United States Patent
Choi et al.

(10) Patent No.: US 11,753,416 B2
(45) Date of Patent: *Sep. 12, 2023

(54) COMPOUNDS AND COMPOSITIONS FOR INDUCING CHONDROGENESIS

(71) Applicant: NOVARTIS AG, Basel (CH)

(72) Inventors: Ha-Soon Choi, San Diego, CA (US); Jiqing Jiang, San Diego, CA (US); James Paul Lajiness, San Diego, CA (US); Bao Nguyen, San Diego, CA (US); Hank Michael James Petrassi, Fallbrook, CA (US)

(73) Assignee: Novartis AG, Basel (CH)

( * ) Notice: Subject to any disclaimer, the term of this patent is extended or adjusted under 35 U.S.C. 154(b) by 17 days.

This patent is subject to a terminal disclaimer.

(21) Appl. No.: 17/368,537

(22) Filed: Jul. 6, 2021

(65) Prior Publication Data

US 2021/0347784 A1  Nov. 11, 2021

Related U.S. Application Data

(63) Continuation of application No. 16/620,407, filed as application No. PCT/IB2018/054123 on Jun. 7, 2018, now Pat. No. 11,091,499.

(60) Provisional application No. 62/517,394, filed on Jun. 9, 2017.

(51) Int. Cl.
  *C07D 493/08* (2006.01)
  *A61K 9/00* (2006.01)
  *A61K 31/343* (2006.01)

(52) U.S. Cl.
  CPC .......... *C07D 493/08* (2013.01); *A61K 9/0053* (2013.01); *A61K 31/343* (2013.01)

(58) Field of Classification Search
  CPC ... C07D 493/08; A61K 9/0053; A61K 31/343
  USPC .......................................................... 514/456
  See application file for complete search history.

(56) References Cited

U.S. PATENT DOCUMENTS

| | | | |
|---|---|---|---|
| 6,077,864 A | 6/2000 | Burgess et al. | |
| 6,653,468 B1 | 11/2003 | Guzaev et al. | |
| 9,233,106 B2 | 1/2016 | Hess et al. | |
| 11,091,499 B2 * | 8/2021 | Choi | C07D 493/08 |
| 2006/0211730 A1 | 9/2006 | Levin et al. | |
| 2010/0256385 A1 | 10/2010 | Woodward et al. | |

FOREIGN PATENT DOCUMENTS

| | | |
|---|---|---|
| AU | 2018279306 C1 | 1/2021 |
| EC | SP98-2358 A | 1/1998 |
| JP | 200568052 A | 3/2005 |
| JP | 2016204316 A | 12/2016 |
| WO | 0222620 A2 | 3/2002 |
| WO | 0222621 A2 | 3/2002 |
| WO | 2002042310 A2 | 5/2002 |
| WO | 2006/038112 A1 | 4/2006 |
| WO | 2009052237 A1 | 4/2009 |
| WO | 2011008773 A2 | 1/2011 |
| WO | 2012080729 A2 | 6/2012 |
| WO | 2012129562 A2 | 9/2012 |
| WO | 2012177856 A2 | 12/2012 |
| WO | 2013007765 A1 | 1/2013 |
| WO | 2015175487 A1 | 11/2015 |
| WO | 2018225009 A1 | 12/2018 |

OTHER PUBLICATIONS

Fugami, et al., "Novel Palladium-Catalyzed Diarylation and Dialkenylation Reactions of Norbornene Derivatives", Synlett, May 1998, Issue 5, pp. 477-478, Georg Thieme Verlag.

Pachuta-Stec, et al., "New Norcantharidin Analogs: Synthesis and Anticancer Activity", Arch. Harm. Chem. Life Sci., 2015, vol. 348, pp. 897-907, Wiley-VCH Verlag GmbH & Co.

* cited by examiner

*Primary Examiner* — Kristin A Vajda
(74) *Attorney, Agent, or Firm* — Emily T. Wu

(57) ABSTRACT

The present invention provides a compound of formula (I) or a pharmaceutically acceptable salt thereof;

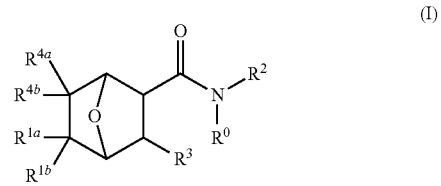

(I)

or a pharmaceutically acceptable salt, tautomer, or stereoisomer thereof, wherein the variables are as defined herein. The present invention further provides pharmaceutical compositions comprising such compounds; and methods of using such compounds for treating joint damage or injury in a mammal, for inducing hyaline cartilage production or for inducing differentiation of chondrogenic progenitor cells into mature chondrocytes.

16 Claims, No Drawings

COMPOUNDS AND COMPOSITIONS FOR INDUCING CHONDROGENESIS

CROSS-REFERENCE TO RELATED APPLICATIONS

This application is a continuation of U.S. application Ser. No. 16/620,407 filed 6 Dec. 2019, which is a 371 U.S. national phase application of international application number PCT/IB2018/054123, filed 7 Jun. 2018, which claims the benefit of U.S. provisional application Ser. No. 62/517,394 filed 9 Jun. 2017; each of which is incorporated by reference herein in its entirety.

FIELD OF THE INVENTION

The present invention relates to compositions and methods for treating or preventing joint damage resulting from joint injury and arthritis.

BACKGROUND OF THE INVENTION

Osteoarthritis (OA) represents the most common musculoskeletal disorder. Approximately 40 million Americans are currently affected and this number is predicted to increase to 60 million within the next twenty years as a result of the aging population and an increase in life expectancy, making it the fourth leading cause of disability. OA is characterized by a slow degenerative breakdown of the joint including both the articular cartilage (containing the cells and matrix which produce lubrication and cushioning for the joint) and the subchondral bone underlying the articular cartilage. OA can be considered a consequence of various etiologic factors. For example, it can be caused by abnormal biomechanical stress or genetic or acquired abnormalities of articular cartilage or bone. Current OA therapies include pain relief with oral NSAIDs or selective cyclooxygenase 2 (COX-2) inhibitors, intra-articular (IA) injection with agents such as corticorsteroids and hyaluronan, and surgical approaches.

Joint damage, e.g., acute joint injury, such as a meniscal or ligament tear, or an intra-articular fracture can also lead to arthritis, e.g., posttraumatic arthritis. Because articular cartilage has a limited ability to repair, even small undetectable damage can often get worse over time and lead to OA. Current treatments for joint injury can include surgery and other invasive procedures focused on regeneration of damaged joints as well as treatment with agents to reduce pain and inflammation.

Mesenchymal stem cells (MSCs) are present in adult articular cartilage and upon isolation can be programmed in vitro to undergo differentiation to chondrocytes and other mesenchymal cell lineages, and may be used for cartilage regeneration. In part, the process is regulated by growth factors (TGFβs, BMPs), serum conditions and cell-cell contact.

WO2011/008773 describes peptide compositions and use of those compositions for treating or preventing arthritis and joint injury and for inducing differentiation of mesenchymal cells into chondrocytes. Additionally, WO2012/129562 describes small molecule compounds, compositions and use of those compositions for amelioration of arthritis and joint injury and for inducing differentiation of mesenchymal cells into chondrocytes.

Though surgical techniques, and regenerative technology have made some progress in restoration of cartilage, slowing degeneration, and improved repair of joint damage, a continued need exists for improvement of compositions and methods for effective cartilage regeneration, treatment of joint damage and amelioration or prevention of OA.

SUMMARY OF THE INVENTION

The present invention relates to compositions and methods for treating or preventing joint damage resulting from joint injury and arthritis.

In one aspect, the invention provides a compound of Formula (I), or a pharmaceutically acceptable salt, or stereoisomer thereof;

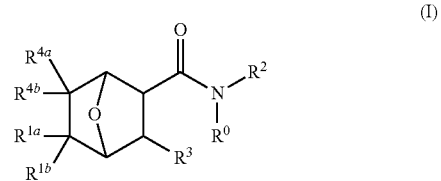

(I)

wherein $R^0$ is hydrogen or $C_{1-6}$alkyl;

$R^2$ is phenyl; a 5- or 6-membered heteroaryl or a 5- or 6-membered heterocyclyl, each having 1 to 3 heteroatoms selected from N, O and S; wherein $R^2$ is unsubstituted or substituted;

$R^3$ is a 5- or 6-membered heteroaryl having 1 to 2 heteroatoms selected from N, O and S; wherein $R^3$ is unsubstituted or substituted, $R^{1a}$, $R^{1b}$, $R^{4a}$, and $R^{4b}$ are each independently hydrogen, halo, hydroxyl, $C_{1-6}$alkoxy, $C_{1-6}$alkyl, —$NR^7R^8$ or —$NR^7$—$(CR^9R^{10})_{2-4}$—$OR^{11}$; or wherein one of $R^{1a}$ and $R^{1b}$ together with one of $R^{4a}$ and $R^{4b}$ form a cyclopropyl with the two carbon atoms to which said $R^{1a}$, $R^{1b}$, $R^{4a}$ and $R^{4b}$ are respectively attached;

$R^5$, $R^6$, $R^7$, $R^9$, $R^{10}$ and $R^{11}$ are each independently hydrogen or $C_{1-6}$alkyl;

$R^8$ is hydrogen, $C_{3-7}$ cycloalkyl or a 5- or 6-membered heterocyclyl having 1-3 heteroatoms selected from N, O and S; wherein said $C_{3-7}$ cycloalkyl or 5- or 6-membered heterocyclyl of $R^8$ is unsubstituted or substituted;

alternatively, $R^5$ and $R^6$ or $R^7$ and $R^8$ together with the nitrogen atom to which they are attached in —$NR^5R^6$ or —$NR^7R^8$ respectively form a 5- or 6-membered heterocyclyl having 1-3 heteroatoms selected from N, O and S;

provided that $R^{1a}$, $R^{1b}$, $R^{4a}$, and $R^{4b}$ cannot all be hydrogen; and further provided that when $R^{1a}$, $R^{1b}$, $R^{4a}$, or $R^{4b}$ is $C_{1-6}$alkyl, the other substituent on the same carbon ring atom is not hydrogen.

In another aspect, the invention provides a pharmaceutical composition comprising a therapeutically effective amount of a compound of Formula (I) or subformulae thereof, or a pharmaceutically acceptable salt or stereoisomer thereof; and one or more pharmaceutically acceptable carriers.

In yet another aspect, the invention provides a combination, in particular a pharmaceutical combination, comprising a therapeutically effective amount of a compound of Formula (I) or subformulae thereof, or a pharmaceutically acceptable salt or stereoisomer thereof; and one or more therapeutically active agent(s).

The compounds of the invention, alone or in combination with one or more therapeutically active agent(s), can be used for treating, ameliorating or preventing acute joint damage or injury, such as arthritis (osteoarthritis, traumatic arthritis, systemic rheumatoid arthritis) or degenerative disc disease. Furthermore, the compounds of the invention, alone or in combination with one or more therapeutically active agent(s), can be used for inducing hyaline cartilage production or for inducing differentiation of chondrogenic progenitor cells into mature chondrocytes mature chondrocytes producing hyaline cartilage extracellular matrix.

Unless specified otherwise, the term "compounds of the present invention" refers to compounds of Formula (I) and subformulae thereof (e.g., Formula (1A), (1B), (1C), (1D), (1E), (1F), (1G), (1H), (1I), (1J), (1K), (1L), (2A), (2B), (2C), (2D), (2E), (2F), (2G), (2H), (2I), (2J), (2K), (2L)), and salts thereof, as well as all stereoisomers (including diastereoisomers and enantiomers), rotamers, tautomers and isotopically labeled compounds (including deuterium substitutions), as well as inherently formed moieties.

DETAILED DESCRIPTION OF THE INVENTION

The present invention provides novel compounds that stimulate hyaline cartilage production in injured joints.

In one aspect, the present invention provides novel compounds and compositions for repairing cartilage. Also provided are compositions and methods to treat, prevent or ameliorate arthritis or joint injury by administering a compound or composition of the invention into a joint, a cartilage tissue or a cartilage proximal tissue, or systemically. Further, the invention provides compositions and methods for induction of chondrogenic progenitor differentiation into normal hyaline chondrocytes.

Definitions

For purposes of interpreting this specification, the following definitions will apply and whenever appropriate, terms used in the singular will also include the plural and vice versa.

As used herein, the term "$C_{1-6}$alkoxy" refers to a radical of the formula —$OR_a$ where $R_a$ is a $C_{1-6}$ alkyl radical as generally defined above. Examples of $C_{1-6}$alkoxy include, but are not limited to, methoxy, ethoxy, propoxy, isopropoxy, butoxy, isobutoxy, pentoxy, and hexoxy. The alkyl portion of the alkoxy may be optionally substituted, and the substituents include those described for the alkyl group below.

As used herein, the term "$C_{1-6}$ alkyl" refers to a straight or branched hydrocarbon chain radical consisting solely of carbon and hydrogen atoms, containing no unsaturation, having from one to six carbon atoms, and which is attached to the rest of the molecule by a single bond. The term "$C_{1-4}$alkyl" is to be construed accordingly. Examples of $C_{1-6}$alkyl include, but are not limited to, methyl, ethyl, n-propyl, 1-methylethyl (iso-propyl), n-butyl, n-pentyl and 1,1-dimethylethyl (t-butyl). Typical substituents include, but are not limited to halo, hydroxyl, alkoxy, cyano, amino, acyl, aryl, arylalkyl, and cycloalkyl, or an heteroform of one of these groups, and each of which can be substituted by the substituents that are appropriate for the particular group.

"Amino", as used herein, refers to the radical —$NH_2$. When an amino is described as "substituted" or "optionally substituted", the term includes NR'R" wherein each R' and R" is independently H, or is an alkyl, alkenyl, alkynyl, acyl, aryl, aryl, cycloalkyl, arylalkyl cycloalkylalkyl group or a heteroform of one of these groups, and each of the alkyl, alkenyl, alkynyl, acyl, aryl, arylalkyl or groups or heteroforms of one of these groups, each of which is optionally substituted with the substituents described herein as suitable for the corresponding group. Unless otherwise indicated, the compounds of the invention containing amino moieties may include protected derivatives thereof. Suitable protecting groups for amino moieties include acetyl, tert-butoxycarbonyl, benzyloxycarbonyl, and the like.

As used herein, the term "amino$C_{1-6}$alkyl" refers to a $C_{1-6}$alkyl radical as defined above, wherein one of the hydrogen atoms of the $C_{1-6}$alkyl group is replaced by a primary amino group.

Representative examples of amino$C_{1-6}$alkyl include, but are not limited to, amino-methyl, 2-amino-ethyl, 2-amino-propyl, 3-amino-propyl, 3-amino-pentyl and 5-amino-pentyl.

As used herein, the term "$C_{1-4}$alkylamino" refers to a radical of the formula —NH—$R_a$ where $R_a$ is a $C_{1-4}$alkyl radical as defined above.

"Aromatic", as used herein, refers to a moiety wherein the constituent atoms make up an unsaturated ring system, where all atoms in the ring system are $sp^2$ hybridized and the total number of pi electrons is equal to 4n+2. An aromatic ring may be such that the ring atoms are only carbon atoms or may include carbon and non-carbon atoms (see Heteroaryl).

"Aryl", as used herein, refers to a monocyclic or polycyclic aromatic ring assembly containing 6-14 ring atoms where all the ring atoms are carbon atoms. Typically, the aryl is a 6-membered (ring atoms) monocyclic, a 10- to 12-membered bicyclic or a 14-membered fused tricyclic aromatic ring system. Six to fourteen membered aryls include, but are not limited to, phenyl, biphenyl, naphthyl, azulenyl, and anthracenyl. An aryl may be unsubstituted or substituted by 1-5 (such as one, or two, or three) substituents independently selected from the group consisting of hydroxy, thiol, cyano, nitro, $C_{1-4}$alkyl, $C_{1-4}$alkenyl, $C_{1-4}$alkynyl, $C_{1-4}$alkoxy, thio$C_{1-4}$alkyl, $C_{1-4}$alkenyloxy, $C_{1-4}$alkynyloxy, halogen, $C_{1-4}$alkylcarbonyl, carboxy, $C_{1-4}$alkoxycarbonyl, amino, $C_{1-4}$alkylamino, di-$C_{1-4}$alkylamino, $C_{1-4}$alkylaminocarbonyl, di-$C_{1-4}$alkylaminocarbonyl, $C_{1-4}$alkylcarbonylamino, $C_{1-4}$alkylcarbonyl($C_{1-4}$alkyl)amino, sulfonyl, sulfamoyl, alkylsulfamoyl, $C_{1-4}$alkylaminosulfonyl, aryl, heteroaryl, cycloalkyl and heterocyclyl, wherein each of the aforementioned substitutents may be further substituted by one or more substituents independently selected from halogen, alkyl, hydroxyl or $C_{1-4}$alkoxy groups. When an "aryl" is represented along with another radical like "arylalkyl", "aryloxyalkyl", "aryloxycarbonyl", "aryloxy-carbonylalkyl", the aryl portion shall have the same meaning as described in the above-mentioned definition of "aryl".

"Bicyclic" or "bicyclyl", as used here, in refers to a ring assembly of two rings where the two rings are fused together, linked by a single bond or linked by two bridging atoms. The rings may be a carbocyclyl, a heterocyclyl, or a mixture thereof.

"Bridging ring", as used herein, refers to a polycyclic ring system where two ring atoms that are common to two rings are not directly bound to each other. One or more rings of the ring system may also comprise heteroatoms as ring atoms. Non-exclusive examples of bridging rings include norbornanyl, oxabicyclo[2.2.1]heptanyl, azabicyclo[2.2.1]heptanyl, adamantanyl, and the like.

"Cycloalkyl", as used herein, means a radical comprising a non-aromatic, saturated monocyclic, bicyclic, tricyclic, fused, bridged or spiro polycyclic hydrocarbon ring system of 3- to 14-ring members where all the ring members are carbon atoms. Exemplary monocyclic cycloalkyl include, but are not limited to, cyclopropyl, cyclobutyl, cyclopentyl, cyclohexyl, cycloheptanyl, cyclooctanyl, and the like. Exemplary bicyclic cycloalkyls include bicyclo[2.2.1]heptane, bicyclo[2.2.1]octanyl, bornyl, norbornanyl, decahydronaphthyl, bicyclo[2.1.1]hexyl, bicyclo[2.2.1]heptyl, bicyclo[3.1.1]heptyl, bicyclo[2.2.2]octyl. Exemplary tricyclic cycloalkyl groups include, for example, adamantanyl. A cycloalkyl may be unsubstituted or substituted by one, or two, or three, or more substituents independently selected from the group consisting of hydroxyl, thiol, cyano, nitro, oxo, alkylimino, $C_{1-4}$alkyl, $C_{1-4}$alkenyl, $C_{1-4}$alkynyl, $C_{1-4}$alkoxy, $C_{1-4}$thioalkyl, $C_{1-4}$alkenyloxy, $C_{1-4}$alkynyloxy, halogen, $C_{1-4}$alkylcarbonyl, carboxy, $C_{1-4}$alkoxycarbonyl, amino, $C_{1-4}$alkylamino, di-$C_{1-4}$alkylamino, $C_{1-4}$alkylaminocarbonyl, di-$C_{1-4}$alkylaminocarbonyl, $C_{1-4}$alkylcarbonylamino, $C_{1-4}$alkylcarbonyl($C_{1-4}$alkyl)amino, sulfonyl, sulfamoyl, alkylsulfamoyl, $C_{1-4}$alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_{1-4}$alkoxy groups.

"Cyano", as used herein, refers to the radical —CN.

"$EC_{50}$", as used herein, refers to the molar concentration of a modulator that produces 50% efficacy.

"$IC_{50}$", as used herein, refers to the molar concentration of an inhibitor or modulator that produces 50% inhibition.

"Fused ring", as used herein, refers to a multi-ring assembly wherein the rings comprising the ring assembly are so linked that the ring atoms that are common to two rings are directly bound to each other. The fused ring assemblies may be saturated, partially saturated, aromatics, carbocyclics, heterocyclics, and the like. Non-exclusive examples of common fused rings include decalin, naphthalene, anthracene, phenanthrene, indole, benzofuran, purine, quinoline, and the like.

"Halo" or "halogen", as used herein, refers to fluoro, chloro, bromo, and iodo.

"Halo-substituted $C_{1-6}$alkyl", as used herein, refers to a $C_{1-6}$alkyl radical as defined above, substituted by one or more halo radicals as defined above. Examples of halo-substituted $C_{1-6}$alkyl include, but are not limited to, trifluoromethyl, difluoromethyl, fluoromethyl, trichloromethyl, 2,2,2-trifluoroethyl, 1,3-dibromopropan-2-yl, 3-bromo-2-fluoropropyl and 1,4,4-trifluorobutan-2-yl.

"Heteroaryl", as used herein, refers to a 5- or 6-membered aromatic monocyclic ring radical which comprises 1, 2, 3 or 4 heteroatoms individually selected from nitrogen, oxygen and sulfur. The heteroaryl radical may be bonded via a carbon atom or heteroatom. Examples of heteroaryl include, but are not limited to, furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl or pyridyl. A heteroaryl may be unsubstituted or substituted with one or more substituents independently selected from hydroxyl, thiol, cyano, nitro, $C_{1-4}$alkyl, $C_{1-4}$alkenyl, $C_{1-4}$alkynyl, $C_{1-4}$alkoxy, thio$C_{1-4}$alkyl, $C_{1-4}$alkenyloxy, $C_{1-4}$alkynyloxy, halogen, $C_{1-4}$alkylcarbonyl, carboxy, $C_{1-4}$alkoxycarbonyl, amino, $C_{1-4}$alkylamino, di-$C_{1-4}$alkylamino, $C_{1-4}$alkylaminocarbonyl, di-$C_{1-4}$alkylaminocarbonyl, $C_{1-4}$alkylcarbonylamino, $C_{1-4}$alkylcarbonyl($C_{1-4}$alkyl)amino, sulfonyl, sulfamoyl, alkylsulfamoyl, $C_{1-4}$alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_{1-4}$alkoxy groups. When a heteroaryl is represented along with another radical like "heteroaryloxy", "heteroaryloxyalkyl", "heteroaryloxycarbonyl", the heteroaryl portion shall have the same meaning as described in the above-mentioned definition of "heteroaryl".

"Heteroatom", as used herein, refers to an atom that is not a carbon atom. Particular examples of heteroatoms include, but are not limited to nitrogen, oxygen, and sulfur.

"Heterocyclyl" or "heterocyclic", as used herein, refers to a stable 5- or 6-membered non-aromatic monocyclic ring radical which comprises 1, 2, or 3, heteroatoms individually selected from nitrogen, oxygen and sulfur. The heterocyclyl radical may be bonded via a carbon atom or heteroatom. Examples of heterocyclyl include, but are not limited to, azetidinyl, oxetanyl, pyrrolinyl, pyrrolidyl, tetrahydrofuryl, tetrahydrothienyl, piperidyl, piperazinyl, tetrahydropyranyl, morpholinyl or perhydroazepinyl." A heterocyclyl may be unsubstituted or substituted with 1-5 substituents (such as one, or two, or three) each independently selected from hydroxyl, thiol, cyano, nitro, oxo, alkylimino, $C_{1-4}$alkyl, $C_{1-4}$alkenyl, $C_{1-4}$alkynyl, $C_{1-4}$alkoxy, $C_{1-4}$thioalkyl, $C_{1-4}$alkenyloxy, $C_{1-4}$alkynyloxy, halogen, $C_{1-4}$alkylcarbonyl, carboxy, $C_{1-4}$alkoxycarbonyl, amino, $C_{1-4}$alkylamino, di-$C_{1-4}$alkylamino, $C_{1-4}$alkylaminocarbonyl, di-$C_{1-4}$alkylaminocarbonyl, $C_{1-4}$alkylcarbonylamino, $C_{1-4}$alkylcarbonyl($C_{1-4}$alkyl)amino, sulfonyl, sulfamoyl, alkylsulfamoyl, $C_{1-4}$alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_{1-4}$alkoxy groups.

Hydroxy, as used herein, refers to the radical —OH.

"Protected derivatives", as used herein, refers to derivatives of inhibitors in which a reactive site or sites are blocked with protecting groups. Protected derivatives are useful in the preparation of inhibitors or in themselves may be active as inhibitors. Examples of protected group includes, but are not limited to, acetyl, tetrahydropyran, methoxymethyl ether, β-methoxyethoxymethyl ether, ρ-methoxybenzyl, methylthiomethyl ether, pivaloyl, silyl ether, carbobenzyloxy, benzyl, tert-butoxycarbonyl, ρ-methoxyphenyl, 9-fluorenylmethyloxycarbonyl, acetals, ketals, acylals, dithianes, methylesters, benzyl esters, tert-butyl esters, and silyl esters. A comprehensive list of suitable protecting groups can be found in T. W. Greene, *Protecting Groups in Organic Synthesis,* 3rd edition, John Wiley & Sons, Inc. 1999.

"Unsubstituted or substituted" or "optionally substituted", as used herein, indicate the substituent bound on the available valance of a named group or radical. "Unsubstituted" as used herein indicates that the named group or radical will have no further non-hydrogen substituents. "Substituted" or "optionally substituted" as used herein indicates that at least one of the available hydrogen atoms of named group or radical has been (or may be) replaced by a non-hydrogen substituent. Unless otherwise specified, examples of substituents may include, but are not limited to, halo, nitro, cyano, thio, oxy, hydroxy, carbonyloxy, $C_{1-6}$alkoxy, 6- to 10-membered aryloxy, 5- to 10-membered heteroaryloxy, carbonyl, oxycarbonyl, aminocarbonyl, amino, $C_{1-6}$alkylamino, sulfonamido, imino, sulfonyl, sulfinyl, $C_{1-6}$alkyl, $C_{1-6}$haloalkyl, hydroxy$C_{1-6}$alkyl, carbonyl$C_{1-6}$alkyl, thiocarbonyl$C_{1-10}$alkyl, sulfonyl$C_{1-6}$alkyl, sulfinyl$C_{1-6}$alkyl, $C_{1-10}$azaalkyl, imino$C_{1-6}$alkyl, 3- to 12-membered cycloalkyl$C_{1-6}$alkyl, 4- to 15-membered heterocycloalkyl$C_{1-6}$alkyl, 6- to 10-membered aryl$C_{1-6}$alkyl, 5- to 10-membered heteroaryl$C_{1-6}$alkyl, 10- to 12-membered bicycloaryl$C_{1-6}$alkyl, 9- to 12-membered heterobicycloaryl$C_{1-6}$alkyl, 3- to 12-membered cycloalkyl, 4- to 12-membered heterocyclyl, 9- to 12-membered bicycloalkyl, 3- to 12-membered heterobicycloalkyl, 6- to 12-membered aryl, and 5- to 12-membered heteroaryl, "Sulfonyl", as used herein, means the radical —S(O)$_2$—. It is noted that the term "sulfonyl" when referring to a monovalent substituent can alternatively refer to a substituted sulfonyl group, —S(=O)$_2$R, where R is hydrogen or a non-hydrogen substituent on the sulfur atom forming different sulfonyl groups including sulfonic acids, sulfonamides, sulfonate esters, and sulfones.

Any definition herein may be used in combination with any other definition to describe a composite structural group. By convention, the trailing element of any such definition is that which attaches to the parent moiety. For example, the composite group alkoxyalkyl would represent an alkoxy group attached to the parent molecule through an alkyl group.

As used herein, the term "chondrocytes" refers to differentiated cartilage cells. Chondrocytes produce and maintain the cartilaginous matrix which is composed of collagen and proteoglycans. Chondrocytes are derived from the differentiation of chondrogenic progenitor cells (CPCs). Differentiation is the process a specialized cell type is formed from a less specialized cell type, for example, a chondrocyte from a chondrogenic progenitor cell (CPC).

As used herein, the term "chondrocyte differentiation agent" refers to an agent that induces chondrogenic cells to differentiate into mature chondrocyte, which then synthesize the cartilage extra-cellular matrix (ECM).

As used herein, the term "subject" refers to primates (e.g., humans, male or female), dogs, rabbits, guinea pigs, pigs, rats and mice. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing" or "prevention" of any disease or disorder refers to the prophylactic treatment of the disease or disorder; or delaying the onset or progression of the disease or disorder As used herein, a subject is "in need of" a treatment if such subject would benefit biologically, medically or in quality of life from such treatment.

As used herein, the term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate joint damage resulting from joint injury and arthritis. In another non-limiting embodiment, the term "a therapeutically effective amount" refers to the amount of the compound of the present invention that, when administered to a cell, or a tissue, or a non-cellular biological material, or a medium, is effective to promote chondrogenesis.

As used herein, the terms "treat", "treating", "treatment" plus "ameliorate" and "ameliorating" refer to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

As used herein, "administering" refers to administration to a specific joint.

As used herein, the term "pharmaceutical composition" refers to a compound of the invention, or a pharmaceutically acceptable salt thereof, together with at least one pharmaceutically acceptable carrier, in a form suitable for oral or parenteral administration.

As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, 22$^{nd}$ Ed. Pharmaceutical Press, 2013, pp. 1049-1070).

As used herein, the term "a," "an," "the" and similar terms used in the context of the present invention (especially in the context of the claims) are to be construed to cover both the singular and plural unless otherwise indicated herein or clearly contradicted by the context.

DESCRIPTION OF PREFERRED EMBODIMENTS

The present invention relates to compositions and methods for treating or preventing joint damage resulting from joint injury and arthritis.

Various enumerated embodiments of the invention are described herein. Features specified in each embodiment may be combined with other specified features to provide further embodiments of the present invention.

In one aspect, the present invention provides a compound of Formula (I), or a pharmaceutically acceptable salt or stereoisomer thereof, as described above.

Embodiment 1. A compound of Formula (I), or a pharmaceutically acceptable salt or stereoisomer thereof;

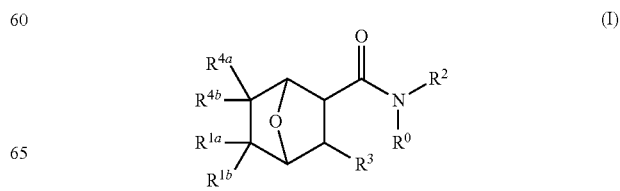

wherein $R^0$ is hydrogen or $C_{1-6}$alkyl;

$R^2$ is phenyl; a 5- or 6-membered heteroaryl or a 5- or 6-membered heterocyclyl, each having 1 to 3 heteroatoms selected from N, O and S; wherein $R^2$ is unsubstituted or substituted by 1 to 3 substituents independently selected from halo, $C_{1-6}$alkyl, halo-substituted $C_{1-6}$alkyl, $C_{1-6}$alkoxy, halo-substituted $C_{1-6}$alkoxy, cyano, $C_{1-6}$alkylsulfonyl, phenyl unsubstituted or substituted by halo;

$R^3$ is a 5- or 6-membered heteroaryl having 1 to 2 heteroatoms selected from N, O and S; wherein $R^3$ is unsubstituted or substituted by 1 to 3 substituents independently selected from halo, $C_{1-6}$alkyl, halo-substituted $C_{1-6}$alkyl, $C_{1-6}$alkoxy or —$NR^5R^6$;

$R^{1a}$, $R^{1b}$, $R^{4a}$, and $R^{4b}$ are each independently hydrogen, halo, hydroxyl, $C_{1-6}$alkoxy, $C_{1-6}$alkyl, —$NR^7R^8$ or —$NR^7$—$(CR^9R^{10})_{2-4}$—$OR^{11}$; or wherein one of $R^{1a}$ and $R^{1b}$ together with one of $R^{4a}$ and $R^{4b}$ form a cyclopropyl with the two carbon atoms to which said $R^{1a}$, $R^{1b}$, $R^{4a}$ and $R^{4b}$ are respectively attached;

$R^5$, $R^6$, $R^7$, $R^9$, $R^{10}$ and $R^{11}$ are each independently hydrogen or $C_{1-6}$alkyl;

$R^8$ is hydrogen, $C_{3-7}$ cycloalkyl or a 5- or 6-membered heterocyclyl having 1-3 heteroatoms selected from N, O and S; wherein said $C_{3-7}$ cycloalkyl or 5- or 6-membered heterocyclyl of $R^8$ is unsubstituted or substituted by hydroxy or $C_{1-6}$ alkyl;

alternatively, $R^5$ and $R^6$ or $R^7$ and $R^8$ together with the nitrogen atom to which they are attached in —$NR^5R^6$ or —$NR^7R^8$ respectively form a 5- or 6-membered heterocyclyl having 1-3 heteroatoms selected from N, O and S;

provided that $R^{1a}$, $R^{1b}$, $R^{4a}$, and $R^{4b}$ cannot all be hydrogen; and further provided that when $R^{1a}$, $R^{1b}$, $R^{4a}$, or $R^{4b}$ is $C_{1-6}$alkyl, the other substituent on the same carbon ring atom is not hydrogen.

Embodiment 2. A compound according to Embodiment 1, selected from Formula (1A), (1B), (1C), (1D), (1E), (1F), (1G), (1H), (1I), (1J), (1K), (1L), (2A), (2B), (2C), (2D), (2E), (2F), (2G), (2H), (2I), (2J), (2K) and (2L), or a pharmaceutically acceptable salt, or stereoisomer thereof;

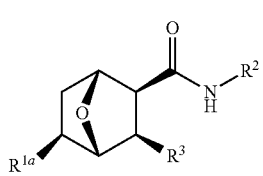

(1A)

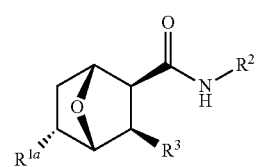

(1B)

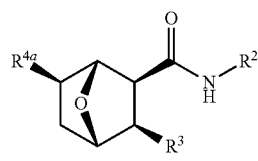

(1C)

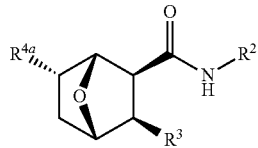

(1D)

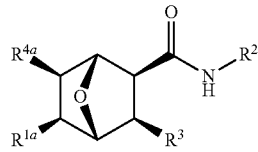

(1E)

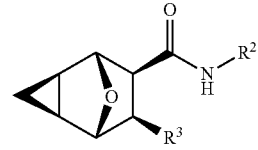

(1F)

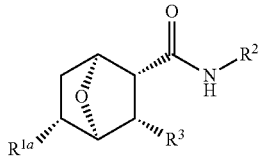

(1G)

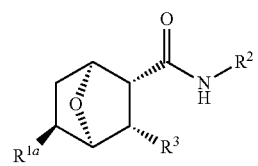

(1H)

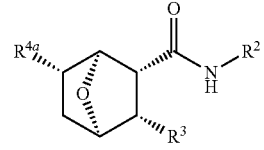

(1I)

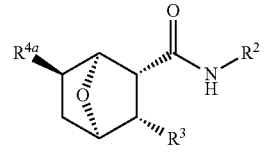

(1J)

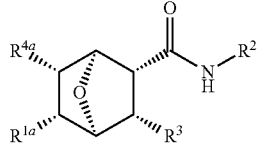

(1K)

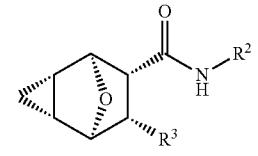

(1L)

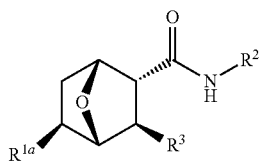 (2A)

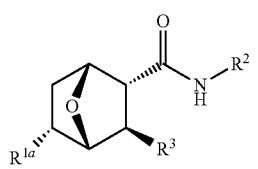 (2B)

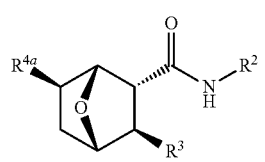 (2C)

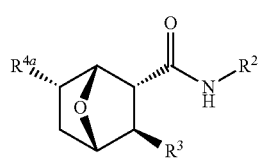 (2D)

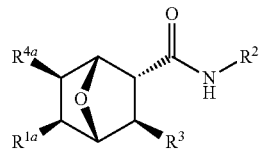 (2E)

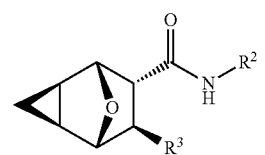 (2F)

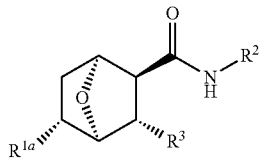 (2G)

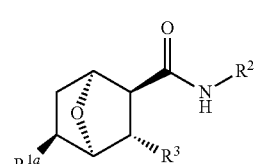 (2H)

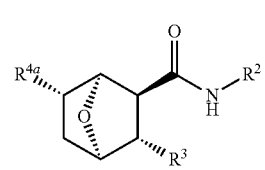 (2I)

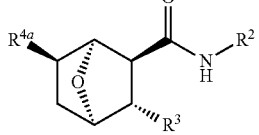 (2J)

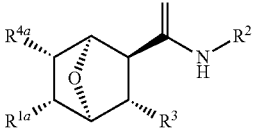 (2K)

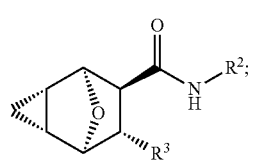 (2L)

Embodiment 3. A compound according to Embodiment 2, selected from:
(a) Formula (1A) or (2A);
(b) Formula (1B) or (2B);
(c) Formula (1C) or (2C);
(d) Formula (1D) or (2D);
(e) Formula (1E) or (2E);
(f) Formula (1F) or (2F);
(g) Formula (1G) or (2G)
(h) Formula (1H) or (2H);
(i) Formula (1I) or (2I);
(j) Formula (1J) or (2J);
(k) Formula (1K) or (2K); and
(l) Formula (1L) or (2L);
or a pharmaceutically salt, or stereoisomer thereof; wherein various substituents are as defined in any of the above embodiments.

Embodiment 3A. A compound according to Embodiment 3, of Formula (1A) or Formula (2A).
Embodiment 3B. A compound according to Embodiment 3, of Formula (1B) or Formula (2B).
Embodiment 3C. A compound according to Embodiment 3, of Formula (1C) or Formula (2C).
Embodiment 3D. A compound according to Embodiment 3, of Formula (1D) or Formula (2D).
Embodiment 3E. A compound according to Embodiment 3, of Formula (1E) or Formula (2E).
Embodiment 3F. A compound according to Embodiment 3, of Formula (1F) or Formula (2F).
Embodiment 3G. A compound according to Embodiment 3, of Formula (1G) or Formula (2G).
Embodiment 3H. A compound according to Embodiment 3, of Formula (1H) or Formula (2H).
Embodiment 3I. A compound according to Embodiment 3, of Formula (1I) or Formula (2I).
Embodiment 3J. A compound according to Embodiment 3, of Formula (1J) or Formula (2J).
Embodiment 3K. A compound according to Embodiment 3, of Formula (1K) or Formula (2K).
Embodiment 3L. A compound according to Embodiment 3, of Formula (1 L) or Formula (2L).
Embodiment 4. A compound according to Embodiment 2, selected from Formula (1A), (1C), (1E), (1F), (1G), (1I), (1L), (1K), (2A), (2C), (2E), (2F), (2G), (2I), (2K) and (2L), or a pharmaceutically acceptable salt, or stereoisomer thereof.

Embodiment 5. A compound according to Embodiment 2, selected from Formula (1A), (1C), (1G), (1L), (2A), (2C), (2G) and (2L), or a pharmaceutically acceptable salt, or stereoisomer thereof; wherein various substituents are as defined in any of the above embodiments. In some embodiments, $R^{1a}$ and $R^{4a}$ are hydroxyl.

Embodiment 5A. A compound according to Embodiment 5, selected from Formula (1A), (1G), (2A) and (2G), or a pharmaceutically acceptable salt or stereoisomer thereof; wherein various substituents are as defined in any of the above embodiments. In some embodiments, $R^{1a}$ and $R^{4a}$ are hydroxyl.

Embodiment 5B. A compound according to Embodiment 5, of Formula (2A) or (2G), or a pharmaceutically acceptable salt or stereoisomer thereof; wherein various substituents are as defined in any of the above embodiments. In some embodiments, $R^{1a}$ and $R^{4a}$ are hydroxyl.

Embodiment 6. A compound according to any of the above Embodiments, or a pharmaceutically acceptable salt or stereoisomer thereof; wherein $R^1$, $R^{1b}$, $R^{4a}$, and $R^{4b}$ are each independently hydrogen, halo, hydroxyl, $C_{1-6}$alkoxy, —$NR^7R^8$ or —$NR^7$—$(CR^9R^{10})_{2-4}$—$OR^{11}$; or wherein one of $R^{1a}$ and $R^{1b}$ together with one of $R^{4a}$ and $R^{4b}$ form a cyclopropyl with the two carbon atoms to which said $R^1$, $R^{1b}$, $R^{4a}$ and $R^{4b}$ are respectively attached.

Embodiment 7. compound according to Embodiment $^a$6, or a pharmaceutically acceptable salt or stereoisomer thereof; wherein one of $R^{1a}$ and $R^{1b}$ is hydrogen and the other is hydroxyl, fluoro, methoxy, methylamino, (2-hydroxyethyl)amino, di-methylamino, morpholin-4-yl, methyl, ((tetrahydro-2H-pyran-4-yl)amino) or (3-hydroxycyclobutyl)amino.

Embodiment 8. compound according to Embodiment 7, or a pharmaceutically acceptable salt or stereoisomer thereof; wherein one of $R^{1a}$ and $R^{1b}$ is hydrogen and the other hydroxyl; and $R^{4a}$ and $R^{4b}$ are hydrogen.

Embodiment 9. A compound according to Embodiment 64 or 5, or a pharmaceutically acceptable salt or stereoisomer thereof; wherein $R^{1a}$ and $R^{1b}$ are hydrogen, and one of $R^{4a}$ and $R^{4b}$ is hydrogen and the other is hydroxyl or fluoro.

Embodiment 10. A compound according to Embodiment 6, or a pharmaceutically acceptable salt or stereoisomer thereof; wherein one of $R^{1a}$ and $R^{1b}$ and one of $R^{4a}$ and $R^{4b}$ together with the carbon ring atoms form a cyclopropyl fused to the bicyclic ring.

Embodiment 11. A compound according to any one of the above Embodiments, or a pharmaceutically acceptable salt or stereoisomer thereof; wherein $R^2$ is phenyl, pyridyl, pyrazolyl, thiazolyl or piperidinyl, each of which is unsubstituted or substituted by 1 to 2 substituents independently selected from halo, $C_{1-6}$alkyl, halo-substituted $C_{1-6}$alkyl, $C_{1-6}$alkoxy, halo-substituted $C_{1-6}$alkoxy, cyano, $C_{1-6}$alkylsulfonyl, phenyl unsubstituted or substituted by halo.

Embodiment 11A. A compound according to Embodiment 11, wherein $R^2$ is phenyl substituted by 1-2 substituents independently selected from chloro, fluoro, trifluoromethyl, trifluoromethoxy, cyano and halo-substituted phenyl.

Embodiment 11B. A compound according to Embodiment 11, wherein $R^2$ is pyridyl substituted by 1-2 substituents independently selected from chloro, methyl, methoxy and trifluoromethyl, Embodiment 11C. A compound according to Embodiment 11, wherein $R^2$ is pyrazolyl or thiazolyl, each substituted by methyl.

Embodiment 11D. A compound according to Embodiment 11, wherein $R^2$ is pyridinyl substituted by methylsulfonyl.

Embodiment 12. A compound according to Embodiment 11, or a pharmaceutically acceptable salt or stereoisomer thereof; wherein $R^2$ is selected from:
phenyl substituted by 3,4-dichloro; 2-trifluoromethyl; 3-trifluoromethyl; 3-cyano-4-chloro;
2-cyano-4-chloro; 3-fluoro-4-chloro; 3-trifluoromethoxy; 3-fluoro-4-trifluoromethoxy; or 3-chloro-4-(2-fluorophenyl);
pyridin-4-yl substituted by 6-methoxy or 2-trifluoromethyl;
pyridin-3-yl substituted by 5,6-dichloro; 6-methoxy; 5-chloro-6-methyl or 5-trifluoromethyl-6-methyl;
pyridin-2-yl substituted by 4,5-dichloro;
1H-pyrazol-3-yl substituted 1-methyl;
thiazol-2-yl substituted by 5-methyl; and
piperidin-4-yl substituted by 1-methylsulfonyl.

Embodiment 13. A compound according to any one of the above Embodiments, or a pharmaceutically acceptable salt or stereoisomer thereof; wherein $R^3$ is pyridyl, pyrimidinyl or pyrazolyl, each of which is unsubstituted or substituted by 1 to 2 substituents independently selected from halo, $C_{1-6}$alkyl, halo-substituted $C_{1-6}$alkyl, $C_{1-6}$alkoxy or —$NR^5R^6$.

Embodiment 13A. A compound according to Embodiment 13, wherein $R^3$ is pyridyl unsubstituted or substituted by 1 to 2 substituents independently selected from fluoro, trifluoromethyl, methyl and methoxy.

Embodiment 13B. A compound according to Embodiment 13, wherein $R^3$ is pyrimidyl unsubstituted or substituted by 1 to 2 substituents independently selected from fluoro, trifluoromethyl, methyl, amino, di-methylamino and morpholinyl. Embodiment 13C. A compound according to Embodiment 13, wherein $R^3$ is 1-methyl-1H-pyrazo-4-lyl or 1-methyl-1H-pyrazol-3-yl.

Embodiment 14. A compound according to Embodiment 13, or a pharmaceutically acceptable salt or stereoisomer thereof; wherein $R^3$ is selected from:
4-pyridyl unsubstituted or substituted by 2-methyl; 2-trifluoromethyl; 2-methoxy; 2-amino;
2-fluoro; 2,3-difluoro; or 2,5-difluoro;
3-pyridyl unsubstituted or substituted by 6-methyl; 6-methoxy; or 5,6-dichloro;
2-pyridyl substituted by 6-trifluoromethyl;
pyrimidin-5-yl unsubstituted or substituted by 2-fluoro, 2-methyl, 2-amino, 2-trifluoromethyl, 2-morpholinyl or 2-di-methylamino;
pyrimidin-4-yl substituted by 2-methyl; and
1H-pyrazol-4-yl or 1H-pyrazolyl-3-yl substituted by 1-methyl.

Embodiment 15. A compound according to Embodiment 1, or a pharmaceutically acceptable salt or stereoisomer thereof; wherein the compound is selected from compounds 1-181 in Table 3.

Embodiment 15A. A compound according to Embodiment 1, or a pharmaceutically acceptable salt or stereoisomer thereof; wherein the compound is selected from:
(1R,2S,3S,4R,5S)-5-hydroxy-3-(pyridin-4-yl)-N-(3-(trifluoromethyl)phenyl)-7-oxabicyclo[2.2.1]heptane-2-carboxamide;
1S,2S,4R,5R,6S,7S)—N-(3,4-dichlorophenyl)-7-(pyrimidin-5-yl)-8-oxatricyclo[3.2.1.0$^{2,4}$]octane-6-carboxamide;
(1R,2R,4S,5S,6R,7R)—N-(5,6-dichloropyridin-3-yl)-7-(pyridin-4-yl)-8-oxatricyclo[3.2.1.0$^{2,4}$]octane-6-carboxamide;
(1R,2S,3S,4R,5S)—N-(3,4-dichlorophenyl)-5-hydroxy-3-(pyridin-4-yl)-7-oxabicyclo[2.2.1]heptane-2-carboxamide;

(1R,2S,3S,4R,5S)—N-(3,4-dichlorophenyl)-3-(2-fluoro-pyridin-4-yl)-5-hydroxy-7-oxabicyclo[2.2.1]heptane-2-carboxamide;

(1R,2S,3S,4R,5S)—N-(3,4-dichlorophenyl)-5-hydroxy-3-(2-methylpyridin-4-yl)-7-oxabicyclo[2.2.1]heptane-2-carboxamide;

(1R,2R,3S,4R,5S)—N-(3,4-dichlorophenyl)-5-hydroxy-3-(2-methylpyridin-4-yl)-7-oxabicyclo[2.2.1]heptane-2-carboxamide;

(1R,2R,3S,4R,5S)—N-(5,6-dichloropyridin-3-yl)-3-(2-fluoropyridin-4-yl)-5-hydroxy-7-oxabicyclo[2.2.1]heptane-2-carboxamide;

(1R,2R,3S,4R,5S)—N-(3,4-dichlorophenyl)-3-(2-fluoro-pyridin-4-yl)-5-hydroxy-7-oxabicyclo[2.2.1]heptane-2-carboxamide; and (1S,2R,3S,4R,5S,6R)—N-(3,4-dichlorophenyl)-5,6-dihydroxy-3-(2-methylpyridin-4-yl)-7-oxabicyclo[2.2.1]heptane-2-carboxamide.

Embodiment 16. A compound of Formula (I) according to Embodiment 15 or 15A, wherein said compound is a mono-hydrate.

Embodiment 17. A pharmaceutical composition comprising a compound according to any one of the above Embodiments 1-16 and sub-embodiments, or a pharmaceutically acceptable salt or stereoisomer thereof, and one or more pharmaceutically acceptable carriers.

Embodiment 18. A combination comprising a compound according to any one of the above Embodiments 1-16 and sub-embodiments, or a pharmaceutically acceptable salt or stereoisomer thereof, and one or more therapeutically active agents.

Embodiment 19. A compound according to any one of Embodiments 1-16 and sub-embodiments, or a pharmaceutically acceptable salt or enantiomer thereof, and optionally in combination with a second therapeutic agent; for use in treating, ameliorating or preventing arthritis or joint injury in a mammal; or for cartilage repair.

Embodiment 20. Use of a compound according to any one of Embodiments 1-16 and sub-embodiments, or a pharmaceutically acceptable salt or enantiomer thereof, and optionally in combination with a second therapeutic agent; in the manufacture of a medicament for arthritis or joint injury, or for cartilage repair.

Embodiment 21. A method for treating, ameliorating or preventing arthritis or joint injury, or for cartilage repair in a mammal in need thereof, comprising administering a therapeutically effective amount of a compound according to any one of Embodiments 1-16 and sub-embodiments, and optionally in combination with a second therapeutic agent; thereby treating, ameliorating or preventing arthritis or joint damage, or repairing cartilage in said mammal.

Embodiment 22. The compound according to Embodiment 19, the use according to Embodiment 20, or the method according to Embodiment 21, wherein the arthritis is osteoarthritis, trauma arthritis, or autoimmune arthritis.

Embodiment 23. The method according to Embodiment 21, wherein said compound is administered orally.

Embodiment 24. A method of inducing hyaline cartilage production or a method of inducing differentiation of chondrogenic progenitor cells into mature chondrocytes, comprising contacting chondrogenic progenitor cells with a therapeutically effective amount of a compound according to any one of Embodiments 1-16 and sub-embodiments, and optionally in combination with a second therapeutic agent; thereby inducing differentiation of chondrocyte progenitor cells into mature chondrocytes producing hyaline cartilage extracellular matrix.

Embodiment 25. The method according to Embodiment 24, wherein said contacting step is performed in vitro or in vivo in a mammal; and when in vivo, stem cells are present in the mammal.

Embodiment 26. The method according to Embodiment 24 or 25, wherein said contacting step occurs in a matrix or biocompatible scaffold.

Embodiment 27. The compound according to Embodiment 19, the use according to Embodiment 20, or the method according to any one of Embodiments 21-26, wherein said second therapeutic agent is a chondrocyte differentiation agent.

Embodiment 28. The compound according to Embodiment 19, the use according to Embodiment 20, or the method according to any one of Embodiments 21-26, wherein said second therapeutic agent is selected from angiopoietin-like 3 protein (ANGPTL3), insulin growth factor (IGF1), SM04690, Janus kinase inhibitor, oral salmon calcitonin, SD-6010, vitamin D3, collagen hydrolyzate, bone morphogenetic protein 7 (BMP7), rusalatide acetate, avocado soy unsaponifiables (ASU), a steroid, a non-steroidal anti-inflammatory agent (NSAID), hyaluronic acid, kartogenin, TPX-100, and a compound having Formula (II);

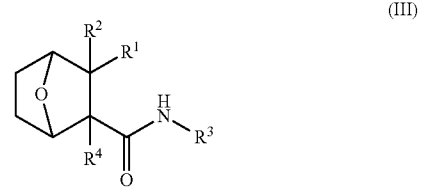

(III)

or a pharmaceutically acceptable salt, or a stereoisomer thereof, wherein $R^1$ is phenyl or 5- or 6-membered heteroaryl; and $R^1$ is unsubstituted or substituted by 1 to 2 substituents independently selected from halo, cyano, $C_{1-6}$alkyl, $C_{1-4}$haloalkyl, —C(O)$R^{13}$, —C(O)O$R^{13}$, —N$R^{14a}R^{14b}$, 5- and 6-membered heterocyclyl, phenyl, and 5- and 6-membered heteroaryl;

wherein $R^{13}$ is $C_{1-6}$alkyl or amino; $R^{14a}$ and $R^{14b}$ are independently is selected from hydrogen, $C_{1-6}$alkyl, —C(O)$R^{15}$, and —C(O)O$R^{15}$; and $R^{15}$ is $C_{1-4}$alkyl; and wherein said heterocyclyl, phenyl, or heteroaryl substituent of $R^1$ is unsubstituted or substituted by 1 to 2 substituents independently selected from halo, hydroxy, and $C_{1-6}$alkyl;

$R^3$ is phenyl or 5- or 6-membered heteroaryl; and $R^3$ is unsubstituted or substituted by 1 to 2 substituents independently selected from halo, cyano, $C_{1-6}$alkyl, $C_{1-6}$haloalkyl, $C_{1-6}$alkoxy, $C_{1-6}$haloalkoxy, —C(O)$R^{16}$, —C(O)O$R^{16}$, 5- and 6-membered heterocyclyl, and phenyl; wherein $R^{16}$ is $C_{1-6}$alkyl; and said heterocyclyl or phenyl of $R^3$ is unsubstituted or substituted by 1 to 2 substituents selected from halo and cyano;

$R^2$ and $R^4$ are independently hydrogen or $C_{1-6}$alkyl; or $R^2$ and $R^4$ taken together form a cyclopropyl fused to the bicyclic ring, or $R^2$ and $R^4$ taken together form a bond, producing a double bond between the two carbons to which $R^2$ and $R^4$ are attached.

Embodiment 29. The compound according to Embodiment 19, the use according to Embodiment 20, or the method according to any one of Embodiments 21-26, wherein said compound having Formula (II) is selected from:

(1R,2S,3R,4S)—N-(3,4-dichlorophenyl)-3-(1-methyl-3-(trifluoromethyl)-1H-pyrazol-5-yl)-7-oxabicyclo[2.2.1]heptane-2-carboxamide;
(1S,2R,3R,4R)—N-(3,4-dichlorophenyl)-3-(pyridin-4-yl)-7-oxabicyclo[2.2.1]heptane-2-carboxamide;
(1S,2S,3R,4R)-3-(2-aminopyridin-4-yl)-N-(3,4-dichlorophenyl)-7-oxabicyclo[2.2.1]heptane-2-carboxamide;
(1R,2S,3S,4S)—N-(3,4-dichlorophenyl)-3-(pyridin-4-yl)-7-oxabicyclo[2.2.1]heptane-2-carboxamide
N-(2-chloro-2'-fluoro-[1,1'-biphenyl]-4-yl)-3-(1H-pyrazol-5-yl)-7-oxabicyclo[2.2.1]hept-2-ene-2-carboxamide
(1R,2R,3S,4S)—N-(3,4-dichlorophenyl)-3-(pyridin-4-yl)-7-oxabicyclo[2.2.1]heptane-2-carboxamide
(1S,2S,3R,4R)—N-(3,4-dichlorophenyl)-3-(pyridin-4-yl)-7-oxabicyclo[2.2.1]heptane-2-carboxamide
(1R,2R,3S,4S)-3-(2-aminopyridin-4-yl)-N-(3,4-dichlorophenyl)-7-oxabicyclo[2.2.1]heptane-2-carboxamide
(1R,2R,4S,5S)—N-(3,4-dichlorophenyl)-4-(pyridin-4-yl)-8-oxatricyclo[3.2.1.02,4]octane-2-carboxamide
(1R,2R,3S,4S)—N-(3,4-dichlorophenyl)-3-(pyridin-4-yl)-7-oxabicyclo[2.2.1]heptane-2-carboxamide; and
N-(2,2'-difluoro-[1,1'-biphenyl]-4-yl)-3-(pyrazin-2-yl)-7-oxabicyclo[2.2.1]hept-2-ene-2-carboxamide.

Embodiment 30. A compound having Formula (III):

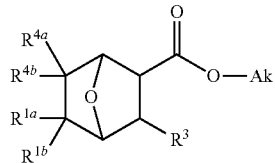

(III)

wherein Ak is $C_{1-6}$ alkyl;
$R^3$ is a 5- or 6-membered heteroaryl having 1 to 2 heteroatoms selected from N, O and S; wherein $R^3$ is unsubstituted or substituted by 1 to 3 substituents independently selected from halo, $C_{1-6}$alkyl, halo-substituted $C_{1-6}$alkyl, $C_{1-6}$alkoxy or —$NR^5R^6$;
$R^{1a}$, $R^{1b}$, $R^{4a}$, and $R^{4b}$ are each independently hydrogen, halo, hydroxyl, $C_{1-6}$alkoxy, $C_{1-6}$alkyl, —$NR^7R^8$ or —$NR^7$—$(CR^9R^{10})_{2-4}$—$OR^{11}$; or wherein one of $R^{1a}$ and $R^{1b}$ together with one of $R^{4a}$ and $R^{4b}$ form a cyclopropyl with the two carbon atoms to which said $R^{1a}$, $R^{1b}$, $R^{4a}$ and $R^{4b}$ are respectively attached;
$R^5$, $R^6$, $R^7$, $R^9$, $R^{10}$ and $R^{11}$ are each independently hydrogen or $C_{1-6}$alkyl;
$R^8$ is hydrogen, $C_{3-7}$ cycloalkyl or a 5- or 6-membered heterocyclyl having 1-3 heteroatoms selected from N, O and S; wherein said $C_{3-7}$ cycloalkyl or 5- or 6-membered heterocyclyl of $R^8$ is unsubstituted or substituted by hydroxy or $C_{1-6}$ alkyl;
alternatively, $R^5$ and $R^6$ or $R^7$ and $R^8$ together with the nitrogen atom to which they are attached in —$NR^5R^6$ or —$NR^7R^8$ respectively form a 5- or 6-membered heterocyclyl having 1-3 heteroatoms selected from N, O and S;
provided that $R^{1a}$, $R^{1b}$, $R^{4a}$, and $R^{4b}$ cannot all be hydrogen; and
further provided that when $R^{1a}$, $R^{1b}$, $R^{4a}$, or $R^{4b}$ is $C_{1-6}$alkyl, the other substituent on the same carbon ring atom is not hydrogen.

Depending on the choice of the starting materials and procedures, the compounds can be present in the form of one of the possible stereoisomers or as mixtures thereof, for example as pure optical isomers, or as stereoisomer mixtures, such as racemates and diastereoisomer mixtures, depending on the number of asymmetric carbon atoms. The present invention is intended to encompass all such possible stereoisomers, including racemic mixtures, diasteriomeric mixtures and optically pure forms. Optically active (R)- and (S)-stereoisomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible stereoisomers, rotamers, atropisomers, tautomers or mixtures thereof, for example, as substantially pure geometric (cis or trans) stereoisomers, diastereomers, optical isomers (antipodes), racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Unless otherwise indicated, a compound represented herein as a single stereoisomer includes an enantiomeric mixture (e.g., the enantiomer of the depicted compound and mixtures of the enantiomers). Furthermore, where a compound is described as a single regioisomer, it is understood that a sample of the compound may still contain small amounts of the other regioisomer and may also exist as an enantiomeric mixture. Typically, where a compound is described as a single regioisomer or enantiomer, the specified structure accounts for at least 90% by weight of total weight of depicted compound plus its isomers; preferably, the specified isomer, diastereomer or enantiomer accounts for at least 95% by weight of the total weight including other isomers.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Isotopes that can be incorporated into compounds of the invention include, for example, isotopes of hydrogen.

Further, incorporation of certain isotopes, particularly deuterium (i.e., $^2$H or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of the formula (I). The concentration of deuterium, may be defined by the isotopic enrichment factor. The term "isotopic enrichment factor" as used herein means the ratio between the isotopic abundance and the natural abundance of a specified isotope. If a substituent in a compound of this invention is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

Other examples of isotopes that can be incorporated into compounds of the invention include isotopes of hydrogen, carbon, nitrogen, oxygen, phosphorous, fluorine, and chlorine, such as 3H, $^{11}C$, $^{13}C$, $^{14}C$, $^{15}N$, $^{18}F$, $^{31}P$, $^{32}P$, $^{35}S$, $^{36}Cl$, $^{123}I$, $^{124}I$, $^{125}I$ respectively. Accordingly it should be understood that the invention includes compounds that incorporate one or more of any of the aforementioned isotopes, including for example, radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

The compounds of the present invention are either obtained in the free form, as a salt thereof. As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of the present invention in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

Processes for Making Compounds of the Invention

All methods described herein can be performed in any suitable order, unless otherwise indicated or otherwise clearly contradicted by context.

Compounds of Formula (1A)-(1L) and Formula (2A)-(2L) can be prepared as generally illustrated in Schemes 1-7, wherein $R^1$ encompasses $R^{1a}$, $R^{1b}$, $R^{4a}$ and $R^{4b}$ groups that are attached to ring carbons 5 or 6; Ar encompasses $R^3$ aryl and heteroaryl groups; and $R^{1a}$, $R^{1b}$, $R^2$, $R^3$, $R^{4a}$, $R^{4b}$, $R^5$ and $R^6$ are defined as above. In the schemes below, the formula depicted as Formula (1A)-(1L)* and Formula (2A)-(2L)* includes a mixture of the formulae as shown and their corresponding enantiomers and regioisomers.

Scheme 1

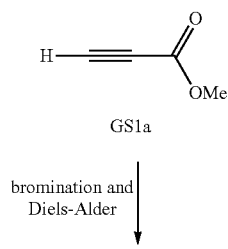

GS1a bromination and
Diels-Alder

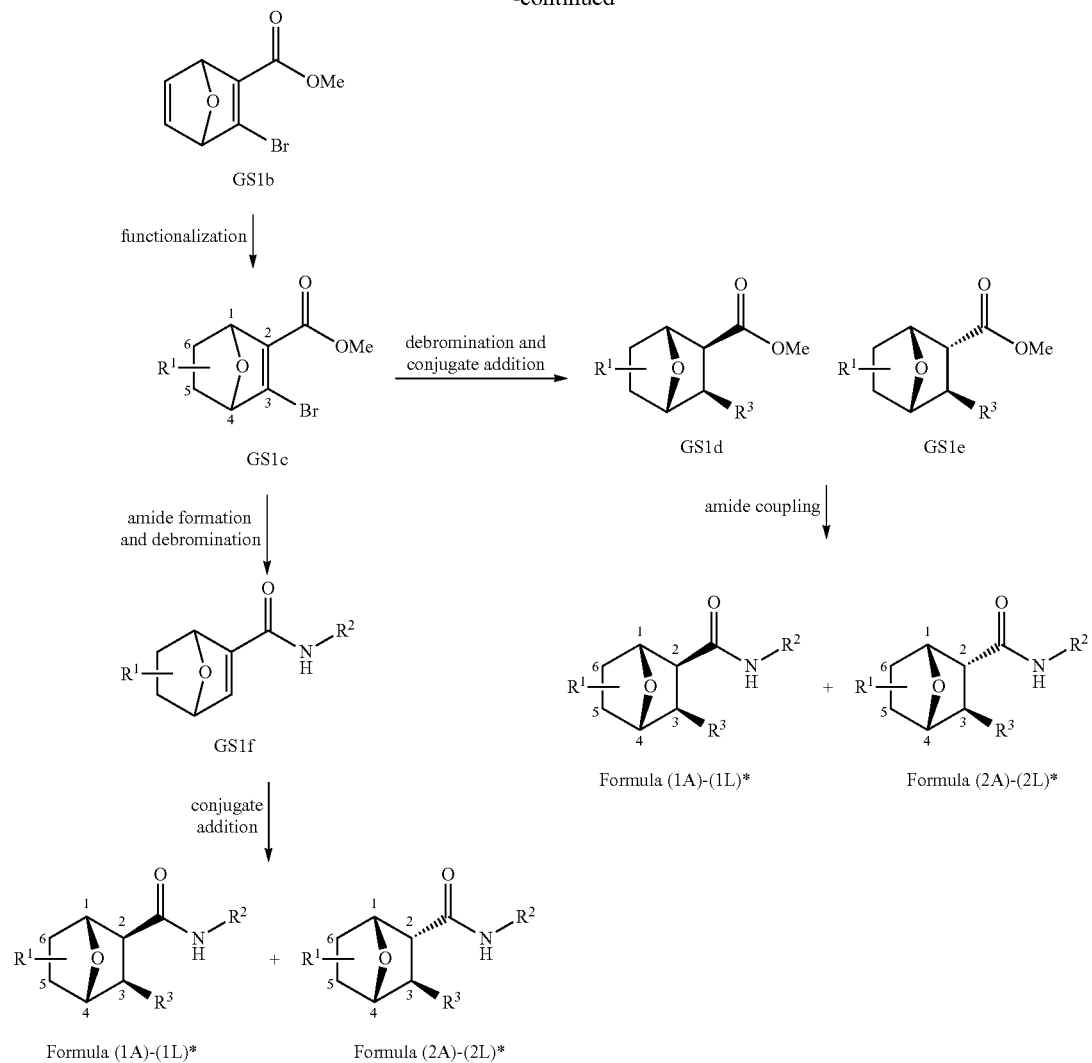

Intermediate GS1b can be prepared from commercially available methyl propiolate, GS1a, via bromination and Diels-Alder reaction with furan. Intermediate GS1c can be prepared via functionalization of GSb1 utilizing reactions including but not limited to cyclopropanation and hydroboration/oxidation followed by further functionization including methylation, fluorination, oxidation and reduction. Intermediates GS1d and GS1e can be prepared from GS1c by debromination and conjugate addition. Subsequent amide bond formation can afford compounds of Formula (1A)-(1L)* and Formula (2A)-(2L)*. Alternatively, amide bond formation and debromination of GS1c can afford GS1f, which after conjugate addition can provide compounds of Formula (1A)-(1L)* and Formula (2A)-(2L)*.

Scheme 2

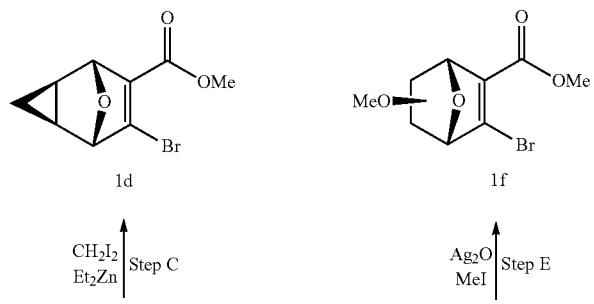

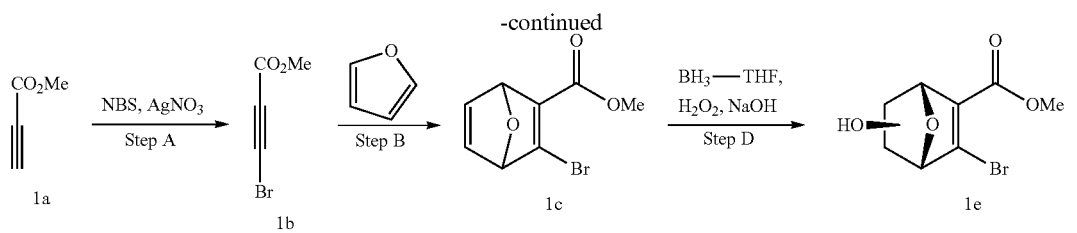

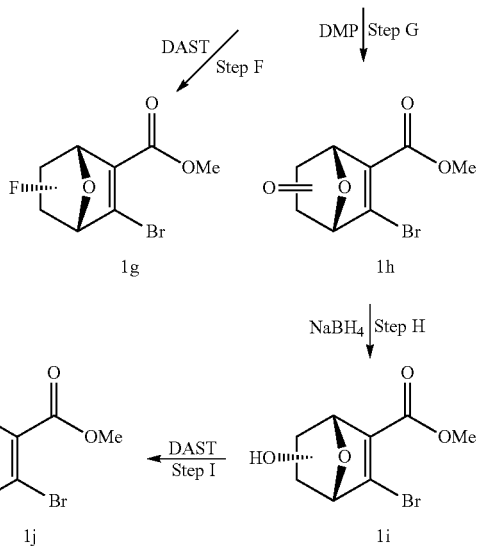

In Scheme 2, bromination of methyl propiolate, 1a, using N-bromosuccinimide or a similar brominating reagent in the presence of a silver catalyst such as silver nitrate afforded intermediate 1b. Diels-Alder cycloaddition of 1b in excess furan with mild heating (ca. 80° C.) provided intermediate 1c. Cyclopropanation of 1c using diethylzinc and diiodomethane afforded intermediate 1d. Hydroboration of 1c using borane-tetrahydrofuran complex followed by oxidation with hydrogen peroxide afforded intermediate 1e as a mixture of alcohol regioisomers. Methylation of 1e using silver oxide and iodomethane provided 1f as a mixture of methoxy regioisomers. Fluorination of 1e using DAST afforded 1g as a mixture of fluorine regioisomers. Oxidation of 1e using DMP afforded 1h as a mixture of ketone regioisomers. Reduction of 1h with sodium borohydride provided 1i as a mixture of alcohol regioisomers. Fluorination of 1i using DAST afforded 1j as a mixture of fluorine regioisomers.

Scheme 3

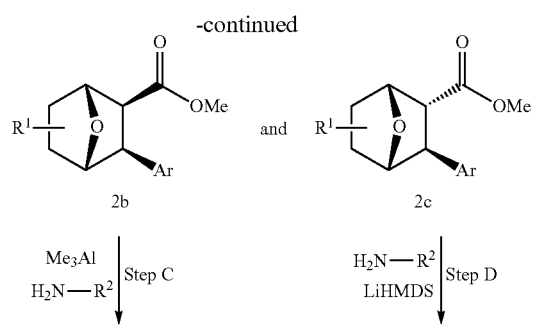

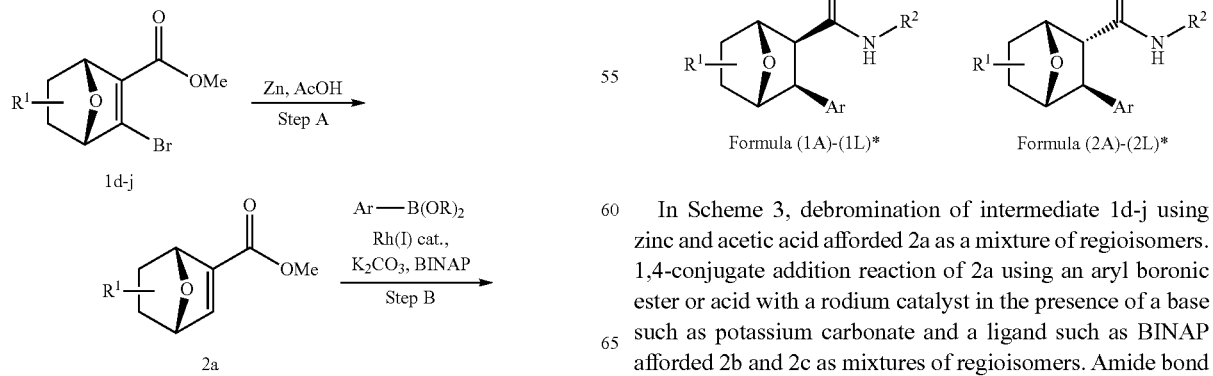

In Scheme 3, debromination of intermediate 1d-j using zinc and acetic acid afforded 2a as a mixture of regioisomers. 1,4-conjugate addition reaction of 2a using an aryl boronic ester or acid with a rhodium catalyst in the presence of a base such as potassium carbonate and a ligand such as BINAP afforded 2b and 2c as mixtures of regioisomers. Amide bond formation using 2b, trimethylaluminum and an amine or aniline provided compounds of Formula (1A)-(1L)* as a mixture of regioisomers. Amide bond formation using 2c, LiHMDS and an amine or aniline provided compounds of Formula (2A)-(2L)* as a mixture of regioisomers.

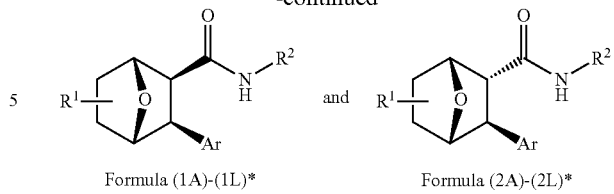

Formula (1A)-(1L)*    and    Formula (2A)-(2L)*

In Scheme 4, amide bond formation using 1d-j, trimethylaluminum and an aniline provided 3a as a mixture of regioisomers. Debromination of intermediate 3a using zinc and acetic acid afforded 3b as a mixture of regioisomers. 1,4-conjugate addition reaction of 3b using an aryl boronic ester or acid with a rodium catalyst in the presence of a base such as potassium carbonate and a ligand such as BINAP afforded compounds of Formula (1A)-(1L)* and Formula (2A)-(2L)* as mixtures of regioisomers.

Scheme 4

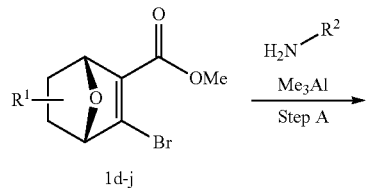

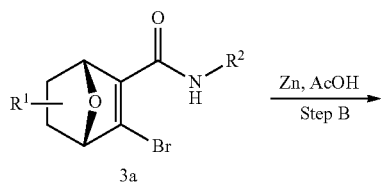

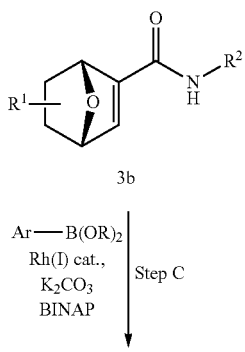

Scheme 5

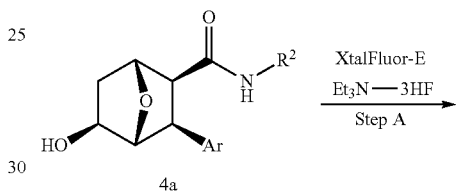

In Scheme 5, compounds 4b of Formula I can be prepared from 4a via fluorination using XtalFluor-E and triethylamine trihydrofluoride.

Scheme 6

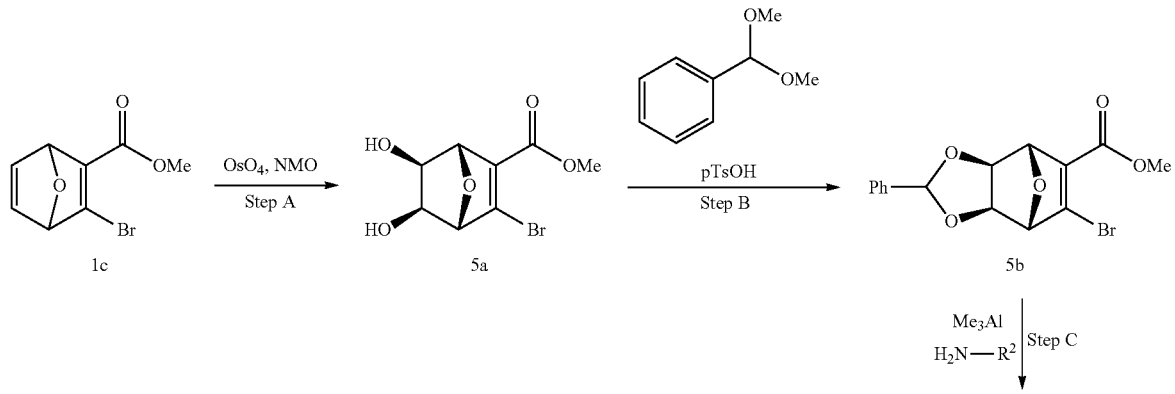

-continued

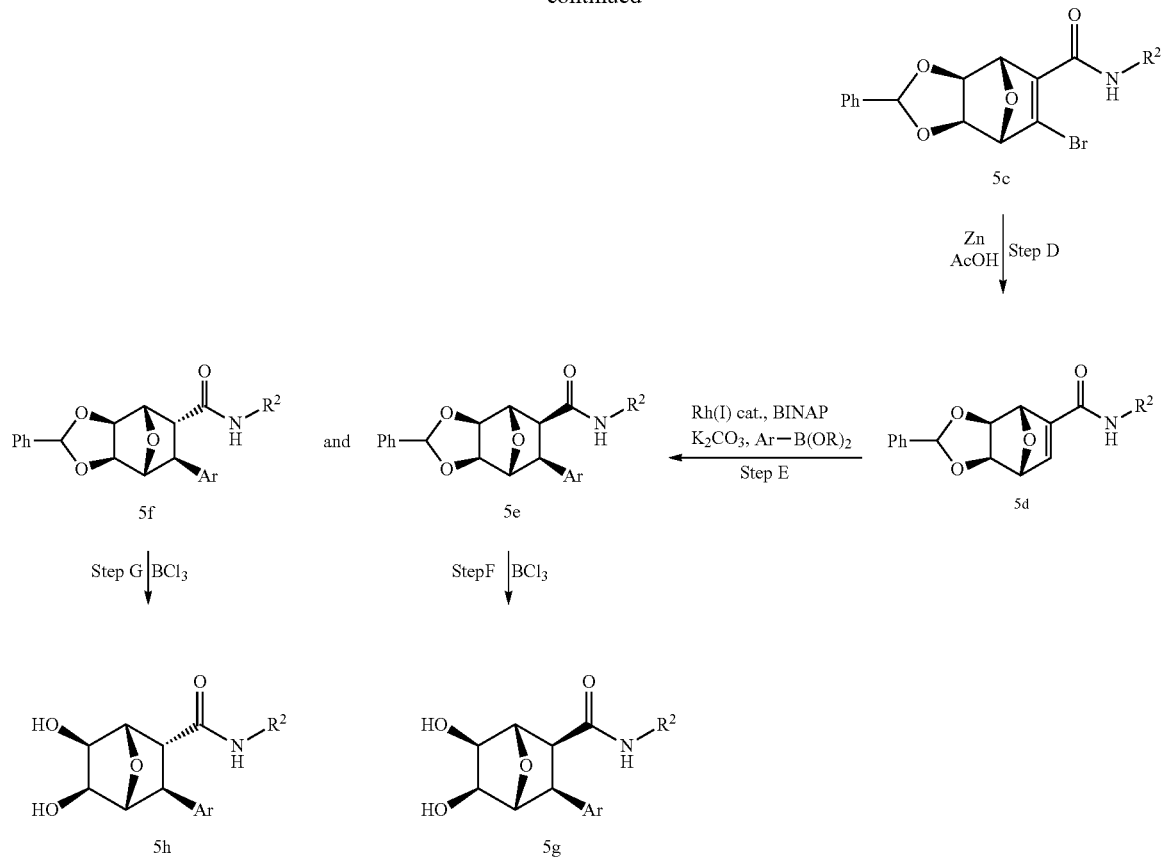

In Scheme 6, dihydroxylation of 1c using osmium tetroxide and N-methylmorpholine N-oxide afforded 5a. Protection of the diol in 5a using (dimethoxymethyl)benzene afforded 5b. Amide bond formation using 5b, trimethylaluminum and an aniline provided 5c. Debromination of intermediate 5c using zinc and acetic acid afforded 5d. 1,4-conjugate addition reaction of 5d using an aryl boronic ester or acid with a rodium catalyst in the presence of a base such as potassium carbonate and a ligand such as BINAP afforded intermediates 5e and 5f. Intermediates 5e and 5f were deprotected using boron trichloride to afford 5g and 5h respectively.

Scheme 7

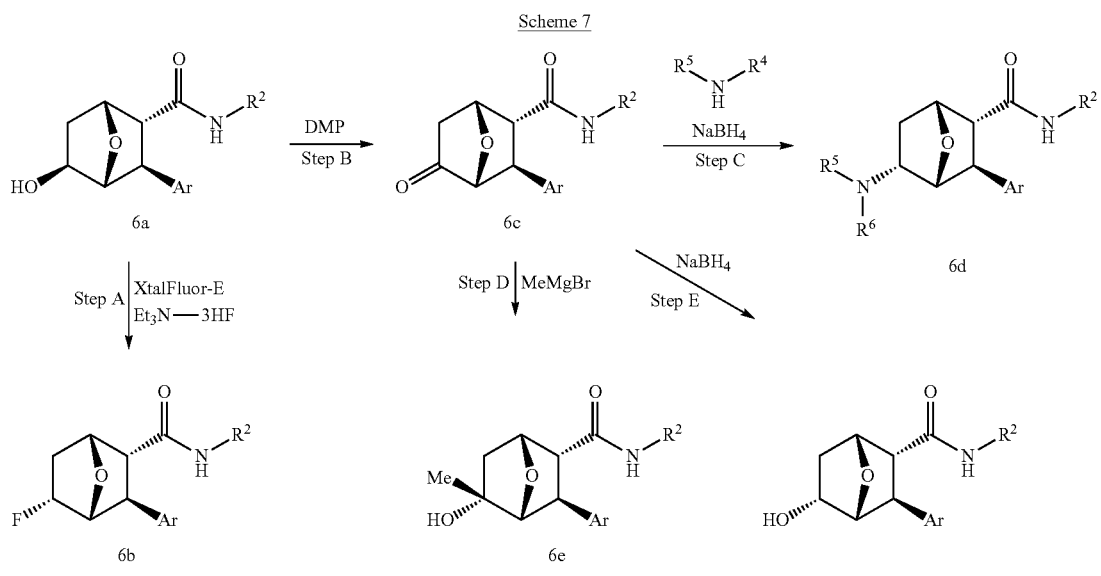

In Scheme 7, fluorination of 6a using XtalFluor-E and triethylamine trihydrofluoride afforded 6b. Oxidation of 6a using DMP afforded 6c. Reductive amination on 6c using an amine and sodium borohydride afforded 6d. Treatment of 6c with methylmagnesium bromide provided 6e. Reduction of 6c using sodium borohydride afforded 6f.

The invention further includes any variant of the present processes; for example, wherein an intermediate product obtainable at any stage thereof is used as starting material and the remaining steps are carried out; wherein starting materials are formed in situ under the reaction conditions; or wherein the reaction components are used in the form of their salts or optically pure material. Compounds of the invention and intermediates can also be converted into each other according to methods generally known to those skilled in the art.

Pharmacology and Utility

The present invention provides a method of treating, ameliorating or preventing arthritis of joint injury in a mammal in need thereof, the method including administering to the mammal a therapeutically effective amount of a compound of the invention, wherein the subject has or is at risk of joint damage or arthritis. The invention also provides a method of treating, ameliorating or preventing arthritis or joint injury in a human patient, the method comprising: administering orally the patient a composition comprising an effective amount of a compound of the invention, thereby treating, ameliorating or preventing arthritis or joint injury in the patient. In some embodiments, the patient has arthritis or joint injury. In some embodiments, the individual does not have, but is at risk for, arthritis or joint injury. In some embodiments, the arthritis is osteoarthritis, trauma arthritis, or autoimmune arthritis.

The compounds of the present invention are also useful for inducing hyaline cartilage production of chondrogenic progenitor cells. In some embodiment, the present invention provides a method for preventing chondrocyte hypertrophy of chondrocytic progenitor cells. In some embodiment, the present invention provides a method of inducing differentiation of chondrogenic progenitor cells into mature chondrocytes, the method including contacting chondrogenic progenitor cells with a sufficient amount of a compound of the invention, thereby inducing differentiation into mature chondrocytes producing hyaline cartilage extracellular matrix.

CPCs can differentiate into different types of cells including, but not limited to, osteoblasts, hyaline chondrocytes and hypertrophic chondrocytes. Differentiation is the process by which a specialized cell type is formed from a less specialized cell type, for example, a chondrocyte from a chondrogenic progenitor. In some embodiments, the method is performed in vitro. In some embodiments, the method is performed in vivo in a mammal and the progenitor cells are present in the mammal.

Inducing chondrocyte differentiation of chondrogenic progenitor can be accomplished using any suitable amount of a compound of the present invention. In some embodiment, the compound of the present invention can be present in an amount form about 0.1 mg to about 10000 mg, e.g., 1.0 mg to 1000 mg, e.g., 10 mg to 500 mg, according to the particular application and potency of the active component. In some embodiments, the compounds of the present invention can be administered orally once daily at a dose of 1 mg/kg to about 300 mg/kg. Treatment duration can vary from a week or less to chronic treatment in severe osteoarthritis.

It is contemplated that compounds, compositions, and methods of the present invention may be used to treat, ameliorate or prevent any type of articular cartilage damage (e.g., joint damage or injury) including, for example, damage arising from a traumatic event or tendon or ligament tear. In some embodiments, the compounds or compositions of the invention are administered to prevent or ameliorate arthritis or joint damage, for example where there is a genetic or family history of arthritis or joint damage or joint injury or prior or during joint surgery. In some embodiments, compounds, compositions and methods are used to treat joint damage. In particular embodiments, the joint damage is traumatic joint injury. In other embodiments, the joint damage is damage arising from age or inactivity. In yet other embodiments, the joint damage is damage arising from an autoimmune disorder. In other embodiments, the joint damage is damage arising from a metabolic disorder (e.g. diabetes). In some embodiments of the invention, compounds, compositions, and methods of the present invention may be used to treat, ameliorate or prevent osteoarthritis. In some embodiments, the compounds, compositions and methods are used to ameliorate or prevent arthritis in a subject at risk of having or acquiring arthritis. In some embodiments, the compounds, compositions and methods are used to ameliorate or prevent joint damage in a subject at risk of having or acquiring joint damage.

In some embodiments, compounds, compositions, and methods of the present invention provide a method for stimulating chondrocyte proliferation and hyaline cartilage production in cartilagenous tissues that have been damaged, e.g., due to traumatic injury or chondropathy. In particular embodiments compounds, compositions, and methods of the present invention are useful for treatment of cartilage damage in joints, e.g., at articulated surfaces, e.g., spine, shoulder, elbow, wrist, joints of the fingers, hip, knee, ankle, and joints of the feet. Examples of diseases or disorders that may benefit from treatment include osteoarthritis, rheumatoid arthritis, other autoimmune diseases, or osteochondritis dessicans. In addition, cartilage damage or disruption occurs as a result of certain genetic or metabolic disorders, cartilage malformation is often seen in forms of dwarfism in humans, and/or cartilage damage or disruption is often a result of reconstructive surgery; thus compounds, compositions, and methods would be useful therapy in these patients, whether alone or in connection with other approaches.

It is further contemplated that compounds, compositions, and methods of the present invention may be used to treat, ameliorate or prevent various cartilagenous disorders and/or associated symptoms or effects of such conditions. Exemplary conditions or disorders for treatment, amelioration and/or prevention with compounds, compositions, and methods of the invention, include, but are not limited to systemic lupus erythematosis, rheumatoid arthritis, juvenile chronic arthritis, osteoarthritis, degenerative disc disease, spondyloarthropathies, Ehlers Danlos syndrome, systemic sclerosis (scleroderma) or tendon disease. Other conditions or disorders that may benefit from treatment with compounds for amelioration of associated effects include idiopathic inflammatory myopathies (dermatomyositis, polymyositis), Sjogren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barr syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease.

It is contemplated that compounds and/or compositions of the present invention can promote expression of collagen in human dermal fibroblast. Collagen is the major structural component of the dermi. Collagen is vital for skin health and has been widely used in dermal treatment of wrinkles and skin aging, and as a healing aid for burn patients. Collagen is produced in fibroblast, and both human and bovine collagen is widely used. The invention therefore provides a method of increasing production of collagen in fibroblast by contacting the fibroblasts with a compound or composition of the invention, thereby increasing the production of collagen in the fibroblast. The contacting may be in vivo by direct injection of the compound in the areas to be treated. The contacting may be in vitro into a population of fibroblasts.

Pharmaceutical Compositions, Dosage and Administration

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. The pharmaceutical composition can be formulated for particular routes of administration such as oral administration, parenteral administration (e.g. by injection, infusion, transdermal or topical administration), and rectal administration. Topical administration may also pertain to inhalation or intranasal application. The pharmaceutical compositions of the present invention can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of:
a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and
e) absorbents, colorants, flavors and sweeteners.

In general, compounds of the invention will be administered in therapeutically effective amounts via any of the usual and acceptable modes known in the art, either singly or in combination with one or more therapeutic agents. In some embodiments, compounds and compositions of the present invention are applied by direct injection into the synovial fluid of a joint, systemic administration (oral or intravenously) or directly into a cartilage defect, either alone or complexed with a suitable carrier for extended release of the compound. In some embodiments, compounds or compositions are administered in a biocompatible matrix or scaffold.

Compounds, compositions, and methods of the present invention can also be used in conjunction with a surgical procedure at an affected joint. Administration of a compounds or composition of the invention may occur prior to, during or in conjunction with, and/or after a surgical procedure. For example, compounds, compositions and methods of the invention can be used to expand chondrocyte populations in culture for autologous or allogenic chondrocyte implantation (ACI). Chondrocytes can be optionally implanted with concurrent treatment consisting of administration of compounds and compositions of the present invention. In these procedures, for example, chondrocytes can be harvested arthroscopically from an uninjured minor load-bearing area of a damaged joint, and can be cultured in vitro, optionally in the presence of compounds and compositions of the present invention and/or other growth factors to increase the number of cells prior to transplantation. Expanded cultures are then optionally admixed with compounds and compositions of the present invention and/or placed in the joint space or directly into the defect. In certain embodiments, expanded cultures (optionally with compounds of the present invention) are placed in the joint space suspended in a matrix or membrane.

In other embodiments, compounds and compositions of the present invention can be used in combination with one or more periosteal or perichondrial grafts that contain cartilage forming cells and/or help to hold the transplanted chondrocytes or chondrocyte precursor cells in place. In some embodiments, compounds and compositions of the present invention are used to repair cartilage damage in conjunction with other procedures, including but not limited to lavage of a joint, stimulation of bone marrow, abrasion arthroplasty, subchondral drilling, or microfracture of proximal subchondral bone. Optionally, following administration of compounds and compositions of the present invention and growth of cartilage, additional surgical treatment may be beneficial to suitably contour newly formed cartilage surface(s).

The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention.

In one embodiment, the invention provides a product comprising a compound of formula (I) and at least one other therapeutic agent as a combined preparation for simultaneous, separate or sequential use in therapy. In one embodiment, the therapy is the treatment of joint damage resulting from joint injury or arthritis. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and a second therapeutic agent(s). The second agent may be one or more additional chondrocyte differentiation agent. Examples of chondrocyte differentiation agent include but are not limited to angiopoietin-like 3 protein (ANGPTL3), insulin growth factor (IGF1), SM04690 (Wnt inhibitor), Janus kinase inhibitors (such as Ruxolitinib, Tofacitinib, Baricitinib), oral salmon calcitonin, SD-6010 (iNOS inhibitor), vitamin D3 (choliecalciferol), collagen hydrolyzate, bone morphogenetic protein 7 (BMP7), rusalatide acetate, avocado soy unsaponifiables (ASU), a steroid, a non-steroidal anti-inflammatory agent (NSAID), hyaluronic acid, kartogenin and TPX-100. The second agent may be a chondrocyte differentiation agent having Formula (I) as described in WO 2015/175487. Optionally, the pharmaceutical composition may comprise a pharmaceutically acceptable carrier, as described above.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about 10-3 molar and 10-9 molar concentrations. A therapeutically effective amount in vivo may range depending on the route of administration, between about 0.1-500 mg/kg, or between about 1-100 mg/kg.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

EXAMPLES

Temperatures are given in degrees Celsius. The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Unless otherwise specified, starting materials are generally available from commercial sources, such as but not limited to, TCI Fine Chemical (Japan), Aurora Fine Chemicals LLC (San Diego, CA), FCH Group (Ukraine), Aldrich Chemicals Co. (Milwaukee, Wis.), Acros Organics (Fairlawn, N.J.), Maybridge Chemical Company, Ltd. (Cornwall, England), Matrix Scientific (USA), Enamine Ltd (Ukraine), Combi-Blocks, Inc. (San Diego, Calif.), Oakwood Products, Inc. (USA), Apollo Scientific, Ltd. (UK).

The Examples herein merely illuminate the invention and does not limit the scope of the invention otherwise claimed. Further, the compounds of the present invention can be produced by organic synthesis methods known to one of ordinary skill in the art as shown in the following examples. Where desired, conventional protecting groups are used to protect reactive functional groups in accordance with standard practice, for example, see T. W. Greene and P. G. M. Wuts in "Protecting Groups in Organic Synthesis", John Wiley and Sons, 1991.

Abbreviations

Abbreviations as used herein, are defined as follows: "1×" for once, "2×" for twice, "3×" for thrice, "° C." for degrees Celsius, "aq" for aqueous, "FCC" for flash column chromatography, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" or "hrs" for hour or hours, "RT" for room temperature, "ON" for overnight, "atm" for atmosphere, "psi" for pounds per square inch, "conc." for concentrate, "sat" or "sat'd" for saturated, "MW" for molecular weight, "mw" or "pwave" for microwave, "mp" for melting point, "Wt" for weight, "MS" or "Mass Spec" for mass spectrometry, "ESI" for electrospray ionization mass spectroscopy, "HR" for high resolution, "HRMS" for high resolution mass spectrometry, "LCMS" or "LC-MS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "¹H" for proton, "b" for delta, "δ" for singlet, "d" for doublet, "t" for triplet, "q" for quartet, "m" for multiplet, "br" for broad, "Hz" for hertz, "ee" for "enantiomeric excess" and "α", "β", "R", "r", "S", "s", "E", and "Z" are stereochemical designations familiar to one skilled in the art.

The following abbreviations used herein below have the corresponding meanings:

AcOH acetic acid
app apparent
ATP adenosine 5-triphosphate
BINAP racemic 2,2'-bis(diphenylphosphino)-1,1'-binaphthyl
BOC tertiary butyl carboxy
BSA bovine serum albumin
cProp cyclopropyl
DAST diethylaminosulfur trifluoride
dd doublet of doublets
DCE dichloroethane
DCM dichloromethane
DIEA diethylisopropylamine
DME 1,4-dimethoxyethane
DMF N,N-dimethylformamide
DMP Dess-Martin periodinane
DMSO dimethylsulfoxide
EDTA ethylenediamine tetraacetic acid
ESI electrospray ionization
Et₃N-3HF triethylamine trihydrofluoride
EtOAc ethyl acetate
HCl hydrochloric acid
LiHMDS lithium bis(trimethylsilyl)amide
MeOH methanol
MHz megahertz
MTBE methyl tert-butyl ether
m/z mass to charge ratio
NBS N-bromosuccinimide
NMO N-methylmorpholine N-oxide
PE petroleum ether
ppm parts per million
pTsOH p-toluenesulfonic acid
rac-racemic
Rt retention time
TFA trifluoroacetic acid
THF tetrahydrofuran
Tris-HCl aminotris(hydroxymethyl)methane hydrochloride
XtalFluor-E (Diethylamino)difluorosulfonium tetrafluoroborate Instrumentation LCMS Methods Employed in Characterization of Examples Analytical LC/MS is carried out on Agilent systems using ChemStation software. The system consists of:
Agilent G1312 Binary Pump
Agilent G1367 Well Plate Autosampler
Agilent G1316 Thermostated Column Compartment
Agilent G1315 Diode Array Detector
Agilent 6140/6150 Mass Spectrometer
SOFTA Evaporative Light Scattering Detector Typical method conditions are as follows:
Flow rate: 0.9 mL/min
Column: 1.8 μm 2.1×50 mm Waters Acquity HSS T3 C18 column
Mobile Phase A: Water+0.05% TFA
Mobile Phase B: Acetonitrile+0.035% TFA
Run Time: 2.25 minutes
Method A: Unless otherwise stated, the system runs a gradient from 10% B to 90% B in 1.35 minutes. A 0.6 minute wash at 100% B follows the gradient. The remaining duration of the method returns the system to initial conditions.
Method B: The system starts the gradient at 20% B rather than 10% B.
Method C: The system starts the gradient at 30% B rather than 10% B.
Method D: The system starts the gradient at 40% B rather than 10% B.

Typical mass spectrometer scan range is 100 to 1000 amu.

NMR Methods

Proton spectra are recorded on a Bruker AVANCE II 400 MHz with 5 mm QNP Cryoprobe or a Bruker AVANCE III 500 MHz with 5 mm QNP probe unless otherwise noted. Chemical shifts are reported in ppm relative to dimethyl sulfoxide (b 2.50), chloroform (b 7.26), methanol (b 3.34), dichloromethane (b 5.32), acetone (b 2.05), or acetonitrile (b 1.94). A small amount of the dry sample (2-5 mg) is dissolved in an appropriate deuterated solvent (0.6 mL).

ISCO Methods Employed in Purification of Examples

ISCO flash chromatography is performed on Teledyne COMBIFLASH® system with prepacked silica RediSep® column.

Preparative HPLC Methods Employed in Purification of Examples

Preparative HPLC is carried out on Waters Autoprep systems using MassLynx and FractionLynx software. The system consists of:
Waters 2767 Autosampler/Fraction Collector
Waters 2525 Binary Pump
Waters 515 Makeup Pump
Waters 2487 Dual Wavelength UV Detector
Waters ZQ Mass Spectrometer Typical method conditions are as follows:
Flow Rate: 100 mL/min
Column: 10 μm 19×50 mm Waters Atlantis T3 C18 column
Injection Volume: 0-1000 μL
Mobile Phase A: Water+0.05% TFA
Mobile Phase B: Acetonitrile+0.035% TFA
Run Time: 4.25 minutes The system runs a gradient from X % B to Y % B as appropriate for the examples in 3 minutes following a 0.25 minute hold at initial conditions. A 0.5 minute wash at 100% B follows the gradient. The remaining duration of the method returns the system to initial conditions. Fraction collection is triggered by mass detection through FractionLynx software.

Chiral Preparative HPLC Methods Employed in Purification of Examples

SFC chiral screening is carried out on a Thar Instruments Prep Investigator system coupled to a Waters ZQ mass spectrometer. The Thar Prep Investigator system consists of:
Leap HTC PAL autosampler
Thar Fluid Delivery Module (0 to 10 mL/min)
Thar SFC 10 position column oven
Waters 2996 PDA
Jasco CD-2095 Chiral Detector
Thar Automated Back Pressure Regulator All of the Thar components are part of the SuperPure Discovery Series line. The system flows at 2 mL/min (4 mL/min for the WhelkO-1 column) and kept at 30° C. The system back pressure is set to 125 bar. Each sample is screened through a battery of six 3 μm columns:
3 μm 4.6×50 mm ChiralPak AD
3 μm 4.6×50 mm ChiralPak OD
3 μm 4.6×50 mm ChiralPak OJ
5 μm 4.6×250 mm Whelk O-1
3 μm 4.6×50 mm ChiralPak AS
3 μm 4.6×50 mm Lux-Cellulose-2

The system runs a gradient from 5% co-solvent to 50% co-solvent in 5 minutes followed by a 0.5 minute hold at 50% co-solvent, a switch back to 5% co-solvent and a 0.25 minute hold at initial conditions. In between each gradient there is a 4 minute equilibration method that flows 5% co-solvent through the next column to be screened. The typical solvents screened are MeOH, MeOH+20 mM NH$_3$, MeOH+0.5% DEA, IPA, and IPA+20 mM NH$_3$. Once separation is detected using one of the gradient methods, an isocratic method can be developed, and if necessary, scaled up for purification on the Thar Prep80 system.

Intermediates

Intermediates 1c-1j were prepared following the general procedures in Scheme 1.

Intermediate 1c. Methyl 3-bromo-7-oxabicyclo[2.2.1]hepta-2,5-diene-2-carboxylate

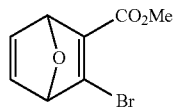

Step A: To a stirring solution of methyl propiolate (200 g, 2.38 mol, 198 mL) in acetone (2.50 L) was added AgNO$_3$ (36.4 g, 214 mmol, 36.0 mL). After 5 min, NBS (445 g, 2.50 mol) was added portionwise, and the reaction mixture was stirred at 25° C. for 12 h. The reaction mixture was filtered, the filtrate was concentrated, and the residue was triturated with 10% EtOAc/PE (1500 mL), and the filtrate was concentrated again. The residue was purified by column chromatography (0-5% EtOAc/PE) to give methyl 3-bromopropiolate (1b) as a yellow oil which was used for the next step directly.

Step B: A solution of methyl 3-bromopropiolate (1b, 200 g, 1.23 mol), furan (419 g, 6.15 mol, 445 mL) in toluene (2.50 L) was degassed by passing nitrogen gas through the reaction vessel for 2 min at 0° C., then the reaction mixture was warmed to 90° C. for 72 hour to give a black solution. The reaction mixture was concentrated, and the residue was purified by column chromatography (2-5% EtOAc/PE) to give methyl 3-bromo-7-oxabicyclo[2.2.1]hepta-2,5-diene-2-carboxylate. Four batches were purified separately and combined to afford methyl 3-bromo-7-oxabicyclo[2.2.1]hepta-2,5-diene-2-carboxylate (1c) as a yellow oil. $^1$H NMR (400 MHz, CDCl$_3$) δ=7.25-7.17 (m, 2H), 5.70 (t, J=1.6 Hz, 1H), 5.33 (t, J=1.7 Hz, 1H), 3.82-3.75 (m, 3H).

Intermediate 1d. Methyl (1S,2S,4R,5R)-7-bromo-8-oxatricyclo[3.2.1.0$^{2,4}$]oct-6-ene-6-carboxylate

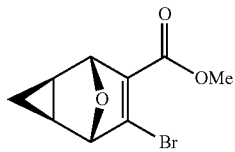 [SMILES: COC(=O)C1=C(Br)[C@H]2O[C@@H]1[C@@H]1C[C@@H]12]

Step C: A solution of 2,2,2-trichloroacetic acid (91.2 g, 558 mmol, 56.3 mL) in 1,2-dichloroethane (300 mL) was added to a cooled solution of diethylzinc (1 M, 558 mL, 558 mmol) in 1,2-dichloroethane (1200 mL) at −45° C. The solution was warmed to 0° C. and was stirred for 20 min. Diiodomethane (150 g, 558 mmol, 45.0 mL) was added to the reaction mixture and it was allowed to stir at 0° C. for another 10 min. A solution of methyl 3-bromo-7-oxabicyclo[2.2.1]hepta-2,5-diene-2-carboxylate (1c, 60.0 g, 260 mmol) in 1,2-dichloroethane (300 mL) was added to the reaction mixture which was stirred at 15° C. for 16 h. The reaction mixture was diluted with 1 M HCl (1200 mL) and the aqueous phase was extracted with DCM (2000 mL 2×). The combined organic layers were washed with sat. aq. NaHCO$_3$ (1000 mL), brine (1000 mL), dried over Na$_2$SO$_4$, filtered and concentrated to give a yellow oil. The crude was purified by column chromatography (0-10% EtOAc/PE) to give methyl (1S,2S,4R,5R)-7-bromo-8-oxatricyclo[3.2.1.0$^{2,4}$]oct-6-ene-6-carboxylate (1d) as a yellow oil. $^1$H NMR (400 MHz, DMSO-d$_6$) δ 4.97-4.92 (m, 1H), 4.89-4.85 (m, 1H), 3.73 (s, 3H), 1.58-1.52 (m, 2H), 1.44-1.38 (m, 1H), 1.04-0.95 (m, 1H).

Intermediate 1e

Methyl (1R,4S,5S)-3-bromo-5-hydroxy-7-oxabicyclo[2.2.1]hept-2-ene-2-carboxylate and Methyl (1S,4S,6R)-3-bromo-6-hydroxy-7-oxabicyclo[2.2.1]hept-2-ene-2-carboxylate

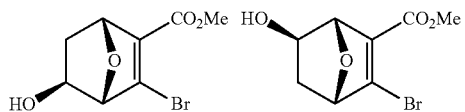 [SMILES: COC(=O)C1=C(Br)[C@H]2O[C@@H]1C[C@@H]2O ; COC(=O)C1=C(Br)[C@@H]2C[C@@H](O)[C@H]1O2]

Step D: A solution of methyl 3-bromo-7-oxabicyclo[2.2.1]hepta-2,5-diene-2-carboxylate (1c, 130 g, 563 mmol, 1.00 eq) in THF (800 mL) was treated with BH$_3$-THF (1 M, 563 mL, 563 mmol) and was stirred at 0° C. for 2 hr. A solution of phosphate buffer, pH=7 (1000 mL) was added dropwise, followed by a mixture of H$_2$O$_2$ (270 mL, 2.81 mol, 30% v/v) and NaOH (2 M, 338 mL, 676 mmol) was added slowly and the mixture was stirred at 0° C. for 2 hr. The reaction mixture was extracted with ethyl acetate (500 mL 3×), and the combined organic layers was washed with sat. aq. NaHSO$_3$ solution (500 mL 2×), brine (500 mL), dried (Na$_2$SO$_4$) and concentrated. The residue was purified by column chromatography (2-50% EtOAc/PE) to give the desired product. Two batches were combined to afford 1e as a 1.3:1 mixture of alcohol regioisomers favoring the 5-hydroxy product as a yellow solid. 1.3:1 mixture of alcohol regioisomers: $^1$H NMR (400 MHz, CDCl$_3$) δ 5.25-5.02 (m, 1H), 4.94-4.74 (m, 1H), 4.23-4.14 (m, 1H), 3.80-3.78 (m, 3H), 2.14-2.01 (m, 1H), 1.91-1.81 (m, 1H), 1.69-1.60 (m, 1H).

Intermediate 1f

Methyl (1R,4S,5S)-3-bromo-5-methoxy-7-oxabicyclo[2.2.1]hept-2-ene-2-carboxylate and Methyl (1S,4S,6R)-3-bromo-6-methoxy-7-oxabicyclo[2.2.1]hept-2-ene-2-carboxylate

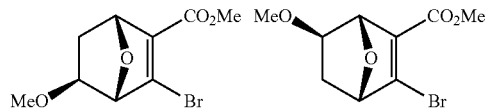 [SMILES: COC(=O)C1=C(Br)[C@H]2O[C@@H]1C[C@@H]2OC ; COC(=O)C1=C(Br)[C@@H]2C[C@@H](OC)[C@H]1O2]

Step E: A suspension of 1e (500 mg, 2.01 mmol) and silver oxide (465 mg, 2.01 mmol) in acetonitrile (5 mL) at RT was treated with iodomethane (0.125 mL, 2.01 mmol) and was warmed at 80° C. for 16 h. The reaction was cooled to room temperature and filtered through a pad of celite. The solvent was concentrated and the resulting residue was purified by column chromatography using hexanes and EtOAc to afford 1f as a mixture of methoxy regioisomers. LC-MS: Rt=1.25 min; MS m/z [M+H]$^+$ 263.0.

Intermediate 1g

Methyl (1R,4S,5R)-3-bromo-5-fluoro-7-oxabicyclo[2.2.1]hept-2-ene-2-carboxylate and Methyl (1S,4S,6S)-3-bromo-6-fluoro-7-oxabicyclo[2.2.1]hept-2-ene-2-carboxylate

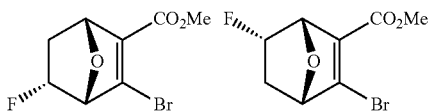 [SMILES: COC(=O)C1=C(Br)[C@H]2O[C@@H]1C[C@H]2F ; COC(=O)C1=C(Br)[C@@H]2C[C@H](F)[C@H]1O2]

Step F: A solution of 1e (1.00 g, 4.02 mmol) in DCM (80 mL) at RT was treated with DAST (3.71 mL, 28.1 mmol) and was stirred for 18 h. The reaction mixture was concentrated and was purified by FCC (0-50% EtOAc/DCM) to afford 1g as a mixture of fluorine regioisomers. LC-MS: Rt=1.15 min; MS m/z [M+H]$^+$ 251.1.

Intermediate 1h

Methyl 3-bromo-5-oxo-7-oxabicyclo[2.2.1]hept-2-ene-2-carboxylate and methyl 3-bromo-6-oxo-7-oxabicyclo[2.2.1]hept-2-ene-2-carboxylate

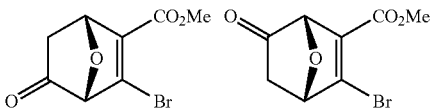 [SMILES: COC(=O)C1=C(Br)[C@H]2O[C@@H]1CC2=O ; COC(=O)C1=C(Br)[C@@H]2CC(=O)[C@H]1O2]

Step G: A solution of 1e (2.00 g, 8.03 mmol) in DCM (40 mL) at 0° C. was treated portion-wise with Dess-Martin reagent (10.2 g, 24.1 mmol) over 5 minutes. The reaction mixture was warmed to RT and was stirred for 6 h. The reaction was cooled to 0° C. and quenched with a solution of saturated aqueous sodium bicarbonate. The aqueous layer was washed with DCM×3. The combined organic layers were dried over anhydrous sodium sulfate. The crude compound was purified by silica column chromatography to afford 1h as a mixture of ketone regioisomers. LC-MS: Rt=1.10 min; MS m/z [M+H]$^+$ 246.9.

Intermediate 1i

Methyl (1R,4S,5R)-3-bromo-5-hydroxy-7-oxabicyclo[2.2.1]hept-2-ene-2-carboxylate and Methyl (1S,4S,6S)-3-bromo-6-hydroxy-7-oxabicyclo[2.2.1]hept-2-ene-2-carboxylate

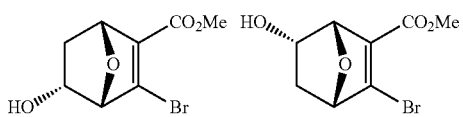 [SMILES: COC(=O)C1=C(Br)[C@H]2O[C@@H]1C[C@H]2O ; COC(=O)C1=C(Br)[C@@H]2C[C@H](O)[C@H]1O2]

Step H: A solution of 1h (50.0 mg, 0.202 mmol) in THF (2 ml) at RT was treated with NaBH$_4$ (15.3 mg, 0.405 mmol) and was stirred at RT for 16 h. The reaction mixture was diluted with EtOAc and sat. aq. NH$_4$Cl, washed with water and brine, dried (Na$_2$SO$_4$), filtered, and concentrated to afford 1i as a mixture of alcohol regioisomers. LC-MS: Rt=0.57 min; MS m/z [M+H]$^+$ 249.0.

Intermediate 1j

Methyl (1R,4S,5S)-3-bromo-5-fluoro-7-oxabicyclo[2.2.1]hept-2-ene-2-carboxylate and Methyl (1S,4S,6R)-3-bromo-6-fluoro-7-oxabicyclo[2.2.1]hept-2-ene-2-carboxylate

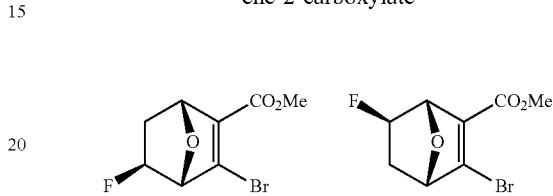

Step I: A solution of 1i (3.70 g, 14.9 mmol) in DCE (74 ml) was treated with triethylamine trihydrofluoride (7.26 ml, 44.6 mmol) and then XtalFluor-E (6.83 g, 29.7 mmol) and was warmed at 80° C. for 1 h. The reaction mixture was cooled to RT, diluted with DCM, washed with sat. aq. NaHCO$_3$ and brine, dried (Na$_2$SO$_4$), filtered, and concentrated. The resulting residue was purified by FCC to afford 1j as a mixture of fluorine regioisomers. LC-MS: Rt=1.18 min; MS m/z [M+H]$^+$ 251.1.

EXAMPLES

Unless otherwise stated, the examples described below consist of a mixture of enantiomers; and in some examples a mixture of alcohol, fluorine, or methoxy regioisomers. In the case of a mixture of regioisomers, the structure and name for the major regioisomer is provided with the approximate ratio of the regioisomers.

Example 1: (1S,2S,4R,5R,6S,7S)—N-(5,6-dichloropyridin-3-yl)-7-(2-methoxypyridin-4-yl)-8-oxatricyclo[3.2.1.0$^{2,4}$]octane-6-carboxamide

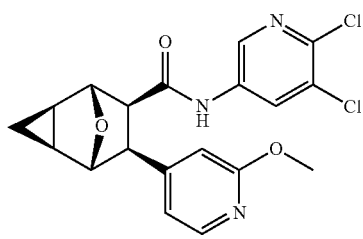 [SMILES: COc1cc([C@H]2[C@H]3O[C@H]([C@@H]4C[C@@H]43)[C@H]2C(=O)Nc2cnc(Cl)c(Cl)c2)ccn1]

Title compound was prepared from methyl (1S,2S,4R,5R)-7-bromo-8-oxatricyclo[3.2.1.0$^{2,4}$]oct-6-ene-6-carboxylate (Intermediate 1d) using Steps A-C as in Scheme 2.

Step A: To a stirring solution of 1d (4.70 g, 19.2 mmol) in THF (25 mL) and water (6 mL) at 0° C. was added acetic acid (4.40 mL) and portion-wise Zn (5.00 g, 77.0 mmol). The reaction slurry was stirred to room temperature for 15 minutes. The reaction was filtered and neutralized with saturated sodium bicarbonate to pH 7. The compound was extracted with ethyl acetate. The organic layer was washed with water and brine and dried over anhydrous sodium sulfate. The solvent was concentrated and dried under vacuo. The crude compound (1S,2S,4R,5R)-methyl 8-oxatricyclo[3.2.1.0$^{2,4}$]oct-6-ene-6-carboxylate was used in the next step without further purification. LC-MS: Rt=1.16 min; MS m/z [M+H]$^+$ 167.1.

Step B: A mixture of (1S,2S,4R,5R)-methyl 8-oxatricyclo [3.2.1.0$^{2,4}$]oct-6-ene-6-carboxylate (500 mg, 3.01 mmol), (2-methoxypyridin-4-yl)boronic acid (598 mg, 3.91 mmol), 2,2'-bis(diphenylphosphino)-1,1'-binaphthalene (187 mg, 0.301 mmol), chloro(1,5-cyclooctadiene)rhodium(I) dimer (74.0 mg, 0.150 mmol) and potassium carbonate (208 mg, 1.50 mmol) in dioxane (10 mL) and water (2.5 mL) was heated at 100° C. for 1 h in the microwave. The material was taken in celite and the solvent was concentrated. The compound was purified by silica column chromatography afford (1S,2S,4R,5R,6S,7S)-methyl 7-(2-methoxypyridin-4-yl)-8-oxatricyclo[3.2.1.0$^{2,4}$]octane-6-carboxylate (cis) and (1S,2S,4R,5R,6R,7S)-methyl 7-(2-methoxypyridin-4-yl)-8-oxatricyclo[3.2.1.02,4]octane-6-carboxylate (trans). cis LC-MS: Rt=1.15 min; MS m/z [M+H]$^+$ 276.1. trans LC-MS: Rt=1.26 min; MS m/z [M+H]$^+$ 276.1.

Step C: To a stirring solution of 5,6-dichloropyridin-3-amine (68.0 mg, 0.418 mmol) in anhydrous toluene (2 mL) at 0° C. under nitrogen was added trimethylaluminum in toluene (2 M, 0.623 mL, 1.25 mmol). After 10 minutes, the ice bath was removed and the mixture was stirred at room temperature for 30 minutes. (1S,2S,4R,5R,6S,7S)-methyl 7-(2-methoxypyridin-4-yl)-8-oxatricyclo[3.2.1.0$^{2,4}$]octane-6-carboxylate (115 mg, 0.418 mmol) was added as a solid and the reaction was stirred at room temperature for 1h and then heated to 80° C. overnight. The reaction was cooled to 0° C. and quenched with methanol. The solvent was removed under a stream of nitrogen. The solid was taken up in methanol and filtered through a pad of celite. The solvent was concentrated the crude compound was purified by silica column chromatography to afford (1S,2S,4R,5R,6S,7S)—N-(5,6-dichloropyridin-3-yl)-7-(2-methoxypyridin-4-yl)-8-oxatricyclo[3.2.1.0$^{2,4}$]octane-6-carboxamide. LC-MS: Rt=1.38 min; MS m/z [M+H]$^+$ 406.0. $^1$H NMR (400 MHz, DMSO-d$_6$) δ 9.98 (s, 1H), 8.03 (d, J=2.4 Hz, 1H), 7.84 (d, J=5.3 Hz, 1H), 7.77 (d, J=2.4 Hz, 1H), 6.83 (dd, J=5.3, 1.4 Hz, 1H), 6.68 (s, 1H), 4.66 (s, 1H), 4.31 (s, 1H), 3.67 (s, 3H), 3.49 (d, J=9.7 Hz, 1H), 3.30 (d, J=9.7 Hz, 1H), 1.36-1.26 (m, 2H), 0.45-0.39 (m, 1H), 0.22-0.15 (m, 1H).

Example 2: rac-(1S,2S,4R,5R,6S,7S)—N-(6-methoxypyridin-3-yl)-7-(6-methylpyridin-3-yl)-8-oxatricyclo[3.2.1.0$^{2,4}$]octane-6-carboxamide Example 2 was synthesized according to the protocol described for Example 1 using methyl (1S,2S,4R,5R)-7-bromo-8-oxatricyclo[3.2.1.0$^{2,4}$]oct-6-ene-6-carboxylate (Intermediate 1d) and (6-methylpyridin-3-yl)boronic acid in Step B and 6-methoxypyridin-3-amine in Step C. LC-MS: Rt=0.95 min; MS m/z [M+H]$^+$ 352.0. $^1$H NMR (400 MHz, DMSO-d$_6$) δ 9.42 (s, 1H), 8.31 (d, J=2.1 Hz, 1H), 7.71-7.68 (m, 1H), 7.550 2 (dd, J=8.0, 2.3 Hz, 1H), 7.14 (dd, J=8.9, 2.7 Hz, 1H), 7.00 (d, J=8.0 Hz, 1H), 6.62-6.57 (m, 1H), 4.62 (s, 1H), 4.24 (s, 1H), 3.73 (s, 3H), 3.49 (d, J=9.6 Hz, 1H), 3.21 (d, J=9.6 Hz, 1H), 2.27 (s, 3H), 1.36-1.29 (m, 1H), 1.29-1.24 (m, 1H), 0.44-0.38 (m, 1H), 0.20-0.15 (m, 1H).

Examples 3 and 4 (Corresponding to Peak 1 and Peak 2)

(1S,2S,4R,5R,6S,7S)—N-(6-methoxypyridin-3-yl)-7-(6-methylpyridin-3-yl)-8-oxatricyclo[3.2.1.0$^{2,4}$] octane-6-carboxamide or (1R,2R,4S,5S,6R,7R)—N-(6-methoxypyridin-3-yl)-7-(6-methylpyridin-3-yl)-8-oxatricyclo[3.2.1.0$^{2,4}$]octane-6-carboxamide

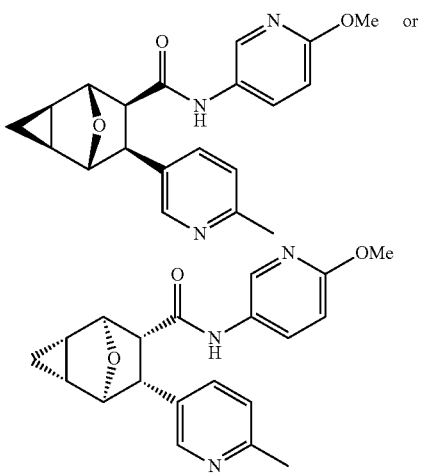

Chiral separation of rac-(1S,2S,4R,5R,6S,7S)—N-(6-methoxypyridin-3-yl)-7-(6-methylpyridin-3-yl)-8-oxatricyclo[3.2.1.0$^{2,4}$]octane-6-carboxamide by Supercritical Fluid Chromatography using the following conditions afforded the compounds listed hereafter:

Method Details:
Column: 21×250 mm Cellulose-2 @ 30° C.
Mobile Phase: 70% CO$_2$/30% MeOH+0.5% isopropylamine
Detection: UV @ 220 nm
Flow: 2 mL/min
Peak 1: SFC Retention Time=1.64 min. LC-MS: Rt=1.00 min; MS m/z [M+H]$^+$ 352.1. $^1$H NMR (400 MHz, DMSO-d$_6$) δ 9.42 (s, 1H), 8.31 (dd, J=2.4, 0.8 Hz, 1H), 7.70 (dd, J=2.7, 0.7 Hz, 1H), 7.52 (dd, J=8.0, 2.3 Hz, 1H), 7.14 (dd, J=8.8, 2.7 Hz, 1H), 7.00 (d, J=8.0 Hz, 1H), 6.60 (dd, J=8.8, 0.7 Hz, 1H), 4.62 (s, 1H), 4.24 (s, 1H), 3.73 (s, 3H), 3.49 (d, J=9.6 Hz, 1H), 3.21 (d, J=9.6 Hz, 1H), 2.27 (s, 3H), 1.36-1.30 (m, 1H), 1.30-1.21 (m, 1H), 0.44-0.38 (m, 1H), 0.20-0.15 (m, 1H).

Peak 2: SFC Retention Time=3.30 min. LC-MS: Rt=1.00 min; MS m/z [M+H]$^+$ 352.1. $^1$H NMR (400 MHz, DMSO-d$_6$) δ 9.42 (s, 1H), 8.31 (dd, J=2.4, 0.8 Hz, 1H), 7.70 (dd, J=2.7, 0.7 Hz, 1H), 7.52 (dd, J=8.0, 2.3 Hz, 1H), 7.14 (dd, J=8.8, 2.7 Hz, 1H), 7.00 (d, J=8.0 Hz, 1H), 6.60 (dd, J=8.8, 0.7 Hz, 1H), 4.62 (s, 1H), 4.24 (s, 1H), 3.73 (s, 3H), 3.49 (d, J=9.6 Hz, 1H), 3.21 (d, J=9.6 Hz, 1H), 2.27 (s, 3H), 1.36-1.30 (m, 1H), 1.30-1.21 (m, 1H), 0.44-0.38 (m, 1H), 0.20-0.15 (m, 1H).

Examples 5-13 described infra were synthesized according to the protocol described for Example 1 using methyl (1R,4S,5S)-3-bromo-5-hydroxy-7-oxabicyclo[2.2.1]hept-2-ene-2-carboxylate and methyl (1S,4S,6R)-3-bromo-6-hydroxy-7-oxabicyclo[2.2.1]hept-2-ene-2-carboxylate (Intermediate 1e) and various boronic acids/esters in Step B and various anilines in Step C to give a mixture of alcohol regioisomers.

Example 5: (1R,2S,3S,4R,5S)—N-(4,5-dichloropyridin-2-yl)-5-hydroxy-3-(2-methylpyridin-4-yl)-7-oxabicyclo[2.2.1]heptane-2-carboxamide

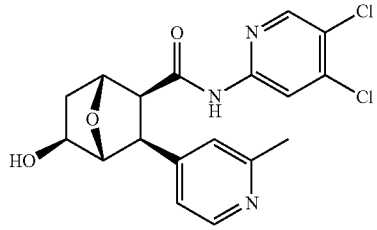 [SMILES: Cc1cc([C@H]2[C@H]3O[C@H](C[C@@H]3O)[C@H]2C(=O)Nc2cc(Cl)c(Cl)cn2)ccn1]

LC-MS: Rt=0.62 min; MS m/z [M+H]$^+$ 394.1.

Example 6: (1R,2S,3S,4R,5S)—N-(5-chloro-6-methylpyridin-3-yl)-5-hydroxy-3-(2-methylpyridin-4-yl)-7-oxabicyclo[2.2.1]heptane-2-carboxamide

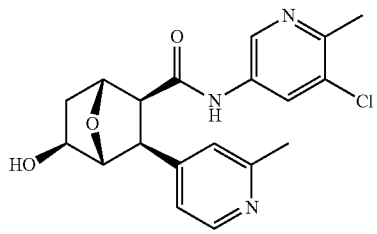 [SMILES: Cc1cc([C@H]2[C@H]3O[C@H](C[C@@H]3O)[C@H]2C(=O)Nc2cnc(C)c(Cl)c2)ccn1]

LC-MS: Rt=0.53 min; MS m/z [M+H]$^+$ 374.1. $^1$H NMR (500 MHz, DMSO-d$_6$) δ 9.62 (s, 1H), 8.12 (dd, J=5.2, 0.8 Hz, 1H), 8.00 (d, J=2.2 Hz, 1H), 7.55 (d, J=2.3 Hz, 1H), 7.12 (s, 1H), 7.03 (dd, J=5.2, 1.6 Hz, 1H), 4.95-4.92 (m, 1H), 4.85-4.81 (m, 1H), 4.18 (s, 1H), 4.04-4.00 (m, 1H), 3.26 (d, J=9.8 Hz, 1H), 3.04 (d, J=9.8 Hz, 1H), 2.38 (s, 3H), 2.27 (s, 3H), 2.04-1.97 (m, 1H), 1.50-1.44 (m, 1H). ~6:1 mixture of alcohol regioisomers.

Examples 7 and 8 (Corresponding to Peak 1 and Peak 2)

(1R,2S,3S,4R,5S)—N-(5,6-dichloropyridin-3-yl)-5-hydroxy-3-(2-methylpyridin-4-yl)-7-oxabicyclo[2.2.1]heptane-2-carboxamide or (1S,2R,3R,4S,5R)—N-(5,6-dichloropyridin-3-yl)-5-hydroxy-3-(2-methylpyridin-4-yl)-7-oxabicyclo[2.2.1]heptane-2-carboxamide

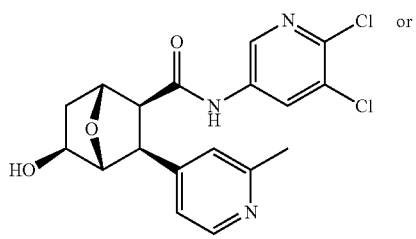

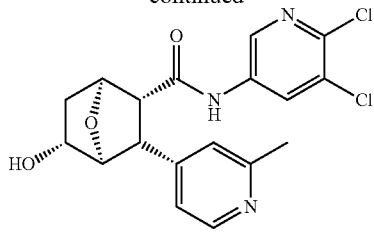

Chiral separation of rac-(1R,2S,3S,4R,5S)—N-(5,6-dichloropyridin-3-yl)-5-hydroxy-3-(2-methylpyridin-4-yl)-7-oxabicyclo[2.2.1]heptane-2-carboxamide by Supercritical Fluid Chromatography using the following conditions afforded the compounds listed hereafter:

Method Details:

Column: 21×250 mm IC @ 30° C.

Mobile Phase: 65% CO$_2$/35% MeOH+0.5% isopropylamine

Detection: UV @ 220 nm

Flow: 2 mL/min

Peak 1: SFC Retention Time=1.28 min. LC-MS: Rt=0.95 min; MS m/z [M+H]$^+$ 394.2. $^1$H NMR (400 MHz, DMSO-d$_6$) δ 9.88 (s, 1H), 8.11 (d, J=5.2 Hz, 1H), 8.01 (d, J=2.4 Hz, 1H), 7.79 (d, J=2.4 Hz, 1H), 7.10 (s, 1H), 7.04-7.00 (m, 1H), 4.99-4.93 (m, 1H), 4.87-4.80 (m, 1H), 4.19 (s, 1H), 4.06-4.00 (m, 1H), 3.30-3.25 (m, 1H), 3.07 (d, J=9.8 Hz, 1H), 2.26 (s, 3H), 2.05-1.94 (m, 1H), 1.52-1.43 (m, 1H).

Peak 2: SFC Retention Time=2.85 min. LC-MS: Rt=0.95 min; MS m/z [M+H]$^+$ 394.2. $^1$H NMR (400 MHz, DMSO-d$_6$) δ 9.88 (s, 1H), 8.11 (d, J=5.2 Hz, 1H), 8.01 (d, J=2.4 Hz, 1H), 7.79 (d, J=2.4 Hz, 1H), 7.10 (s, 1H), 7.04-7.00 (m, 1H), 4.99-4.93 (m, 1H), 4.87-4.80 (m, 1H), 4.19 (s, 1H), 4.06-4.00 (m, 1H), 3.30-3.25 (m, 1H), 3.07 (d, J=9.8 Hz, 1H), 2.26 (s, 3H), 2.05-1.94 (m, 1H), 1.52-1.43 (m, 1H).

Example 9: (1R,2S,3S,4R,5S)-5-hydroxy-3-(2-methylpyridin-4-yl)-N-(3-(trifluoromethyl)phenyl)-7-oxabicyclo[2.2.1]heptane-2-carboxamide

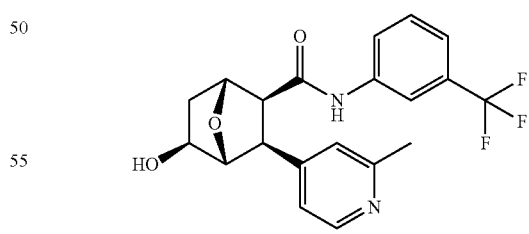

LC-MS: Rt=1.04 min; MS m/z [M+H]$^+$ 393.2. $^1$H NMR (400 MHz, DMSO-d$_6$) δ 9.64 (s, 1H), 8.10-8.07 (m, 1H), 7.46 (s, 1H), 7.38-7.33 (m, 1H), 7.28-7.22 (m, 2H), 7.12 (s, 1H), 7.03 (dd, J=5.2, 1.7 Hz, 1H), 4.99-4.92 (m, 1H), 4.88-4.82 (m, 1H), 4.17 (s, 1H), 4.05-3.99 (m, 1H), 3.27 (d, J=9.8 Hz, 1H), 3.04 (d, J=9.8 Hz, 1H), 2.23 (s, 3H), 2.05-1.96 (m, 1H), 1.51-1.43 (m, 1H). >20:1 mixture of alcohol regioisomers.

Example 10: (1S,2S,3S,4S,6R)-6-hydroxy-3-(2-methylpyridin-4-yl)-N-(3-(trifluoromethyl)phenyl)-7-oxabicyclo[2.2.1]heptane-2-carboxamide

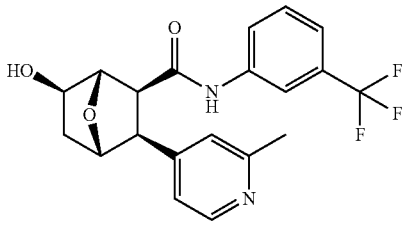 [SMILES: Cc1cc([C@@H]2[C@H](C(=O)Nc3cccc(C(F)(F)F)c3)[C@@H]3O[C@H]2C[C@H]3O)ccn1]

LC-MS: Rt=1.00 min; MS m/z [M+H]+ 393.2. $^1$H NMR (400 MHz, DMSO-$d_6$) δ 9.75 (s, 1H), 8.09 (dd, J=5.2, 0.8 Hz, 1H), 7.46 (s, 1H), 7.39-7.34 (m, 1H), 7.30-7.23 (m, 2H), 7.13 (s, 1H), 7.06 (dd, J=5.2, 1.6 Hz, 1H), 4.97-4.91 (m, 1H), 4.59 (s, 1H), 4.51-4.47 (m, 1H), 4.01-3.95 (m, 1H), 3.24 (d, J=9.7 Hz, 1H), 3.05 (d, J=9.7 Hz, 1H), 2.22 (s, 3H), 2.05-1.97 (m, 1H), 1.53-1.45 (m, 1H). >20:1 mixture of alcohol regioisomers.

Example 11: rac-(1R,2S,3S,4R,5S)—N-(5,6-dichloropyridin-3-yl)-5-hydroxy-3-(pyridin-4-yl)-7-oxabicyclo[2.2.1]heptane-2-carboxamide LC-MS: Rt=0.92 min; MS m/z [M+H]+ 381.1. $^1$H NMR (400 MHz, DMSO-$d_6$) δ 9.96 (s, 1H), 8.30-8.27 (m, 2H), 8.00 (d, J=2.4 Hz, 1H), 7.80 (d, J=2.4 Hz, 1H), 7.28-7.23 (m, 2H), 4.98-4.95 (m, 1H), 4.87-4.83 (m, 1H), 4.21 (s, 1H), 4.07-4.02 (m, 1H), 3.36-3.29 (m, 1H), 3.09 (d, J=9.8 Hz, 1H), 2.06-1.98 (m, 1H), 1.52-1.44 (m, 1H). ~3:1 mixture of alcohol regioisomers.

Example 11a: (Corresponding to Peak 1)

(1R,2S,3S,4R,5S)—N-(5,6-dichloropyridin-3-yl)-5-hydroxy-3-(pyridin-4-yl)-7-oxabicyclo[2.2.1]heptane-2-carboxamide or (1 S,2R,3R,4S,5R)—N-(5,6-dichloropyridin-3-yl)-5-hydroxy-3-(pyridin-4-yl)-7-oxabicyclo[2.2.1]heptane-2-carboxamide

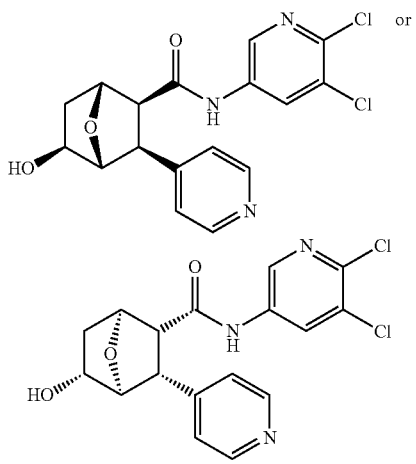

Chiral separation of rac-(1R,2S,3S,4R,5S)—N-(5,6-dichloropyridin-3-yl)-5-hydroxy-3-(pyridin-4-yl)-7-oxabicyclo[2.2.1]heptane-2-carboxamide (Example 10) by Supercritical Fluid Chromatography using the following conditions afforded the compound listed hereafter:

Method Details:
Column: 21×250 mm IC @ 30° C.
Mobile Phase: 65% CO$_2$/35% MeOH+0.5% isopropylamine
Detection: UV @ 220 nm
Flow: 2 mL/min
Peak 1: SFC Retention Time=1.74 min. LC-MS: Rt=0.92 min; MS m/z [M+H]+ 381.1. $^1$H NMR (400 MHz, DMSO-$d_6$) δ 9.97 (s, 1H), 8.30-8.26 (m, 2H), 7.99 (d, J=2.3 Hz, 1H), 7.80 (d, J=2.4 Hz, 1H), 7.26-7.22 (m, 2H), 4.97 (s, 1H), 4.88-4.82 (m, 1H), 4.20 (s, 1H), 4.07-4.00 (m, 1H), 3.36-3.31 (m, 1H), 3.09 (d, J=9.8 Hz, 1H), 2.06-1.98 (m, 1H), 1.53-1.43 (m, 1H).

Example 12: rac-(1R,2S,3S,4R,5S)-5-hydroxy-3-(pyridin-4-yl)-N-(3-(trifluoromethyl)phenyl)-7-oxabicyclo[2.2.1]heptane-2-carboxamide LC-MS: Rt=0.96 min; MS m/z [M+H]+ 379.2. $^1$H NMR (400 MHz, DMSO-$d_6$) δ 9.70 (s, 1H), 8.27-8.24 (m, 2H), 7.47 (s, 1H), 7.37-7.31 (m, 1H), 7.27-7.22 (m, 4H), 4.99-4.93 (m, 1H), 4.90-4.83 (m, 1H), 4.18 (s, 1H), 4.06-4.01 (m, 1H), 3.34-3.31 (m, 1H), 3.07 (d, J=9.8 Hz, 1H), 2.07-1.95 (m, 1H), 1.52-1.41 (m, 1H). >20:1 mixture of alcohol regioisomers.

Example 12a: (Corresponding to Peak 1)

(1R,2S,3S,4R,5S)-5-hydroxy-3-(pyridin-4-yl)-N-(3-(trifluoromethyl)phenyl)-7-oxabicyclo[2.2.1]heptane-2-carboxamide or (1 S,2R,3R,4S,5R)-5-hydroxy-3-(pyridin-4-yl)-N-(3-(trifluoromethyl)phenyl)-7-oxabicyclo[2.2.1]heptane-2-carboxamide

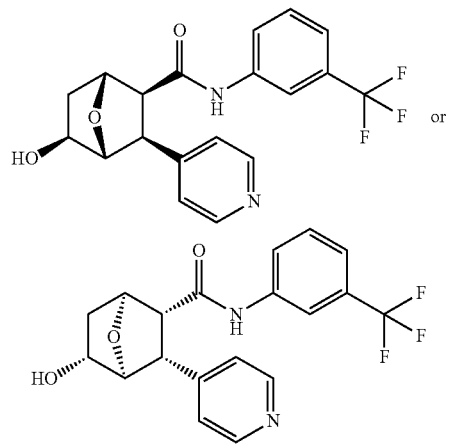

Chiral separation of rac-(1R,2S,3S,4R,5S)-5-hydroxy-3-(pyridin-4-yl)-N-(3-(trifluoromethyl)phenyl)-7-oxabicyclo[2.2.1]heptane-2-carboxamide (Example 11) by Supercritical Fluid Chromatography using the following conditions afforded the compound listed hereafter:

Method Details:
Column: 21×250 mm IC @ 30° C.
Mobile Phase: 95-50% CO$_2$/5-50% MeOH+0.5% isopropylamine in 5 minutes
Detection: UV @ 220 nm
Flow: 2 mL/min
Peak 1: SFC Retention Time=2.59 min. LC-MS: Rt=0.96 min; MS m/z [M+H]+ 379.2. $^1$H NMR (400 MHz, DMSO-$d_6$) δ 9.70 (s, 1H), 8.27-8.24 (m, 2H), 7.47 (s, 1H), 7.37-7.31

(m, 1H), 7.27-7.22 (m, 4H), 4.99-4.93 (m, 1H), 4.90-4.83 (m, 1H), 4.18 (s, 1H), 4.06-4.01 (m, 1H), 3.34-3.31 (m, 1H), 3.07 (d, J=9.8 Hz, 1H), 2.07-1.95 (m, 1H), 1.52-1.41 (m, 1H).

Example 13: (1S,2S,3S,4S,6R)-6-hydroxy-3-(pyridin-4-yl)-N-(3-(trifluoromethyl)phenyl)-7-oxabicyclo[2.2.1]heptane-2-carboxamide

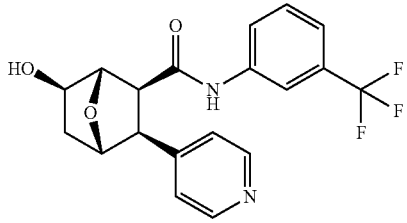 [SMILES: O=C(Nc1cccc(C(F)(F)F)c1)[C@@H]1[C@@H]2O[C@@H](C[C@H]2O)[C@@H]1c1ccncc1]

LC-MS: Rt=0.84 min; MS m/z [M+H]$^+$ 379.2. $^1$H NMR (400 MHz, DMSO-d$_6$) δ 9.79 (s, 1H), 8.26-8.24 (m, 2H), 7.47 (s, 1H), 7.38-7.33 (m, 1H), 7.29-7.23 (m, 4H), 4.97-4.93 (m, 1H), 4.60 (s, 1H), 4.52-4.49 (m, 1H), 4.02-3.96 (m, 1H), 3.32-3.29 (m, 1H), 3.07 (d, J=9.6 Hz, 1H), 2.05-1.99 (m, 1H), 1.55-1.47 (m, 1H). >20:1 mixture of alcohol regioisomers.

Examples 14-16 described infra were synthesized according to the protocol described for Example 1 using methyl (1R,4S,5R)-3-bromo-5-fluoro-7-oxabicyclo[2.2.1]hept-2-ene-2-carboxylate and methyl (1S,4S,6S)-3-bromo-6-fluoro-7-oxabicyclo[2.2.1]hept-2-ene-2-carboxylate (Intermediate 1g) and various boronic acids/esters in Step B and various anilines in Step C.

Example 14: (1R,2S,3S,4R,5R)—N-(3,4-dichlorophenyl)-5-fluoro-3-(2-methylpyridin-4-yl)-7-oxabicyclo[2.2.1]heptane-2-carboxamide

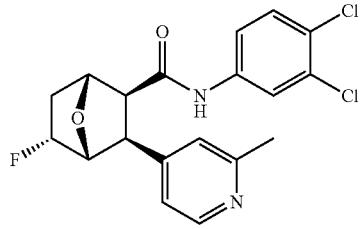 [SMILES: Cc1cc([C@H]2[C@H]3O[C@H](C[C@H]3F)[C@H]2C(=O)Nc2ccc(Cl)c(Cl)c2)ccn1]

LC-MS: Rt=1.16 min; MS m/z [M+H]$^+$ 395.2. Mixture of fluorine regioisomers.

Example 15: (1R,2S,3S,4R,5R)-5-fluoro-N-(6-methoxypyridin-3-yl)-3-(2-methylpyridin-4-yl)-7-oxabicyclo[2.2.1]heptane-2-carboxamide

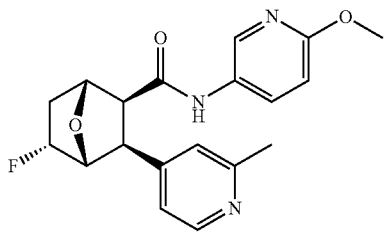 [SMILES: COc1ccc(NC(=O)[C@H]2[C@@H](c3ccnc(C)c3)[C@H]3O[C@@H]2C[C@H]3F)cn1]

LC-MS: Rt=0.42 min; MS m/z [M+H]$^+$ 358.2. $^1$H NMR (400 MHz, DMSO-d$_6$) δ 9.48 (s, 1H), 8.18 (dd, J=5.1, 0.8 Hz, 1H), 7.77-7.73 (m, 1H), 7.26 (dd, J=8.8, 2.7 Hz, 1H), 7.18 (s, 1H), 7.12-7.09 (m, 1H), 6.62 (dd, J=8.8, 0.7 Hz, 1H), 5.29-5.08 (m, 1H), 4.90-4.84 (m, 1H), 4.69-4.63 (m, 1H), 3.94-3.89 (m, 1H), 3.74 (s, 3H), 3.40-3.35 (m, 1H), 2.29 (s, 3H), 2.27-2.13 (m, 1H), 1.72-1.58 (m, 1H). >20:1 mixture of fluorine regioisomers.

Example 16: (1R,2S,3S,4R,5R)-5-fluoro-3-(2-methylpyridin-4-yl)-N-(3-(trifluoromethyl)phenyl)-7-oxabicyclo[2.2.1]heptane-2-carboxamide

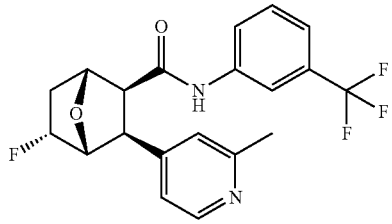 [SMILES: Cc1cc([C@H]2[C@H]3O[C@H](C[C@H]3F)[C@H]2C(=O)Nc2cccc(C(F)(F)F)c2)ccn1]

LC-MS: Rt=1.14 min; MS m/z [M+H]$^+$ 395.2. $^1$H NMR (400 MHz, DMSO-d$_6$) δ 9.80 (s, 1H), 8.11 (dd, J=5.1, 0.8 Hz, 1H), 7.48 (s, 1H), 7.40-7.34 (m, 1H), 7.30-7.24 (m, 2H), 7.18 (d, J=1.6 Hz, 1H), 7.10-7.06 (m, 1H), 5.29-5.08 (m, 1H), 4.91-4.87 (m, 1H), 4.70-4.64 (m, 1H), 3.97-3.90 (m, 1H), 3.44-3.38 (m, 1H), 2.28-2.18 (m, 1H), 2.23 (s, 3H), 1.71-1.59 (m, 1H). >20:1 mixture of fluorine regioisomers.

Examples 17-23 described infra were synthesized according to the protocol described for Example 1 using methyl (1R,4S,5S)-3-bromo-5-fluoro-7-oxabicyclo[2.2.1]hept-2-ene-2-carboxylate and methyl (1S,4S,6R)-3-bromo-6-fluoro-7-oxabicyclo[2.2.1]hept-2-ene-2-carboxylate (Intermediate 1j) and various boronic acids/esters in Step B and various anilines in Step C.

Example 17: (1R,2S,3S,4R,5S)—N-(3,4-dichlorophenyl)-5-fluoro-3-(2-methylpyridin-4-yl)-7-oxabicyclo[2.2.1]heptane-2-carboxamide

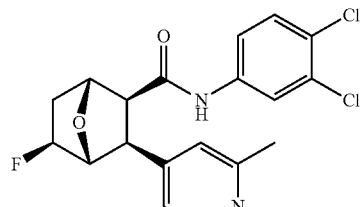

LC-MS: Rt=1.19 min; MS m/z [M+H]$^+$ 395.2. $^1$H NMR (500 MHz, DMSO-d6) δ 9.60 (s, 1H), 8.13 (dd, J=5.2, 0.7 Hz, 1H), 7.40-7.35 (m, 2H), 7.11 (s, 1H), 7.02 (dd, J=5.3, 1.6 Hz, 1H), 6.99 (dd, J=8.8, 2.4 Hz, 1H), 5.24-5.08 (m, 1H), 4.97-4.92 (m, 1H), 4.63-4.55 (m, 1H), 3.34-3.27 (m, 1H), 3.05 (d, J=9.9 Hz, 1H), 2.27 (s, 3H), 2.21-2.11 (m, 1H), 1.85-1.70 (m, 1H). >20:1 mixture of fluorine regioisomers.

Example 18: (1R,2S,3S,4R,5S)-5-fluoro-3-(2-methylpyridin-4-yl)-N-(3-(trifluoromethyl)phenyl)-7-oxabicyclo[2.2.1]heptane-2-carboxamide

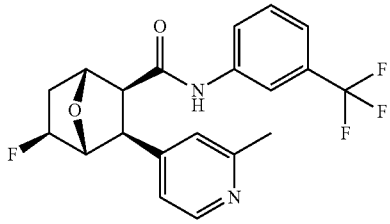 [SMILES: Cc1cc([C@H]2[C@H]3O[C@H](C[C@@H]3F)[C@H]2C(=O)Nc2cccc(C(F)(F)F)c2)ccn1]

LC-MS: Rt=1.15 min; MS m/z [M+H]$^+$ 395.2. $^1$H NMR (400 MHz, Acetonitrile-d$_3$) δ 8.15 (dd, J=5.2, 0.8 Hz, 1H), 8.06 (s, 1H), 7.43 (s, 1H), 7.32 (dd, J=7.9, 0.8 Hz, 1H), 7.28-7.24 (m, 2H), 7.15 (s, 1H), 7.05 (dd, J=5.2, 1.7 Hz, 1H), 5.15-4.98 (m, 1H), 5.06-5.02 (m, 1H), 4.74-4.68 (m, 1H), 3.36-3.30 (m, 1H), 3.07-3.02 (m, 1H), 2.29 (s, 3H), 2.24-2.16 (m, 1H), 1.93-1.79 (m, 1H). >20:1 mixture of fluorine regioisomers.

Example 19: (1R,2S,3S,4R,5S)—N-(5,6-dichloropyridin-3-yl)-5-fluoro-3-(2-methylpyridin-4-yl)-7-oxabicyclo[2.2.1]heptane-2-carboxamide

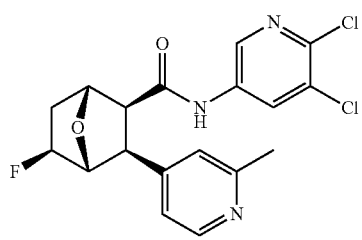 [SMILES: Cc1cc([C@H]2[C@H]3O[C@H](C[C@@H]3F)[C@H]2C(=O)Nc2cnc(Cl)c(Cl)c2)ccn1]

LC-MS: Rt=1.06 min; MS m/z [M+H]$^+$ 396.1. $^1$H NMR (400 MHz, Acetonitrile-d$_3$) δ 8.20-8.14 (m, 2H), 7.97 (d, J=2.4 Hz, 1H), 7.75 (d, J=2.4 Hz, 1H), 7.12 (s, 1H), 7.04 (dd, J=5.2, 1.7 Hz, 1H), 5.14-4.97 (m, 1H), 5.03-5.01 (m, 1H), 4.73-4.68 (m, 1H), 3.33 (d, J=9.7 Hz, 1H), 3.07 (d, J=9.7 Hz, 1H), 2.32 (s, 3H), 2.24-2.13 (m, 1H), 1.93-1.79 (m, 1H). >20:1 mixture of fluorine regioisomers.

Example 20: (1R,2S,3S,4R,5S)—N-(3,4-dichlorophenyl)-5-fluoro-3-(2-methoxypyridin-4-yl)-7-oxabicyclo[2.2.1]heptane-2-carboxamide

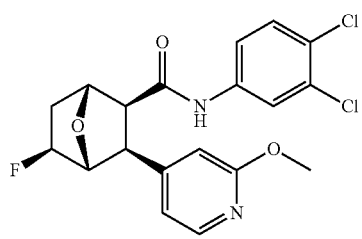

LC-MS: Rt=1.36 min; MS m/z [M+H]$^+$ 411.2. $^1$H NMR (500 MHz, DMSO-d$_6$) δ 9.61 (s, 1H), 7.85 (dd, J=5.3, 0.7 Hz, 1H), 7.40-7.36 (m, 2H), 7.00 (dd, J=8.8, 2.5 Hz, 1H), 6.83 (dd, J=5.3, 1.5 Hz, 1H), 6.68 (s, 1H), 5.23-5.08 (m, 1H), 4.97-4.90 (m, 1H), 4.61-4.55 (m, 1H), 3.69 (s, 3H), 3.32 (d, J=9.9 Hz, 1H), 3.04 (d, J=9.8 Hz, 1H), 2.21-2.11 (m, 1H), 1.83-1.70 (m, 1H). >20:1 mixture of fluorine regioisomers.

Example 21: (1R,2S,3S,4R,5S)-3-(2-aminopyrimidin-5-yl)-N-(3,4-dichlorophenyl)-5-fluoro-7-oxabicyclo[2.2.1]heptane-2-carboxamide

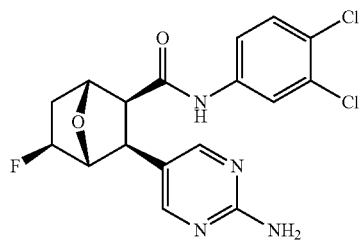 [SMILES: Nc1ncc([C@H]2[C@H]3O[C@H](C[C@@H]3F)[C@H]2C(=O)Nc2ccc(Cl)c(Cl)c2)cn1]

LC-MS: Rt=1.14 min; MS m/z [M+H]$^+$ 397.1. $^1$H NMR (400 MHz, DMSO-d6) δ 9.80 (s, 1H), 8.05 (s, 2H), 7.50 (d, J=2.4 Hz, 1H), 7.42 (d, J=8.8 Hz, 1H), 7.08 (dd, J=8.8, 2.5 Hz, 1H), 6.32 (s, 2H), 5.23-5.05 (m, 1H), 4.91-4.87 (m, 1H), 4.58-4.52 (m, 1H), 3.19 (d, J=9.6 Hz, 1H), 2.94 (d, J=9.7 Hz, 1H), 2.20-2.09 (m, 1H), 1.81-1.63 (m, 1H). >20:1 mixture of fluorine regioisomers.

Example 22: (1R,2S,3S,4R,5S)—N-(3,4-dichlorophenyl)-5-fluoro-3-(6-methylpyridin-3-yl)-7-oxabicyclo[2.2.1]heptane-2-carboxamide

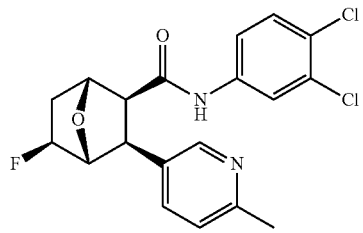 [SMILES: Cc1ccc([C@H]2[C@H]3O[C@H](C[C@@H]3F)[C@H]2C(=O)Nc2ccc(Cl)c(Cl)c2)cn1]

LC-MS: Rt=1.23 min; MS m/z [M+H]$^+$ 395.1. $^1$H NMR (500 MHz, DMSO-d$_6$) δ 9.63 (s, 1H), 8.29 (dd, J=2.3, 0.8 Hz, 1H), 7.50 (dd, J=8.0, 2.4 Hz, 1H), 7.38 (d, J=8.7 Hz, 1H), 7.24 (d, J=2.4 Hz, 1H), 6.99 (d, J=8.0 Hz, 1H), 6.94 (dd, J=8.8, 2.4 Hz, 1H), 5.26-5.10 (m, 1H), 4.96-4.89 (m, 1H), 4.58-4.53 (m, 1H), 3.36 (d, J=9.7 Hz, 1H), 3.01 (d, J=9.8 Hz, 1H), 2.25 (s, 3H), 2.21-2.11 (m, 1H), 1.83-1.69 (m, 1H). >20:1 mixture of fluorine regioisomers.

Example 23: (1R,2S,3S,4R,5S)—N-(3,4-dichlorophenyl)-5-fluoro-3-(2-fluoropyridin-4-yl)-7-oxabicyclo[2.2.1]heptane-2-carboxamide

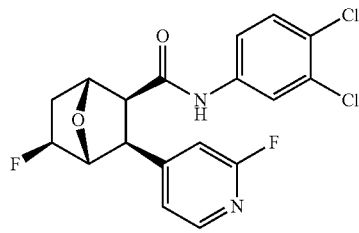

LC-MS: Rt=1.40 min; MS m/z [M+H]$^+$ 399.1. $^1$H NMR (400 MHz, DMSO-d$_6$) δ 9.80 (s, 1H), 7.97 (d, J=5.2 Hz, 1H), 7.44 (d, J=2.4 Hz, 1H), 7.40 (d, J=8.8 Hz, 1H), 7.21-7.17 (m, 1H), 7.02 (dd, J=8.8, 2.4 Hz, 1H), 6.96 (s, 1H), 5.25-5.07 (m, 1H), 4.97-4.94 (m, 1H), 4.69-4.64 (m, 1H), 3.47 (d, J=9.8 Hz, 1H), 3.11 (d, J=9.8 Hz, 1H), 2.24-2.13 (m, 1H), 1.86-1.70 (m, 1H). >20:1 mixture of fluorine regioisomers.

Example 24: rac-(1S,2S,4R,5R,6S,7S)—N-(3,4-dichlorophenyl)-7-(2-methylpyridin-4-yl)-8-oxatricyclo[3.2.1.0$^{2,4}$]octane-6-carboxamide Title compound was prepared from methyl (1S,2S,4R,5R)-7-bromo-8-oxatricyclo[3.2.1.0$^{2,4}$]oct-6-ene-6-carboxylate (Intermediate 1d) using Steps A-C as in Scheme 3.

Step A: To a stirring solution of 3,4-dichloroaniline (568 mg, 3.51 mmol) in anhydrous toluene (10 mL) at 0° C. under nitrogen was added trimethylaluminum in toluene (2 M, 3.90 mL, 7.79 mmol). After 10 minutes, the ice bath was removed and the mixture was stirred at room temperature for 30 minutes. The reaction was cooled back to 0° C. and 1d (955 mg, 3.90 mmol, dissolved in 2 mL of toluene) was added and the reaction was stirred at room temperature for 6 h. The reaction was cooled to 0° C. and quenched with a solution of saturated aqueous NH$_4$Cl and methanol. The suspension was filtered and the solid was washed with EtOAc. The organic layer was separated and washed with brine and dried over anhydrous sodium sulfate and concentrated. The crude compound was purified by silica column chromatography using DCM and EtOAc to afford (1 S,2S,4R,5R)-7-bromo-N-(3,4-dichlorophenyl)-8-oxatricyclo[3.2.1.0$^{2,4}$]oct-6-ene-6-carboxamide. LC-MS: Rt=1.63 min; MS m/z [M+H]$^+$ 373.9. $^1$H NMR (400 MHz, DMSO-d$_6$) δ 10.10 (s, 1H), 8.04 (d, J=2.3 Hz, 1H), 7.65 (dd, J=8.9, 2.3 Hz, 1H), 7.60 (d, J=8.8 Hz, 1H), 5.15 (s, 1H), 4.87 (s, 1H), 1.70-1.66 (m, 1H), 1.60-1.55 (m, 1H), 1.42-1.39 (m, 1H), 1.02-0.98 (m, 1H).

Step B: To a stirring solution of (1S,2S,4R,5R)-7-bromo-N-(3,4-dichlorophenyl)-8-oxatricyclo[3.2.1.0$^{2,4}$]oct-6-ene-6-carboxamide (525 mg, 1.40 mmol) in THF (10 mL) and water (2.5 mL) at 0° C. was added acetic acid (0.321 mL) and portion-wise Zn (366 mg, 5.60 mmol). The reaction slurry was stirred to room temperature for 15 minutes. The reaction was filtered and neutralized with saturated sodium bicarbonate to pH ~7. The compound was extracted with ethyl acetate. The organic layer was washed with water and brine and dried over anhydrous sodium sulfate and concentrated. The crude compound was purified by silica column chromatography (hexanes:EtOAc) to afford (1S,2S,4R,5R)—N-(3,4-dichlorophenyl)-8-oxatricyclo[3.2.1.0$^{2,4}$]oct-6-ene-6-carboxamide. LC-MS: Rt=1.54 min; MS m/z [M+H]$^+$ 296.0. $^1$H NMR (400 MHz, DMSO-d$_6$) δ 10.11 (s, 1H), 8.05 (d, J=2.3 Hz, 1H), 7.64 (dd, J=8.9, 2.4 Hz, 1H), 7.59 (d, J=8.8 Hz, 1H), 7.37 (d, J=1.7 Hz, 1H), 4.98 (s, 1H), 4.89 (d, J=1.7 Hz, 1H), 1.42-1.36 (m, 3H), 0.96-0.90 (m, 1H).

Step C: A mixture of (1S,2S,4R,5R)—N-(3,4-dichlorophenyl)-8-oxatricyclo[3.2.1.0$^{2,4}$]oct-6-ene-6-carboxamide (150 mg, 0.507 mmol), 2-methyl-4-(4,4,5,5-tetramethyl-1,3,2-dioxaborolan-2-yl)pyridine (133 mg, 0.608 mmol), 2,2-bis(diphenylphosphino)-1,1-binapthalene (32 mg, 0.051 mmol), chloro(1,5-cyclooctadiene)rhodium(I) dimer (12 mg, 0.025 mmol) and potassium carbonate (35 mg, 0.253 mmol) in 1,4-dioxane (2 mL) and water (0.5 mL) was heated in the microwave at 100° C. for 1 h. The crude reaction was taken in celite and the solvent was concentrated to dryness. The crude compound was purified by silica column chromatography using DCM and EtOAc to afford (1S,2S,4R,5R,6S,7S)—N-(3,4-dichlorophenyl)-7-(2-methylpyridin-4-yl)-8-oxatricyclo[3.2.1.0$^{2,4}$]octane-6-carboxamide (Example 23) and (1S,2S,4R,5R,6R,7S)—N-(3,4-dichlorophenyl)-7-(2-methylpyridin-4-yl)-8-oxatricyclo[3.2.1.0$^{2,4}$]octane-6-carboxamide (trans). LC-MS: Rt=1.29 min; MS m/z [M+H]+ 389.0. $^1$H NMR (400 MHz, DMSO-d$_6$) δ 9.70 (s, 1H), 8.14 (d, J=5.2 Hz, 1H), 7.40-7.37 (m, 2H), 7.16-7.13 (m, 1H), 7.06 (dd, J=5.3, 1.6 Hz, 1H), 6.99 (dd, J=8.8, 2.4 Hz, 1H), 4.65 (s, 1H), 4.30 (s, 1H), 3.48 (d, J=9.7 Hz, 1H), 3.28 (d, J=9.7 Hz, 1H), 2.28 (s, 3H), 1.35-1.23 (m, 2H), 0.44-0.39 (m, 1H), 0.22-0.15 (m, 1H).

Examples 24a and 24b (Corresponding to Peak 1 and Peak 2)

(1S,2S,4R,5R,6S,7S)—N-(3,4-dichlorophenyl)-7-(2-methylpyridin-4-yl)-8-oxatricyclo[3.2.1.02,4]octane-6-carboxamide or (1R,2R,4S,5S,6R,7R)—N-(3,4-dichlorophenyl)-7-(2-methylpyridin-4-yl)-8-oxatricyclo[3.2.1.02,4]octane-6-carboxamide

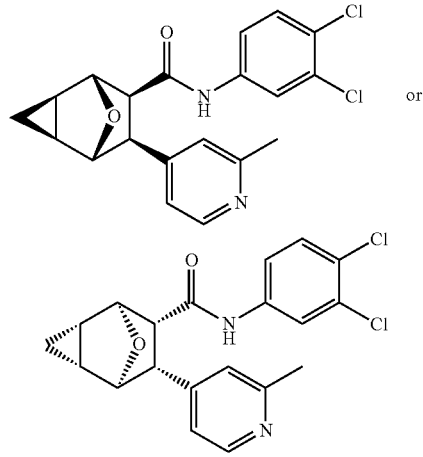

Chiral separation of rac-(1S,2S,4R,5R,6S,7S)—N-(3,4-dichlorophenyl)-7-(2-methylpyridin-4-yl)-8-oxatricyclo[3.2.1.0$^{2,4}$]octane-6-carboxamide (Example 23) by Supercritical Fluid Chromatography using the following conditions afforded the compounds listed hereafter:

Method Details:

Column: 21×250 mm IC @ 30° C.

Mobile Phase: 85% CO$_2$/15% MeOH+0.5% isopropylamine

Detection: UV @ 220 nm

Flow: 2 mL/min

Peak 1: SFC Retention Time=2.80 min. Method B LC-MS: Rt=1.06 min; MS m/z [M+H]+ 388.9. $^1$H NMR (400 MHz, DMSO-d$_6$) δ 9.68 (s, 1H), 8.11 (d, J=5.1 Hz, 1H), 7.39 (s, 1H), 7.38 (d, J=6.6 Hz, 1H), 7.11 (s, 1H), 7.03-6.97 (m, 2H), 4.65 (s, 1H), 4.29 (s, 1H), 3.46 (d, J=9.7 Hz, 1H), 3.26 (d, J=9.7 Hz, 1H), 2.26 (s, 3H), 1.35-1.25 (m, 2H), 0.43-0.39 (m, 1H), 0.22-0.16 (m, 1H).

Peak 2: SFC Retention Time=3.26 min. Method B LC-MS: Rt=1.06 min; MS m/z [M+H]+ 388.9. $^1$H NMR (400 MHz, DMSO-$d_6$) δ 9.68 (s, 1H), 8.11 (d, J=5.1 Hz, 1H), 7.39 (s, 1H), 7.38 (d, J=6.6 Hz, 1H), 7.11 (s, 1H), 7.03-6.97 (m, 2H), 4.65 (s, 1H), 4.29 (s, 1H), 3.46 (d, J=9.7 Hz, 1H), 3.26 (d, J=9.7 Hz, 1H), 2.26 (s, 3H), 1.35-1.25 (m, 2H), 0.43-0.39 (m, 1H), 0.22-0.16 (m, 1H).

Examples 25-46 described infra were synthesized according to the protocol described for Example 23 using methyl (1S,2S,4R,5R)-7-bromo-8-oxatricyclo[3.2.1.0$^{2,4}$]oct-6-ene-6-carboxylate (Intermediate 1d) and various anilines in Step A and various boronic esters/acids in Step C.

Example 25: (1S,2S,4R,5R,6S,7S)—N-(3,4-dichlorophenyl)-7-(2-methoxypyridin-4-yl)-8-oxatricyclo[3.2.1.0$^{2,4}$]octane-6-carboxamide

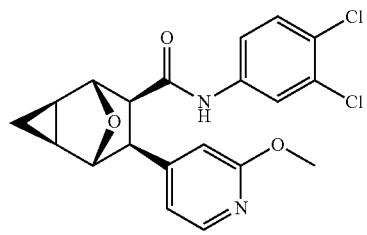 [SMILES: COc1cc([C@H]2[C@H]3O[C@H]([C@@H]4C[C@@H]43)[C@H]2C(=O)Nc2ccc(Cl)c(Cl)c2)ccn1]

Method B LC-MS: Rt=1.40 min; MS m/z [M+H]$^+$ 405.0. $^1$H NMR (400 MHz, DMSO-$d_6$) δ 9.72 (s, 1H), 7.83 (dd, J=5.3, 0.6 Hz, 1H), 7.39 (d, J=5.1 Hz, 1H), 7.38 (d, J=1.2 Hz, 1H), 7.01 (dd, J=8.8, 2.4 Hz, 1H), 6.83 (dd, J=5.4, 1.4 Hz, 1H), 6.69-6.66 (m, 1H), 4.65 (s, 1H), 4.28 (s, 1H), 3.68 (s, 3H), 3.47 (d, J=9.7 Hz, 1H), 3.26 (d, J=9.7 Hz, 1H), 1.35-1.29 (m, 1H), 1.29-1.24 (m, 1H), 0.44-0.38 (m, 1H), 0.21-0.14 (m, 1H).

Example 26: (1S,2S,4R,5R,6S,7S)—N-(3,4-dichlorophenyl)-7-(2-fluoropyridin-4-yl)-8-oxatricyclo[3.2.1.0$^{2,4}$]octane-6-carboxamide

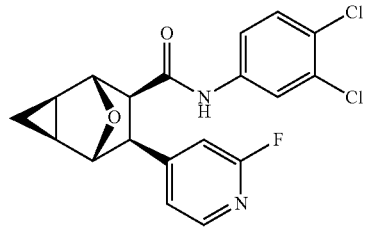 [SMILES: O=C(Nc1ccc(Cl)c(Cl)c1)[C@@H]1[C@@H]2O[C@@H]([C@H]3C[C@H]32)[C@@H]1c1ccnc(F)c1]

LC-MS: Rt=1.63 min; MS m/z [M+H]$^+$ 393.0. $^1$H NMR (400 MHz, DMSO-$d_6$) δ 9.83 (s, 1H), 7.95 (d, J=5.2 Hz, 1H), 7.45 (d, J=2.4 Hz, 1H), 7.40 (d, J=8.8 Hz, 1H), 7.19 (d, J=5.0 Hz, 1H), 7.02 (dd, J=8.9, 2.5 Hz, 1H), 6.95 (s, 1H), 4.67 (d, J=2.7 Hz, 1H), 4.35 (d, J=2.7 Hz, 1H), 3.61 (d, J=9.6 Hz, 1H), 3.31 (d, J=9.6 Hz, 1H), 1.36-1.25 (m, 2H), 0.44-0.39 (m, 1H), 0.23-0.18 (m, 1H).

Example 27: (1S,2S,4R,5R,6S,7S)-7-(2-methylpyridin-4-yl)-N-(3-(trifluoromethyl)phenyl)-8-oxatricyclo[3.2.1.0$^{2,4}$]octane-6-carboxamide

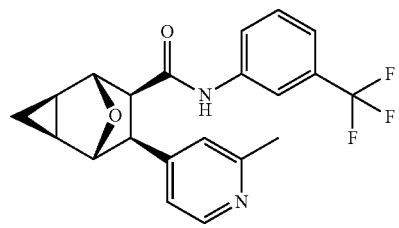 [SMILES: Cc1cc([C@H]2[C@H]3O[C@H]([C@@H]4C[C@@H]43)[C@H]2C(=O)Nc2cccc(C(F)(F)F)c2)ccn1]

LC-MS: Rt=1.29 min; MS m/z [M+H]$^+$ 389.1. $^1$H NMR (400 MHz, DMSO-$d_6$) δ 9.73 (s, 1H), 8.08 (d, J=5.1 Hz, 1H), 7.46 (s, 1H), 7.36 (t, J=7.9 Hz, 1H), 7.26 (t, J=9.2 Hz, 2H), 7.12 (s, 1H), 7.03 (dd, J=5.1, 1.2 Hz, 1H), 4.66 (s, 1H), 4.29 (s, 1H), 3.47 (d, J=9.7 Hz, 1H), 3.29 (d, J=9.7 Hz, 1H), 2.23 (s, 3H), 1.35-1.26 (m, 2H), 0.44-0.41 (m, 1H), 0.21-0.16 (m, 1H).

Examples 28 and 29 (Corresponding to Peak 1 and Peak 2)

(1S,2S,4R,5R,6S,7S)—N-(3,4-dichlorophenyl)-7-(pyrimidin-5-yl)-8-oxatricyclo[3.2.1.0$^{2,4}$]octane-6-carboxamide or (1R,2R,4S,5S,6R,7R)—N-(3,4-dichlorophenyl)-7-(pyrimidin-5-yl)-8-oxatricyclo[3.2.1.0$^{2,4}$]octane-6-carboxamide

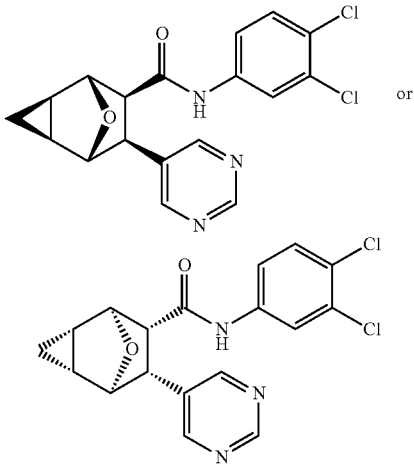

Chiral separation of rac-(1S,2S,4R,5R,6S,7S)—N-(3,4-dichlorophenyl)-7-(pyrimidin-5-yl)-8-oxatricyclo[3.2.1.0$^{2,4}$]octane-6-carboxamide by Supercritical Fluid Chromatography using the following conditions afforded the compounds listed hereafter:

Method Details:

Column: 21×250 mm IB @ 30° C.

Mobile Phase: 75% $CO_2$/25% MeOH+0.5% isopropylamine

Detection: UV @ 220 nm

Flow: 2 mL/min

Peak 1: SFC Retention Time=1.28 min. Method C LC-MS: Rt=1.03 min; MS m/z [M+H]⁺ 375.8. ¹H NMR (400 MHz, DMSO-d₆) δ 9.93 (s, 1H), 8.82 (s, 1H), 8.61 (s, 2H), 7.40 (d, J=8.0 Hz, 2H), 7.01-6.98 (m, 1H), 4.66 (s, 1H), 4.41 (s, 1H), 3.57 (d, J=9.5 Hz, 1H), 3.29 (d, J=9.7 Hz, 1H), 1.38-1.27 (m, 2H), 0.45-0.40 (m, 1H), 0.24-0.18 (m, 1H).

Peak 2: SFC Retention Time=2.76 min. Method C LC-MS: Rt=1.03 min; MS m/z [M+H]⁺ 375.9. ¹H NMR (400 MHz, DMSO-d₆) δ 9.93 (s, 1H), 8.82 (s, 1H), 8.61 (s, 2H), 7.40 (d, J=8.0 Hz, 2H), 7.01-6.98 (m, 1H), 4.66 (s, 1H), 4.41 (s, 1H), 3.57 (d, J=9.5 Hz, 1H), 3.29 (d, J=9.7 Hz, 1H), 1.38-1.27 (m, 2H), 0.45-0.40 (m, 1H), 0.24-0.18 (m, 1H).

Examples 30 and 31 (Corresponding to Peak 1 and Peak 2)

(1S,2S,4R,5R,6S,7S)—N-(3,4-dichlorophenyl)-7-(2,3-difluoropyridin-4-yl)-8-oxatricyclo[3.2.1.0²,⁴]octane-6-carboxamide or (1R,2R,4S,5S,6R,7R)—N-(3,4-dichlorophenyl)-7-(2,3-difluoropyridin-4-yl)-8-oxatricyclo[3.2.1.0²,⁴]octane-6-carboxamide

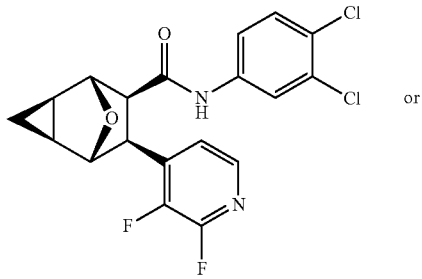

or

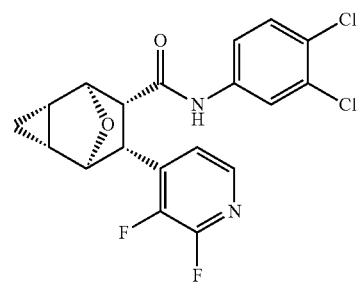

Chiral separation of rac-(1S,2S,4R,5R,6S,7S)—N-(3,4-dichlorophenyl)-7-(2,3-difluoropyridin-4-yl)-8-oxatricyclo[3.2.1.0²,⁴]octane-6-carboxamide by Supercritical Fluid Chromatography using the following conditions afforded the compounds listed hereafter:

Method Details:

Column: 21×250 mm IA @ 30° C.

Mobile Phase: 85% CO₂/15% MeOH+0.5% isopropylamine

Detection: UV @ 220 nm

Flow: 2 mL/min

Peak 1: SFC Retention Time=2.63 min. Method D LC-MS: Rt=1.23 min; MS m/z [M+H]⁺ 410.8. ¹H NMR (400 MHz, DMSO-d₆) δ 10.02 (s, 1H), 7.84 (dd, J=5.2, 0.9 Hz, 1H), 7.44 (d, J=1.7 Hz, 1H), 7.43 (d, J=4.6 Hz, 1H), 7.31 (t, J=4.9 Hz, 1H), 7.04 (dd, J=8.8, 2.4 Hz, 1H), 4.67 (s, 1H), 4.44 (s, 1H), 3.89 (d, J=9.6 Hz, 1H), 3.36 (d, J=9.6 Hz, 1H), 1.42-1.37 (m, 1H), 1.34-1.28 (m, 1H), 0.46-0.40 (m, 1H), 0.24-0.19 (m, 1H).

Peak 2: SFC Retention Time=3.19 min. Method D LC-MS: Rt=1.23 min; MS m/z [M+H]⁺ 410.8. ¹H NMR (400 MHz, DMSO-d₆) δ 10.02 (s, 1H), 7.84 (dd, J=5.2, 0.9 Hz, 1H), 7.44 (d, J=1.7 Hz, 1H), 7.43 (d, J=4.6 Hz, 1H), 7.31 (t, J=4.9 Hz, 1H), 7.04 (dd, J=8.8, 2.4 Hz, 1H), 4.67 (s, 1H), 4.44 (s, 1H), 3.89 (d, J=9.6 Hz, 1H), 3.36 (d, J=9.6 Hz, 1H), 1.42-1.37 (m, 1H), 1.34-1.28 (m, 1H), 0.46-0.40 (m, 1H), 0.24-0.19 (m, 1H).

Example 32: (1S,2S,4R,5R,6S,7S)—N-(5,6-dichloropyridin-3-yl)-7-(2,3-difluoropyridin-4-yl)-8-oxatricyclo[3.2.1.0²,⁴]octane-6-carboxamide

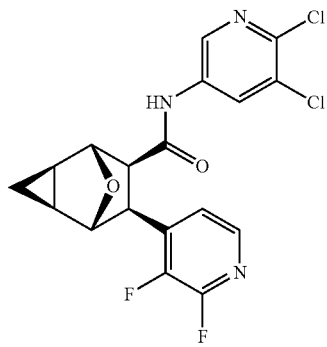 [SMILES: O=C(Nc1cnc(Cl)c(Cl)c1)[C@@H]1[C@@H]2O[C@@H]([C@H]3C[C@H]32)[C@@H]1c1ccnc(F)c1F]

Method C LC-MS: Rt=1.29 min; MS m/z [M+H]⁺ 411.8. ¹H NMR (400 MHz, DMSO-d₆) δ 10.34 (s, 1H), 8.07 (d, J=2.4 Hz, 1H), 7.84 (d, J=2.4 Hz, 2H), 7.31 (t, J=4.9 Hz, 1H), 4.70 (s, 1H), 4.44 (s, 1H), 3.90 (d, J=9.6 Hz, 1H), 3.39 (d, J=9.6 Hz, 1H), 1.43-1.37 (m, 1H), 1.33-1.28 (m, 1H), 0.46-0.40 (m, 1H), 0.25-0.19 (m, 1H).

Example 33: (1S,2S,4R,5R,6S,7S)—N-(6-methoxypyridin-3-yl)-7-(pyridin-4-yl)-8-oxatricyclo[3.2.1.0²,⁴]octane-6-carboxamide

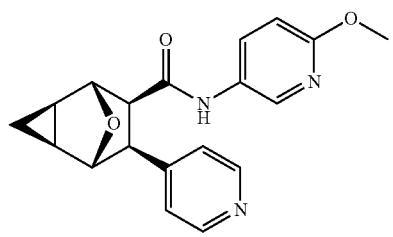 [SMILES: COc1ccc(NC(=O)[C@@H]2[C@@H]3O[C@@H]([C@H]4C[C@H]43)[C@@H]2c2ccncc2)cn1]

LC-MS: Rt=0.92 min; MS m/z [M+H]⁺ 338.0. ¹H NMR (400 MHz, DMSO-d₆) δ 9.63 (s, 1H), 8.62 (d, J=5.9 Hz, 2H), 7.76 (dd, J=2.7, 0.7 Hz, 1H), 7.73 (d, J=5.9 Hz, 2H), 7.31 (dd, J=8.9, 2.7 Hz, 1H), 6.62 (dd, J=8.8, 0.7 Hz, 1H), 4.71 (s, 1H), 4.40 (s, 1H), 3.75 (dt, J=9.6, 0.6 Hz, 1H), 3.73 (s, 3H), 3.39 (d, J=9.6 Hz, 1H), 1.40-1.29 (m, 2H), 0.47-0.41 (m, 1H), 0.25-0.18 (m, 1H).

Example 34: (1S,2S,4R,5R,6S,7S)-7-(2,3-difluoropyridin-4-yl)-N-(6-methoxypyridin-3-yl)-8-oxatricyclo[3.2.1.0$^{2,4}$]octane-6-carboxamide

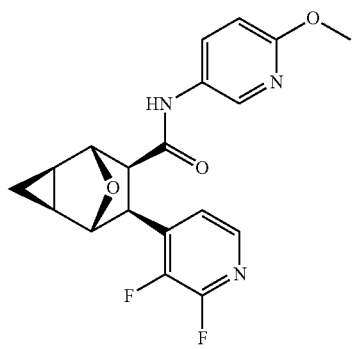 [SMILES: COc1ccc(NC(=O)[C@@H]2[C@@H]3O[C@@H]([C@H]4C[C@H]43)[C@@H]2c2ccnc(F)c2F)cn1]

Method C LC-MS: Rt=0.89 min; MS m/z [M+H]$^+$ 373.9. $^1$H NMR (400 MHz, DMSO-d6) δ 9.70 (s, 1H), 7.85 (d, J=5.2 Hz, 1H), 7.79 (d, J=2.7 Hz, 1H), 7.33 (t, J=4.9 Hz, 1H), 7.28 (dd, J=8.9, 2.7 Hz, 1H), 6.65 (dd, J=8.9, 0.7 Hz, 1H), 4.67 (s, 1H), 4.42 (s, 1H), 3.88 (d, J=9.6 Hz, 1H), 3.74 (s, 3H), 3.35 (d, J=9.6 Hz, 1H), 1.42-1.37 (m, 1H), 1.34-1.29 (m, 1H), 0.46-0.40 (m, 1H), 0.23-0.16 (m, 1H).

Example 35: (1S,2S,4R,5R,6S,7S)—N-(6-methoxypyridin-3-yl)-7-(6-(trifluoromethyl)pyridin-2-yl)-8-oxatricyclo[3.2.1.0$^{2,4}$]octane-6-carboxamide

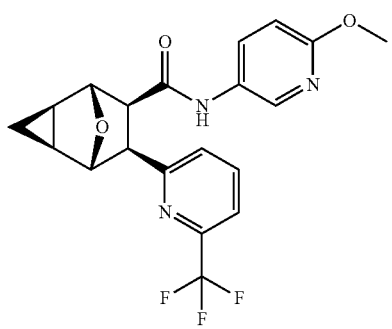 [SMILES: COc1ccc(NC(=O)[C@@H]2[C@@H]3O[C@@H]([C@H]4C[C@H]43)[C@@H]2c2cccc(C(F)(F)F)n2)cn1]

LC-MS: Rt=1.47 min; MS m/z [M+H]$^+$ 406.0. $^1$H NMR (400 MHz, DMSO-d$_6$) δ 9.63 (s, 1H), 7.90 (t, J=7.9 Hz, 1H), 7.76 (d, J=2.7 Hz, 1H), 7.63 (d, J=8.0 Hz, 1H), 7.60-7.57 (m, 1H), 7.27 (dd, J=8.9, 2.7 Hz, 1H), 6.59 (d, J=8.9 Hz, 1H), 4.66 (s, 1H), 4.48 (s, 1H), 3.78 (d, J=9.7 Hz, 1H), 3.72 (s, 3H), 3.36 (d, J=9.7 Hz, 1H), 1.42-1.36 (m, 1H), 1.31-1.26 (m, 1H), 0.46-0.41 (m, 1H), 0.23-0.18 (m, 1H).

Example 36: (1S,2S,4R,5R,6S,7S)—N-(3,4-dichlorophenyl)-7-(2-fluoropyrimidin-5-yl)-8-oxatricyclo[3.2.1.0$^{2,4}$]octane-6-carboxamide

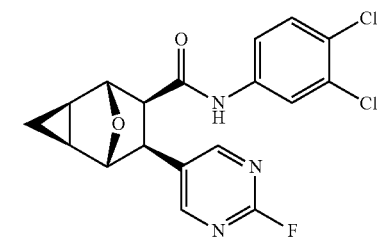 [SMILES: O=C(Nc1ccc(Cl)c(Cl)c1)[C@@H]1[C@@H]2O[C@@H]([C@H]3C[C@H]32)[C@@H]1c1cnc(F)nc1]

Method B LC-MS: Rt=1.50 min; MS m/z [M+H]$^+$ 394.0. $^1$H NMR (400 MHz, DMSO-d$_6$) δ 10.03 (s, 1H), 8.57 (d, J=1.5 Hz, 2H), 7.43 (d, J=6.1 Hz, 1H), 7.42 (s, 1H), 7.04 (dd, J=8.8, 2.4 Hz, 1H), 4.66 (s, 1H), 4.42 (s, 1H), 3.66 (d, J=9.5 Hz, 1H), 3.29 (d, J=9.5 Hz, 1H), 1.37-1.26 (m, 2H), 0.46-0.40 (m, 1H), 0.25-0.17 (m, 1H).

Example 37: (1S,2S,4R,5R,6S,7S)-7-(pyrimidin-5-yl)-N-(3-(trifluoromethyl)phenyl)-8-oxatricyclo[3.2.1.0$^{2,4}$]octane-6-carboxamide

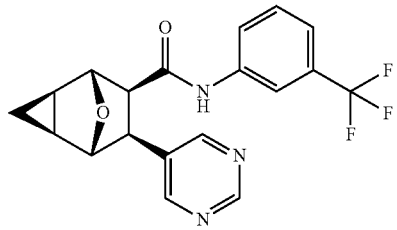 [SMILES: O=C(Nc1cccc(C(F)(F)F)c1)[C@@H]1[C@@H]2O[C@@H]([C@H]3C[C@H]32)[C@@H]1c1cncnc1]

LC-MS: Rt=1.41 min; MS m/z [M+H]$^+$ 376.1. $^1$H NMR (400 MHz, DMSO-d$_6$) δ 9.96 (s, 1H), 8.79 (s, 1H), 8.63 (s, 2H), 7.44 (s, 1H), 7.38 (t, J=8.0 Hz, 1H), 7.29-7.24 (m, 2H), 4.68 (s, 1H), 4.41 (s, 1H), 3.59 (d, J=9.6 Hz, 1H), 3.30 (s, 1H), 1.40-1.35 (m, 1H), 1.34-1.28 (m, 1H), 0.46-0.41 (m, 1H), 0.23-0.18 (m, 1H).

Example 38: (1S,2S,4R,5R,6S,7S)-7-(pyridin-4-yl)-N-(3-(trifluoromethyl)phenyl)-8-oxatricyclo[3.2.1.0$^{2,4}$]octane-6-carboxamide

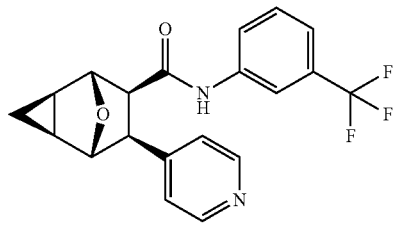 [SMILES: O=C(Nc1cccc(C(F)(F)F)c1)[C@@H]1[C@@H]2O[C@@H]([C@H]3C[C@H]32)[C@@H]1c1ccncc1]

LC-MS: Rt=1.28 min; MS m/z [M+H]$^+$ 375.1. $^1$H NMR (400 MHz, DMSO-d$_6$) δ 9.79 (s, 1H), 8.28 (d, J=6.0 Hz, 2H), 7.48 (s, 1H), 7.36 (t, J=7.9 Hz, 1H), 7.29 (dd, J=4.6, 1.4 Hz, 2H), 7.24 (d, J=8.1 Hz, 2H), 4.68 (s, 1H), 4.31 (s, 1H), 3.54 (d, J=9.7 Hz, 1H), 3.31 (d, J=9.7 Hz, 1H), 1.37-1.32 (m, 1H), 1.31-1.26 (m, 1H), 0.46-0.40 (m, 1H), 0.22-0.16 (m, 1H).

Example 39: (1S,2S,4R,5R,6S,7S)-7-(2-aminopyrimidin-5-yl)-N-(3,4-dichlorophenyl)-8-oxatricyclo[3.2.1.0²,⁴]octane-6-carboxamide

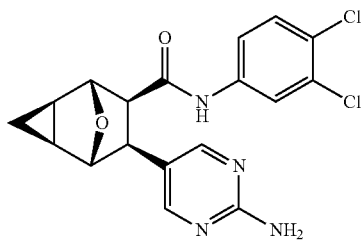 [SMILES: Nc1ncc([C@H]2[C@H]3O[C@H]([C@@H]4C[C@@H]43)[C@H]2C(=O)Nc2ccc(Cl)c(Cl)c2)cn1]

LC-MS: Rt=1.24 min; MS m/z [M+H]⁺ 391.0. ¹H NMR (400 MHz, DMSO-d₆) δ 9.85 (s, 1H), 8.05 (s, 2H), 7.51 (d, J=2.4 Hz, 1H), 7.42 (d, J=8.8 Hz, 1H), 7.08 (dd, J=8.8, 2.4 Hz, 1H), 6.27 (s, 2H), 4.59 (s, 1H), 4.23 (s, 1H), 3.33 (d, J=9.3 Hz, 1H), 3.15 (d, J=9.5 Hz, 1H), 1.32-1.26 (m, 1H), 1.26-1.20 (m, 1H), 0.42-0.37 (m, 1H), 0.20-0.15 (m, 1H).

Example 40: (1S,2S,4R,5R,6S,7S)—N-(3,4-dichlorophenyl)-7-(2-morpholinopyrimidin-5-yl)-8-oxatricyclo[3.2.1.0²,⁴]octane-6-carboxamide

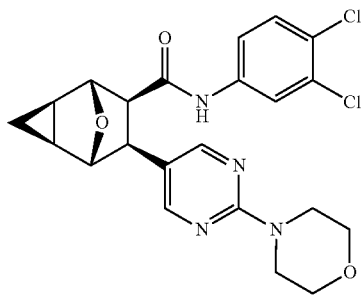 [SMILES: O=C(Nc1ccc(Cl)c(Cl)c1)[C@@H]1[C@@H]2O[C@@H]([C@H]3C[C@H]32)[C@@H]1c1cnc(N2CCOCC2)nc1]

LC-MS: Rt=1.55 min; MS m/z [M+H]⁺ 461.1. ¹H NMR (400 MHz, DMSO-d₆) δ 9.84 (s, 1H), 8.18 (s, 2H), 7.43-7.39 (m, 2H), 7.04 (dd, J=8.8, 2.4 Hz, 1H), 4.60 (s, 1H), 4.28 (s, 1H), 3.48 (s, 8H), 3.39 (d, J=9.4 Hz, 1H), 3.18 (d, J=9.5 Hz, 1H), 1.34-1.28 (m, 1H), 1.28-1.23 (m, 1H), 0.44-0.38 (m, 1H), 0.21-0.14 (m, 1H).

Example 41: (1S,2S,4R,5R,6S,7S)-7-(2-fluoropyridin-4-yl)-N-(3-(trifluoromethyl)phenyl)-8-oxatricyclo[3.2.1.0²,⁴]octane-6-carboxamide

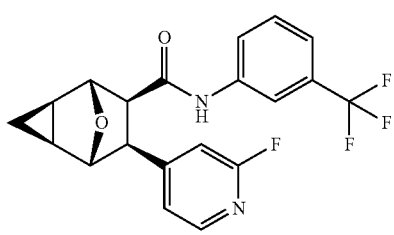 [SMILES: O=C(Nc1cccc(C(F)(F)F)c1)[C@@H]1[C@@H]2O[C@@H]([C@H]3C[C@H]32)[C@@H]1c1ccnc(F)c1]

LC-MS: Rt=1.58 min; MS m/z [M+H]⁺ 393.1. ¹H NMR (400 MHz, DMSO-d₆) δ 9.84 (s, 1H), 7.92 (d, J=5.2 Hz, 1H), 7.50 (d, J=2.0 Hz, 1H), 7.38 (t, J=7.9 Hz, 1H), 7.31-7.24 (m, 2H), 7.24-7.18 (m, 1H), 6.96 (d, J=1.4 Hz, 1H), 4.69 (s, 1H), 4.35 (s, 1H), 3.62 (d, J=9.6 Hz, 1H), 3.33 (d, J=9.6 Hz, 1H), 1.39-1.27 (m, 2H), 0.46-0.40 (m, 1H), 0.23-0.17 (m, 1H).

Example 42: (1S,2S,4R,5R,6S,7S)—N-(3,4-dichlorophenyl)-7-(2-methylpyrimidin-5-yl)-8-oxatricyclo[3.2.1.0²,⁴]octane-6-carboxamide

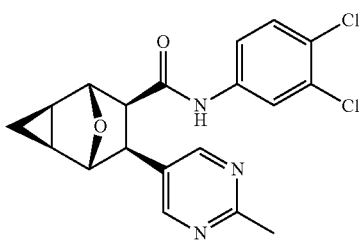 [SMILES: Cc1ncc([C@H]2[C@H]3O[C@H]([C@@H]4C[C@@H]43)[C@H]2C(=O)Nc2ccc(Cl)c(Cl)c2)cn1]

Method B LC-MS: Rt=1.35 min; MS m/z [M+H]⁺ 390.0. ¹H NMR (400 MHz, DMSO-d₆) δ 9.92 (s, 1H), 8.48 (s, 2H), 7.41 (d, J=8.8 Hz, 1H), 7.30 (d, J=2.4 Hz, 1H), 6.98 (dd, J=8.8, 2.4 Hz, 1H), 4.64 (s, 1H), 4.36 (s, 1H), 3.53 (d, J=9.5 Hz, 1H), 3.25 (d, J=9.6 Hz, 1H), 2.38 (s, 3H), 1.37-1.31 (m, 1H), 1.30-1.25 (m, 1H), 0.46-0.40 (m, 1H), 0.23-0.17 (m, 1H).

Example 43: rac-(1S,2S,4R,5R,6S,7S)—N-(5,6-dichloropyridin-3-yl)-7-(pyridin-4-yl)-8-oxatricyclo[3.2.1.0²,⁴]octane-6-carboxamide LC-MS: Rt=1.17 min; MS m/z [M+H]⁺ 376.0. ¹H NMR (400 MHz, DMSO-d₆) δ 10.17 (s, 1H), 8.50-8.42 (m, 2H), 8.03 (d, J=2.4 Hz, 1H), 7.85 (d, J=2.4 Hz, 1H), 7.54-7.49 (m, 2H), 4.70 (s, 1H), 4.39 (s, 1H), 3.68 (d, J=9.6 Hz, 1H), 3.40 (d, J=9.7 Hz, 1H), 1.41-1.29 (m, 2H), 0.46-0.42 (m, 1H), 0.26-0.18 (m, 1H).

Examples 43a and 43b (Corresponding to Peak 1 and Peak 2)

(1S,2S,4R,5R,6S,7S)—N-(5,6-dichloropyridin-3-yl)-7-(pyridin-4-yl)-8-oxatricyclo[3.2.1.0²,⁴]octane-6-carboxamide or (1R,2R,4S,5S,6R,7R)—N-(5,6-dichloropyridin-3-yl)-7-(pyridin-4-yl)-8-oxatricyclo[3.2.1.0²,⁴]octane-6-carboxamide

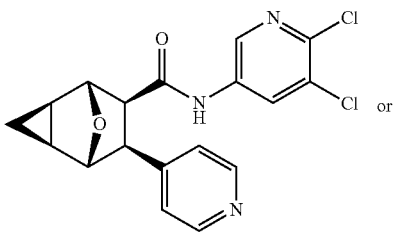

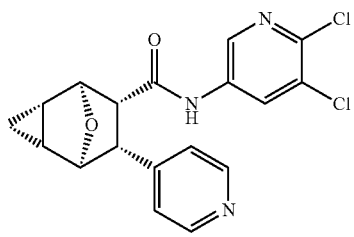

Chiral separation of rac-(1S,2S,4R,5R,6S,7S)—N-(5,6-dichloropyridin-3-yl)-7-(pyridin-4-yl)-8-oxatricyclo[3.2.1.0²,⁴]octane-6-carboxamide (Example 43) by Supercritical Fluid Chromatography using the following conditions afforded the compounds listed hereafter:

Method Details:

Column: 30×250 mm IC @ 30° C.

Mobile Phase: 65% $CO_2$/35% MeOH+0.5% isopropylamine

Detection: UV @ 220 nm

Flow: 2 mL/min

Peak 1: SFC Retention Time=1.64 min. LC-MS: Rt=1.17 min; MS m/z [M+H]⁺ 376.0. ¹H NMR (400 MHz, DMSO-$d_6$) δ 10.17 (s, 1H), 8.50-8.42 (m, 2H), 8.03 (d, J=2.4 Hz, 1H), 7.85 (d, J=2.4 Hz, 1H), 7.54-7.49 (m, 2H), 4.70 (s, 1H), 4.39 (s, 1H), 3.68 (d, J=9.6 Hz, 1H), 3.40 (d, J=9.7 Hz, 1H), 1.41-1.29 (m, 2H), 0.46-0.42 (m, 1H), 0.26-0.18 (m, 1H).

Peak 2: SFC Retention Time=2.80 min. LC-MS: Rt=1.17 min; MS m/z [M+H]⁺ 376.0. ¹H NMR (400 MHz, DMSO-$d_6$) δ 10.17 (s, 1H), 8.50-8.42 (m, 2H), 8.03 (d, J=2.4 Hz, 1H), 7.85 (d, J=2.4 Hz, 1H), 7.54-7.49 (m, 2H), 4.70 (s, 1H), 4.39 (s, 1H), 3.68 (d, J=9.6 Hz, 1H), 3.40 (d, J=9.7 Hz, 1H), 1.41-1.29 (m, 2H), 0.46-0.42 (m, 1H), 0.26-0.18 (m, 1H).

Example 44: (1S,2S,4R,5R,6S,7S)—N-(3,4-dichlorophenyl)-7-(pyridin-4-yl)-8-oxatricyclo[3.2.1.0²,⁴]octane-6-carboxamide

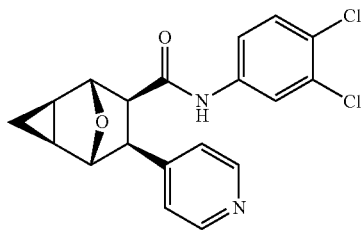 [SMILES: O=C(Nc1ccc(Cl)c(Cl)c1)[C@@H]1[C@@H]2O[C@@H]([C@H]3C[C@H]32)[C@@H]1c1ccncc1]

LC-MS: Rt=1.27 min; MS m/z [M+H]⁺ 375.0. ¹H NMR (500 MHz, DMSO-$d_6$) δ 9.73 (s, 1H), 8.29-8.25 (m, 2H), 7.41-7.32 (m, 2H), 7.26-7.21 (m, 2H), 7.01-6.96 (m, 1H), 4.69-4.62 (m, 1H), 4.33-4.27 (m, 1H), 3.53-3.48 (m, 1H), 3.30-3.25 (m, 1H), 1.37-1.31 (m, 1H), 1.31-1.25 (m, 1H), 0.45-0.38 (m, 1H), 0.24-0.17 (m, 1H).

Examples 45 and 46 (Corresponding to Peak 1 and Peak 2)

(1S,2S,4R,5R,6S,7S)—N-(5,6-dichloropyridin-3-yl)-7-(2-methylpyridin-4-yl)-8-oxatricyclo[3.2.1.0²,⁴]octane-6-carboxamide or (1R,2R,4S,5S,6R,7R)—N-(5,6-dichloropyridin-3-yl)-7-(2-methylpyridin-4-yl)-8-oxatricyclo[3.2.1.0²,⁴]octane-6-carboxamide Chiral separation of rac-(1S,2S,4R,5R,6S,7S)—N-(5,6-dichloropyridin-3-yl)-7-(2-methylpyridin-4-yl)-8-oxatricyclo[3.2.1.0²,⁴]octane-6-carboxamide by Supercritical Fluid Chromatography using the following conditions afforded the compounds listed hereafter:

Method Details:

Column: 21×250 mm IC @ 30° C.

Mobile Phase: 70% $CO_2$/30% MeOH+0.5% isopropylamine

Detection: UV @ 220 nm

Flow: 2 mL/min

Peak 1: SFC Retention Time=1.50 min. LC-MS: Rt=1.19 min; MS m/z [M+H]⁺ 390.0. ¹H NMR (400 MHz, DMSO-$d_6$) δ 9.97 (s, 1H), 8.11 (d, J=5.2 Hz, 1H), 8.01 (d, J=2.4 Hz, 1H), 7.79 (d, J=2.4 Hz, 1H), 7.10 (s, 1H), 7.01 (dd, J=5.1, 1.3 Hz, 1H), 4.66 (s, 1H), 4.32 (s, 1H), 3.48 (d, J=9.7 Hz, 1H), 3.31 (d, J=10.1 Hz, 1H), 2.25 (s, 3H), 1.36-1.26 (m, 2H), 0.45-0.39 (m, 1H), 0.22-0.16 (m, 1H).

Peak 2: SFC Retention Time=2.54 min. LC-MS: Rt=1.19 min; MS m/z [M+H]⁺ 390.0. ¹H NMR (400 MHz, DMSO-$d_6$) δ 9.97 (s, 1H), 8.11 (d, J=5.2 Hz, 1H), 8.01 (d, J=2.4 Hz, 1H), 7.79 (d, J=2.4 Hz, 1H), 7.10 (s, 1H), 7.01 (dd, J=5.1, 1.3 Hz, 1H), 4.66 (s, 1H), 4.32 (s, 1H), 3.48 (d, J=9.7 Hz, 1H), 3.31 (d, J=10.1 Hz, 1H), 2.25 (s, 3H), 1.36-1.26 (m, 2H), 0.45-0.39 (m, 1H), 0.22-0.16 (m, 1H).

Example 47: rac-(1R,2S,3S,4R,5S)—N-(3,4-dichlorophenyl)-5-hydroxy-3-(pyridin-4-yl)-7-oxabicyclo[2.2.1]heptane-2-carboxamide Title compound was prepared from methyl (1R,4S,5S)-3-bromo-5-hydroxy-7-oxabicyclo[2.2.1]hept-2-ene-2-carboxylate and methyl (1S,4S,6R)-3-bromo-6-hydroxy-7-oxabicyclo[2.2.1]hept-2-ene-2-carboxylate (Intermediate 1e) using Steps A-C as in Scheme 3.

Step A: To a stirring solution of 3,4-dichloroaniline (44.0 g, 271 mmol) in anhydrous toluene (100 mL) at 0° C. under nitrogen was added trimethylaluminum in toluene (2 M, 313 mL, 626 mmol). After 10 minutes, the ice bath was removed and the mixture was stirred at RT for 30 minutes. The reaction was cooled back to 0° C. and the mixture of methyl (1R,4S,5S)-3-bromo-5-hydroxy-7-oxabicyclo[2.2.1]hept-2-ene-2-carboxylate and methyl (1S,4S,6R)-3-bromo-6-hydroxy-7-oxabicyclo[2.2.1]hept-2-ene-2-carboxylate (Intermediate 1e, 26.0 g, 104 mmol) in 600 mL of toluene was added and the reaction was stirred ar RT for 6 h. The reaction was cooled to 0° C. and was slowly quenched with saturated aqueous ammonium chloride (500 ml). The suspension was filtered and the solid was washed with EtOAc (500 mL 3×) and methanol (100 mL 2×). The combined organic layer was washed with sat. aq. NH$_4$Cl (300 mL), water (300 mL), brine (300 mL) and dried over anhydrous sodium sulfate. The crude compound was purified by silica column chromatography using PE and EtOAc to give the mixture of (1R,4S,5S)-3-bromo-N-(3,4-dichlorophenyl)-5-hydroxy-7-oxabicyclo[2.2.1]hept-2-ene-2-carboxamide and (1S,4S,6R)-3-bromo-N-(3,4-dichlorophenyl)-6-hydroxy-7-oxabicyclo[2.2.1]hept-2-ene-2-carboxamide as a 2:1 mixture of alcohol regioisomers favoring the 5-hydroxy product as a light-yellow solid. $^1$H NMR (400 MHz, CDCl$_3$) b ppm 7.99-7.95 (m, 1H), 7.79-7.78 (m, 1H), 7.43-7.38 (m, 2H), 5.38-5.36 (m, 0.7H), 5.18-5.17 (m, 0.3H), 5.02-5.01 (m, 0.3H), 4.88-4.86 (m, 0.7H), 4.29-4.24 (m, 1H), 2.22-2.19 (m, 0.7H), 2.15-2.08 (m, 0.3H), 1.74-1.69 (m, 1H), 0.89-0.85 (m, 1H).

Step B: To a stirring solution of a mixture of (1R,4S,5S)-3-bromo-N-(3,4-dichlorophenyl)-5-hydroxy-7-oxabicyclo[2.2.1]hept-2-ene-2-carboxamide and (1S,4S,6R)-3-bromo-N-(3,4-dichlorophenyl)-6-hydroxy-7-oxabicyclo[2.2.1]hept-2-ene-2-carboxamide (14.5 g, 38.3 mmol) in THF (240 mL) and H$_2$O (60 mL) at 0° C. was added AcOH (18.0 mL) and Zn powder (20.0 g, 306 mmol). The reaction slurry was stirred at RT for 2 h. The reaction was filtered and neutralized with saturated aqueous sodium bicarbonate to pH 7. The compound was extracted with ethyl acetate (200 mL 3×). The organic layer was washed with water (200 mL), brine (100 mL) and dried over anhydrous sodium sulfate and concentrated. The resulting solid was triturated with MTBE (30 mL), then filtered to collect the solid to give a regioisomeric mixture of (1R,4R,5S)—N-(3,4-dichlorophenyl)-5-hydroxy-7-oxabicyclo[2.2.1]hept-2-ene-2-carboxamide and (1S,4S,6R)—N-(3,4-dichlorophenyl)-6-hydroxy-7-oxabicyclo[2.2.1]hept-2-ene-2-carboxamide as a yellow solid. $^1$H NMR (400 MHz, DMSO-d$_6$) δ 10.12 (s, 1H), 8.03-8.02 (d, 1H), 7.64-7.57 (m, 2H), 7.09-7.07 (d, 1H), 5.15-5.08 (m, 2H), 4.87-4.81 (m, 1H), 3.91-3.89 (m, 1H), 1.76-1.72 (m, 1H), 1.44-1.40 (m, 1H).

Step C: A mixture of (1R,4R,5S)—N-(3,4-dichlorophenyl)-5-hydroxy-7-oxabicyclo[2.2.1]hept-2-ene-2-carboxamide and (1S,4S,6R)—N-(3,4-dichlorophenyl)-6-hydroxy-7-oxabicyclo[2.2.1]hept-2-ene-2-carboxamide (250 mg, 0.833 mmol), pyridin-4-ylboronic acid (133 mg, 1.08 mmol), 2,2-bis(diphenylphosphino)-1,1-binapthalene (52 mg, 0.083 mmol), chloro(1,5-cyclooctadiene)rhodium(I) dimer (21 mg, 0.042 mmol) and potassium carbonate (58.0 mg, 0.416 mmol) in 1,4-dioxane (6 mL) and water (1.5 mL) was heated at 100° C. for 1 h in the microwave. The reaction mixture was concentrated onto celite and was purified by silica column chromatography to afford rac-(1R,2S,3S,4R,5S)—N-(3,4-dichlorophenyl)-5-hydroxy-3-(pyridin-4-yl)-7-oxabicyclo[2.2.1]heptane-2-carboxamide as a ~2:1 mixture of alcohol regioisomers favoring the 5-hydroxy product. LC-MS: Rt=1.10 min; MS m/z [M+H]$^+$ 379.0.

Example 47a: (Corresponding to Peak 1)

(1R,2S,3S,4R,5S)—N-(3,4-dichlorophenyl)-5-hydroxy-3-(pyridin-4-yl)-7-oxabicyclo[2.2.1]heptane-2-carboxamide or (1 S,2R,3R,4S,5R)—N-(3,4-dichlorophenyl)-5-hydroxy-3-(pyridin-4-yl)-7-oxabicyclo[2.2.1]heptane-2-carboxamide

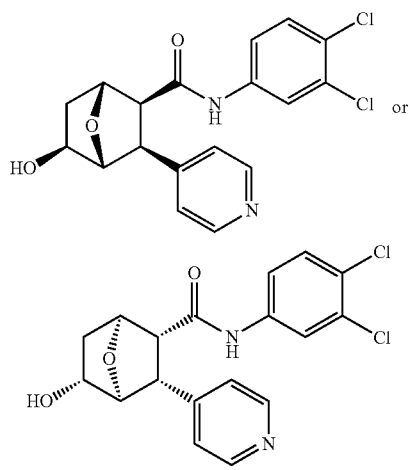

Chiral separation of rac-(1R,2S,3S,4R,5S)—N-(3,4-dichlorophenyl)-5-hydroxy-3-(pyridin-4-yl)-7-oxabicyclo[2.2.1]heptane-2-carboxamide (Example 47) by Supercritical Fluid Chromatography using the following conditions afforded the compound listed hereafter:

Method Details:

Column: 30×250 mm IC @ 30° C.

Mobile Phase: 70% CO$_2$/30% MeOH+0.5% isopropylamine

Detection: UV @ 220 nm

Flow: 2 mL/min

Peak 1: SFC Retention Time=3.59 min. LC-MS: Rt=1.10 min; MS m/z [M+H]$^+$ 379.0. $^1$H NMR (400 MHz, DMSO-d$_6$) δ 9.84 (s, 1H), 8.55-8.52 (m, 2H), 7.65-7.62 (m, 2H), 7.44 (d, J=2.4 Hz, 1H), 7.39 (d, J=8.8 Hz, 1H), 7.00 (dd, J=8.8, 2.4 Hz, 1H), 5.12-4.96 (m, 1H), 4.91-4.86 (m, 1H), 4.26 (s, 1H), 4.08-4.04 (m, 1H), 3.53 (d, J=9.7 Hz, 1H), 3.15 (d, J=9.8 Hz, 1H), 2.08-2.00 (m, 1H), 1.54-1.47 (m, 1H).

Examples 48-62 described infra were synthesized according to the protocol described for Example 47 using methyl (1R,4S,5S)-3-bromo-5-hydroxy-7-oxabicyclo[2.2.1]hept-2-ene-2-carboxylate and methyl (1S,4S,6R)-3-bromo-6-hydroxy-7-oxabicyclo[2.2.1]hept-2-ene-2-carboxylate (Intermediate 1e) and various anilines in Step A and various boronic esters/acids in Step C.

Example 48: (1R,2S,3S,4R,5S)—N-(3,4-dichlorophenyl)-5-hydroxy-3-(6-methylpyridin-3-yl)-7-oxabicyclo[2.2.1]heptane-2-carboxamide

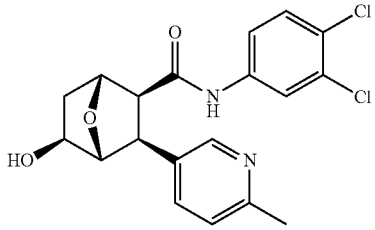 [SMILES: Cc1ccc([C@H]2[C@H]3O[C@H](C[C@@H]3O)[C@H]2C(=O)Nc2ccc(Cl)c(Cl)c2)cn1]

LC-MS: Rt=1.20 min; MS m/z [M+H]$^+$ 393.0. $^1$H NMR (500 MHz, DMSO-d$_6$) δ 9.66 (s, 1H), 8.32 (d, J=2.2 Hz, 1H), 7.65-7.59 (m, 1H), 7.38 (d, J=8.8 Hz, 1H), 7.27 (d, J=2.4 Hz, 1H), 7.11-7.06 (m, 1H), 6.95 (dd, J=8.9, 2.4 Hz, 1H), 4.98-4.86 (m, 1H), 4.82 (d, J=5.5, 1.2 Hz, 1H), 4.17 (s, 1H), 4.05-4.02 (m, 1H), 3.37-3.32 (m, 1H), 3.00 (d, J=9.7 Hz, 1H), 2.28 (s, 3H), 2.04-1.98 (m, 1H), 1.49-1.43 (m, 1H). ~3:1 mixture of alcohol regioisomers.

Example 49: rac-(1R,2S,3S,4R,5S)—N-(3,4-dichlorophenyl)-5-hydroxy-3-(2-methoxypyridin-4-yl)-7-oxabicyclo[2.2.1]heptane-2-carboxamide LC-MS: Rt=1.32 min; MS m/z [M+H]$^+$ 409.0. $^1$H NMR (400 MHz, DMSO-d$_6$) δ 9.61 (s, 1H), 7.83 (d, J=5.3 Hz, 1H), 7.39 (d, J=6.0 Hz, 1H), 7.37 (s, 1H), 6.99 (dd, J=8.8, 2.4 Hz, 1H), 6.84 (dd, J=5.4, 1.5 Hz, 1H), 6.68 (s, 1H), 4.96-4.93 (m, 1H), 4.84-4.77 (m, 1H), 4.15 (s, 1H), 4.03-3.98 (m, 1H), 3.68 (s, 3H), 3.27 (d, J=9.7 Hz, 1H), 3.01 (d, J=9.8 Hz, 1H), 2.03-1.93 (m, 1H), 1.51-1.42 (m, 1H). ~3:1 mixture of alcohol regioisomers.

Examples 49a and 49b (Corresponding to Peak 1 and Peak 2)

(1R,2S,3S,4R,5S)—N-(3,4-dichlorophenyl)-5-hydroxy-3-(2-methoxypyridin-4-yl)-7-oxabicyclo[2.2.1]heptane-2-carboxamide or (1S,2R,3R,4S,5R)—N-(3,4-dichlorophenyl)-5-hydroxy-3-(2-methoxypyridin-4-yl)-7-oxabicyclo[2.2.1]heptane-2-carboxamide

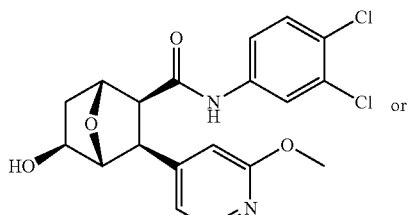

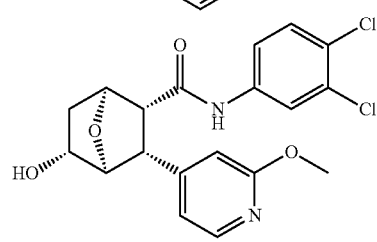

Chiral separation of rac-(1R,2S,3S,4R,5S)—N-(3,4-dichlorophenyl)-5-hydroxy-3-(2-methoxypyridin-4-yl)-7-oxabicyclo[2.2.1]heptane-2-carboxamide (Example 49) by Supercritical Fluid Chromatography using the following conditions afforded the compounds listed hereafter:

Method Details:
Column: 21×250 mm IF @ 30° C.
Mobile Phase: 65% CO$_2$/35% MeOH+0.5% isopropylamine
Detection: UV @ 220 nm
Flow: 2 mL/min Peak 1: SFC Retention Time=1.10 min. LC-MS: Rt=1.23 min; MS m/z [M+H]$^+$ 409.0. $^1$H NMR (400 MHz, DMSO-d6) δ 9.61 (s, 1H), 7.83 (d, J=5.3 Hz, 1H), 7.39 (d, J=6.1 Hz, 1H), 7.37 (s, 1H), 6.99 (dd, J=8.8, 2.4 Hz, 1H), 6.84 (dd, J=5.3, 1.4 Hz, 1H), 6.68 (d, J=0.8 Hz, 1H), 4.97-4.92 (m, 1H), 4.86-4.80 (m, 1H), 4.15 (s, 1H), 4.05-3.97 (m, 1H), 3.68 (s, 3H), 3.27 (d, J=9.7 Hz, 1H), 3.01 (d, J=9.8 Hz, 1H), 2.02-1.95 (m, 1H), 1.50-1.42 (m, 1H).

Peak 2: SFC Retention Time=2.81 min. LC-MS: Rt=1.23 min; MS m/z [M+H]$^+$ 409.0. $^1$H NMR (400 MHz, DMSO-d6) δ 9.61 (s, 1H), 7.83 (d, J=5.3 Hz, 1H), 7.39 (d, J=6.1 Hz, 1H), 7.37 (s, 1H), 6.99 (dd, J=8.8, 2.4 Hz, 1H), 6.84 (dd, J=5.3, 1.4 Hz, 1H), 6.68 (d, J=0.8 Hz, 1H), 4.97-4.92 (m, 1H), 4.86-4.80 (m, 1H), 4.15 (s, 1H), 4.05-3.97 (m, 1H), 3.68 (s, 3H), 3.27 (d, J=9.7 Hz, 1H), 3.01 (d, J=9.8 Hz, 1H), 2.02-1.95 (m, 1H), 1.50-1.42 (m, 1H).

Example 50: (1R,2S,3S,4R,5S)—N-(3,4-dichlorophenyl)-5-hydroxy-3-(6-(trifluoromethyl)pyridin-2-yl)-7-oxabicyclo[2.2.1]heptane-2-carboxamide

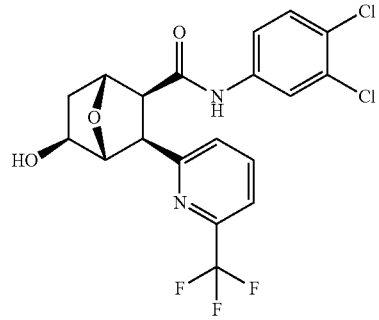 [SMILES: O=C(Nc1ccc(Cl)c(Cl)c1)[C@H]1[C@@H](c2cccc(C(F)(F)F)n2)[C@H]2O[C@@H]1C[C@@H]2O]

LC-MS: Rt=1.57 min; MS m/z [M+H]$^+$ 447.0. Mixture of alcohol regioisomers.

Example 51: (1R,2S,3S,4R,5S)—N-(3,4-dichlorophenyl)-5-hydroxy-3-(pyrimidin-5-yl)-7-oxabicyclo[2.2.1]heptane-2-carboxamide

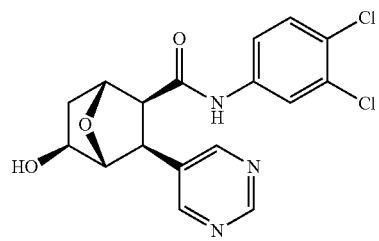 [SMILES: O=C(Nc1ccc(Cl)c(Cl)c1)[C@H]1[C@@H](c2cncnc2)[C@H]2O[C@@H]1C[C@@H]2O]

LC-MS: Rt=1.26 min; MS m/z [M+H]+ 380.0. ¹H NMR (400 MHz, DMSO-d₆) δ 9.86 (s, 1H), 8.82 (s, 1H), 8.62 (s, 2H), 7.40 (d, J=4.5 Hz, 1H), 7.39 (d, J=1.9 Hz, 1H), 6.99 (dd, J=8.8, 2.4 Hz, 1H), 5.03-4.99 (m, 1H), 4.86-4.82 (m, 1H), 4.28 (s, 1H), 4.07-4.02 (m, 1H), 3.38 (d, J=9.7 Hz, 1H), 3.05 (d, J=9.7 Hz, 1H), 2.07-2.00 (m, 1H), 1.52-1.44 (m, 1H). ~3:1 mixture of alcohol regioisomers.

Example 52: rac-(1R,2S,3S,4R,5S)—N-(3,4-dichlorophenyl)-3-(2-fluoropyridin-4-yl)-5-hydroxy-7-oxabicyclo[2.2.1]heptane-2-carboxamide LC-MS: Rt=1.39 min; MS m/z [M+H]+ 397.0. ¹H NMR (400 MHz, DMSO-d₆) δ 9.74 (s, 1H), 7.95 (d, J=5.2 Hz, 1H), 7.44 (d, J=2.4 Hz, 1H), 7.40 (d, J=8.8 Hz, 1H), 7.21-7.18 (m, 1H), 7.01 (dd, J=8.8, 2.5 Hz, 1H), 6.96 (s, 1H), 5.00-4.97 (m, 1H), 4.87-4.83 (m, 1H), 4.21 (s, 1H), 4.05-4.00 (m, 1H), 3.41 (d, J=9.8 Hz, 1H), 3.07 (d, J=9.8 Hz, 1H), 2.05-1.97 (m, 1H), 1.52-1.44 (m, 1H). ~3:1 mixture of alcohol regioisomers.

Examples 52a and 52b (Corresponding to Peak 1 and Peak 2)

(1R,2S,3S,4R,5S)—N-(3,4-dichlorophenyl)-3-(2-fluoropyridin-4-yl)-5-hydroxy-7-oxabicyclo[2.2.1]heptane-2-carboxamide or (1S,2R,3R,4S,5R)—N-(3,4-dichlorophenyl)-3-(2-fluoropyridin-4-yl)-5-hydroxy-7-oxabicyclo[2.2.1]heptane-2-carboxamide

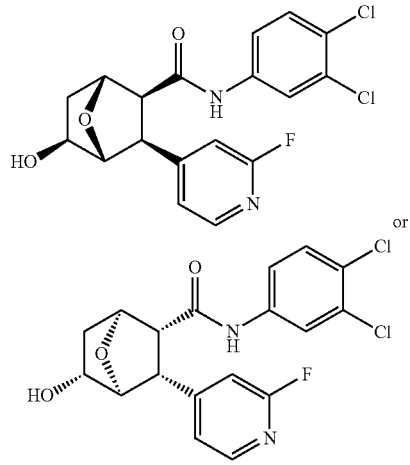

Chiral separation of rac-(1R,2S,3S,4R,5S)—N-(3,4-dichlorophenyl)-3-(2-fluoropyridin-4-yl)-5-hydroxy-7-oxabicyclo[2.2.1]heptane-2-carboxamide (Example 52) by Supercritical Fluid Chromatography using the following conditions afforded the compounds listed hereafter:
Method Details:
Column: 21×250 mm IF @ 30° C.
Mobile Phase: 95-50% CO₂/5-50% MeOH+0.5% isopropylamine in 5 minutes
Detection: UV @ 220 nm
Flow: 2 mL/min
Peak 1: SFC Retention Time=3.15 min. LC-MS: Rt=1.30 min; MS m/z [M+H]+ 397.0. ¹H NMR (400 MHz, DMSO-d₆) δ 9.75 (s, 1H), 7.95 (d, J=5.2 Hz, 1H), 7.44 (d, J=2.4 Hz, 1H), 7.40 (d, J=8.8 Hz, 1H), 7.20 (d, J=4.9 Hz, 1H), 7.01 (dd, J=8.8, 2.4 Hz, 1H), 6.96 (s, 1H), 5.04-4.95 (m, 1H), 4.89-4.82 (m, 1H), 4.21 (s, 1H), 4.05-4.00 (m, 1H), 3.41 (d, J=9.7 Hz, 1H), 3.07 (d, J=9.9 Hz, 1H), 2.05-1.96 (m, 1H), 1.52-1.44 (m, 1H).

Peak 2: SFC Retention Time=4.12 min. LC-MS: Rt=1.30 min; MS m/z [M+H]+ 397.0. ¹H NMR (400 MHz, DMSO-d₆) δ 9.75 (s, 1H), 7.95 (d, J=5.2 Hz, 1H), 7.44 (d, J=2.4 Hz, 1H), 7.40 (d, J=8.8 Hz, 1H), 7.20 (d, J=4.9 Hz, 1H), 7.01 (dd, J=8.8, 2.4 Hz, 1H), 6.96 (s, 1H), 5.04-4.95 (m, 1H), 4.89-4.82 (m, 1H), 4.21 (s, 1H), 4.05-4.00 (m, 1H), 3.41 (d, J=9.7 Hz, 1H), 3.07 (d, J=9.9 Hz, 1H), 2.05-1.96 (m, 1H), 1.52-1.44 (m, 1H).

Example 53: rac-(1R,2S,3S,4R,5S)—N-(3,4-dichlorophenyl)-5-hydroxy-3-(2-methylpyridin-4-yl)-7-oxabicyclo[2.2.1]heptane-2-carboxamide LC-MS: Rt=1.18 min; MS m/z [M+H]+ 393.0. ~3:1 mixture of alcohol regioisomers.

Examples 53a and 53b (Corresponding to Peak 1 and Peak 2)

(1R,2S,3S,4R,5S)—N-(3,4-dichlorophenyl)-5-hydroxy-3-(2-methylpyridin-4-yl)-7-oxabicyclo[2.2.1]heptane-2-carboxamide or (1S,2R,3R,4S,5R)—N-(3,4-dichlorophenyl)-5-hydroxy-3-(2-methylpyridin-4-yl)-7-oxabicyclo[2.2.1]heptane-2-carboxamide

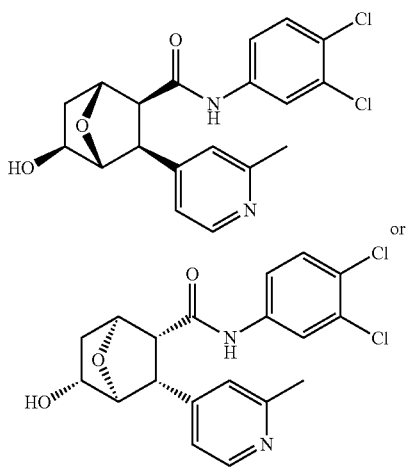

Chiral separation of rac-(1R,2S,3S,4R,5S)—N-(3,4-dichlorophenyl)-5-hydroxy-3-(2-methylpyridin-4-yl)-7-oxabicyclo[2.2.1]heptane-2-carboxamide (Example 53) by Supercritical Fluid Chromatography using the following conditions afforded the compounds listed hereafter:
Method Details:
Column: 21×250 mm IC @ 30° C.
Mobile Phase: 80% CO₂/20% MeOH+0.5% isopropylamine
Detection: UV @ 220 nm
Flow: 2 mL/min
Peak 1: SFC Retention Time=2.14 min. LC-MS: Rt=1.10 min; MS m/z [M+H]+ 393.1. ¹H NMR (400 MHz, DMSO-d₆) δ 9.59 (s, 1H), 8.11 (dd, J=5.1, 0.8 Hz, 1H), 7.40-7.36 (m, 2H), 7.11 (s, 1H), 7.03-7.00 (m, 1H), 6.98 (dd, J=8.8, 2.4 Hz, 1H), 4.98-4.91 (m, 1H), 4.86-4.80 (m, 1H), 4.17 (s, 1H), 4.04-3.99 (m, 1H), 3.25 (d, J=9.7 Hz, 1H), 3.02 (d, J=9.7 Hz, 1H), 2.26 (s, 3H), 2.04-1.95 (m, 1H), 1.50-1.42 (m, 1H).

Peak 2: SFC Retention Time=2.79 min. LC-MS: Rt=1.10 min; MS m/z [M+H]⁺ 393.1. ¹H NMR (400 MHz, DMSO-d₆) δ 9.59 (s, 1H), 8.11 (dd, J=5.1, 0.8 Hz, 1H), 7.40-7.36 (m, 2H), 7.11 (s, 1H), 7.03-7.00 (m, 1H), 6.98 (dd, J=8.8, 2.4 Hz, 1H), 4.98-4.91 (m, 1H), 4.86-4.80 (m, 1H), 4.17 (s, 1H), 4.04-3.99 (m, 1H), 3.25 (d, J=9.7 Hz, 1H), 3.02 (d, J=9.7 Hz, 1H), 2.26 (s, 3H), 2.04-1.95 (m, 1H), 1.50-1.42 (m, 1H).

Example 54: rac-(1R,2S,3S,4R,5S)—N-(3,4-dichlorophenyl)-5-hydroxy-3-(2-(trifluoromethyl)pyridin-4-yl)-7-oxabicyclo[2.2.1]heptane-2-carboxamide LC-MS: Rt=1.48 min; MS m/z [M+H]⁺ 447.0. ¹H NMR (500 MHz, DMSO-d₆) δ 9.70 (s, 1H), 8.47 (d, J=5.0 Hz, 1H), 7.73 (s, 1H), 7.52 (dd, J=5.1, 1.5 Hz, 1H), 7.37-7.33 (m, 2H), 6.96 (dd, J=8.8, 2.4 Hz, 1H), 4.99-4.97 (m, 1H), 4.89-4.86 (m, 1H), 4.26 (s, 1H), 4.07-4.03 (m, 1H), 3.49 (d, J=9.7 Hz, 1H), 3.10 (d, J=9.9 Hz, 1H), 2.06-2.00 (m, 1H), 1.52-1.46 (m, 1H). ~3:1 mixture of alcohol regioisomers.

Examples 54a and 54b (Corresponding to Peak 1 and Peak 2)

(1R,2S,3S,4R,5S)—N-(3,4-dichlorophenyl)-5-hydroxy-3-(2-(trifluoromethyl)pyridin-4-yl)-7-oxabicyclo[2.2.1]heptane-2-carboxamide or (1S,2R,3R,4S,5R)—N-(3,4-dichlorophenyl)-5-hydroxy-3-(2-(trifluoromethyl)pyridin-4-yl)-7-oxabicyclo[2.2.1]heptane-2-carboxamide

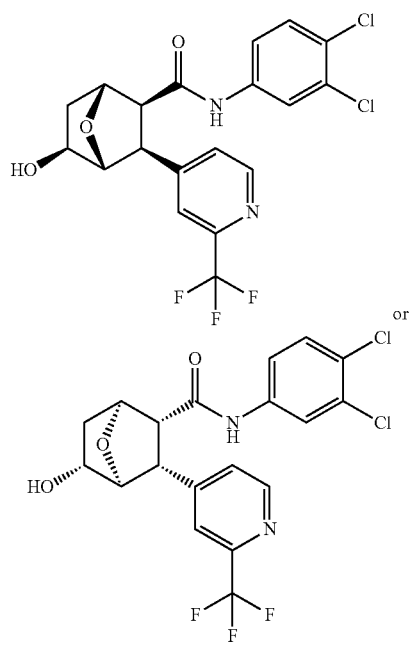

Chiral separation of rac-(1R,2S,3S,4R,5S)—N-(3,4-dichlorophenyl)-5-hydroxy-3-(2-(trifluoromethyl)pyridin-4-yl)-7-oxabicyclo[2.2.1]heptane-2-carboxamide (Example 54) by Supercritical Fluid Chromatography using the following conditions afforded the compounds listed hereafter:
Method Details:
Column: 21×250 mm AD @ 30° C.
Mobile Phase: 80% CO₂/20% MeOH+0.5% isopropylamine
Detection: UV @ 220 nm
Flow: 2 mL/min
Peak 1: SFC Retention Time=0.80 min. LC-MS: Rt=1.42 min; MS m/z [M+H]⁺ 447.0. ¹H NMR (400 MHz, DMSO-d₆) δ 9.73 (s, 1H), 8.47 (d, J=5.0 Hz, 1H), 7.73 (s, 1H), 7.52 (dd, J=5.1, 1.6 Hz, 1H), 7.38-7.34 (m, 2H), 6.96 (dd, J=8.8, 2.4 Hz, 1H), 5.04-4.96 (m, 1H), 4.90-4.84 (m, 1H), 4.25 (s, 1H), 4.07-4.00 (m, 1H), 3.49 (d, J=9.8 Hz, 1H), 3.10 (d, J=9.8 Hz, 1H), 2.06-1.99 (m, 1H), 1.54-1.45 (m, 1H).
Peak 2: SFC Retention Time=1.28 min. LC-MS: Rt=1.42 min; MS m/z [M+H]⁺ 447.0. ¹H NMR (400 MHz, DMSO-d₆) δ 9.73 (s, 1H), 8.47 (d, J=5.0 Hz, 1H), 7.73 (s, 1H), 7.52 (dd, J=5.1, 1.6 Hz, 1H), 7.38-7.34 (m, 2H), 6.96 (dd, J=8.8, 2.4 Hz, 1H), 5.04-4.96 (m, 1H), 4.90-4.84 (m, 1H), 4.25 (s, 1H), 4.07-4.00 (m, 1H), 3.49 (d, J=9.8 Hz, 1H), 3.10 (d, J=9.8 Hz, 1H), 2.06-1.99 (m, 1H), 1.54-1.45 (m, 1H).

Example 55: (1R,2S,3S,4R,5S)—N-(3,4-dichlorophenyl)-3-(2-(dimethylamino)pyrimidin-5-yl)-5-hydroxy-7-oxabicyclo[2.2.1]heptane-2-carboxamide

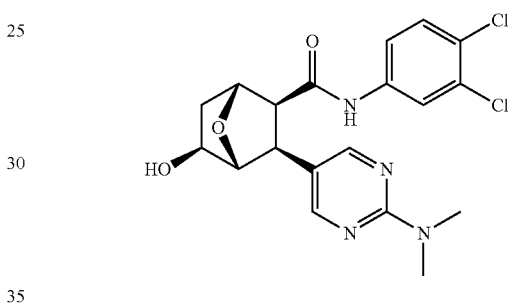

LC-MS: Rt=1.28 min; MS m/z [M+H]⁺ 423.0. ¹H NMR (500 MHz, DMSO-d₆) δ 9.71 (s, 1H), 8.15 (s, 2H), 7.40 (d, J=8.8 Hz, 1H), 7.35 (d, J=2.4 Hz, 1H), 7.03 (dd, J=8.9, 2.4 Hz, 1H), 4.93-4.89 (m, 1H), 4.80-4.77 (m, 1H), 4.15 (s, 1H), 4.02-3.97 (m, 1H), 3.16 (d, J=9.5 Hz, 1H), 2.93 (s, 6H), 2.91 (d, J=9.5 Hz, 1H), 2.01-1.96 (m, 1H), 1.46-1.40 (m, 1H). ~3:1 mixture of alcohol regioisomers.

Example 56: (1R,2S,3S,4R,5S)—N-(3,4-dichlorophenyl)-5-hydroxy-3-(2-methylpyrimidin-5-yl)-7-oxabicyclo[2.2.1]heptane-2-carboxamide

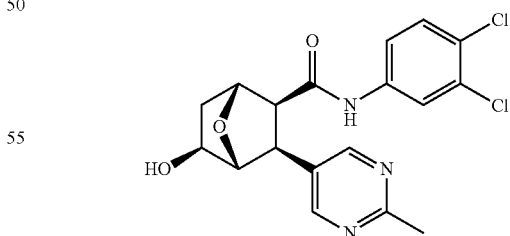

LC-MS: Rt=1.20 min; MS m/z [M+H]⁺ 394.0. ¹H NMR (400 MHz, DMSO-d₆) δ 9.81 (s, 1H), 8.49 (s, 2H), 7.41 (d, J=8.8 Hz, 1H), 7.29 (d, J=2.4 Hz, 1H), 6.96 (dd, J=8.8, 2.4 Hz, 1H), 4.85-4.79 (m, 1H), 4.59-4.53 (m, 1H), 4.24 (s, 1H), 4.06-4.01 (m, 1H), 3.33 (d, J=9.6 Hz, 1H), 3.01 (d, J=9.7 Hz, 1H), 2.38 (s, 3H), 2.05-1.98 (m, 1H), 1.50-1.43 (m, 1H). ~3:1 mixture of alcohol regioisomers.

Example 57: (1R,2S,3S,4R,5S)-3-(2-aminopyridin-4-yl)-N-(3,4-dichlorophenyl)-5-hydroxy-7-oxabicyclo[2.2.1]heptane-2-carboxamide

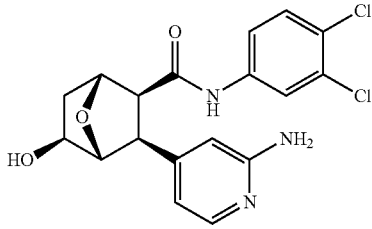 [SMILES: Nc1cc([C@H]2[C@H]3O[C@H](C[C@@H]3O)[C@H]2C(=O)Nc2ccc(Cl)c(Cl)c2)ccn1]

LC-MS: Rt=1.10 min; MS m/z [M+H]+ 394.0. $^1$H NMR (400 MHz, DMSO-d$_6$) δ 9.73 (s, 1H), 7.61 (d, J=6.3 Hz, 1H), 7.55 (d, J=2.4 Hz, 1H), 7.41 (d, J=8.8 Hz, 1H), 7.08 (dd, J=8.8, 2.4 Hz, 1H), 6.86 (s, 2H), 6.64 (s, 1H), 6.58-6.55 (m, 1H), 4.98-4.95 (m, 1H), 4.85-4.82 (m, 1H), 4.16 (s, 1H), 4.03-3.99 (m, 1H), 3.21 (d, J=9.9 Hz, 1H), 3.04 (d, J=9.8 Hz, 1H), 2.01-1.96 (m, 1H), 1.49-1.43 (m, 1H). ~3:1 mixture of alcohol regioisomers.

Example 58: (1R,2S,3S,4R,5S)—N-(3,4-dichlorophenyl)-3-(2,5-difluoropyridin-4-yl)-5-hydroxy-7-oxabicyclo[2.2.1]heptane-2-carboxamide

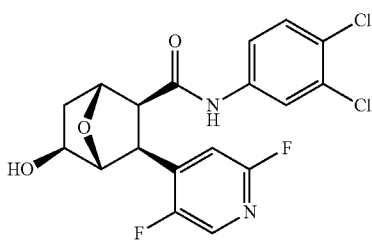 [SMILES: O=C(Nc1ccc(Cl)c(Cl)c1)[C@H]1[C@@H](c2cc(F)ncc2F)[C@H]2O[C@@H]1C[C@@H]2O]

LC-MS: Rt=1.38 min; MS m/z [M+H]+ 415.0. $^1$H NMR (400 MHz, DMSO-d$_6$) δ 9.98 (s, 1H), 7.99 (d, J=1.3 Hz, 1H), 7.46-7.41 (m, 2H), 7.10-7.05 (m, 2H), 5.06-5.01 (m, 1H), 4.85-4.81 (m, 1H), 4.37 (s, 1H), 4.10-4.03 (m, 1H), 3.63 (d, J=10.0 Hz, 1H), 3.11 (d, J=9.7 Hz, 1H), 2.06-1.99 (m, 1H), 1.52-1.46 (m, 1H). ~2:1 mixture of alcohol regioisomers.

Example 59: (1R,2S,3S,4R,5S)—N-(3,4-dichlorophenyl)-3-(2,3-difluoropyridin-4-yl)-5-hydroxy-7-oxabicyclo[2.2.1]heptane-2-carboxamide

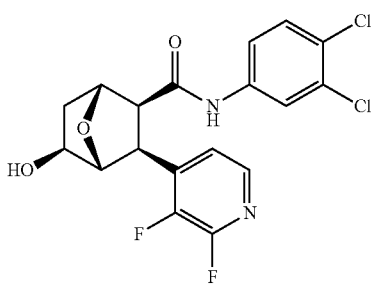 [SMILES: O=C(Nc1ccc(Cl)c(Cl)c1)[C@H]1[C@@H](c2ccnc(F)c2F)[C@H]2O[C@@H]1C[C@@H]2O]

LC-MS: Rt=1.40 min; MS m/z [M+H]+ 415.0. $^1$H NMR (400 MHz, DMSO-d$_6$) δ 9.92 (s, 1H), 7.84 (d, J=5.2 Hz, 1H), 7.45-7.40 (m, 2H), 7.34 (t, J=4.9 Hz, 1H), 7.04 (dd, J=8.8, 2.5 Hz, 1H), 5.04-5.01 (m, 1H), 4.88-4.83 (m, 1H), 4.30 (s, 1H), 4.10-4.05 (m, 1H), 3.70 (d, J=10.0 Hz, 1H), 3.12 (d, J=9.7 Hz, 1H), 2.08-2.00 (m, 1H), 1.53-1.46 (m, 1H). ~2:1 mixture of alcohol regioisomers.

Example 60: (1R,2S,3S,4R,5S)-3-(2-aminopyrimidin-5-yl)-N-(3,4-dichlorophenyl)-5-hydroxy-7-oxabicyclo[2.2.1]heptane-2-carboxamide

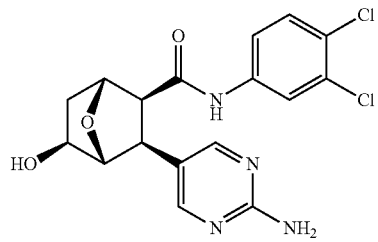 [SMILES: Nc1ncc([C@H]2[C@H]3O[C@H](C[C@@H]3O)[C@H]2C(=O)Nc2ccc(Cl)c(Cl)c2)cn1]

LC-MS: Rt=1.11 min; MS m/z [M+H]+ 395.0. $^1$H NMR (500 MHz, DMSO-d$_6$) δ 9.74 (s, 1H), 8.06 (s, 2H), 7.50 (d, J=2.4 Hz, 1H), 7.41 (d, J=8.8 Hz, 1H), 7.09-7.06 (m, 1H), 6.25 (s, 2H), 4.92-4.89 (m, 1H), 4.81-4.76 (m, 1H), 4.12 (s, 1H), 4.01-3.97 (m, 1H), 3.13 (d, J=9.6 Hz, 1H), 2.91 (d, J=9.8 Hz, 1H), 2.00-1.94 (m, 1H), 1.46-1.40 (m, 1H). ~3:1 mixture of alcohol regioisomers.

Example 61: (1R,2S,3S,4R,5S)—N-(3,4-dichlorophenyl)-3-(2-fluoropyrimidin-5-yl)-5-hydroxy-7-oxabicyclo[2.2.1]heptane-2-carboxamide

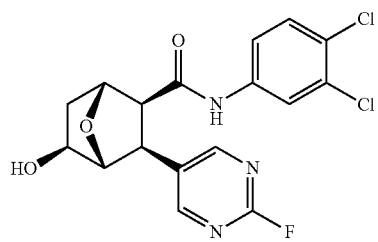 [SMILES: O=C(Nc1ccc(Cl)c(Cl)c1)[C@H]1[C@@H](c2cnc(F)nc2)[C@H]2O[C@@H]1C[C@@H]2O]

LC-MS: Rt=1.33 min; MS m/z [M+H]+ 398.0. $^1$H NMR (500 MHz, DMSO-d$_6$) δ 9.91 (s, 1H), 8.57 (d, J=1.5 Hz, 2H), 7.42-7.41 (m, 2H), 7.03 (dd, J=8.8, 2.5 Hz, 1H), 5.02-4.98 (m, 1H), 4.86-4.82 (m, 1H), 4.30 (s, 1H), 4.06-4.02 (m, 1H), 3.47 (d, J=9.6 Hz, 1H), 3.05 (d, J=9.7 Hz, 1H), 2.07-2.01 (m, 1H), 1.52-1.46 (m, 1H). ~2:1 mixture of alcohol regioisomers.

Example 62: (1R,2S,3S,4R,5S)—N-(3,4-dichlorophenyl)-5-hydroxy-3-(2-(trifluoromethyl)pyrimidin-5-yl)-7-oxabicyclo[2.2.1]heptane-2-carboxamide

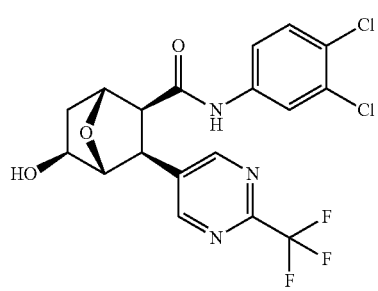 [SMILES: O=C(Nc1ccc(Cl)c(Cl)c1)[C@H]1[C@@H](c2cnc(C(F)(F)F)nc2)[C@H]2O[C@@H]1C[C@@H]2O]

LC-MS: Rt=1.03 min; MS m/z [M+H]+ 448.1. $^1$H NMR (500 MHz, DMSO-$d_6$) δ 9.90 (s, 1H), 8.83 (s, 2H), 7.38 (d, J=8.8 Hz, 1H), 7.28 (d, J=2.4 Hz, 1H), 6.94 (dd, J=8.8, 2.5 Hz, 1H), 5.08-5.03 (m, 1H), 4.89-4.85 (m, 1H), 4.41 (s, 1H), 4.09-4.05 (m, 1H), 3.53 (d, J=9.6 Hz, 1H), 3.11 (d, J=9.6 Hz, 1H), 2.09-2.03 (m, 1H), 1.56-1.47 (m, 1H). ~3:1 mixture of alcohol regioisomers.

Example 63: (1R,2S,3S,4R,5S)—N-(3,4-dichlorophenyl)-5-methoxy-3-(2-methylpyridin-4-yl)-7-oxabicyclo[2.2.1]heptane-2-carboxamide

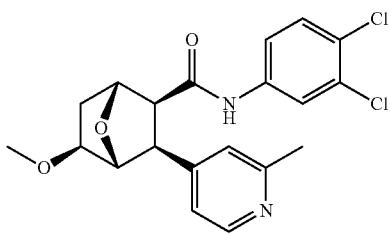 [SMILES: CO[C@H]1C[C@H]2O[C@@H]1[C@H](c1ccnc(C)c1)[C@@H]2C(=O)Nc1ccc(Cl)c(Cl)c1]

Example 63 described was synthesized according to the protocol described for Example 47 using methyl (1R,4S,5S)-3-bromo-5-methoxy-7-oxabicyclo[2.2.1]hept-2-ene-2-carboxylate and methyl (1S,4S,6R)-3-bromo-6-methoxy-7-oxabicyclo[2.2.1]hept-2-ene-2-carboxylate (Intermediate 1f) and 3,4-dichloroaniline in Step A and (2-methylpyridin-4-yl)boronic acid in Step C. LC-MS: Rt=1.23 min; MS m/z [M+H]+ 407.0. $^1$H NMR (500 MHz, DMSO-$d_6$) δ 9.61 (s, 1H), 8.11 (d, J=5.1 Hz, 1H), 7.39-7.36 (m, 2H), 7.12 (s, 1H), 7.03 (d, J=5.4 Hz, 1H), 6.99 (dd, J=8.9, 2.5 Hz, 1H), 4.86-4.81 (m, 1H), 4.48 (s, 1H), 3.76-3.72 (m, 1H), 3.28-3.24 (m, 1H), 3.21 (s, 3H), 3.06 (d, J=9.5 Hz, 1H), 2.27 (s, 3H), 2.03-1.97 (m, 1H), 1.54-1.48 (m, 1H). ~4:1 mixture of methoxy regioisomers.

Example 64: (1R,2S,3S,4R,5R)—N-(3,4-dichlorophenyl)-5-fluoro-3-(6-methylpyridin-3-yl)-7-oxabicyclo[2.2.1]heptane-2-carboxamide

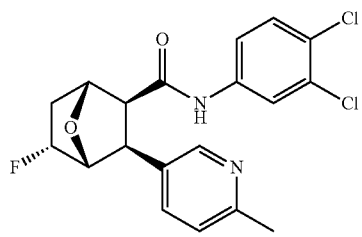 [SMILES: Cc1ccc([C@H]2[C@H]3O[C@H](C[C@H]3F)[C@H]2C(=O)Nc2ccc(Cl)c(Cl)c2)cn1]

Title compound was prepared from (1R,2S,3S,4R,5S)—N-(3,4-dichlorophenyl)-5-hydroxy-3-(6-methylpyridin-3-yl)-7-oxabicyclo[2.2.1]heptane-2-carboxamide (intermediate 4a, Example 48) using Step A as in Scheme 4.

Step A: To a stirring solution of (1R,2S,3S,4R,5S)—N-(3,4-dichlorophenyl)-5-hydroxy-3-(6-methylpyridin-3-yl)-7-oxabicyclo[2.2.1]heptane-2-carboxamide (25 mg, 0.064 mmol) in DCM (1 mL) at room temperature was added Xtalfluor-E (36 mg, 0.16 mmol) and Et$_3$N-3HF (0.031 mL, 0.19 mmol) and the reaction was stirred for 16 h. The reaction was cooled to 0° C. and was quenched with saturated aqueous sodium bicarbonate solution. The crude compound was extracted with DCM 3×. The combined organic layer was dried over anhydrous sodium sulfate, filtered, and concentrated. The crude compound was purified by silica column chromatography to afford (1R,2S,3S,4R,5R)—N-(3,4-dichlorophenyl)-5-fluoro-3-(6-methylpyridin-3-yl)-7-oxabicyclo[2.2.1]heptane-2-carboxamide as an unknown mixture of fluorine regioisomers. LC-MS: Rt=1.38 min; MS m/z [M+H]+ 395.0.

Example 65: (1R,2S,3S,4R,5R)—N-(3,4-dichlorophenyl)-5-fluoro-3-(2-methoxypyridin-4-yl)-7-oxabicyclo[2.2.1]heptane-2-carboxamide

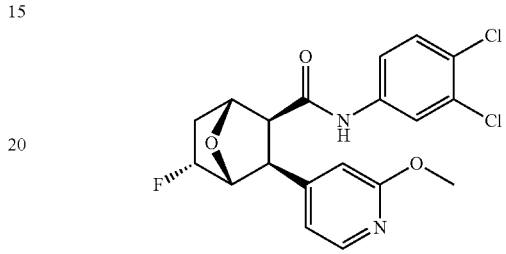

Example 65 was synthesized according to the protocol described for Example 64 using (1R,2S,3S,4R,5S)—N-(3,4-dichlorophenyl)-5-hydroxy-3-(2-methoxypyridin-4-yl)-7-oxabicyclo[2.2.1]heptane-2-carboxamide (Intermediate 4a, Example 49) in Step A. LC-MS: Rt=1.53 min; MS m/z [M+H]+ 411.0. $^1$H NMR (500 MHz, DMSO-$d_6$) δ 10.13 (s, 1H), 7.97-7.94 (m, 1H), 7.77 (d, J=2.5 Hz, 1H), 7.49 (d, J=8.8 Hz, 1H), 7.29 (dd, J=8.8, 2.5 Hz, 1H), 6.69 (dd, J=5.5, 1.5 Hz, 1H), 6.58 (s, 1H), 5.64 (d, J=72.4 Hz, 1H), 4.85-4.80 (m, 1H), 3.79 (s, 3H), 3.70-3.66 (m, 1H), 3.46-3.42 (m, 1H), 3.16-3.13 (m, 1H), 1.99-1.95 (m, 1H), 1.79-1.75 (m, 1H). ~4:1 mixture of fluorine regioisomers.

Example 66: (1S,2S,4R,5R,6R,7S)—N-(4-chloro-3-cyanophenyl)-7-(2-methylpyridin-4-yl)-8-oxatricyclo[3.2.1.0$^{2,4}$]octane-6-carboxamide

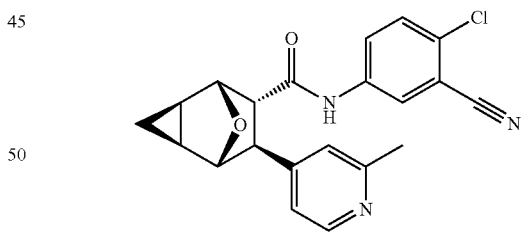

Title compound was prepared from methyl (1S,2S,4R,5R)-7-bromo-8-oxatricyclo[3.2.1.0$^{2,4}$]oct-6-ene-6-carboxylate (Intermediate 1d) using Steps A-B and Step D as in Scheme 2.

Step A: To a stirring solution of methyl (1S,2S,4R,5R)-7-bromo-8-oxatricyclo[3.2.1.0$^{2,4}$]oct-6-ene-6-carboxylate (1d, 4.70 g, 19.2 mmol) in THF (25 mL) and water (6 mL) at 0° C. was added acetic acid (4.40 mL) and portion-wise Zn powder (5.00 g, 77.0 mmol). The reaction slurry was stirred to room temperature for 15 minutes. The reaction was filtered and neutralized with saturated aqueous sodium bicarbonate to pH ~7. The compound was extracted with ethyl acetate. The organic layer was washed with water and brine and dried over anhydrous sodium sulfate. The solvent was concentrated and dried under vacuo. The crude compound (1S,2S,4R,5R)-methyl 8-oxatricyclo[3.2.1.0²,⁴]oct-6-ene-6-carboxylate was used in the next step without further purification. LC-MS: Rt=1.16 min; MS m/z [M+H]⁺ 167.1.

Step B: A mixture of (1S,2S,4R,5R)-methyl 8-oxatricyclo[3.2.1.02,4]oct-6-ene-6-carboxylate (800 mg, 4.81 mmol), 2-methyl-4-(4,4,5,5-tetramethyl-1,3,2-dioxaborolan-2-yl)pyridine (1.27 g, 5.78 mmol), 2,2-bis(diphenylphosphino)-1,1-binapthalene (300 mg, 0.481 mmol), chloro(1,5-cyclooctadiene)rhodium(I) dimer (119 mg, 0.241 mol) and potassium carbonate (332 mg, 2.41 mmol) in 1,4-dioxane (10 mL) and water (2.5 mL) was heated at 100° C. for 1 h in the microwave. Celite was added to the reaction mixture and the solvent was removed under reduced pressure. The compound was purified by FCC to afford (1S,2S,4R,5R,6S,7S)-methyl 7-(2-methylpyridin-4-yl)-8-oxatricyclo[3.2.1.0²,⁴]octane-6-carboxylate (cis) and (1S,2S,4R,5R,6R,7S)-methyl 7-(2-methylpyridin-4-yl)-8-oxatricyclo[3.2.1.02,4]octane-6-carboxylate (trans). cis LC-MS: Rt=0.88 min; MS m/z [M+H]⁺ 260.1. trans LC-MS: Rt=0.96 min; MS m/z [M+H]⁺ 260.1.

Step C: To a stirring solution of (1S,2S,4R,5R,6R,7S)-methyl 7-(2-methylpyridin-4-yl)-8-oxatricyclo[3.2.1.0²,⁴]octane-6-carboxylate (75.0 mg, 0.289 mmol) and 5-amino-2-chlorobenzonitrile (44.0 mg, 0.289 mmol) in THF (2 mL) at 0° C. was added LiHMDS (1 M, 0.434 mL, 0.434 mmol). The reaction was stirred at room temperature for 1 h. LiHMDS (1 M, 0.434 mL, 0.434 mmol) was added and the reaction was continued stirring at room temperature for 4 h. Celite was added and the solvent was concentrated. The crude compound was purified by FCC to afford the title compound (1S,2S,4R,5R,6R,7S)—N-(4-chloro-3-cyanophenyl)-7-(2-methylpyridin-4-yl)-8-oxatricyclo[3.2.1.0²,⁴]octane-6-carboxamide. Method B LC-MS: Rt=1.11 min; MS m/z [M+H]⁺ 380.1. ¹H NMR (400 MHz, DMSO-d₆) δ 10.42 (s, 1H), 8.33 (d, J=5.1 Hz, 1H), 8.22 (d, J=2.5 Hz, 1H), 7.77 (dd, J=8.9, 2.5 Hz, 1H), 7.69 (d, J=8.9 Hz, 1H), 7.11 (s, 1H), 7.05 (d, J=4.0 Hz, 1H), 4.76 (d, J=4.9 Hz, 1H), 4.39 (s, 1H), 3.51 (d, J=4.8 Hz, 1H), 3.09 (t, J=4.8 Hz, 1H), 2.42 (s, 3H), 1.34-1.28 (m, 1H), 1.20-1.15 (m, 1H), 0.43-0.39 (m, 1H), 0.21-0.15 (m, 1H).

Examples 67-76 described infra were synthesized according to the protocol described for Example 66 using methyl (1S,2S,4R,5R)-7-bromo-8-oxatricyclo[3.2.1.0²,⁴]oct-6-ene-6-carboxylate (Intermediate 1d) and various boronic acids/esters in Step B and various anilines in Step D.

Example 67: (1S,2S,4R,5R,6R,7S)—N-(4-chloro-2-cyanophenyl)-7-(2-methylpyridin-4-yl)-8-oxatricyclo[3.2.1.0²,⁴]octane-6-carboxamide

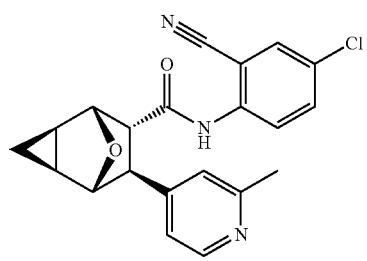 [SMILES: Cc1cc([C@H]2[C@H]3O[C@H]([C@@H]4C[C@@H]43)[C@@H]2C(=O)Nc2ccc(Cl)cc2C#N)ccn1]

Method B LC-MS: Rt=1.04 min; MS m/z [M+H]⁺ 380.1. ¹H NMR (400 MHz, DMSO-d₆) δ 10.36 (s, 1H), 8.34 (d, J=5.1 Hz, 1H), 8.04 (d, J=2.5 Hz, 1H), 7.77 (dd, J=8.8, 2.5 Hz, 1H), 7.52 (d, J=8.8 Hz, 1H), 7.12 (s, 1H), 7.06 (dd, J=5.1, 1.3 Hz, 1H), 4.77 (d, J=4.9 Hz, 1H), 4.39 (s, 1H), 3.50 (d, J=4.8 Hz, 1H), 3.14 (t, J=4.9 Hz, 1H), 2.43 (s, 3H), 1.42-1.37 (m, 1H), 1.33-1.27 (m, 1H), 0.45-0.40 (m, 1H), 0.21-0.17 (m, 1H).

Example 68: (1S,2S,4R,5R,6R,7S)—N-(4-chloro-3-fluorophenyl)-7-(2-methylpyridin-4-yl)-8-oxatricyclo[3.2.1.0²,⁴]octane-6-carboxamide

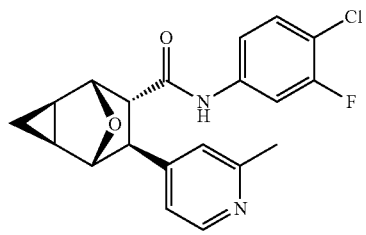 [SMILES: Cc1cc([C@H]2[C@H]3O[C@H]([C@@H]4C[C@@H]43)[C@@H]2C(=O)Nc2ccc(Cl)c(F)c2)ccn1]

Method C LC-MS: Rt=1.47 min; MS m/z [M+H]⁺ 373.1. ¹H NMR (400 MHz, DMSO-d₆) δ 10.30 (s, 1H), 8.38 (d, J=5.2 Hz, 1H), 7.80 (dd, J=12.0, 2.3 Hz, 1H), 7.52 (t, J=8.7 Hz, 1H), 7.31-7.28 (m, 1H), 7.19 (s, 1H), 7.12 (d, J=4.9 Hz, 1H), 4.76 (d, J=4.9 Hz, 1H), 4.39 (s, 1H), 3.54 (d, J=4.8 Hz, 1H), 3.09 (t, J=4.8 Hz, 1H), 2.45 (s, 3H), 1.33-1.28 (m, 1H), 1.18-1.13 (m, 1H), 0.43-0.39 (m, 1H), 0.21-0.15 (m, 1H).

Example 69: (1S,2S,4R,5R,6R,7S)-7-(2-methylpyridin-4-yl)-N-(3-(trifluoromethoxy)phenyl)-8-oxatricyclo[3.2.1.0²,⁴]octane-6-carboxamide

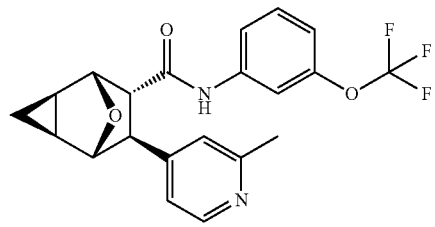 [SMILES: Cc1cc([C@H]2[C@H]3O[C@H]([C@@H]4C[C@@H]43)[C@@H]2C(=O)Nc2cccc(OC(F)(F)F)c2)ccn1]

LC-MS: Rt=1.47 min; MS m/z [M+H]⁺ 405.1. ¹H NMR (400 MHz, DMSO-d₆) δ 10.26 (s, 1H), 8.34 (d, J=5.1 Hz, 1H), 7.80 (s, 1H), 7.46-7.41 (m, 2H), 7.12 (s, 1H), 7.08-7.01 (m, 2H), 4.76 (d, J=4.9 Hz, 1H), 4.38 (s, 1H), 3.51 (d, J=4.8 Hz, 1H), 3.09 (t, J=4.8 Hz, 1H), 2.42 (s, 3H), 1.35-1.29 (m, 1H), 1.19-1.13 (m, 1H), 0.43-0.37 (m, 1H), 0.22-0.16 (m, 1H).

Example 70: (1S,2S,4R,5R,6R,7S)-7-(2-methylpyridin-4-yl)-N-(5-methylthiazol-2-yl)-8-oxatricyclo[3.2.1.0²,⁴]octane-6-carboxamide

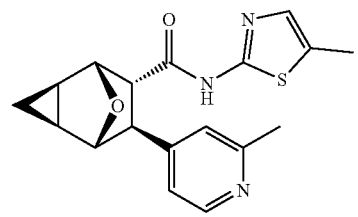 [SMILES: Cc1cc([C@H]2[C@H]3O[C@H]([C@@H]4C[C@@H]43)[C@@H]2C(=O)Nc2ncc(C)s2)ccn1]

LC-MS: Rt=1.20 min; MS m/z [M+H]+ 342.1. ¹H NMR (400 MHz, DMSO-d₆) δ 12.12 (s, 1H), 8.55 (d, J=5.9 Hz, 1H), 7.51 (s, 1H), 7.44 (s, 1H), 7.14 (s, 1H), 4.87 (d, J=4.8 Hz, 1H), 4.48 (d, J=1.8 Hz, 1H), 3.73 (d, J=4.6 Hz, 1H), 3.21 (d, J=4.9 Hz, 1H), 2.58 (s, 3H), 2.34 (s, 3H), 1.37-1.32 (m, 1H), 1.09-1.03 (m, 1H), 0.44-0.38 (m, 1H), 0.23-0.17 (m, 1H).

Example 71: (1S,2S,4R,5R,6R,7S)—N-(3-fluoro-4-(trifluoromethoxy)phenyl)-7-(2-methylpyridin-4-yl)-8-oxatricyclo[3.2.1.0²,⁴]octane-6-carboxamide

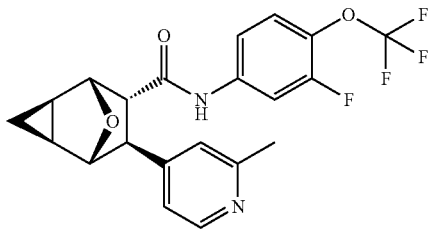 [SMILES: Cc1cc([C@H]2[C@H]3O[C@H]([C@@H]4C[C@@H]43)[C@@H]2C(=O)Nc2ccc(OC(F)(F)F)c(F)c2)ccn1]

LC-MS: Rt=1.50 min; MS m/z [M+H]+ 423.1. ¹H NMR (400 MHz, DMSO-d₆) δ 10.38 (s, 1H), 8.41 (d, J=5.1 Hz, 1H), 7.86 (d, J=12.9 Hz, 1H), 7.52 (t, J=8.9 Hz, 1H), 7.35 (d, J=8.9 Hz, 1H), 7.25 (s, 1H), 7.19 (d, J=5.4 Hz, 1H), 4.78 (d, J=4.5 Hz, 1H), 4.41 (s, 1H), 3.57 (d, J=4.4 Hz, 1H), 3.11 (t, J=4.3 Hz, 1H), 2.48 (s, 3H), 1.36-1.28 (m, 1H), 1.21-1.13 (m, 1H), 0.44-0.37 (m, 1H), 0.22-0.16 (m, 1H).

Examples 72 and 73 (Corresponding to Peak 1 and Peak 2)

(1S,2S,4R,5R,6R,7S)—N-(5,6-dichloropyridin-3-yl)-7-(2,3-difluoropyridin-4-yl)-8-oxatricyclo[3.2.1.0²,⁴]octane-6-carboxamidecarboxamide or (1R,2R,4S,5S,6S,7R)—N-(5,6-dichloropyridin-3-yl)-7-(2,3-difluoropyridin-4-yl)-8-oxatricyclo[3.2.1.0²,⁴]octane-6-carboxamide

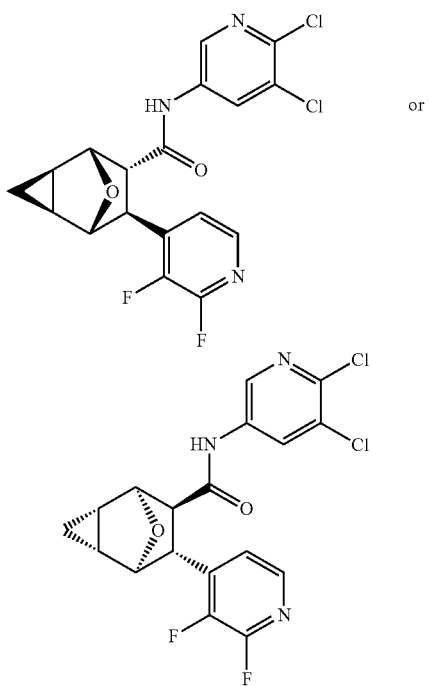

Chiral separation of rac-(1S,2S,4R,5R,6R,7S)—N-(5,6-dichloropyridin-3-yl)-7-(2,3-difluoropyridin-4-yl)-8-oxatricyclo[3.2.1.0²,⁴]octane-6-carboxamidecarboxamide by Supercritical Fluid Chromatography using the following conditions afforded the compounds listed hereafter:

Method Details:
  Column: 21×250 mm IA @ 30° C.
  Mobile Phase: 85% CO₂/15% MeOH+0.5% isopropylamine
  Detection: UV @ 220 nm
  Flow: 2 mL/min Peak 1: SFC Retention Time=2.61 min. LC-MS: Rt=1.69 min; MS m/z [M+H]+ 412.0. ¹H NMR (500 MHz, DMSO-d₆) δ 10.55 (s, 1H), 8.48 (d, J=2.4 Hz, 1H), 8.41 (d, J=2.4 Hz, 1H), 8.00 (dd, J=5.2, 1.1 Hz, 1H), 7.37 (t, J=4.9 Hz, 1H), 4.81 (d, J=5.0 Hz, 1H), 4.52 (s, 1H), 3.95 (d, J=4.7 Hz, 1H), 3.20-3.11 (m, 1H), 1.38-1.31 (m, 1H), 1.26-1.21 (m, 1H), 0.45-0.39 (m, 1H), 0.24-0.16 (m, 1H).

Peak 2: SFC Retention Time=3.23 min. LC-MS: Rt=1.69 min; MS m/z [M+H]+ 412.0. ¹H NMR (500 MHz, DMSO-d₆) δ 10.55 (s, 1H), 8.48 (d, J=2.4 Hz, 1H), 8.41 (d, J=2.4 Hz, 1H), 8.00 (dd, J=5.2, 1.1 Hz, 1H), 7.37 (t, J=4.9 Hz, 1H), 4.81 (d, J=5.0 Hz, 1H), 4.52 (s, 1H), 3.95 (d, J=4.7 Hz, 1H), 3.20-3.11 (m, 1H), 1.38-1.31 (m, 1H), 1.26-1.21 (m, 1H), 0.45-0.39 (m, 1H), 0.24-0.16 (m, 1H).

Example 74: (1S,2S,4R,5R,6R,7S)—N-(5,6-dichloropyridin-3-yl)-7-(6-methylpyridin-3-yl)-8-oxatricyclo[3.2.1.0²,⁴]octane-6-carboxamide

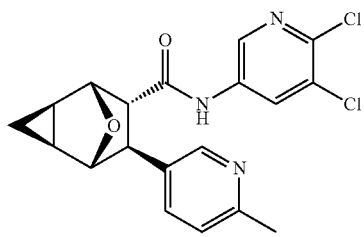 [SMILES: Cc1ccc([C@H]2[C@H]3O[C@H]([C@@H]4C[C@@H]43)[C@@H]2C(=O)Nc2cnc(Cl)c(Cl)c2)cn1]

LC-MS: Rt=1.28 min; MS m/z [M+H]+ 390.0. ¹H NMR (400 MHz, DMSO-d₆) δ 10.51 (s, 1H), 8.48 (d, J=2.4 Hz, 1H), 8.41 (d, J=2.4 Hz, 1H), 8.32 (d, J=2.1 Hz, 1H), 7.54 (dd, J=8.0, 2.3 Hz, 1H), 7.19 (d, J=8.0 Hz, 1H), 4.77 (d, J=4.9 Hz, 1H), 4.32 (s, 1H), 3.54 (d, J=4.7 Hz, 1H), 3.10 (t, J=4.8 Hz, 1H), 2.42 (s, 3H), 1.35-1.29 (m, 1H), 1.24-1.17 (m, 1H), 0.44-0.39 (m, 1H), 0.21-0.15 (m, 1H).

Example 75: (1S,2S,4R,5R,6R,7S)—N-(5,6-dichloropyridin-3-yl)-7-(pyrimidin-5-yl)-8-oxatricyclo[3.2.1.0²,⁴]octane-6-carboxamide

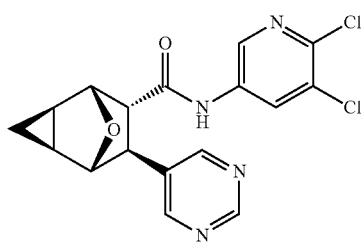 [SMILES: O=C(Nc1cnc(Cl)c(Cl)c1)[C@H]1[C@@H]2O[C@@H]([C@H]3C[C@H]32)[C@@H]1c1cncnc1]

LC-MS: Rt=1.43 min; MS m/z [M+H]+ 377.0. ¹H NMR (400 MHz, DMSO-$d_6$) δ 10.52 (s, 1H), 9.06 (s, 1H), 8.69 (s, 2H), 8.49 (d, J=2.4 Hz, 1H), 8.42 (d, J=2.4 Hz, 1H), 4.83 (d, J=4.9 Hz, 1H), 4.43 (s, 1H), 3.62 (d, J=4.7 Hz, 1H), 3.22 (t, J=4.8 Hz, 1H), 1.37-1.32 (m, 1H), 1.28-1.21 (m, 1H), 0.44-0.40 (m, 1H), 0.22-0.17 (m, 1H).

Example 76: (1S,2S,4R,5R,6R,7S)—N-(5,6-dichloropyridin-3-yl)-7-(2-methoxypyridin-4-yl)-8-oxatricyclo[3.2.1.0²,⁴]octane-6-carboxamide

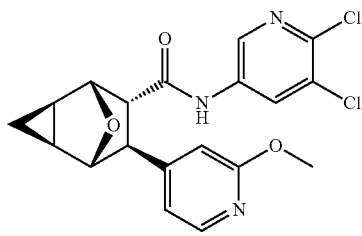 [SMILES: COc1cc([C@H]2[C@H]3O[C@H]([C@@H]4C[C@@H]43)[C@@H]2C(=O)Nc2cnc(Cl)c(Cl)c2)ccn1]

LC-MS: Rt=1.52 min; MS m/z [M+H]+ 406.1. ¹H NMR (400 MHz, DMSO-$d_6$) δ 10.52 (s, 1H), 8.49 (d, J=2.4 Hz, 1H), 8.41 (d, J=2.4 Hz, 1H), 8.07 (d, J=5.3 Hz, 1H), 6.87 (dd, J=5.3, 1.4 Hz, 1H), 6.65 (s, 1H), 4.76 (d, J=4.9 Hz, 1H), 4.39 (s, 1H), 3.81 (s, 3H), 3.52 (d, J=4.8 Hz, 1H), 3.11 (t, J=4.8 Hz, 1H), 1.34-1.27 (m, 1H), 1.23-1.17 (m, 1H), 0.43-0.38 (m, 1H), 0.19-0.14 (m, 1H).

Example 77: rac-(1R,2R,3S,4R,5S)—N-(3,4-dichlorophenyl)-5-hydroxy-3-(2-methylpyridin-4-yl)-7-oxabicyclo[2.2.1]heptane-2-carboxamide Title compound was prepared from methyl (1R,4S,5S)-3-bromo-5-hydroxy-7-oxabicyclo[2.2.1]hept-2-ene-2-carboxylate and methyl (1S,4S,6R)-3-bromo-6-hydroxy-7-oxabicyclo[2.2.1]hept-2-ene-2-carboxylate (Intermediate 1e) using Steps A-B and Step D as in Scheme 2.

Step A: A solution of methyl (1R,4S,5S)-3-bromo-5-hydroxy-7-oxabicyclo[2.2.1]hept-2-ene-2-carboxylate and methyl (1S,4S,6R)-3-bromo-6-hydroxy-7-oxabicyclo[2.2.1]hept-2-ene-2-carboxylate (1e, 1.40 g, 5.62 mmol) and AcOH (1.61 mL, 28.1 mmol) in 1:1 THF:water (15 mL) was treated with Zn powder (735 mg, 11.2 mmol) and was stirred at RT for 1 h. The reaction mixture was diluted with EtOAc and washed with sat. aq. NaHCO₃ and brine. The aqueous layer was further extracted with EtOAc and the combined EtOAc layers were dried (Na₂SO₄), filtered, and concentrated. The resulting crude (1R,4R,5S)-methyl 5-hydroxy-7-oxabicyclo[2.2.1]hept-2-ene-2-carboxylate and (1S,4S,6R)-methyl 6-hydroxy-7-oxabicyclo[2.2.1]hept-2-ene-2-carboxylate was used directly in the next step without purification. LC-MS: Rt=0.29 min; MS m/z [M+H]+ 171.1.

Step B: A solution of crude (1R,4R,5S)-methyl 5-hydroxy-7-oxabicyclo[2.2.1]hept-2-ene-2-carboxylate and (1S,4S,6R)-methyl 6-hydroxy-7-oxabicyclo[2.2.1]hept-2-ene-2-carboxylate (250 mg, 1.469 mmol) from Step A, 2-methyl-4-(4,4,5,5-tetramethyl-1,3,2-dioxaborolan-2-yl)pyridine (386 mg, 1.763 mmol), 2,2-bis(diphenylphosphino)-1,1-binaphthalene (91 mg, 0.147 mmol), chloro(1,5-cyclooctadiene)rhodium(I) dimer (36.2 mg, 0.073 mmol), and potassium carbonate (101 mg, 0.735 mmol) in 4:1 1,4-dioxane:water (15 mL) was degassed with nitrogen and was warmed at 110° C. for 1 h in a microwave reactor. The reaction was repeated on the same scale a total of four times under identical conditions. The reaction mixtures were combined and concentrated onto celite and purified by FCC to afford (1R,2S,3S,4R,5S)-methyl 5-hydroxy-3-(2-methylpyridin-4-yl)-7-oxabicyclo[2.2.1]heptane-2-carboxylate and (1S,2S,3S,4S,6R)-methyl 6-hydroxy-3-(2-methylpyridin-4-yl)-7-oxabicyclo[2.2.1]heptane-2-carboxylate as a mixture of alcohol regioisomers (cis) and (1R,2R,3S,4R,5S)-methyl 5-hydroxy-3-(2-methylpyridin-4-yl)-7-oxabicyclo[2.2.1]heptane-2-carboxylate and (1S,2R,3S,4S,6R)-methyl 6-hydroxy-3-(2-methylpyridin-4-yl)-7-oxabicyclo[2.2.1]heptane-2-carboxylate as a mixture of alcohol regioisomers (trans). cis: LC-MS: Rt=0.29 min; MS m/z [M+H]+ 264.2. trans: LC-MS: Rt=0.33 min; MS m/z [M+H]+ 264.2.

Step C: A solution of (1R,2R,3S,4R,5S)-methyl 5-hydroxy-3-(2-methylpyridin-4-yl)-7-oxabicyclo[2.2.1]heptane-2-carboxylate and (1S,2R,3S,4S,6R)-methyl 6-hydroxy-3-(2-methylpyridin-4-yl)-7-oxabicyclo[2.2.1]heptane-2-carboxylate (338 mg, 1.284 mmol) and 3,4-dichloroaniline (416 mg, 2.57 mmol) in THF (Volume: 16 mL) at RT was treated with LiHMDS (5.14 mL, 5.14 mmol) and was stirred at RT for 1 h. The reaction mixture was concentrated onto celite and was purified by FCC to afford rac-(1R,2R,3S,4R,5S)—N-(3,4-dichlorophenyl)-5-hydroxy-3-(2-methylpyridin-4-yl)-7-oxabicyclo[2.2.1]heptane-2-carboxamide as an ~8:1 mixture of alcohol regioisomers favoring the 5-hydroxy product. LC-MS: Rt=1.20 min; MS m/z [M+H]+ 393.1. ¹H NMR (500 MHz, DMSO-$d_6$) δ 10.31 (s, 1H), 8.34 (d, J=5.0 Hz, 1H), 7.97 (d, J=2.5 Hz, 1H), 7.55 (d, J=8.8 Hz, 1H), 7.42 (dd, J=8.8, 2.4 Hz, 1H), 7.11 (s, 1H), 7.05 (dd, J=5.3, 1.7 Hz, 1H), 4.98-4.95 (m, 1H), 4.90-4.87 (m, 1H), 4.23 (s, 1H), 3.98-3.95 (m, 1H), 3.18-3.14 (m, 1H), 2.96-2.93 (m, 1H), 2.43 (s, 3H), 2.09-2.04 (m, 1H), 1.45-1.37 (m, 1H).

Examples 77a and 77c (Corresponding to Peak 1 and Peak 3a)

(1R,2R,3S,4R,5S)—N-(3,4-dichlorophenyl)-5-hydroxy-3-(2-methylpyridin-4-yl)-7-oxabicyclo[2.2.1]heptane-2-carboxamide or (1S,2S,3R,4S,5R)—N-(3,4-dichlorophenyl)-5-hydroxy-3-(2-methylpyridin-4-yl)-7-oxabicyclo[2.2.1]heptane-2-carboxamide

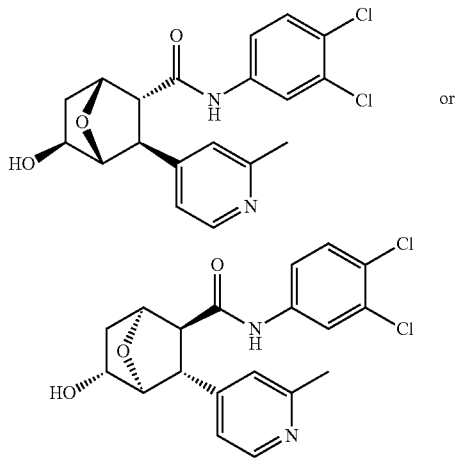

Example 77b and 77d (Corresponding to Peak 2 and Peak 3b)

(1S,2R,3S,4S,6R)—N-(3,4-dichlorophenyl)-6-hydroxy-3-(2-methylpyridin-4-yl)-7-oxabicyclo[2.2.1]heptane-2-carboxamide or (1R,2S,3R,4R,6S)—N-(3,4-dichlorophenyl)-6-hydroxy-3-(2-methylpyridin-4-yl)-7-oxabicyclo[2.2.1]heptane-2-carboxamide

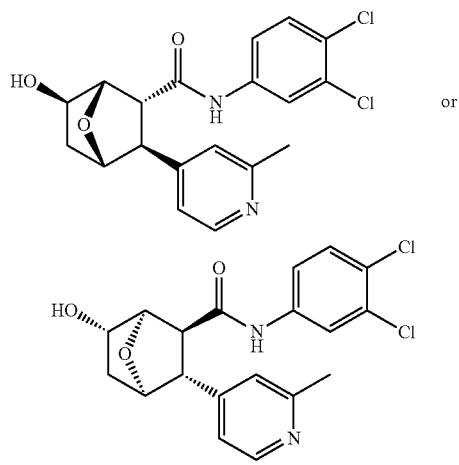

Chiral separation of rac-(1R,2R,3S,4R,5S)—N-(3,4-dichlorophenyl)-5-hydroxy-3-(2-methylpyridin-4-yl)-7-oxabicyclo[2.2.1]heptane-2-carboxamide as an ~8:1 mixture of alcohol regioisomers (Example 77) by Supercritical Fluid Chromatography using the following conditions afforded the compounds listed hereafter:

Method Details:
Column: 21×250 mm AD-H @ 30° C.
Mobile Phase: 80% $CO_2$/20% MeOH+0.5% isopropylamine
Detection: UV @ 220 nm
Flow: 2 mL/min Peak 1: SFC Retention Time=2.14 min. LC-MS: Rt=1.16 min; MS m/z $[M+H]^+$ 393.1. $^1$H NMR (400 MHz, DMSO-$d_6$) δ 10.31 (s, 1H), 8.34 (dd, J=5.2, 0.8 Hz, 1H), 7.98 (d, J=2.4 Hz, 1H), 7.56 (d, J=8.8 Hz, 1H), 7.41 (dd, J=8.8, 2.5 Hz, 1H), 7.11 (s, 1H), 7.05 (dd, J=5.2, 1.7 Hz, 1H), 5.00-4.97 (m, 1H), 4.91-4.86 (m, 1H), 4.22 (s, 1H), 3.99-3.94 (m, 1H), 3.19-3.14 (m, 1H), 2.96-2.92 (m, 1H), 2.43 (s, 3H), 2.10-2.04 (m, 1H), 1.44-1.37 (m, 1H).

Peak 2: SFC Retention Time=3.56 min. LC-MS: Rt=1.16 min; MS m/z $[M+H]^+$ 393.1. $^1$H NMR (400 MHz, DMSO-$d_6$) δ 10.42 (s, 1H), 8.33 (dd, J=5.2, 0.8 Hz, 1H), 8.00 (d, J=2.5 Hz, 1H), 7.58 (d, J=8.8 Hz, 1H), 7.44 (dd, J=8.8, 2.5 Hz, 1H), 7.11 (s, 1H), 7.06 (dd, J=5.2, 1.7 Hz, 1H), 4.95-4.90 (m, 1H), 4.64-4.59 (m, 1H), 4.57-4.51 (m, 1H), 4.02-3.96 (m, 1H), 3.26-3.21 (m, 1H), 3.00-2.95 (m, 1H), 2.42 (s, 3H), 2.10-2.01 (m, 1H), 1.55-1.48 (m, 1H).

Peak 3: SFC Retention Time=4.22 min. The third eluted peak isolated using Supercritical Fluid Chromatography was concentrated and repurified by Supercritical Fluid Chromatography using the following conditions to afford the compounds listed hereafter:

Method Details:
Column: 21×250 mm AS-H @ 30° C.
Mobile Phase: 85% $CO_2$/15% MeOH+0.5% isopropylamine
Detection: UV @ 220 nm
Flow: 2 mL/min Peak 3a: SFC Retention Time=1.44 min. LC-MS: Rt=1.16 min; MS m/z $[M+H]^+$ 393.1. $^1$H NMR (400 MHz, DMSO-$d_6$) δ 10.31 (s, 1H), 8.34 (dd, J=5.2, 0.8 Hz, 1H), 7.98 (d, J=2.4 Hz, 1H), 7.56 (d, J=8.8 Hz, 1H), 7.41 (dd, J=8.8, 2.5 Hz, 1H), 7.11 (s, 1H), 7.05 (dd, J=5.2, 1.7 Hz, 1H), 5.00-4.97 (m, 1H), 4.91-4.86 (m, 1H), 4.22 (s, 1H), 3.99-3.94 (m, 1H), 3.19-3.14 (m, 1H), 2.96-2.92 (m, 1H), 2.43 (s, 3H), 2.10-2.04 (m, 1H), 1.44-1.37 (m, 1H).

Peak 3b: SFC Retention Time=2.04 min. LC-MS: Rt=1.16 min; MS m/z $[M+H]^+$ 393.1. $^1$H NMR (400 MHz, DMSO-$d_6$) δ 10.42 (s, 1H), 8.33 (dd, J=5.2, 0.8 Hz, 1H), 8.00 (d, J=2.5 Hz, 1H), 7.58 (d, J=8.8 Hz, 1H), 7.44 (dd, J=8.8, 2.5 Hz, 1H), 7.11 (s, 1H), 7.06 (dd, J=5.2, 1.7 Hz, 1H), 4.95-4.90 (m, 1H), 4.64-4.59 (m, 1H), 4.57-4.51 (m, 1H), 4.02-3.96 (m, 1H), 3.26-3.21 (m, 1H), 3.00-2.95 (m, 1H), 2.42 (s, 3H), 2.10-2.01 (m, 1H), 1.55-1.48 (m, 1H).

Examples 78-91 described infra were synthesized according to the protocol described for Example 77 using methyl (1R,4S,5S)-3-bromo-5-hydroxy-7-oxabicyclo[2.2.1]hept-2-ene-2-carboxylate and methyl (1S,4S,6R)-3-bromo-6-hydroxy-7-oxabicyclo[2.2.1]hept-2-ene-2-carboxylate (Intermediate 1e) and various boronic acids/esters in Step B and various anilines/amines in Step D.

Example 78: (1R,2R,3S,4R,5S)—N-(2-chloro-2'-fluoro-[1,1'-biphenyl]-4-yl)-5-hydroxy-3-(2-methylpyridin-4-yl)-7-oxabicyclo[2.2.1]heptane-2-carboxamide

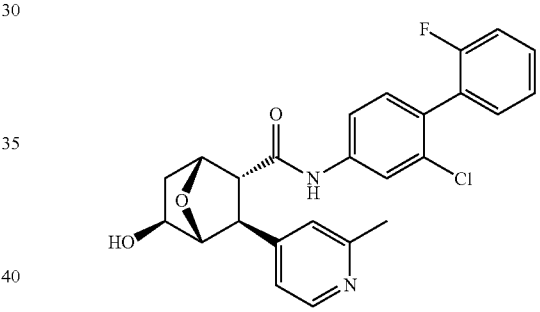

LC-MS: Rt=0.89 min; MS m/z $[M+H]^+$ 453.2. $^1$H NMR (500 MHz, DMSO-$d_6$) δ 10.31 (s, 1H), 8.35 (dd, J=5.2, 0.8 Hz, 1H), 7.93 (d, J=2.1 Hz, 1H), 7.51-7.45 (m, 2H), 7.38-7.27 (m, 4H), 7.13 (s, 1H), 7.07 (dd, J=5.2, 1.6 Hz, 1H), 5.00-4.97 (m, 1H), 4.94-4.89 (m, 1H), 4.24 (s, 1H), 4.01-3.95 (m, 1H), 3.22-3.19 (m, 1H), 3.00-2.96 (m, 1H), 2.44 (s, 3H), 2.12-2.05 (m, 1H), 1.46-1.41 (m, 1H). ~3:1 mixture of alcohol regioisomers.

Example 79: (1R,2R,3S,4R,5S)-5-hydroxy-3-(2-methylpyridin-4-yl)-N-(1-(methylsulfonyl)piperidin-4-yl)-7-oxabicyclo[2.2.1]heptane-2-carboxamide

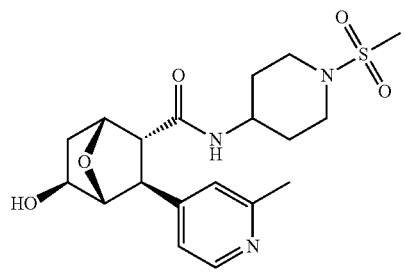 [SMILES: Cc1cc([C@H]2[C@H]3O[C@H](C[C@@H]3O)[C@@H]2C(=O)NC2CCN(S(C)(=O)=O)CC2)ccn1]

LC-MS: Rt=0.20 min; MS m/z [M+H]+ 410.2. Mixture of alcohol regioisomers. Example 80: (1R,2R,3S,4R,5S)—N-(4,5-dichloropyridin-2-yl)-5-hydroxy-3-(2-methylpyridin-4-yl)-7-oxabicyclo[2.2.1]heptane-2-carboxamide

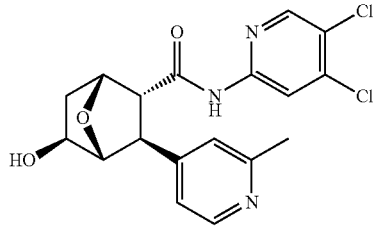 [SMILES: Cc1cc([C@H]2[C@H]3O[C@H](C[C@@H]3O)[C@@H]2C(=O)Nc2cc(Cl)c(Cl)cn2)ccn1]

LC-MS: Rt=0.73 min; MS m/z [M+H]+ 394.1. ¹H NMR (500 MHz, DMSO-d₆) δ 11.03 (s, 1H), 8.52 (s, 1H), 8.37-8.32 (m, 2H), 7.10 (s, 1H), 7.04 (dd, J=5.3, 1.7 Hz, 1H), 5.00-4.95 (m, 1H), 4.95-4.89 (m, 1H), 4.24 (s, 1H), 4.00-3.94 (m, 1H), 3.22-3.18 (m, 1H), 3.13-3.09 (m, 1H), 2.43 (s, 3H), 2.07-1.99 (m, 1H), 1.43-1.36 (m, 1H). ~5:1 mixture of alcohol regioisomers.

Example 81: (1R,2R,3S,4R,5S)—N-(5-chloro-6-methylpyridin-3-yl)-5-hydroxy-3-(2-methylpyridin-4-yl)-7-oxabicyclo[2.2.1]heptane-2-carboxamide

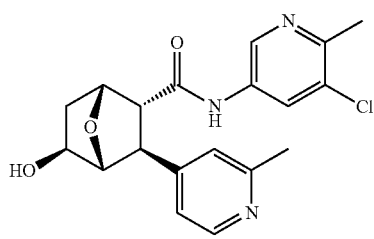 [SMILES: Cc1cc([C@H]2[C@H]3O[C@H](C[C@@H]3O)[C@@H]2C(=O)Nc2cnc(C)c(Cl)c2)ccn1]

LC-MS: Rt=0.57 min; MS m/z [M+H]+ 374.1. ¹H NMR (400 MHz, DMSO-d₆) δ 10.37 (s, 1H), 8.45 (d, J=2.2 Hz, 1H), 8.34 (dd, J=5.2, 0.8 Hz, 1H), 8.17 (d, J=2.2 Hz, 1H), 7.12 (d, J=1.7 Hz, 1H), 7.06 (dd, J=5.3, 1.7 Hz, 1H), 5.00-4.96 (m, 1H), 4.93-4.87 (m, 1H), 4.22 (s, 1H), 3.99-3.91 (m, 1H), 3.21-3.15 (m, 1H), 2.99-2.94 (m, 1H), 2.47 (s, 3H), 2.43 (s, 3H), 2.11-2.04 (m, 1H), 1.44-1.36 (m, 1H). ~5:1 mixture of alcohol regioisomers.

Example 82: (1R,2R,3S,4R,5S)—N-(3,4-dichlorophenyl)-5-hydroxy-3-(2-methylpyrimidin-4-yl)-7-oxabicyclo[2.2.1]heptane-2-carboxamide

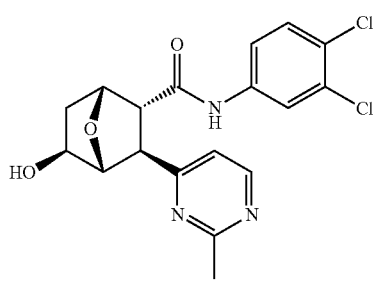 [SMILES: Cc1nccc([C@H]2[C@H]3O[C@H](C[C@@H]3O)[C@@H]2C(=O)Nc2ccc(Cl)c(Cl)c2)n1]

LC-MS: Rt=0.83 min; MS m/z [M+H]+ 394.1. Mixture of alcohol regioisomers.

Examples 83 and 84 (Corresponding to Peak 1 and Peak 2A)

(1R,2R,3S,4R,5S)—N-(5,6-dichloropyridin-3-yl)-5-hydroxy-3-(2-methylpyridin-4-yl)-7-oxabicyclo[2.2.1]heptane-2-carboxamide or (1S,2S,3R,4S,5R)—N-(5,6-dichloropyridin-3-yl)-5-hydroxy-3-(2-methylpyridin-4-yl)-7-oxabicyclo[2.2.1]heptane-2-carboxamide

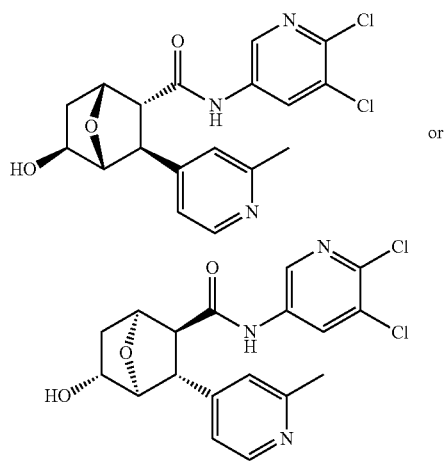

Chiral separation of rac-(1R,2R,3S,4R,5S)—N-(5,6-dichloropyridin-3-yl)-5-hydroxy-3-(2-methylpyridin-4-yl)-7-oxabicyclo[2.2.1]heptane-2-carboxamide as a mixture of alcohol regioisomers by Supercritical Fluid Chromatography using the following conditions afforded the compounds listed hereafter:

Method Details:
Column: 21×250 mm IA @ 30° C.
Mobile Phase: 80% CO₂/20% MeOH+0.5% isopropylamine
Detection: UV @ 220 nm
Flow: 2 mL/min Peak 1: SFC Retention Time=1.96 min. LC-MS: Rt=1.05 min; MS m/z [M+H]+ 394.2. ¹H NMR (400 MHz, DMSO-d₆) δ 10.58 (s, 1H), 8.45 (d, J=2.4 Hz, 1H), 8.38 (d, J=2.4 Hz, 1H), 8.34 (dd, J=5.2, 0.7 Hz, 1H), 7.12 (s, 1H), 7.06 (dd, J=5.2, 1.7 Hz, 1H), 5.02-4.98 (m, 1H), 4.94-4.89 (m, 1H), 4.23 (s, 1H), 4.00-3.94 (m, 1H), 3.19-3.15 (m, 1H), 3.01-2.94 (m, 1H), 2.43 (s, 3H), 2.12-2.03 (m, 1H), 1.45-1.38 (m, 1H).

Peak 2: The second eluted peak isolated using Supercritical Fluid Chromatography with Retention Time=3.03 min was concentrated and repurified by Supercritical Fluid Chromatography using the following conditions to afford the compound listed hereafter:

Method Details:
Column: 21×250 mm AD-H @ 30° C.
Mobile Phase: 80% CO₂/20% IPA+0.5% isopropylamine
Detection: UV @ 220 nm
Flow: 2 mL/min Peak 2A: First eluted peak. SFC Retention Time=2.18 min. LC-MS: Rt=1.05 min; MS m/z [M+H]+ 394.2. ¹H NMR (400 MHz, DMSO-d₆) δ 10.58 (s, 1H), 8.45 (d, J=2.4 Hz, 1H), 8.38 (d, J=2.4 Hz, 1H), 8.34 (dd, J=5.2, 0.7 Hz, 1H), 7.12 (s, 1H), 7.06 (dd, J=5.2, 1.7 Hz, 1H), 5.02-4.98 (m, 1H), 4.94-4.89 (m, 1H), 4.23 (s, 1H), 4.00-3.94 (m, 1H), 3.19-3.15 (m, 1H), 3.01-2.94 (m, 1H), 2.43 (s, 3H), 2.12-2.03 (m, 1H), 1.45-1.38 (m, 1H).

Example 85: (1R,2R,3S,4R,5S)-5-hydroxy-3-(2-methylpyridin-4-yl)-N-(3-(trifluoromethyl)phenyl)-7-oxabicyclo[2.2.1]heptane-2-carboxamide

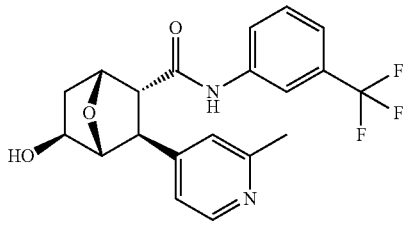 [SMILES: Cc1cc([C@H]2[C@H]3O[C@H](C[C@@H]3O)[C@@H]2C(=O)Nc2cccc(C(F)(F)F)c2)ccn1]

LC-MS: Rt=1.13 min; MS m/z [M+H]$^+$ 393.3. $^1$H NMR (400 MHz, DMSO-d$_6$) δ 10.41 (s, 1H), 8.34 (dd, J=5.2, 0.8 Hz, 1H), 8.09 (s, 1H), 7.73-7.69 (m, 1H), 7.57-7.52 (m, 1H), 7.43-7.38 (m, 1H), 7.12 (s, 1H), 7.07 (dd, J=5.2, 1.7 Hz, 1H), 5.02-4.95 (m, 1H), 4.94-4.88 (m, 1H), 4.23 (s, 1H), 4.01-3.94 (m, 1H), 3.22-3.17 (m, 1H), 3.00-2.96 (m, 1H), 2.43 (s, 3H), 2.13-2.04 (m, 1H), 1.45-1.37 (m, 1H). >20:1 mixture of alcohol regioisomers.

Example 86: (1S,2R,3S,4S,6R)-6-hydroxy-3-(2-methylpyridin-4-yl)-N-(3-(trifluoromethyl)phenyl)-7-oxabicyclo[2.2.1]heptane-2-carboxamide

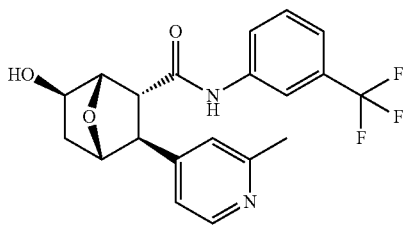 [SMILES: Cc1cc([C@@H]2[C@@H](C(=O)Nc3cccc(C(F)(F)F)c3)[C@@H]3O[C@H]2C[C@H]3O)ccn1]

LC-MS: Rt=1.12 min; MS m/z [M+H]$^+$ 393.3. $^1$H NMR (400 MHz, DMSO-d$_6$) δ 10.51 (s, 1H), 8.34 (dd, J=5.2, 0.7 Hz, 1H), 8.12 (s, 1H), 7.76-7.72 (m, 1H), 7.59-7.53 (m, 1H), 7.45-7.40 (m, 1H), 7.13-7.10 (m, 1H), 7.07 (dd, J=5.2, 1.7 Hz, 1H), 4.92 (s, 1H), 4.66-4.61 (m, 1H), 4.58-4.53 (m, 1H), 4.05-3.98 (m, 1H), 3.28-3.23 (m, 1H), 3.03-2.98 (m, 1H), 2.42 (s, 3H), 2.10-2.02 (m, 1H), 1.56-1.46 (m, 1H). >20:1 mixture of alcohol regioisomers.

Example 87: (1R,2R,3S,4R,5S)—N-(5,6-dichloropyridin-3-yl)-5-hydroxy-3-(pyridin-4-yl)-7-oxabicyclo[2.2.1]heptane-2-carboxamide

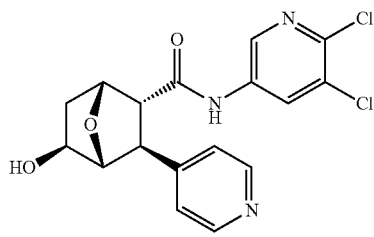

LC-MS: Rt=0.84 min; MS m/z [M+H]$^+$ 380.1. $^1$H NMR (400 MHz, DMSO-d$_6$) δ 10.60 (s, 1H), 8.50-8.46 (m, 2H), 8.45 (d, J=2.4 Hz, 1H), 8.38 (d, J=2.4 Hz, 1H), 7.29-7.25 (m, 2H), 5.04-4.99 (m, 1H), 4.96-4.90 (m, 1H), 4.25 (s, 1H), 4.02-3.95 (m, 1H), 3.26-3.22 (m, 1H), 3.01-2.96 (m, 1H), 2.12-2.04 (m, 1H), 1.48-1.37 (m, 1H). ~5:1 mixture of alcohol regioisomers.

Example 88: (1R,2R,3S,4R,5S)-5-hydroxy-3-(pyridin-4-yl)-N-(3-(trifluoromethyl)phenyl)-7-oxabicyclo[2.2.1]heptane-2-carboxamide

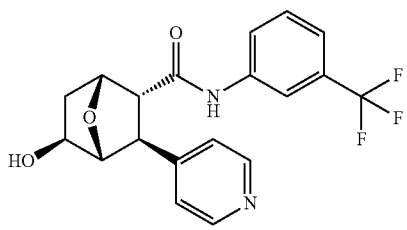 [SMILES: O=C(Nc1cccc(C(F)(F)F)c1)[C@@H]1[C@@H](c2ccncc2)[C@H]2O[C@@H]1C[C@@H]2O]

LC-MS: Rt=1.11 min; MS m/z [M+H]$^+$ 379.2. $^1$H NMR (400 MHz, DMSO-d$_6$) δ 10.47 (s, 1H), 8.49-8.46 (m, 2H), 8.09 (s, 1H), 7.74-7.70 (m, 1H), 7.57-7.51 (m, 1H), 7.42-7.37 (m, 1H), 7.29-7.25 (m, 2H), 5.01 (s, 1H), 4.96-4.90 (m, 1H), 4.25 (s, 1H), 4.02-3.97 (m, 1H), 3.27-3.22 (m, 1H), 3.02-2.98 (m, 1H), 2.14-2.04 (m, 1H), 1.46-1.37 (m, 1H). >20:1 mixture of alcohol regioisomers.

Example 89: (1S,2R,3S,4S,6R)-6-hydroxy-3-(pyridin-4-yl)-N-(3-(trifluoromethyl)phenyl)-7-oxabicyclo[2.2.1]heptane-2-carboxamide

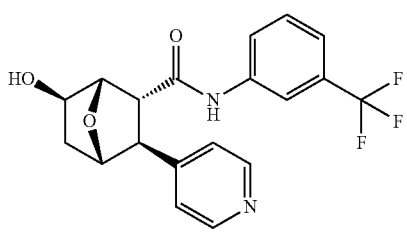 [SMILES: O=C(Nc1cccc(C(F)(F)F)c1)[C@H]1[C@@H]2O[C@@H](C[C@H]2O)[C@@H]1c1ccncc1]

LC-MS: Rt=1.08 min; MS m/z [M+H]$^+$ 379.2. $^1$H NMR (400 MHz, DMSO-d$_6$) δ 10.56 (s, 1H), 8.50-8.45 (m, 2H), 8.12 (s, 1H), 7.77-7.73 (m, 1H), 7.59-7.53 (m, 1H), 7.44-7.40 (m, 1H), 7.29-7.24 (m, 2H), 4.94 (s, 1H), 4.69-4.62 (m, 1H), 4.61-4.55 (m, 1H), 4.04-3.97 (m, 1H), 3.32-3.28 (m, 1H), 3.06-3.00 (m, 1H), 2.13-2.03 (m, 1H), 1.58-1.48 (m, 1H). >20:1 mixture of alcohol regioisomers.

Example 90: rac-(1R,2R,3S,4R,5S)—N-(5,6-dichloropyridin-3-yl)-3-(2-fluoropyridin-4-yl)-5-hydroxy-7-oxabicyclo[2.2.1]heptane-2-carboxamide LC-MS: Rt=1.30 min; MS m/z [M+H]$^+$ 398.1. Mixture of alcohol regioisomers.

Examples 90a and 90b (Corresponding to Peak 1 and Peak 2)

(1R,2R,3S,4R,5S)—N-(5,6-dichloropyridin-3-yl)-3-(2-fluoropyridin-4-yl)-5-hydroxy-7-oxabicyclo[2.2.1]heptane-2-carboxamide or (1S,2S,3R,4S,5R)—N-(5,6-dichloropyridin-3-yl)-3-(2-fluoropyridin-4-yl)-5-hydroxy-7-oxabicyclo[2.2.1]heptane-2-carboxamide

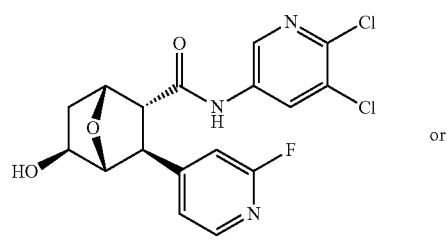

or

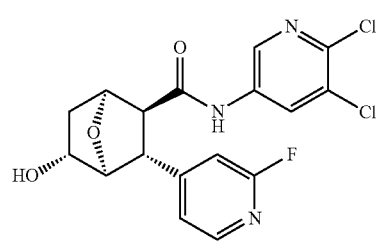

Chiral separation of rac-(1R,2R,3S,4R,5S)—N-(5,6-dichloropyridin-3-yl)-3-(2-fluoropyridin-4-yl)-5-hydroxy-7-oxabicyclo[2.2.1]heptane-2-carboxamide (Example 90) as a mixture of alcohol regioisomers by Supercritical Fluid Chromatography using the following conditions afforded the compounds listed hereafter:

Method Details:

Column: 21×250 mm IF @ 30° C.

Mobile Phase: 70% $CO_2$/30% MeOH+0.5% isopropylamine

Detection: UV @ 220 nm

Flow: 2 mL/min

Peak 1: SFC Retention Time=1.29 min. LC-MS: Rt=1.30 min; MS m/z [M+H]$^+$ 398.1. $^1$H NMR (400 MHz, DMSO-$d_6$) δ 10.58 (s, 1H), 8.45 (d, J=2.4 Hz, 1H), 8.38 (d, J=2.4 Hz, 1H), 8.17 (d, J=5.2 Hz, 1H), 7.27-7.23 (m, 1H), 7.02 (s, 1H), 5.06-5.02 (m, 1H), 4.97-4.92 (m, 1H), 4.28 (s, 1H), 4.01-3.96 (m, 1H), 3.35-3.33 (m, 1H), 3.04-2.99 (m, 1H), 2.13-2.05 (m, 1H), 1.47-1.38 (m, 1H).

Peak 2: SFC Retention Time=1.95 min. LC-MS: Rt=1.30 min; MS m/z [M+H]$^+$ 398.1. $^1$H NMR (400 MHz, DMSO-$d_6$) δ 10.58 (s, 1H), 8.45 (d, J=2.4 Hz, 1H), 8.38 (d, J=2.4 Hz, 1H), 8.17 (d, J=5.2 Hz, 1H), 7.27-7.23 (m, 1H), 7.02 (s, 1H), 5.06-5.02 (m, 1H), 4.97-4.92 (m, 1H), 4.28 (s, 1H), 4.01-3.96 (m, 1H), 3.35-3.33 (m, 1H), 3.04-2.99 (m, 1H), 2.13-2.05 (m, 1H), 1.47-1.38 (m, 1H).

Example 91: (1R,2R,3S,4R,5S)—N-(5,6-dichloropyridin-3-yl)-3-(2,3-difluoropyridin-4-yl)-5-hydroxy-7-oxabicyclo[2.2.1]heptane-2-carboxamide

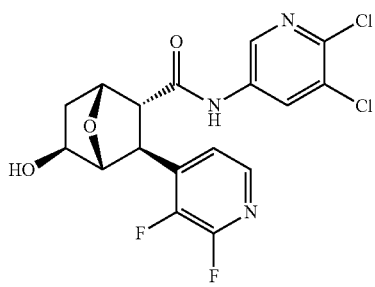 [SMILES: O=C(Nc1cnc(Cl)c(Cl)c1)[C@@H]1[C@@H](c2ccnc(F)c2F)[C@H]2O[C@@H]1C[C@@H]2O]

LC-MS: Rt=1.35 min; MS m/z [M+H]$^+$ 416.1. $^1$H NMR (400 MHz, DMSO-$d_6$) δ 10.61 (s, 1H), 8.44 (d, J=2.4 Hz, 1H), 8.39 (d, J=2.4 Hz, 1H), 8.01 (dd, J=5.2, 1.2 Hz, 1H), 7.42-7.37 (m, 1H), 5.11-5.08 (m, 1H), 4.96-4.93 (m, 1H), 4.36 (s, 1H), 4.02-3.97 (m, 1H), 3.64-3.60 (m, 1H), 3.05-3.02 (m, 1H), 2.15-2.07 (m, 1H), 1.49-1.40 (m, 1H). ~5:1 mixture of alcohol regioisomers.

Examples 92-102 described infra were synthesized according to the protocol described for Example 77 using methyl (1R,4S,5R)-3-bromo-5-fluoro-7-oxabicyclo[2.2.1]hept-2-ene-2-carboxylate and methyl (1S,4S,6S)-3-bromo-6-fluoro-7-oxabicyclo[2.2.1]hept-2-ene-2-carboxylate (Intermediate 1g) and various boronic acids/esters in Step B and various anilines in Step D.

Examples 92 and 94 (Corresponding to Peak 1 and Peak 3)

(1R,2R,3S,4R,5R)—N-(3,4-dichlorophenyl)-5-fluoro-3-(2-methylpyridin-4-yl)-7-oxabicyclo[2.2.1]heptane-2-carboxamide or (1S,2S,3R,4S,5S)—N-(3,4-dichlorophenyl)-5-fluoro-3-(2-methylpyridin-4-yl)-7-oxabicyclo[2.2.1]heptane-2-carboxamide

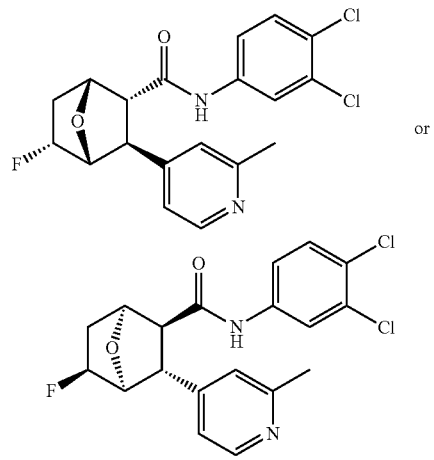

Examples 93 and 95 (Corresponding to Peak 2 and Peak 4)

(1S,2R,3S,4S,6S)—N-(3,4-dichlorophenyl)-6-fluoro-3-(2-methylpyridin-4-yl)-7-oxabicyclo[2.2.1]heptane-2-carboxamide or (1R,2S,3R,4R,6R)—N-(3,4-dichlorophenyl)-6-fluoro-3-(2-methylpyridin-4-yl)-7-oxabicyclo[2.2.1]heptane-2-carboxamide

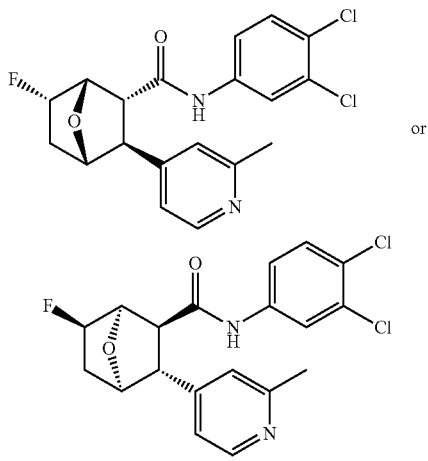

or

Chiral separation of rac-(1R,2R,3S,4R,5R)—N-(3,4-dichlorophenyl)-5-fluoro-3-(2-methylpyridin-4-yl)-7-oxabicyclo[2.2.1]heptane-2-carboxamide as a mixture of fluorine regioisomers by Supercritical Fluid Chromatography using the following conditions afforded the compounds listed hereafter:

Method Details:
 Column: 21×250 mm IF @ 30° C.
 Mobile Phase: 95-50% CO$_2$/5-50% MeOH+0.5% isopropylamine in 5 minutes
 Detection: UV @ 220 nm
 Flow: 2 mL/min Peak 1: SFC Retention Time=2.45 min. LC-MS: Rt=1.35 min; MS m/z [M+H]$^+$ 395.1. $^1$H NMR (400 MHz, Acetonitrile-d$_3$) δ 8.50 (s, 1H), 8.36 (dd, J=5.2, 0.8 Hz, 1H), 7.88 (dd, J=2.3, 0.6 Hz, 1H), 7.46-7.39 (m, 2H), 7.16 (s, 1H), 7.10 (dd, J=5.2, 1.7 Hz, 1H), 5.24-5.02 (m, 1H), 4.92-4.87 (m, 1H), 4.65-4.58 (m, 1H), 4.09-4.02 (m, 1H), 3.18-3.11 (m, 1H), 2.46 (s, 3H), 2.23-2.16 (m, 1H), 1.91-1.79 (m, 1H).

Peak 2: SFC Retention Time=2.75 min. LC-MS: Rt=1.35 min; MS m/z [M+H]$^+$ 395.1. $^1$H NMR (400 MHz, Acetonitrile-d$_3$) δ 8.61 (s, 1H), 8.36 (dd, J=5.2, 0.7 Hz, 1H), 7.87 (d, J=2.4 Hz, 1H), 7.43 (d, J=8.8 Hz, 1H), 7.40-7.37 (m, 1H), 7.13 (s, 1H), 7.07 (dd, J=5.2, 1.7 Hz, 1H), 5.12-4.97 (m, 1H), 4.97-4.95 (m, 1H), 4.68-4.62 (m, 1H), 3.26-3.20 (m, 1H), 2.97-2.91 (m, 1H), 2.46 (s, 3H), 2.41-2.29 (m, 1H), 1.83-1.68 (m, 1H).

Peak 3: SFC Retention Time=2.85 min. LC-MS: Rt=1.35 min; MS m/z [M+H]$^+$ 395.1. $^1$H NMR (400 MHz, Acetonitrile-d$_3$) δ 8.50 (s, 1H), 8.36 (dd, J=5.2, 0.8 Hz, 1H), 7.88 (dd, J=2.3, 0.6 Hz, 1H), 7.46-7.39 (m, 2H), 7.16 (s, OH), 7.10 (dd, J=5.2, 1.7 Hz, 1H), 5.24-5.02 (m, 1H), 4.92-4.87 (m, 1H), 4.65-4.58 (m, 1H), 4.09-4.02 (m, 1H), 3.18-3.11 (m, 1H), 2.46 (s, 3H), 2.23-2.16 (m, 1H), 1.91-1.79 (m, 1H).

Peak 4: SFC Retention Time=3.12 min. LC-MS: Rt=1.35 min; MS m/z [M+H]$^+$ 395.1. $^1$H NMR (400 MHz, Acetonitrile-d$_3$) δ 8.61 (s, 1H), 8.36 (dd, J=5.2, 0.7 Hz, 1H), 7.87 (d, J=2.4 Hz, 1H), 7.43 (d, J=8.8 Hz, 1H), 7.40-7.37 (m, 1H), 7.13 (s, 1H), 7.07 (dd, J=5.2, 1.7 Hz, 1H), 5.12-4.97 (m, 1H), 4.97-4.95 (m, 1H), 4.68-4.62 (m, 1H), 3.26-3.20 (m, 1H), 2.97-2.91 (m, 1H), 2.46 (s, 3H), 2.41-2.29 (m, 1H), 1.83-1.68 (m, 1H).

Example 96: (1R,2R,3S,4R,5R)-5-fluoro-3-(2-methylpyridin-4-yl)-N-(3-(trifluoromethyl)phenyl)-7-oxabicyclo[2.2.1]heptane-2-carboxamide

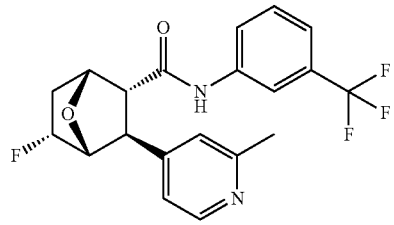 [SMILES: Cc1cc([C@H]2[C@H]3O[C@H](C[C@H]3F)[C@@H]2C(=O)Nc2cccc(C(F)(F)F)c2)ccn1]

LC-MS: Rt=1.29 min; MS m/z [M+H]$^+$ 395.2. $^1$H NMR (400 MHz, DMSO-d$_6$) δ 10.38 (s, 1H), 8.37 (dd, J=5.1, 0.8 Hz, 1H), 8.10 (s, 1H), 7.75-7.71 (m, 1H), 7.55 (t, J=8.0 Hz, 1H), 7.45-7.39 (m, 1H), 7.16 (s, 1H), 7.10 (dd, J=5.2, 1.7 Hz, 1H), 5.25-5.03 (m, 1H), 5.01-4.95 (m, 1H), 4.74-4.68 (m, 1H), 4.06-3.98 (m, 1H), 3.25-3.20 (m, 1H), 2.44 (s, 3H), 2.25-2.10 (m, 1H), 1.82-1.70 (m, 1H). >20:1 mixture of fluorine regioisomers.

Example 97: (1R,2R,3S,4R,5R)-5-fluoro-N-(6-methoxypyridin-3-yl)-3-(2-methylpyridin-4-yl)-7-oxabicyclo[2.2.1]heptane-2-carboxamide

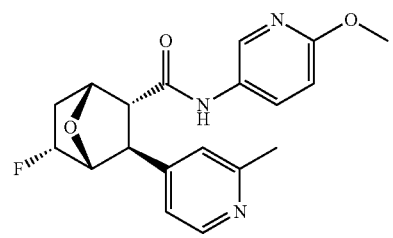 [SMILES: COc1ccc(NC(=O)[C@@H]2[C@@H](c3ccnc(C)c3)[C@H]3O[C@@H]2C[C@H]3F)cn1]

LC-MS: Rt=0.92 min; MS m/z [M+H]$^+$ 358.2. $^1$H NMR (400 MHz, DMSO-d$_6$) δ 10.06 (s, 1H), 8.37 (d, J=5.2 Hz, 1H), 8.31 (dd, J=2.7, 0.7 Hz, 1H), 7.87 (dd, J=8.9, 2.7 Hz, 1H), 7.15 (s, 1H), 7.09 (dd, J=5.2, 1.7 Hz, 1H), 6.79 (dd, J=8.8, 0.7 Hz, 1H), 5.24-5.04 (m, 1H), 4.97-4.91 (m, 1H), 4.71-4.66 (m, 1H), 4.02-3.98 (m, 1H), 3.80 (s, 3H), 3.22-3.15 (m, 1H), 2.44 (s, 3H), 2.24-2.09 (m, 1H), 1.82-1.70 (m, 1H). >20:1 mixture of fluorine regioisomers.

Example 98: (1R,2R,3S,4R,5R)—N-(5,6-dichloro-pyridin-3-yl)-5-fluoro-3-(2-methylpyridin-4-yl)-7-oxabicyclo[2.2.1]heptane-2-carboxamide

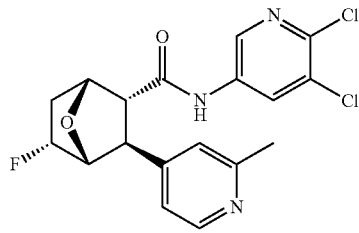 [SMILES: Cc1cc([C@H]2[C@H]3O[C@H](C[C@H]3F)[C@@H]2C(=O)Nc2cnc(Cl)c(Cl)c2)ccn1]

LC-MS: Rt=1.21 min; MS m/z [M+H]$^+$ 396.2. $^1$H NMR (400 MHz, DMSO-d$_6$) δ 10.59 (s, 1H), 8.46 (d, J=2.4 Hz, 1H), 8.41 (d, J=2.4 Hz, 1H), 8.37 (d, J=5.1 Hz, 1H), 7.17-7.14 (m, 1H), 7.09 (dd, J=5.2, 1.7 Hz, 1H), 5.26-5.05 (m, 1H), 5.01-4.94 (m, 1H), 4.75-4.67 (m, 1H), 4.03-3.97 (m, 1H), 3.27-3.21 (m, 1H), 2.44 (s, 3H), 2.24-2.11 (m, 1H), 1.81-1.67 (m, 1H). >20:1 mixture of fluorine regioisomers.

Example 99: (1R,2R,3S,4R,5R)-5-fluoro-3-(2-methylpyridin-4-yl)-N-(3-(trifluoromethoxy)phenyl)-7-oxabicyclo[2.2.1]heptane-2-carboxamide

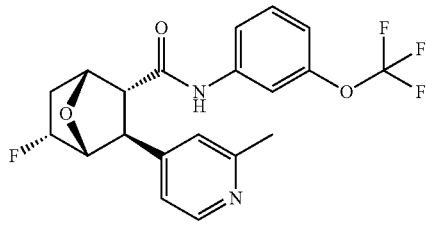 [SMILES: Cc1cc([C@H]2[C@H]3O[C@H](C[C@H]3F)[C@@H]2C(=O)Nc2cccc(OC(F)(F)F)c2)ccn1]

LC-MS: Rt=1.30 min; MS m/z [M+H]$^+$ 411.2. $^1$H NMR (400 MHz, DMSO-d$_6$) δ 10.34 (s, 1H), 8.38 (dd, J=5.2, 0.8 Hz, 1H), 7.78 (s, 1H), 7.49-7.41 (m, 2H), 7.19-7.15 (m, 1H), 7.10 (dd, J=5.2, 1.7 Hz, 1H), 7.08-7.04 (m, 1H), 5.26-5.04 (m, 1H), 4.99-4.94 (m, 1H), 4.75-4.66 (m, 1H), 4.04-4.00 (m, 1H), 3.25-3.20 (m, 1H), 2.45 (s, 3H), 2.24-2.09 (m, 1H), 1.81-1.68 (m, 1H). >20:1 mixture of fluorine regioisomers.

Example 100: (1R,2R,3S,4R,5R)-5-fluoro-N-(3-fluoro-4-(trifluoromethoxy)phenyl)-3-(2-methylpyridin-4-yl)-7-oxabicyclo[2.2.1]heptane-2-carboxamide

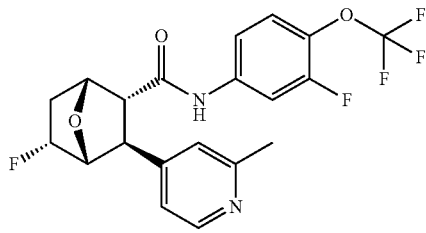 [SMILES: Cc1cc([C@H]2[C@H]3O[C@H](C[C@H]3F)[C@@H]2C(=O)Nc2ccc(OC(F)(F)F)c(F)c2)ccn1]

LC-MS: Rt=1.36 min; MS m/z [M+H]$^+$ 429.2. $^1$H NMR (400 MHz, DMSO-d$_6$) δ 10.43 (s, 1H), 8.37 (d, J=0.7 Hz, 1H), 7.84 (dd, J=12.9, 2.5 Hz, 1H), 7.55-7.50 (m, 1H), 7.36-7.32 (m, 1H), 7.15 (s, 1H), 7.09 (dd, J=5.2, 1.7 Hz, 1H), 5.25-5.04 (m, 1H), 4.99-4.93 (m, 1H), 4.74-4.68 (m, 1H), 4.03-3.99 (m, 1H), 3.25-3.17 (m, 1H), 2.44 (s, 3H), 2.23-2.10 (m, 1H), 1.79-1.65 (m, 1H). >20:1 mixture of fluorine regioisomers.

Example 101: (1R,2R,3S,4R,5R)-5-fluoro-N-(1-methyl-1H-pyrazol-3-yl)-3-(2-methylpyridin-4-yl)-7-oxabicyclo[2.2.1]heptane-2-carboxamide

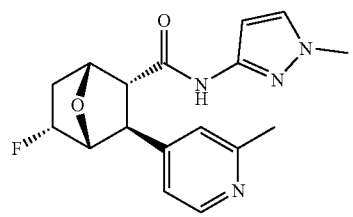 [SMILES: Cc1cc([C@H]2[C@H]3O[C@H](C[C@H]3F)[C@@H]2C(=O)Nc2ccn(C)n2)ccn1]

LC-MS: Rt=0.43 min; MS m/z [M+H]$^+$ 331.3. $^1$H NMR (400 MHz, DMSO-d$_6$) δ 10.54 (s, 1H), 8.36 (dd, J=5.1, 0.8 Hz, 1H), 7.55 (d, J=2.3 Hz, 1H), 7.12 (s, 1H), 7.06 (dd, J=5.2, 1.7 Hz, 1H), 6.46 (d, J=2.2 Hz, 1H), 5.22-5.01 (m, 1H), 4.95-4.89 (m, 1H), 4.70-4.65 (m, 1H), 4.03-3.98 (m, 1H), 3.71 (s, 3H), 3.20-3.15 (m, 1H), 2.44 (s, 3H), 2.19-2.06 (m, 1H), 1.75-1.61 (m, 1H). >20:1 mixture of fluorine regioisomers.

Example 102: (1R,2R,3S,4R,5R)-5-fluoro-3-(2-methylpyridin-4-yl)-N-(5-methylthiazol-2-yl)-7-oxabicyclo[2.2.1]heptane-2-carboxamide

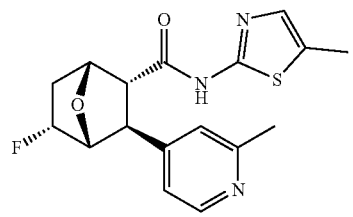 [SMILES: Cc1cc([C@H]2[C@H]3O[C@H](C[C@H]3F)[C@@H]2C(=O)Nc2ncc(C)s2)ccn1]

LC-MS: Rt=1.04 min; MS m/z [M+H]$^+$ 348.2. $^1$H NMR (400 MHz, DMSO-d$_6$) δ 12.11 (s, 1H), 8.37 (dd, J=5.1, 0.7 Hz, 1H), 7.16-7.11 (m, 2H), 7.08 (dd, J=5.3, 1.7 Hz, 1H), 5.25-5.04 (m, 1H), 5.02-4.97 (m, 1H), 4.75-4.69 (m, 1H), 4.06-4.00 (m, 1H), 3.33-3.27 (m, 1H), 2.44 (s, 3H), 2.34 (s, 3H), 2.24-2.10 (m, 1H), 1.68-1.53 (m, 1H). ~8:1 mixture of fluorine regioisomers.

Examples 103-116 described infra were synthesized according to the protocol described for Example 77 using methyl (1R,4S,5S)-3-bromo-5-fluoro-7-oxabicyclo[2.2.1]hept-2-ene-2-carboxylate and methyl (1S,4S,6R)-3-bromo-6-fluoro-7-oxabicyclo[2.2.1]hept-2-ene-2-carboxylate (Intermediate 1j) and various boronic acids/esters in Step B and various anilines in Step D.

Example 103: (1R,2R,3S,4R,5S)—N-(3,4-dichlorophenyl)-5-fluoro-3-(2-methoxypyridin-4-yl)-7-oxabicyclo[2.2.1]heptane-2-carboxamide

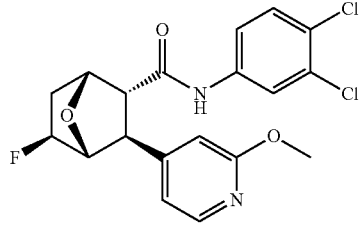 [SMILES: COc1cc([C@H]2[C@H]3O[C@H](C[C@@H]3F)[C@@H]2C(=O)Nc2ccc(Cl)c(Cl)c2)ccn1]

LC-MS: Rt=1.54 min; MS m/z [M+H]+ 411.2. $^1$H NMR (500 MHz, DMSO-$d_6$) δ 10.37 (s, 1H), 8.10 (dd, J=5.3, 0.7 Hz, 1H), 7.97 (d, J=2.4 Hz, 1H), 7.56 (d, J=8.8 Hz, 1H), 7.41 (dd, J=8.8, 2.4 Hz, 1H), 6.88 (dd, J=5.4, 1.5 Hz, 1H), 6.66 (s, 1H), 5.16-5.01 (m, 1H), 5.01-4.98 (m, 1H), 4.67 (d, J=10.6 Hz, 1H), 3.83 (s, 3H), 3.24-3.19 (m, 1H), 3.02-2.96 (m, 1H), 2.30-2.20 (m, 1H), 1.79-1.64 (m, 1H). >20:1 mixture of fluorine regioisomers.

Example 104: (1S,2R,3S,4S,6R)—N-(3,4-dichlorophenyl)-6-fluoro-3-(2-methoxypyridin-4-yl)-7-oxabicyclo[2.2.1]heptane-2-carboxamide

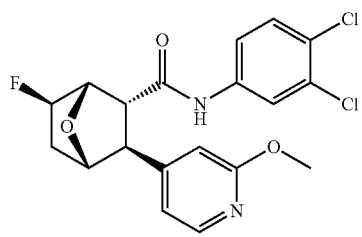 [SMILES: COc1cc([C@@H]2[C@@H](C(=O)Nc3ccc(Cl)c(Cl)c3)[C@@H]3O[C@H]2C[C@H]3F)ccn1]

LC-MS: Rt=1.55 min; MS m/z [M+H]+ 411.1. $^1$H NMR (400 MHz, Acetonitrile-$d_3$) δ 8.55 (s, 1H), 8.07 (dd, J=5.4, 0.7 Hz, 1H), 7.86 (d, J=2.4 Hz, 1H), 7.43 (d, J=8.7 Hz, 1H), 7.37 (dd, J=8.8, 2.4 Hz, 1H), 6.87 (dd, J=5.3, 1.5 Hz, 1H), 6.67 (dd, J=1.5, 0.7 Hz, 1H), 5.11-4.92 (m, 2H), 4.67-4.59 (m, 1H), 3.86 (s, 3H), 3.27-3.21 (m, 1H), 2.97-2.90 (m, 1H), 2.43-2.31 (m, 1H), 1.84-1.65 (m, 1H). >20:1 mixture of fluorine regioisomers.

Example 105: (1R,2R,3S,4R,5S)—N-(3,4-dichlorophenyl)-5-fluoro-3-(2-methylpyridin-4-yl)-7-oxabicyclo[2.2.1]heptane-2-carboxamide

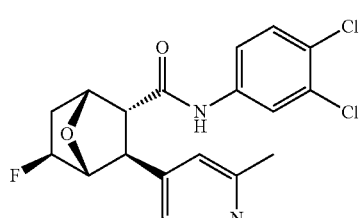

LC-MS: Rt=1.31 min; MS m/z [M+H]+ 395.2. $^1$H NMR (400 MHz, Acetonitrile-$d_3$) δ 8.56 (s, 1H), 8.36 (dd, J=5.2, 0.8 Hz, 1H), 7.87 (d, J=2.4 Hz, 1H), 7.45-7.38 (m, 2H), 7.13 (s, 1H), 7.08-7.06 (m, 1H), 5.13-4.93 (m, 2H), 4.68-4.63 (m, 1H), 3.26-3.22 (m, 1H), 2.96-2.91 (m, 1H), 2.46 (s, 3H), 2.40-2.30 (m, 1H), 1.85-1.77 (m, 1H). >20:1 mixture of fluorine regioisomers.

Example 106: (1S,2R,3S,4S,6R)—N-(3,4-dichlorophenyl)-6-fluoro-3-(2-methylpyridin-4-yl)-7-oxabicyclo[2.2.1]heptane-2-carboxamide

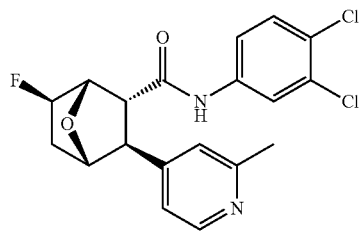

LC-MS: Rt=1.31 min; MS m/z [M+H]+ 395.2. $^1$H NMR (400 MHz, Acetonitrile-ds) δ 8.52 (s, 1H), 8.36 (dd, J=5.2, 0.8 Hz, 1H), 7.89 (d, J=2.0 Hz, 1H), 7.45-7.38 (m, 2H), 7.18-7.15 (m, 1H), 7.10 (dd, J=5.2, 1.7 Hz, 1H), 5.23-5.03 (m, 1H), 4.91-4.86 (m, 1H), 4.64-4.59 (m, 1H), 4.08-4.05 (m, 1H), 3.19-3.13 (m, 1H), 2.46 (s, 3H), 2.20-2.11 (m, 1H), 1.91-1.79 (m, 1H). >20:1 mixture of fluorine regioisomers.

Example 107: (1R,2R,3S,4R,5S)-5-fluoro-3-(2-methylpyridin-4-yl)-N-(3-(trifluoromethyl)phenyl)-7-oxabicyclo[2.2.1]heptane-2-carboxamide

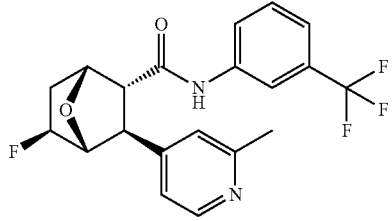 [SMILES: Cc1cc([C@H]2[C@H]3O[C@H](C[C@@H]3F)[C@@H]2C(=O)Nc2cccc(C(F)(F)F)c2)ccn1]

LC-MS: Rt=1.29 min; MS m/z [M+H]+ 395.2. $^1$H NMR (400 MHz, Acetonitrile-ds) δ 8.72 (s, 1H), 8.35 (dd, J=5.2, 0.8 Hz, 1H), 8.02 (s, 1H), 7.68-7.62 (m, 1H), 7.52-7.46 (m, 1H), 7.42-7.36 (m, 1H), 7.14 (s, 1H), 7.07 (dd, J=5.2, 1.7 Hz, 1H), 5.13-4.95 (m, 2H), 4.70-4.63 (m, 1H), 3.29-3.23 (m, 1H), 2.99-2.92 (m, 1H), 2.45 (s, 3H), 2.43-2.34 (m, 1H), 1.86-1.67 (m, 1H). >20:1 mixture of fluorine regioisomers.

Example 108: (1S,2R,3S,4S,6R)-6-fluoro-3-(2-methylpyridin-4-yl)-N-(3-(trifluoromethyl)phenyl)-7-oxabicyclo[2.2.1]heptane-2-carboxamide

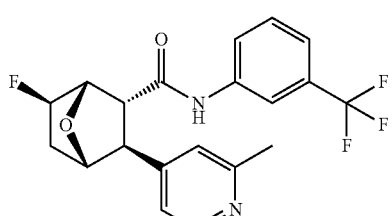

LC-MS: Rt=1.29 min; MS m/z [M+H]+ 395.2. ¹H NMR (400 MHz, Acetonitrile-ds) δ 8.59 (s, 1H), 8.37 (dd, J=5.2, 0.8 Hz, 1H), 8.03 (s, 1H), 7.71-7.67 (m, 1H), 7.53-7.47 (m, 1H), 7.42-7.37 (m, 1H), 7.18 (s, 1H), 7.11 (dd, J=5.3, 1.7 Hz, 1H), 5.24-5.03 (m, 1H), 4.94-4.89 (m, 1H), 4.66-4.60 (m, 1H), 4.12-4.07 (m, 1H), 3.21-3.16 (m, 1H), 2.46 (s, 3H), 2.24-2.14 (m, 1H), 1.90-1.81 (m, 1H). >20:1 mixture of fluorine regioisomers.

Example 109: (1R,2R,3S,4R,5S)—N-(5,6-dichloropyridin-3-yl)-5-fluoro-3-(2-methylpyridin-4-yl)-7-oxabicyclo[2.2.1]heptane-2-carboxamide

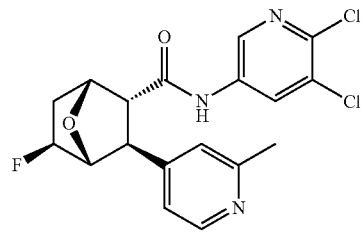 [SMILES: Cc1cc([C@H]2[C@H]3O[C@H](C[C@@H]3F)[C@@H]2C(=O)Nc2cnc(Cl)c(Cl)c2)ccn1]

LC-MS: Rt=1.22 min; MS m/z [M+H]+ 396.2. ¹H NMR (400 MHz, Acetonitrile-ds) δ 8.73 (s, 1H), 8.40 (d, J=2.4 Hz, 1H), 8.36 (dd, J=5.2, 0.8 Hz, 1H), 8.28 (d, J=2.4 Hz, 1H), 7.14-7.13 (m, 1H), 7.07 (dd, J=5.3, 1.7 Hz, 1H), 5.13-4.94 (m, 2H), 4.69-4.62 (m, 1H), 3.27-3.21 (m, 1H), 3.00-2.94 (m, 1H), 2.46 (s, 3H), 2.40-2.30 (m, 1H), 1.86-1.67 (m, 1H). >20:1 mixture of fluorine regioisomers.

Example 110: (1S,2R,3S,4S,6R)—N-(5,6-dichloropyridin-3-yl)-6-fluoro-3-(2-methylpyridin-4-yl)-7-oxabicyclo[2.2.1]heptane-2-carboxamide

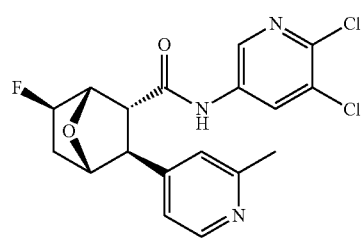 [SMILES: Cc1cc([C@@H]2[C@@H](C(=O)Nc3cnc(Cl)c(Cl)c3)[C@@H]3O[C@H]2C[C@H]3F)ccn1]

LC-MS: Rt=1.22 min; MS m/z [M+H]+ 396.2. ¹H NMR (400 MHz, Acetonitrile-ds) δ 8.69 (s, 1H), 8.42 (d, J=2.4 Hz, 1H), 8.37 (dd, J=5.2, 0.8 Hz, 1H), 8.31 (d, J=2.4 Hz, 1H), 7.17 (s, 1H), 7.10 (dd, J=5.2, 1.7 Hz, 1H), 5.24-5.04 (m, 1H), 4.93-4.89 (m, 1H), 4.64-4.60 (m, 1H), 4.09-4.05 (m, 1H), 3.22-3.18 (m, 1H), 2.46 (s, 3H), 2.25-2.14 (m, 1H), 1.90-1.78 (m, 1H). >20:1 mixture of fluorine regioisomers.

Example 111: (1R,2R,3S,4R,5S)—N-(3,4-dichlorophenyl)-5-fluoro-3-(2-fluoropyridin-4-yl)-7-oxabicyclo[2.2.1]heptane-2-carboxamide

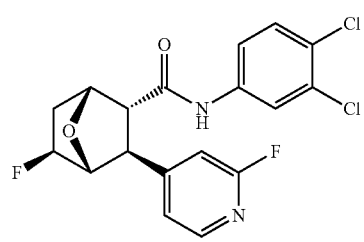

LC-MS: Rt=1.59 min; MS m/z [M+H]+ 399.1. ¹H NMR (400 MHz, Acetonitrile-ds) δ 8.55 (s, 1H), 8.13 (d, J=5.2 Hz, 1H), 7.86 (d, J=2.4 Hz, 1H), 7.44 (d, J=8.8 Hz, 1H), 7.37 (dd, J=8.8, 2.4 Hz, 1H), 7.23-7.20 (m, 1H), 6.97-6.93 (m, 1H), 5.13-4.95 (m, 2H), 4.70-4.65 (m, 1H), 3.39-3.34 (m, 1H), 2.99-2.94 (m, 1H), 2.41-2.30 (m, 1H), 1.85-1.69 (m, 1H). >20:1 mixture of fluorine regioisomers.

Example 112: (1S,2R,3S,4S,6R)—N-(3,4-dichlorophenyl)-6-fluoro-3-(2-fluoropyridin-4-yl)-7-oxabicyclo[2.2.1]heptane-2-carboxamide

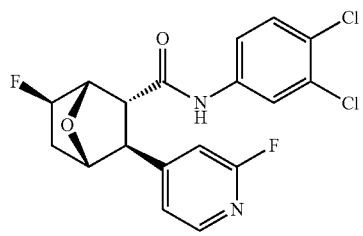 [SMILES: O=C(Nc1ccc(Cl)c(Cl)c1)[C@H]1[C@@H]2O[C@@H](C[C@H]2F)[C@@H]1c1ccnc(F)c1]

LC-MS: Rt=1.59 min; MS m/z [M+H]+ 399.1. ¹H NMR (400 MHz, Acetonitrile-d₃) δ 8.50 (s, 1H), 8.13 (dd, J=5.2, 0.7 Hz, 1H), 7.88 (d, J=2.2 Hz, 1H), 7.45-7.39 (m, 2H), 7.27-7.23 (m, 1H), 6.99-6.97 (m, 1H), 5.25-5.04 (m, 1H), 4.94-4.89 (m, 1H), 4.68-4.65 (m, 1H), 4.21-4.17 (m, 1H), 3.20-3.15 (m, 1H), 2.25-2.17 (m, 1H), 1.91-1.80 (m, 1H). ~5:1 mixture of fluorine regioisomers.

Example 113: (1R,2R,3S,4R,5S)-3-(2-aminopyrimidin-5-yl)-N-(3,4-dichlorophenyl)-5-fluoro-7-oxabicyclo[2.2.1]heptane-2-carboxamide

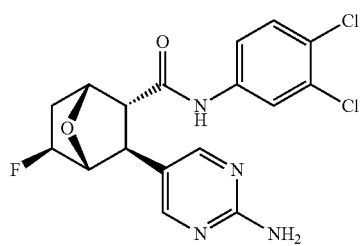 [SMILES: Nc1ncc([C@H]2[C@H]3O[C@H](C[C@@H]3F)[C@@H]2C(=O)Nc2ccc(Cl)c(Cl)c2)cn1]

LC-MS: Rt=1.33 min; MS m/z [M+H]+ 397.2. ¹H NMR (400 MHz, Acetonitrile-d₃) δ 8.57 (s, 1H), 8.18 (s, 2H), 7.85 (d, J=2.4 Hz, 1H), 7.43 (d, J=8.8 Hz, 1H), 7.37 (dd, J=8.8, 2.4 Hz, 1H), 5.37 (s, 2H), 5.10-4.92 (m, 2H), 4.56-4.51 (m, 1H), 3.11-3.07 (m, 1H), 2.93-2.89 (m, 1H), 2.44-2.33 (m, 1H), 1.81-1.65 (m, 1H). >20:1 mixture of fluorine regioisomers.

Example 114: (1S,2R,3S,4S,6R)-3-(2-aminopyrimidin-5-yl)-N-(3,4-dichlorophenyl)-6-fluoro-7-oxabicyclo[2.2.1]heptane-2-carboxamide

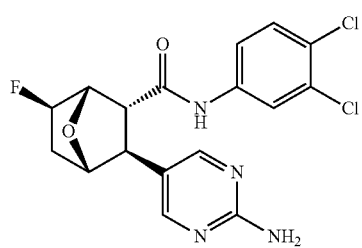 [SMILES: Nc1ncc([C@@H]2[C@@H](C(=O)Nc3ccc(Cl)c(Cl)c3)[C@@H]3O[C@H]2C[C@H]3F)cn1]

LC-MS: Rt=1.33 min; MS m/z [M+H]+ 397.2. ¹H NMR (400 MHz, Acetonitrile-d₃) δ 8.50 (s, 1H), 8.22 (s, 2H), 7.87 (dd, J=2.2, 0.6 Hz, 1H), 7.44-7.39 (m, 2H), 5.36 (s, 2H), 5.20-5.01 (m, 1H), 4.89-4.84 (m, 1H), 4.54-4.50 (m, 1H), 3.94-3.90 (m, 1H), 3.14-3.07 (m, 1H), 2.21-2.10 (m, 1H), 1.93-1.83 (m, 1H). ~5:1 mixture of fluorine regioisomers.

Example 115: (1R,2R,3S,4R,5S)—N-(3,4-dichlorophenyl)-5-fluoro-3-(6-methylpyridin-3-yl)-7-oxabicyclo[2.2.1]heptane-2-carboxamide

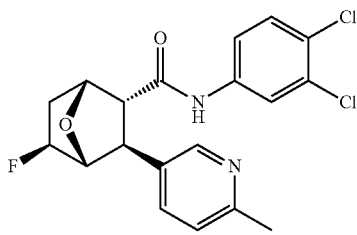 [SMILES: Cc1ccc([C@H]2[C@H]3O[C@H](C[C@@H]3F)[C@@H]2C(=O)Nc2ccc(Cl)c(Cl)c2)cn1]

LC-MS: Rt=1.32 min; MS m/z [M+H]+ 395.2. ¹H NMR (400 MHz, Acetonitrile-ds) δ 8.55 (s, 1H), 8.37-8.34 (m, 1H), 7.86 (d, J=2.4 Hz, 1H), 7.57 (dd, J=8.1, 2.4 Hz, 1H), 7.43 (d, J=8.8 Hz, 1H), 7.37 (dd, J=8.8, 2.4 Hz, 1H), 7.16 (d, J=8.0 Hz, 1H), 5.14-4.93 (m, 2H), 4.61-4.55 (m, 1H), 3.27-3.23 (m, 1H), 2.97-2.92 (m, 1H), 2.45 (s, 3H), 2.44-2.33 (m, 1H), 1.83-1.67 (m, 1H). >20:1 mixture of fluorine regioisomers.

Example 116: (1S,2R,3S,4S,6R)—N-(3,4-dichlorophenyl)-6-fluoro-3-(6-methylpyridin-3-yl)-7-oxabicyclo[2.2.1]heptane-2-carboxamide

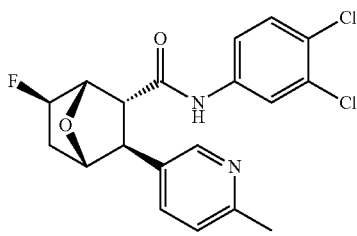 [SMILES: Cc1ccc([C@@H]2[C@@H](C(=O)Nc3ccc(Cl)c(Cl)c3)[C@@H]3O[C@H]2C[C@H]3F)cn1]

LC-MS: Rt=1.32 min; MS m/z [M+H]+ 395.2. ¹H NMR (400 MHz, Acetonitrile-ds) δ 8.57 (s, 1H), 8.39 (d, J=2.4 Hz, 1H), 7.86 (d, J=2.1 Hz, 1H), 7.60 (dd, J=8.1, 2.4 Hz, 1H), 7.43-7.36 (m, 2H), 7.16 (d, J=8.0 Hz, 1H), 5.21-5.01 (m, 1H), 4.91-4.86 (m, 1H), 4.58-4.54 (m, 1H), 4.12-4.06 (m, 1H), 3.18-3.11 (m, 1H), 2.45 (s, 3H), 2.21-2.10 (m, 1H), 1.92-1.81 (m, 1H). >20:1 mixture of fluorine regioisomers.

Example 117: (1S,2S,4R,5R,6R,7S)—N-(3,4-dichlorophenyl)-7-(2-methylpyridin-4-yl)-8-oxatricyclo[3.2.1.0²,⁴]octane-6-carboxamide

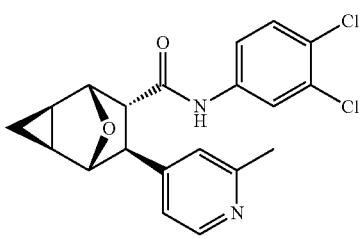 [SMILES: Cc1cc([C@H]2[C@H]3O[C@H]([C@@H]4C[C@@H]43)[C@@H]2C(=O)Nc2ccc(Cl)c(Cl)c2)ccn1]

Title compound was prepared from methyl (1S,2S,4R,5R)-7-bromo-8-oxatricyclo[3.2.1.0²,⁴]oct-6-ene-6-carboxylate (Intermediate 1d) using Steps A-C as in Scheme 3.

Step A: To a stirring solution of 3,4-dichloroaniline (568 mg, 3.51 mmol) in anhydrous toluene (10 mL) at 0° C. under N₂ was added trimethylaluminum in toluene (2 M, 3.9 mL, 7.79 mmol). After 10 minutes, the ice bath was removed and the mixture was stirred at room temperature for 30 minutes. The reaction was cooled back to 0° C. and 1d (955 mg, 3.90 mmol, dissolved in 2 mL of toluene) was added and the reaction was stirred at room temperature for 6 h. The reaction was cooled to 0° C. and quenched with a solution of saturated aqueous NH₄Cl and methanol. The suspension was filtered and the solid was washed with EtOAc. The organic layer was separated and washed with brine and dried over anhydrous sodium sulfate and concentrated. The crude compound was purified by silica column chromatography using DCM and EtOAc to afford (1S,2S,4R,5R)-7-bromo-N-(3,4-dichlorophenyl)-8-oxatricyclo[3.2.1.0²,⁴]oct-6-ene-6-carboxamide. LC-MS: Rt=1.63 min; MS m/z [M+H]+ 373.9. ¹H NMR (400 MHz, DMSO-d₆) δ 10.10 (s, 1H), 8.04 (d, J=2.3 Hz, 1H), 7.65 (dd, J=8.9, 2.3 Hz, 1H), 7.60 (d, J=8.8 Hz, 1H), 5.15 (s, 1H), 4.87 (s, 1H), 1.70-1.66 (m, 1H), 1.60-1.55 (m, 1H), 1.42-1.39 (m, 1H), 1.02-0.98 (m, 1H).

Step B: To a stirring solution of (1S,2S,4R,5R)-7-bromo-N-(3,4-dichlorophenyl)-8-oxatricyclo[3.2.1.0²,⁴]oct-6-ene-6-carboxamide (525 mg, 1.40 mmol) in THF (10 mL) and water (2.5 mL) at 0° C. was added acetic acid (0.321 mL) and portion-wise Zn powder (366 mg, 5.60 mmol). The reaction slurry was stirred to room temperature for 15 minutes. The reaction was filtered and neutralized with saturated sodium bicarbonate to pH ~7. The compound was extracted with ethyl acetate. The organic layer was washed with water and brine and dried over anhydrous sodium sulfate and concentrated. The crude compound was purified by silica column chromatography (hexanes:EtOAc) to afford (1S,2S,4R,5R)—N-(3,4-dichlorophenyl)-8-oxatricyclo[3.2.1.0²,⁴]oct-6-ene-6-carboxamide. LC-MS: Rt=1.54 min; MS m/z [M+H]+ 296.0. ¹H NMR (400 MHz, DMSO-d₆) δ 10.11 (s, 1H), 8.05 (d, J=2.3 Hz, 1H), 7.64 (dd, J=8.9, 2.4 Hz, 1H), 7.59 (d, J=8.8 Hz, 1H), 7.37 (d, J=1.7 Hz, 1H), 4.98 (s, 1H), 4.89 (d, J=1.7 Hz, 1H), 1.42-1.36 (m, 3H), 0.96-0.90 (m, 1H).

Step C: A mixture of (1S,2S,4R,5R)—N-(3,4-dichlorophenyl)-8-oxatricyclo[3.2.1.0²,⁴]oct-6-ene-6-carboxamide (150 mg, 0.507 mmol), 2-methyl-4-(4,4,5,5-tetramethyl-1,3,2-dioxaborolan-2-yl)pyridine (133 mg, 0.608 mmol), 2,2-bis(diphenylphosphino)-1,1-binapthalene (32 mg, 0.051 mmol), chloro(1,5-cyclooctadiene)rhodium(I) dimer (12 mg, 0.025 mmol) and potassium carbonate (35.0 mg, 0.253 mmol) in 1,4-dioxane (2 mL) and water (0.5 mL) was heated in the microwave at 100° C. for 1 h. The crude reaction was taken in celite and the solvent was concentrated to dryness. The crude compound was purified by silica column chromatography to afford (1S,2S,4R,5R,6S,7S)—N-(3,4-dichlorophenyl)-7-(2-methylpyridin-4-yl)-8-oxatricyclo[3.2.1.0²,⁴]octane-6-carboxamide (cis) and (1S,2S,4R,5R,6R,7S)—N-(3,4-dichlorophenyl)-7-(2-methylpyridin-4-yl)-8-oxatricyclo[3.2.1.0²,⁴]octane-6-carboxamide (Example 117). Method B LC-MS: Rt=1.33 min; MS m/z [M+H]+ 389.0. ¹H NMR (400 MHz, DMSO-d₆) δ 10.26 (s, 1H), 8.33 (d, J=5.1 Hz, 1H), 8.02 (d, J=2.4 Hz, 1H), 7.57 (d, J=8.8 Hz, 1H), 7.45 (dd, J=8.8, 2.4 Hz, 1H), 7.12-7.10 (m, 1H), 7.05 (dd, J=5.2, 1.6 Hz, 1H), 4.75 (d, J=4.9 Hz, 1H), 4.38 (s, 1H), 3.50 (d, J=4.8 Hz, 1H), 3.07 (t, J=4.8 Hz, 1H), 2.42 (s, 3H), 1.33-1.28 (m, 1H), 1.18-1.13 (m, 1H), 0.43-0.39 (m, 1H), 0.21-0.15 (m, 1H).

Examples 118-137 described infra were synthesized according to the protocol described for Example 117 using methyl (1S,2S,4R,5R)-7-bromo-8-oxatricyclo[3.2.1.0²,⁴]

oct-6-ene-6-carboxylate (Intermediate 1d) and various anilines in Step A and various boronic esters/acids in Step C.

Example 118: (1S,2S,4R,5R,6R,7S)—N-(3,4-dichlorophenyl)-7-(2-methoxypyridin-4-yl)-8-oxatricyclo[3.2.1.0²,⁴]octane-6-carboxamide

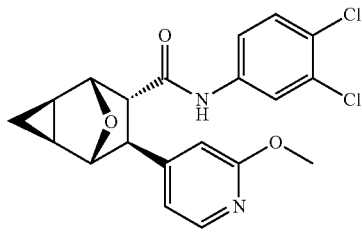 [SMILES: COc1cc([C@H]2[C@H]3O[C@H]([C@@H]4C[C@@H]43)[C@@H]2C(=O)Nc2ccc(Cl)c(Cl)c2)ccn1]

Method B LC-MS: Rt=1.59 min; MS m/z [M+H]⁺ 405.1. ¹H NMR (400 MHz, DMSO-d₆) δ 10.27 (s, 1H), 8.07 (d, J=5.3 Hz, 1H), 8.01 (d, J=2.4 Hz, 1H), 7.57 (d, J=8.8 Hz, 1H), 7.45 (dd, J=8.8, 2.4 Hz, 1H), 6.87 (dd, J=5.3, 1.4 Hz, 1H), 6.47-6.45 (m, 1H), 4.75 (d, J=4.9 Hz, 1H), 4.38 (s, 1H), 3.81 (s, 3H), 3.51 (d, J=4.8 Hz, 1H), 3.07 (t, J=4.9 Hz, 1H), 1.33-1.28 (m, 1H), 1.19-1.13 (m, 1H), 0.42-0.39 (m, 1H), 0.20-0.15 (m, 1H).

Example 119: (1S,2S,4R,5R,6R,7S)—N-(3,4-dichlorophenyl)-7-(2-fluoropyridin-4-yl)-8-oxatricyclo[3.2.1.0²,⁴]octane-6-carboxamide

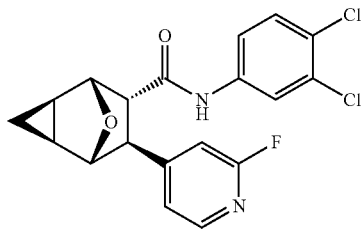 [SMILES: O=C(Nc1ccc(Cl)c(Cl)c1)[C@H]1[C@@H]2O[C@@H]([C@H]3C[C@H]32)[C@@H]1c1ccnc(F)c1]

Method B LC-MS: Rt=1.71 min; MS m/z [M+H]⁺ 393.0. ¹H NMR (400 MHz, DMSO-d₆) δ 10.27 (s, 1H), 8.16 (d, J=5.2 Hz, 1H), 8.02 (d, J=2.4 Hz, 1H), 7.57 (d, J=8.8 Hz, 1H), 7.45 (dd, J=8.8, 2.4 Hz, 1H), 7.23 (dt, J=5.2, 1.8 Hz, 1H), 7.00 (s, 1H), 4.79 (d, J=4.9 Hz, 1H), 4.44 (s, 1H), 3.65 (d, J=4.8 Hz, 1H), 3.12 (t, J=4.8 Hz, 1H), 1.34-1.30 (m, 1H), 1.20-1.16 (m, 1H), 0.43-0.40 (m, 1H), 0.19-0.17 (m, 1H).

Example 120: (1S,2S,4R,5R,6R,7S)—N-(3,4-dichlorophenyl)-7-(6-(trifluoromethyl)pyridin-2-yl)-8-oxatricyclo[3.2.1.0²,⁴]octane-6-carboxamide

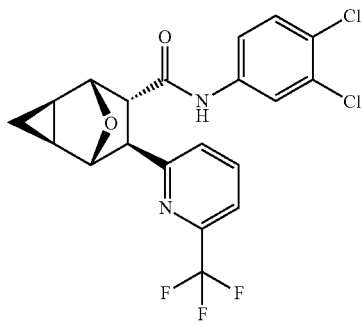 [SMILES: O=C(Nc1ccc(Cl)c(Cl)c1)[C@H]1[C@@H]2O[C@@H]([C@H]3C[C@H]32)[C@@H]1c1cccc(C(F)(F)F)n1]

Method B LC-MS: Rt=1.84 min; MS m/z [M+H]⁺ 443.0. ¹H NMR (400 MHz, DMSO-d₆) δ 10.38 (s, 1H), 8.06 (t, J=7.8 Hz, 1H), 8.02 (d, J=2.4 Hz, 1H), 7.76 (d, J=7.4 Hz, 1H), 7.73 (d, J=8.0 Hz, 1H), 7.57 (d, J=8.8 Hz, 1H), 7.48 (dd, J=8.8, 2.4 Hz, 1H), 4.77 (d, J=5.0 Hz, 1H), 4.50 (s, 1H), 3.87 (d, J=4.8 Hz, 1H), 3.68 (t, J=4.9 Hz, 1H), 1.41-1.37 (m, 1H), 1.19-1.14 (m, 1H), 0.42-0.40 (m, 1H), 0.21-0.16 (m, 1H).

Example 121: rac-(1S,2S,4R,5R,6R,7S)-7-(2-methylpyridin-4-yl)-N-(3-(trifluoromethyl)phenyl)-8-oxatricyclo[3.2.1.0²,⁴]octane-6-carboxamide Method B LC-MS: Rt=1.30 min; MS m/z [M+H]⁺ 389.1. ¹H NMR (400 MHz, DMSO-d₆) δ 10.34 (s, 1H), 8.34 (d, J=5.1 Hz, 1H), 8.13 (s, 1H), 7.74 (d, J=8.4 Hz, 1H), 7.55 (t, J=8.0 Hz, 1H), 7.40 (d, J=7.7 Hz, 1H), 7.12 (s, 1H), 7.06 (d, J=5.1 Hz, 1H), 4.77 (d, J=4.9 Hz, 1H), 4.39 (s, 1H), 3.52 (d, J=4.8 Hz, 1H), 3.10 (t, J=4.8 Hz, 1H), 2.42 (s, 3H), 1.33-1.28 (m, 1H), 1.21-1.16 (m, 1H), 0.43-0.38 (m, 1H), 0.21-0.15 (m, 1H).

Examples 121a and 121b (corresponding to Peak 1 and Peak 2)

(1S,2S,4R,5R,6R,7S)-7-(2-methylpyridin-4-yl)-N-(3-(trifluoromethyl)phenyl)-8-oxatricyclo[3.2.1.02,4]octane-6-carboxamide or (1R,2R,4S,5S,6S,7R)-7-(2-methylpyridin-4-yl)-N-(3-(trifluoromethyl)phenyl)-8-oxatricyclo[3.2.1.0²,⁴]octane-6-carboxamide

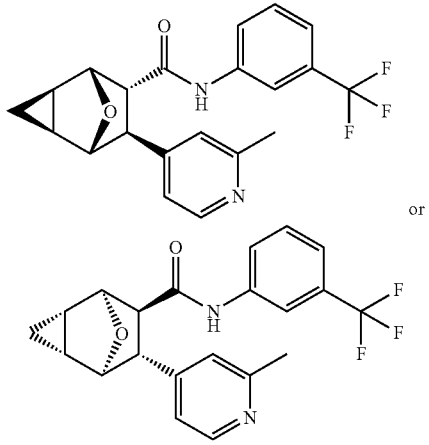

Chiral separation of rac-(1S,2S,4R,5R,6R,7S)-7-(2-methylpyridin-4-yl)-N-(3-(trifluoromethyl)phenyl)-8-oxatricyclo[3.2.1.0²,⁴]octane-6-carboxamide (Example 121) by Supercritical Fluid Chromatography using the following conditions afforded the compounds listed hereafter:

Method Details:
  Column: 21×250 mm IB @ 30° C.
  Mobile Phase: 90% CO₂/10% MeOH+0.5% isopropylamine
  Detection: UV @ 220 nm
  Flow: 2 mL/min
  Peak 1: SFC Retention Time=1.28 min. LC-MS: Rt=1.43 min; MS m/z [M+H]⁺ 389.1. ¹H NMR (400 MHz, DMSO-d₆) δ 10.32 (s, 1H), 8.34 (d, J=5.1 Hz, 1H), 8.13 (s, 1H), 7.74 (d, J=8.5 Hz, 1H), 7.55 (t, J=8.0 Hz, 1H), 7.41 (d, J=7.7 Hz, 1H), 7.12 (s, 1H), 7.06 (dd, J=5.1, 1.4 Hz, 1H), 4.77 (d, J=4.9 Hz, 1H), 4.39 (s, 1H), 3.52 (d, J=4.8 Hz, 1H), 3.10 (t, J=4.8 Hz, 1H), 2.42 (s, 3H), 1.34-1.28 (m, 1H), 1.21-1.15 (m, 1H), 0.43-0.38 (m, 1H), 0.22-0.15 (m, 1H).

Peak 2: SFC Retention Time=1.66 min. LC-MS: Rt=1.43 min; MS m/z [M+H]$^+$ 389.1. $^1$H NMR (400 MHz, DMSO-d$_6$) δ 10.32 (s, 1H), 8.34 (d, J=5.1 Hz, 1H), 8.13 (s, 1H), 7.74 (d, J=8.5 Hz, 1H), 7.55 (t, J=8.0 Hz, 1H), 7.41 (d, J=7.7 Hz, 1H), 7.12 (s, 1H), 7.06 (dd, J=5.1, 1.4 Hz, 1H), 4.77 (d, J=4.9 Hz, 1H), 4.39 (s, 1H), 3.52 (d, J=4.8 Hz, 1H), 3.10 (t, J=4.8 Hz, 1H), 2.42 (s, 3H), 1.34-1.28 (m, 1H), 1.21-1.15 (m, 1H), 0.43-0.38 (m, 1H), 0.22-0.15 (m, 1H).

Example 122: rac-(1S,2S,4R,5R,6R,7S)—N-(3,4-dichlorophenyl)-7-(2,3-difluoropyridin-4-yl)-8-oxatricyclo[3.2.1.0$^{2,4}$]octane-6-carboxamide Method B LC-MS: Rt=1.73 min; MS m/z [M+H]$^+$ 411.0. $^1$H NMR (400 MHz, DMSO-d$_6$) δ 10.29 (s, 1H), 8.01 (d, J=2.4 Hz, 1H), 8.00 (d, J=5.2 Hz, 1H), 7.57 (d, J=8.8 Hz, 1H), 7.45 (dd, J=8.8, 2.4 Hz, 1H), 7.36 (t, J=4.9 Hz, 1H), 4.79 (d, J=4.9 Hz, 1H), 4.51 (s, 1H), 3.94 (d, J=4.7 Hz, 1H), 3.12 (t, J=4.8 Hz, 1H), 1.36-1.31 (m, 1H), 1.21-1.16 (m, 1H), 0.44-0.40 (m, 1H), 0.22-0.17 (m, 1H).

Examples 122a and 122b (Corresponding to Peak 1 and Peak 2)

(1S,2S,4R,5R,6R,7S)—N-(3,4-dichlorophenyl)-7-(2,3-difluoropyridin-4-yl)-8-oxatricyclo[3.2.1.0$^{2,4}$]octane-6-carboxamide or (1R,2R,4S,5S,6S,7R)—N-(3,4-dichlorophenyl)-7-(2,3-difluoropyridin-4-yl)-8-oxatricyclo[3.2.1.0$^{2,4}$]octane-6-carboxamide

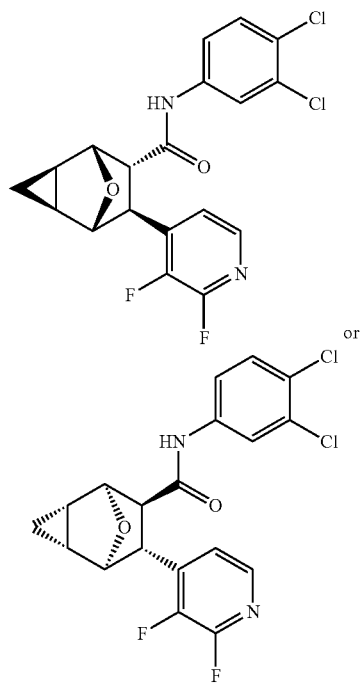

Chiral separation of rac-(1S,2S,4R,5R,6R,7S)—N-(3,4-dichlorophenyl)-7-(2,3-difluoropyridin-4-yl)-8-oxatricyclo[3.2.1.0$^{2,4}$]octane-6-carboxamide (Example 122) by Super-critical Fluid Chromatography using the following conditions afforded the compounds listed hereafter:

Method Details:
Column: 21×250 mm IB @ 30° C.
Mobile Phase: 85% CO$_2$/15% MeOH+0.5% isopropylamine
Detection: UV @ 220 nm
Flow: 2 mL/min Peak 1: SFC Retention Time=1.86 min. Method D LC-MS: Rt=1.79 min; MS m/z [M+H]+ 411.0. $^1$H NMR (400 MHz, DMSO-d$_6$) δ 10.29 (s, 1H), 8.03-7.97 (m, 2H), 7.57 (d, J=8.8 Hz, 1H), 7.45 (dd, J=8.8, 2.4 Hz, 1H), 7.36 (t, J=4.9 Hz, 1H), 4.79 (d, J=4.9 Hz, 1H), 4.51 (s, 1H), 3.94 (d, J=4.7 Hz, 1H), 3.12 (t, J=4.8 Hz, 1H), 1.37-1.31 (m, 1H), 1.22-1.17 (m, 1H), 0.45-0.39 (m, 1H), 0.22-0.17 (m, 1H).

Peak 2: SFC Retention Time=2.43 min. LC-MS: Rt=1.79 min; MS m/z [M+H]$^+$ 410.8. $^1$H NMR (400 MHz, DMSO-d$_6$) δ 10.29 (s, 1H), 8.03-7.97 (m, 2H), 7.57 (d, J=8.8 Hz, 1H), 7.45 (dd, J=8.8, 2.4 Hz, 1H), 7.36 (t, J=4.9 Hz, 1H), 4.79 (d, J=4.9 Hz, 1H), 4.51 (s, 1H), 3.94 (d, J=4.7 Hz, 1H), 3.12 (t, J=4.8 Hz, 1H), 1.37-1.31 (m, 1H), 1.22-1.17 (m, 1H), 0.45-0.39 (m, 1H), 0.22-0.17 (m, 1H).

Example 123: (1S,2S,4R,5R,6R,7S)—N-(6-methoxypyridin-3-yl)-7-(6-methylpyridin-3-yl)-8-oxatricyclo[3.2.1.0$^{2,4}$]octane-6-carboxamide

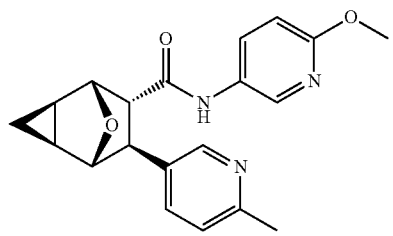 [SMILES: COc1ccc(NC(=O)[C@H]2[C@@H]3O[C@@H]([C@H]4C[C@H]43)[C@@H]2c2ccc(C)nc2)cn1]

LC-MS: Rt=1.03 min; MS m/z [M+H]$^+$ 352.0. $^1$H NMR (400 MHz, DMSO-d$_6$) δ 9.97 (s, 1H), 8.34-8.32 (m, 1H), 8.31 (d, J=2.1 Hz, 1H), 7.87 (dd, J=8.9, 2.7 Hz, 1H), 7.53 (dd, J=8.0, 2.4 Hz, 1H), 7.19 (d, J=8.0 Hz, 1H), 6.79 (dd, J=8.9, 0.5 Hz, 1H), 4.74 (d, J=4.9 Hz, 1H), 4.29 (s, 1H), 3.80 (s, 3H), 3.53 (d, J=4.8 Hz, 1H), 3.05 (t, J=4.8 Hz, 1H), 2.42 (s, 3H), 1.33-1.27 (m, 1H), 1.22-1.16 (m, 1H), 0.44-0.39 (m, 1H), 0.21-0.15 (m, 1H).

Example 124: (1S,2S,4R,5R,6R,7S)—N-(5,6-dichloropyridin-3-yl)-7-(2,3-difluoropyridin-4-yl)-8-oxatricyclo[3.2.1.0$^{2,4}$]octane-6-carboxamide

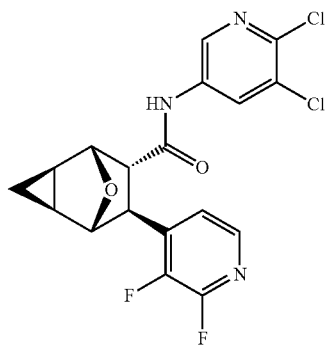 [SMILES: O=C(Nc1cnc(Cl)c(Cl)c1)[C@H]1[C@@H]2O[C@@H]([C@H]3C[C@H]32)[C@@H]1c1ccnc(F)c1F]

Method C LC-MS: Rt=1.49 min; MS m/z [M+H]⁺ 411.8.
¹H NMR (400 MHz, DMSO-d₆) δ 10.59 (s, 1H), 8.48 (d, J=2.4 Hz, 1H), 8.42 (d, J=2.4 Hz, 1H), 8.00 (d, J=5.1 Hz, 1H), 7.36 (t, J=4.9 Hz, 1H), 4.81 (d, J=4.9 Hz, 1H), 4.52 (s, 1H), 3.94 (d, J=4.7 Hz, 1H), 3.17 (t, J=4.8 Hz, 1H), 1.36-1.30 (m, 1H), 1.26-1.20 (m, 1H), 0.45-0.39 (m, 1H), 0.23-0.18 (m, 1H).

Example 125: (1S,2S,4R,5R,6R,7S)—N-(6-methoxypyridin-3-yl)-7-(pyridin-4-yl)-8-oxatricyclo[3.2.1.0²,⁴]octane-6-carboxamide

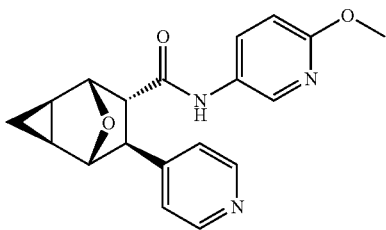 [SMILES: COc1ccc(NC(=O)[C@H]2[C@@H]3O[C@@H]([C@H]4C[C@H]43)[C@@H]2c2ccncc2)cn1]

LC-MS: Rt=1.01 min; MS m/z [M+H]⁺ 338.0. ¹H NMR (400 MHz, DMSO-d₆) δ 10.00 (s, 1H), 8.48 (d, J=5.3 Hz, 2H), 8.35-8.32 (m, 1H), 7.87 (dd, J=8.9, 2.7 Hz, 1H), 7.28-7.24 (m, 2H), 6.82-6.77 (m, 1H), 4.76 (d, J=4.9 Hz, 1H), 4.39 (s, 1H), 3.81 (s, 3H), 3.56 (d, J=4.8 Hz, 1H), 3.08 (t, J=4.8 Hz, 1H), 1.34-1.28 (m, 1H), 1.21-1.16 (m, 1H), 0.44-0.39 (m, 1H), 0.21-0.15 (m, 1H).

Example 126: rac-(1S,2S,4R,5R,6R,7S)—N-(3,4-dichlorophenyl)-7-(pyrimidin-5-yl)-8-oxatricyclo[3.2.1.0²,⁴]octane-6-carboxamide Method B LC-MS: Rt=1.46 min; MS m/z [M+H]⁺ 376.0.
¹H NMR (400 MHz, DMSO-d₆) δ 10.26 (s, 1H), 9.06 (s, 1H), 8.68 (s, 2H), 8.02 (d, J=2.4 Hz, 1H), 7.57 (d, J=8.8 Hz, 1H), 7.45 (dd, J=8.8, 2.4 Hz, 1H), 4.82 (d, J=4.9 Hz, 1H), 4.42 (s, 1H), 3.61 (d, J=4.7 Hz, 1H), 3.17 (t, J=4.8 Hz, 1H), 1.36-1.30 (m, 1H), 1.21-1.16 (m, 1H), 0.45-0.39 (m, 1H), 0.22-0.17 (m, 1H).

Examples 126a and 126b (Corresponding to Peak 1 and Peak 2)

(1S,2S,4R,5R,6R,7S)—N-(3,4-dichlorophenyl)-7-(pyrimidin-5-yl)-8-oxatricyclo[3.2.1.0²,⁴]octane-6-carboxamide or (1R,2R,4S,5S,6S,7R)—N-(3,4-dichlorophenyl)-7-(pyrimidin-5-yl)-8-oxatricyclo[3.2.1.0²,⁴]octane-6-carboxamide

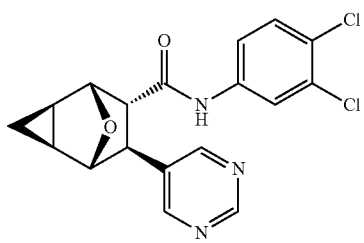

or

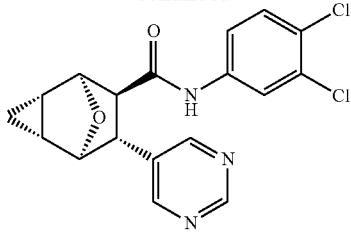

Chiral separation of rac-(1S,2S,4R,5R,6R,7S)—N-(3,4-dichlorophenyl)-7-(pyrimidin-5-yl)-8-oxatricyclo[3.2.1.0²,⁴]octane-6-carboxamide (Example 126) by Supercritical Fluid Chromatography using the following conditions afforded the compounds listed hereafter:

Method Details:

Column: 21×250 mm IB @ 30° C.

Mobile Phase: 85% CO₂/15% MeOH+0.5% isopropylamine

Detection: UV @ 220 nm

Flow: 2 mL/min

Peak 1: SFC Retention Time=1.88 min. Method B LC-MS: Rt=1.44 min; MS m/z [M+H]+ 375.8. ¹H NMR (400 MHz, DMSO-d₆) δ 10.26 (s, 1H), 9.06 (s, 1H), 8.68 (s, 2H), 8.02 (d, J=2.4 Hz, 1H), 7.57 (d, J=8.8 Hz, 1H), 7.45 (dd, J=8.8, 2.4 Hz, 1H), 4.82 (d, J=4.9 Hz, 1H), 4.42 (s, 1H), 3.61 (d, J=4.7 Hz, 1H), 3.18 (t, J=4.8 Hz, 1H), 1.36-1.29 (m, 1H), 1.22-1.17 (m, 1H), 0.44-0.39 (m, 1H), 0.23-0.17 (m, 1H).

Peak 2: SFC Retention Time=2.43 min. Method B LC-MS: Rt=1.44 min; MS m/z [M+H]+ 375.9. ¹H NMR (400 MHz, DMSO-d₆) δ 10.26 (s, 1H), 9.06 (s, 1H), 8.68 (s, 2H), 8.02 (d, J=2.4 Hz, 1H), 7.57 (d, J=8.8 Hz, 1H), 7.45 (dd, J=8.8, 2.4 Hz, 1H), 4.82 (d, J=4.9 Hz, 1H), 4.42 (s, 1H), 3.61 (d, J=4.7 Hz, 1H), 3.18 (t, J=4.8 Hz, 1H), 1.36-1.29 (m, 1H), 1.22-1.17 (m, 1H), 0.44-0.39 (m, 1H), 0.23-0.17 (m, 1H).

Example 127: (1S,2S,4R,5R,6R,7S)-7-(2,3-difluoropyridin-4-yl)-N-(6-methoxypyridin-3-yl)-8-oxatricyclo[3.2.1.0²,⁴]octane-6-carboxamide

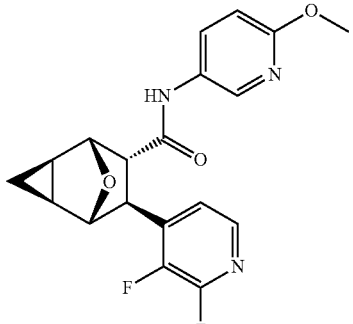

LC-MS: Rt=1.44 min; MS m/z [M+H]⁺ 374.0. ¹H NMR (400 MHz, DMSO-d₆) δ 10.02 (s, 1H), 8.35-8.32 (m, 1H), 8.00 (dd, J=5.0, 0.9 Hz, 1H), 7.88 (dd, J=8.9, 2.7 Hz, 1H), 7.36 (t, J=4.9 Hz, 1H), 6.80 (dd, J=8.9, 0.5 Hz, 1H), 4.78 (d, J=4.9 Hz, 1H), 4.49 (s, 1H), 3.94 (d, J=4.7 Hz, 1H), 3.81 (s, 3H), 3.12 (t, J=4.8 Hz, 1H), 1.36-1.30 (m, 1H), 1.24-1.19 (m, 1H), 0.44-0.38 (m, 1H), 0.23-0.17 (m, 1H).

Example 128: (1S,2S,4R,5R,6R,7S)—N-(6-methoxypyridin-3-yl)-7-(6-(trifluoromethyl)pyridin-2-yl)-8-oxatricyclo[3.2.1.0$^{2,4}$]octane-6-carboxamide

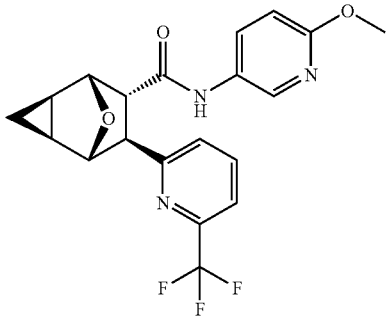 [SMILES: COc1ccc(NC(=O)[C@H]2[C@@H]3O[C@@H]([C@H]4C[C@H]43)[C@@H]2c2cccc(C(F)(F)F)n2)cn1]

LC-MS: Rt=1.76 min; MS m/z [M+H]$^+$ 406.1. $^1$H NMR (400 MHz, DMSO-d$_6$) δ 10.10 (s, 1H), 8.36 (d, J=2.7 Hz, 1H), 8.06 (t, J=7.8 Hz, 1H), 7.89 (dd, J=8.9, 2.7 Hz, 1H), 7.76 (d, J=7.7 Hz, 1H), 7.72 (d, J=8.0 Hz, 1H), 6.80 (d, J=8.9 Hz, 1H), 4.77 (d, J=5.0 Hz, 1H), 4.49 (s, 1H), 3.87 (d, J=4.8 Hz, 1H), 3.81 (s, 3H), 3.66 (t, J=4.9 Hz, 1H), 1.40-1.35 (m, 1H), 1.22-1.16 (m, 1H), 0.44-0.39 (m, 1H), 0.22-0.16 (m, 1H).

Example 129: (1S,2S,4R,5R,6R,7S)—N-(3,4-dichlorophenyl)-7-(2-fluoropyrimidin-5-yl)-8-oxatricyclo[3.2.1.0$^{2,4}$]octane-6-carboxamide

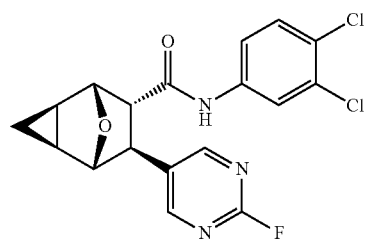 [SMILES: O=C(Nc1ccc(Cl)c(Cl)c1)[C@H]1[C@@H]2O[C@@H]([C@H]3C[C@H]32)[C@@H]1c1cnc(F)nc1]

Method B LC-MS: Rt=1.65 min; MS m/z [M+H]$^+$ 394.0. $^1$H NMR (400 MHz, DMSO-d$_6$) δ 10.26 (s, 1H), 8.64 (d, J=1.6 Hz, 2H), 8.02 (d, J=2.4 Hz, 1H), 7.57 (d, J=8.8 Hz, 1H), 7.46 (dd, J=8.8, 2.4 Hz, 1H), 4.82 (d, J=4.9 Hz, 1H), 4.41 (s, 1H), 3.68 (d, J=4.6 Hz, 1H), 3.17 (t, J=4.8 Hz, 1H), 1.35-1.29 (m, 1H), 1.22-1.16 (m, 1H), 0.45-0.39 (m, 1H), 0.23-0.18 (m, 1H).

Example 130: (1S,2S,4R,5R,6R,7S)-7-(pyrimidin-5-yl)-N-(3-(trifluoromethyl)phenyl)-8-oxatricyclo[3.2.1.0$^{2,4}$]octane-6-carboxamide

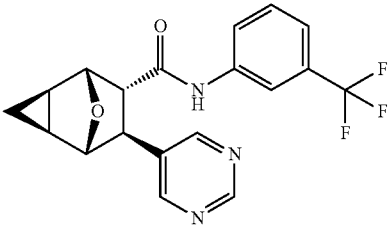 [SMILES: O=C(Nc1cccc(C(F)(F)F)c1)[C@H]1[C@@H]2O[C@@H]([C@H]3C[C@H]32)[C@@H]1c1cncnc1]

LC-MS: Rt=1.56 min; MS m/z [M+H]$^+$ 376.1. $^1$H NMR (400 MHz, DMSO-d$_6$) δ 10.31 (s, 1H), 9.06 (s, 1H), 8.69 (s, 2H), 8.13 (s, 1H), 7.74 (d, J=8.5 Hz, 1H), 7.55 (t, J=8.0 Hz, 1H), 7.41 (d, J=7.7 Hz, 1H), 4.84 (d, J=4.9 Hz, 1H), 4.43 (s, 1H), 3.63 (d, J=4.7 Hz, 1H), 3.20 (t, J=4.8 Hz, 1H), 1.37-1.32 (m, 1H), 1.24-1.18 (m, 1H), 0.45-0.39 (m, 1H), 0.23-0.17 (m, 1H).

Example 131: (1S,2S,4R,5R,6R,7S)-7-(pyridin-4-yl)-N-(3-(trifluoromethyl)phenyl)-8-oxatricyclo[3.2.1.0$^{2,4}$]octane-6-carboxamide

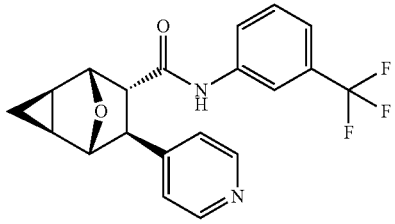 [SMILES: O=C(Nc1cccc(C(F)(F)F)c1)[C@H]1[C@@H]2O[C@@H]([C@H]3C[C@H]32)[C@@H]1c1ccncc1]

LC-MS: Rt=1.40 min; MS m/z [M+H]$^+$ 375.1. $^1$H NMR (400 MHz, DMSO-d$_6$) δ 10.32 (s, 1H), 8.48 (d, J=5.8 Hz, 2H), 8.13 (s, 1H), 7.74 (d, J=8.5 Hz, 1H), 7.55 (t, J=7.9 Hz, 1H), 7.41 (d, J=7.7 Hz, 1H), 7.27 (d, J=6.1 Hz, 2H), 4.79 (d, J=4.9 Hz, 1H), 4.41 (s, 1H), 3.58 (d, J=4.8 Hz, 1H), 3.11 (t, J=4.8 Hz, 1H), 1.36-1.30 (m, 1H), 1.20-1.15 (m, 1H), 0.44-0.40 (m, 1H), 0.22-0.17 (m, 1H).

Example 132: (1S,2S,4R,5R,6R,7S)-7-(2-aminopyrimidin-5-yl)-N-(3,4-dichlorophenyl)-8-oxatricyclo[3.2.1.0$^{2,4}$]octane-6-carboxamide

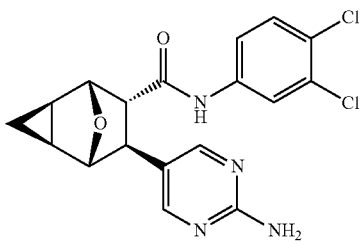 [SMILES: Nc1ncc([C@H]2[C@H]3O[C@H]([C@@H]4C[C@@H]43)[C@@H]2C(=O)Nc2ccc(Cl)c(Cl)c2)cn1]

LC-MS: Rt=1.46 min; MS m/z [M+H]$^+$ 391.0. $^1$H NMR (400 MHz, DMSO-d$_6$) δ 10.24 (s, 1H), 8.10 (s, 2H), 8.02 (d, J=2.4 Hz, 1H), 7.56 (d, J=8.8 Hz, 1H), 7.45 (dd, J=8.8, 2.4 Hz, 1H), 6.52 (s, 2H), 4.73 (d, J=4.9 Hz, 1H), 4.25 (s, 1H), 3.34 (d, J=4.0 Hz, 1H), 3.03 (t, J=4.8 Hz, 1H), 1.29-1.24 (m, 1H), 1.17-1.11 (m, 1H), 0.41-0.36 (m, 1H), 0.18-0.13 (m, 1H).

Example 133: (1S,2S,4R,5R,6R,7S)—N-(3,4-dichlorophenyl)-7-(2-morpholinopyrimidin-5-yl)-8-oxatricyclo[3.2.1.02,4]octane-6-carboxamide

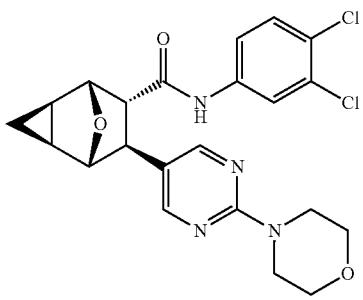 [SMILES: O=C(Nc1ccc(Cl)c(Cl)c1)[C@H]1[C@@H]2O[C@@H]([C@H]3C[C@H]32)[C@@H]1c1cnc(N2CCOCC2)nc1]

LC-MS: Rt=1.72 min; MS m/z [M+H]+ 461.1. ¹H NMR (400 MHz, DMSO-d₆) δ 10.24 (s, 1H), 8.26 (s, 2H), 8.02 (d, J=2.4 Hz, 1H), 7.56 (d, J=8.8 Hz, 1H), 7.45 (dd, J=8.8, 2.4 Hz, 1H), 4.75 (d, J=4.9 Hz, 1H), 4.27 (s, 1H), 3.64 (s, 8H), 3.41 (d, J=4.6 Hz, 1H), 3.05 (t, J=4.8 Hz, 1H), 1.31-1.25 (m, 1H), 1.18-1.13 (m, 1H), 0.43-0.38 (m, 1H), 0.20-0.14 (m, 1H).

Example 134: (1S,2S,4R,5R,6R,7S)-7-(2-fluoropyridin-4-yl)-N-(3-(trifluoromethyl)phenyl)-8-oxatricyclo[3.2.1.0²,⁴]octane-6-carboxamide

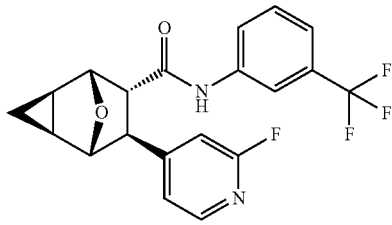 [SMILES: O=C(Nc1cccc(C(F)(F)F)c1)[C@H]1[C@@H]2O[C@@H]([C@H]3C[C@H]32)[C@@H]1c1ccnc(F)c1]

LC-MS: Rt=1.73 min; MS m/z [M+H]+ 393.1. ¹H NMR (400 MHz, DMSO-d₆) δ 10.32 (s, 1H), 8.16 (d, J=5.2 Hz, 1H), 8.13 (s, 1H), 7.74 (d, J=8.5 Hz, 1H), 7.56 (t, J=8.0 Hz, 1H), 7.44-7.35 (m, 1H), 7.27-7.21 (m, 1H), 7.01 (s, 1H), 4.81 (d, J=4.9 Hz, 1H), 4.45 (s, 1H), 3.67 (d, J=4.8 Hz, 1H), 3.14 (t, J=4.8 Hz, 1H), 1.36-1.30 (m, 1H), 1.21-1.16 (m, 1H), 0.45-0.38 (m, 1H), 0.22-1.16 (m, 1H).

Example 135: (1S,2S,4R,5R,6R,7S)—N-(3,4-dichlorophenyl)-7-(2-methylpyrimidin-5-yl)-8-oxatricyclo[3.2.1.0²,⁴]octane-6-carboxamide

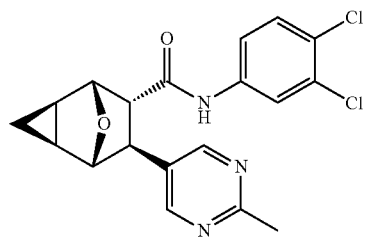 [SMILES: Cc1ncc([C@H]2[C@H]3O[C@H]([C@@H]4C[C@@H]43)[C@@H]2C(=O)Nc2ccc(Cl)c(Cl)c2)cn1]

Method B LC-MS: Rt=1.53 min; MS m/z [M+H]+ 390.0. ¹H NMR (400 MHz, DMSO-d₆) δ 10.26 (s, 1H), 8.55 (s, 2H), 8.02 (d, J=2.4 Hz, 1H), 7.57 (d, J=8.8 Hz, 1H), 7.45 (dd, J=8.8, 2.4 Hz, 1H), 4.80 (d, J=4.9 Hz, 1H), 4.37 (s, 1H), 3.56 (d, J=4.7 Hz, 1H), 3.13 (t, J=4.8 Hz, 1H), 2.58 (s, 3H), 1.35-1.29 (m, 1H), 1.20-1.15 (m, 1H), 0.44-0.38 (m, 1H), 0.22-0.16 (m, 1H).

Example 136: (1S,2S,4R,5R,6R,7S)—N-(5,6-dichloropyridin-3-yl)-7-(pyridin-4-yl)-8-oxatricyclo[3.2.1.0²,⁴]octane-6-carboxamide

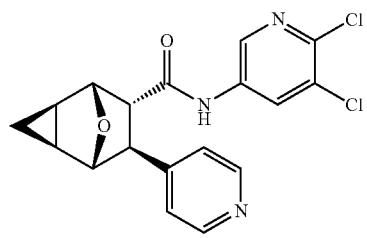 [SMILES: O=C(Nc1cnc(Cl)c(Cl)c1)[C@H]1[C@@H]2O[C@@H]([C@H]3C[C@H]32)[C@@H]1c1ccncc1]

LC-MS: Rt=1.28 min; MS m/z [M+H]+ 376.0. ¹H NMR (400 MHz, DMSO-d₆) δ 10.57 (s, 1H), 8.67 (d, J=5.7 Hz, 2H), 8.50 (d, J=2.4 Hz, 1H), 8.41 (d, J=2.4 Hz, 1H), 7.61 (d, J=5.9 Hz, 2H), 4.87-4.83 (m, 1H), 4.48 (s, 1H), 3.76-3.71 (m, 1H), 3.21-3.17 (m, 1H), 1.38-1.33 (m, 1H), 1.28-1.22 (m, 1H), 0.45-0.40 (m, 1H), 0.24-0.17 (m, 1H).

Example 137: (1S,2S,4R,5R,6R,7S)—N-(3,4-dichlorophenyl)-7-(pyridin-4-yl)-8-oxatricyclo[3.2.1.0²,⁴]octane-6-carboxamide

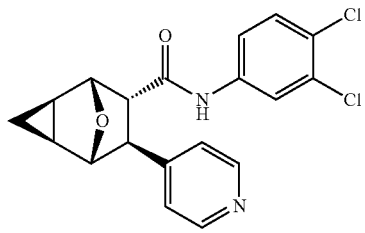 [SMILES: O=C(Nc1ccc(Cl)c(Cl)c1)[C@H]1[C@@H]2O[C@@H]([C@H]3C[C@H]32)[C@@H]1c1ccncc1]

LC-MS: Rt=1.41 min; MS m/z [M+H]+ 375.0. H NMR (500 MHz, DMSO-d₆) δ 10.25 (s, 1H), 8.47 (d, J=6.1 Hz, 2H), 8.01 (d, J=2.5 Hz, 1H), 7.56 (d, J=8.8 Hz, 1H), 7.45 (dd, J=8.8, 2.5 Hz, 1H), 7.25 (d, J=6.2 Hz, 2H), 4.77 (d, J=4.9 Hz, 1H), 4.40 (s, 1H), 3.56 (d, J=4.8 Hz, 1H), 3.09 (t, J=4.9 Hz, 1H), 1.35-1.29 (m, 1H), 1.21-1.14 (m, 1H), 0.45-0.40 (m, 1H), 0.21-0.16 (m, 1H).

Examples 138-154 described infra were synthesized according to the protocol described for Example 117 using methyl (1R,4S,5S)-3-bromo-5-hydroxy-7-oxabicyclo[2.2.1]hept-2-ene-2-carboxylate and methyl (1S,4S,6R)-3-bromo-6-hydroxy-7-oxabicyclo[2.2.1]hept-2-ene-2-carboxylate (Intermediate 1e) and various anilines in Step A and various boronic esters/acids in Step C.

Example 138: (1R,2R,3S,4R,5S)—N-(3,4-dichlorophenyl)-5-hydroxy-3-(6-methylpyridin-3-yl)-7-oxabicyclo[2.2.1]heptane-2-carboxamide

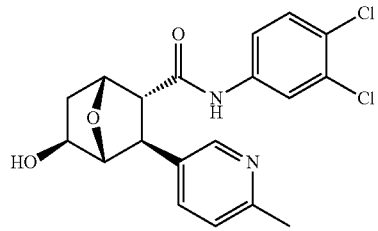 [SMILES: Cc1ccc([C@H]2[C@H]3O[C@H](C[C@@H]3O)[C@@H]2C(=O)Nc2ccc(Cl)c(Cl)c2)cn1]

LC-MS: Rt=1.17 min; MS m/z [M+H]+ 393.0. ¹H NMR (400 MHz, DMSO-d₆) δ 10.30 (s, 1H), 8.31 (dd, J=2.5, 0.8 Hz, 1H), 7.98 (d, J=2.4 Hz, 1H), 7.55 (d, J=8.7 Hz, 1H), 7.54-7.52 (m, 1H), 7.41 (dd, J=8.8, 2.5 Hz, 1H), 7.20 (d, J=8.0 Hz, 1H), 4.96 (d, J=4.7 Hz, 1H), 4.91-4.87 (m, 1H), 4.16 (s, 1H), 4.00-3.96 (m, 1H), 3.20 (d, J=5.3 Hz, 1H), 2.94-2.91 (m, 1H), 2.12-2.05 (m, 1H), 1.43-1.36 (m, 1H). ~4:1 mixture of alcohol regioisomers.

Example 139: rac-(1R,2R,3S,4R,5S)—N-(3,4-dichlorophenyl)-5-hydroxy-3-(2-methoxypyridin-4-yl)-7-oxabicyclo[2.2.1]heptane-2-carboxamide LC-MS: Rt=1.46 min; MS m/z [M+H]+ 409.0. ~4:1 mixture of alcohol regioisomers.

Examples 139a and 139b (Corresponding to Peak 1 and Peak 2)

(1R,2R,3S,4R,5S)—N-(3,4-dichlorophenyl)-5-hydroxy-3-(2-methoxypyridin-4-yl)-7-oxabicyclo[2.2.1]heptane-2-carboxamide or (1S,2S,3R,4S,5R)—N-(3,4-dichlorophenyl)-5-hydroxy-3-(2-methoxypyridin-4-yl)-7-oxabicyclo[2.2.1]heptane-2-carboxamide

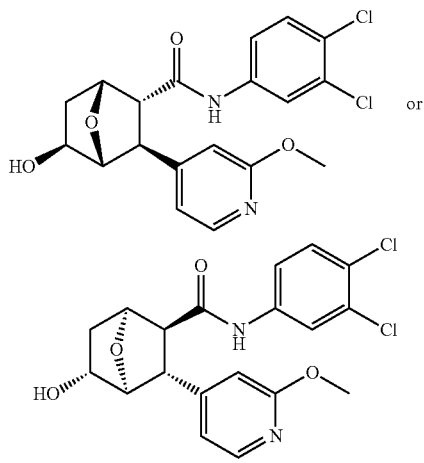

Chiral separation of rac-(1R,2R,3S,4R,5S)—N-(3,4-dichlorophenyl)-5-hydroxy-3-(2-methoxypyridin-4-yl)-7-oxabicyclo[2.2.1]heptane-2-carboxamide (Example 139) as a ~4:1 mixture of alcohol regioisomers by Supercritical Fluid Chromatography using the following conditions afforded the compounds listed hereafter:

Method Details:

Column: 21×250 mm IB @ 30° C.

Mobile Phase: 85% $CO_2$/15% MeOH+0.5% isopropylamine

Detection: UV @ 220 nm

Flow: 2 mL/min

Peak 1: SFC Retention Time=2.40 min. LC-MS: Rt=1.38 min; MS m/z [M+H]$^+$ 409.0. $^1$H NMR (400 MHz, DMSO-d$_6$) δ 10.31 (s, 1H), 8.08 (dd, J=5.3, 0.7 Hz, 1H), 7.97 (d, J=2.5 Hz, 1H), 7.56 (d, J=8.8 Hz, 1H), 7.41 (dd, J=8.8, 2.5 Hz, 1H), 6.87 (dd, J=5.3, 1.5 Hz, 1H), 6.64 (s, 1H), 5.01-4.94 (m, 1H), 4.92-4.84 (m, 1H), 4.21 (s, 1H), 4.00-3.94 (m, 1H), 3.82 (s, 3H), 3.20-3.16 (m, 1H), 2.97-2.91 (m, 1H), 2.10-2.03 (m, 1H), 1.43-1.36 (m, 1H).

Peak 2: SFC Retention Time=3.59 min. LC-MS: Rt=1.38 min; MS m/z [M+H]$^+$ 409.0. $^1$H NMR (400 MHz, DMSO-d$_6$) δ 10.31 (s, 1H), 8.08 (dd, J=5.3, 0.7 Hz, 1H), 7.97 (d, J=2.5 Hz, 1H), 7.56 (d, J=8.8 Hz, 1H), 7.41 (dd, J=8.8, 2.5 Hz, 1H), 6.87 (dd, J=5.3, 1.5 Hz, 1H), 6.64 (s, 1H), 5.01-4.94 (m, 1H), 4.92-4.84 (m, 1H), 4.21 (s, 1H), 4.00-3.94 (m, 1H), 3.82 (s, 3H), 3.20-3.16 (m, 1H), 2.97-2.91 (m, 1H), 2.10-2.03 (m, 1H), 1.43-1.36 (m, 1H).

Example 140: (1R,2R,3S,4R,5S)—N-(3,4-dichlorophenyl)-5-hydroxy-3-(6-(trifluoromethyl)pyridin-2-yl)-7-oxabicyclo[2.2.1]heptane-2-carboxamide

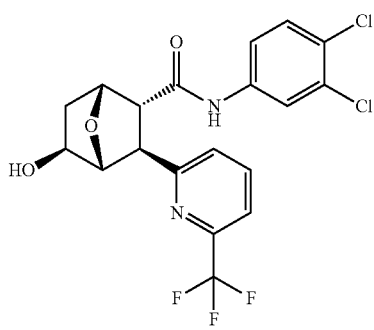 [SMILES: O=C(Nc1ccc(Cl)c(Cl)c1)[C@@H]1[C@@H](c2cccc(C(F)(F)F)n2)[C@H]2O[C@@H]1C[C@@H]2O]

LC-MS: Rt=1.69 min; MS m/z [M+H]$^+$ 447.0. Mixture of alcohol regioisomers.

Example 141: (1R,2R,3S,4R,5S)—N-(3,4-dichlorophenyl)-5-hydroxy-3-(pyrimidin-5-yl)-7-oxabicyclo[2.2.1]heptane-2-carboxamide

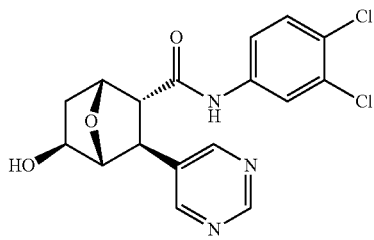

LC-MS: Rt=1.37 min; MS m/z [M+H]$^+$ 380.0. $^1$H NMR (400 MHz, DMSO-d$_6$) δ 10.31 (s, 1H), 9.07 (s, 1H), 8.69 (s, 2H), 7.98 (d, J=2.5 Hz, 1H), 7.56 (d, J=8.8 Hz, 1H), 7.41 (dd, J=8.8, 2.5 Hz, 1H), 5.05-4.99 (m, 1H), 4.98-4.93 (m, 1H), 4.27 (s, 1H), 4.03-3.97 (m, 1H), 3.31-3.28 (m, 1H), 3.05-3.01 (m, 1H), 2.13-2.04 (m, 1H), 1.46-1.35 (m, 1H). ~6:1 mixture of alcohol regioisomers.

Example 142: rac-(1R,2R,3S,4R,5S)—N-(3,4-dichlorophenyl)-3-(2-fluoropyridin-4-yl)-5-hydroxy-7-oxabicyclo[2.2.1]heptane-2-carboxamide LC-MS: Rt=1.54 min; MS m/z [M+H]$^+$ 397.0. $^1$H NMR (400 MHz, DMSO-d$_6$) δ 10.32 (s, 1H), 8.17 (d, J=5.1 Hz, 1H), 7.98 (d, J=2.4 Hz, 1H), 7.58-7.54 (m, 1H), 7.42 (dd, J=8.8, 2.5 Hz, 1H), 7.25-7.22 (m, 1H), 7.01 (s, 1H), 5.03-5.01 (m, 1H), 4.94-4.90 (m, 1H), 4.27 (s, 1H), 3.99-3.95 (m, 1H), 3.35-3.31 (m, 1H), 3.00-2.95 (m, 1H), 2.10-2.02 (m, 1H), 1.46-1.37 (m, 1H). ~4:1 mixture of alcohol regioisomers.

Examples 142a and 142b (Corresponding to Peak 1 and Peak 2A)

(1R,2R,3S,4R,5S)—N-(3,4-dichlorophenyl)-3-(2-fluoropyridin-4-yl)-5-hydroxy-7-oxabicyclo[2.2.1]heptane-2-carboxamide or (1S,2S,3R,4S,5R)—N-(3,4-dichlorophenyl)-3-(2-fluoropyridin-4-yl)-5-hydroxy-7-oxabicyclo[2.2.1]heptane-2-carboxamide

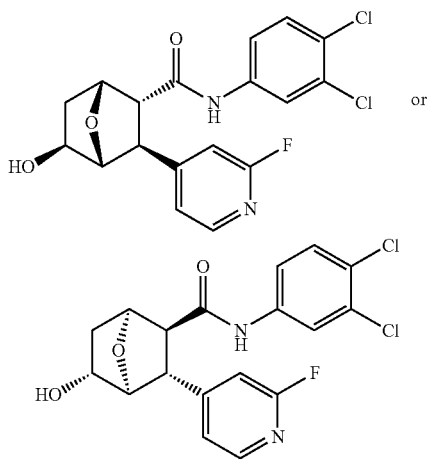

Chiral separation of rac-(1R,2R,3S,4R,5S)—N-(3,4-dichlorophenyl)-3-(2-fluoropyridin-4-yl)-5-hydroxy-7-oxabicyclo[2.2.1]heptane-2-carboxamide (Example 142) as a ~4:1 mixture of alcohol regioisomers by Supercritical Fluid Chromatography using the following conditions afforded the compounds listed hereafter:
Method Details:
 Column: 21×250 mm AD-H @ 30° C.
 Mobile Phase: 75% $CO_2$/25% MeOH+0.5% isopropylamine
 Detection: UV @ 220 nm
 Flow: 2 mL/min
Peak 1: SFC Retention Time=1.30 min. LC-MS: Rt=1.46 min; MS m/z [M+H]$^+$ 397.0. $^1$H NMR (400 MHz, DMSO-d$_6$) δ 10.32 (s, 1H), 8.17 (d, J=5.2 Hz, 1H), 7.98 (d, J=2.4 Hz, 1H), 7.56 (d, J=8.8 Hz, 1H), 7.42 (dd, J=8.8, 2.5 Hz, 1H), 7.26-7.22 (m, 1H), 7.01 (d, J=1.5 Hz, 1H), 5.05-5.00 (m, 1H), 4.95-4.89 (m, 1H), 4.27 (s, 1H), 4.01-3.95 (m, 1H), 3.33-3.30 (m, 1H), 3.01-2.96 (m, 1H), 2.11-2.03 (m, 1H), 1.46-1.39 (m, 1H).
Peak 2: The second eluting peak isolated using Supercritical Fluid Chromatography with Retention Time=4.22 min was concentrated and repurified by Supercritical Fluid Chromatography using the following conditions to afford the compound listed hereafter:
Method Details:
 Column: 21×250 mm IC @ 30° C.
 Mobile Phase: 80% $CO_2$/20% MeOH+0.5% isopropylamine
 Detection: UV @ 220 nm
 Flow: 2 mL/min
Peak 2A: First eluting peak. SFC Retention Time=1.21 min. LC-MS: Rt=1.46 min; MS m/z [M+H]$^+$ 397.0. $^1$H NMR (400 MHz, DMSO-d$_6$) δ 10.32 (s, 1H), 8.17 (d, J=5.2 Hz, 1H), 7.98 (d, J=2.4 Hz, 1H), 7.56 (d, J=8.8 Hz, 1H), 7.42 (dd, J=8.8, 2.5 Hz, 1H), 7.26-7.22 (m, 1H), 7.01 (d, J=1.5 Hz, 1H), 5.05-5.00 (m, 1H), 4.95-4.89 (m, 1H), 4.27 (s, 1H), 4.01-3.95 (m, 1H), 3.33-3.30 (m, 1H), 3.01-2.96 (m, 1H), 2.11-2.03 (m, 1H), 1.46-1.39 (m, 1H).

Example 143: (1R,2R,3S,4R,5S)-3-(2-aminopyrimidin-5-yl)-N-(3,4-dichlorophenyl)-5-hydroxy-7-oxabicyclo[2.2.1]heptane-2-carboxamide

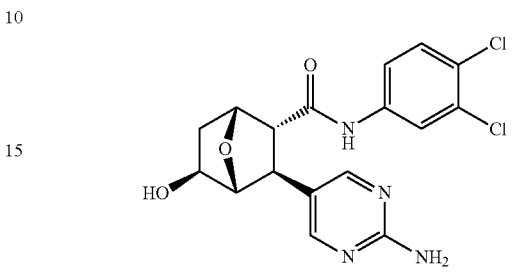

LC-MS: Rt=1.27 min; MS m/z [M+H]$^+$ 395.0. $^1$H NMR (500 MHz, DMSO-d$_6$) δ 10.27 (s, 1H), 8.10 (s, 2H), 7.97 (d, J=2.4 Hz, 1H), 7.55 (d, J=8.8 Hz, 1H), 7.42 (dd, J=8.8, 2.4 Hz, 1H), 6.48 (s, 2H), 4.93-4.90 (m, 1H), 4.88-4.83 (m, 1H), 4.11 (s, 1H), 3.96-3.93 (m, 1H), 3.03-2.99 (m, 1H), 2.91-2.88 (m, 1H), 2.09-2.04 (m, 1H), 1.42-1.34 (m, 1H). ~5:1 mixture of alcohol regioisomers.

Example 144: (1R,2R,3S,4R,5S)—N-(3,4-dichlorophenyl)-3-(2-(dimethylamino)pyrimidin-5-yl)-5-hydroxy-7-oxabicyclo[2.2.1]heptane-2-carboxamide

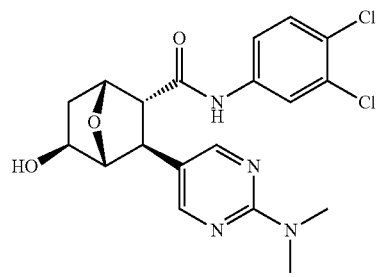 [SMILES: CN(C)c1ncc([C@H]2[C@H]3O[C@H](C[C@@H]3O)[C@@H]2C(=O)Nc2ccc(Cl)c(Cl)c2)cn1]

LC-MS: Rt=1.39 min; MS m/z [M+H]$^+$ 423.0. $^1$H NMR (500 MHz, DMSO-d$_6$) δ 10.27 (s, 1H), 8.22 (s, 2H), 7.97 (d, J=2.4 Hz, 1H), 7.55 (d, J=8.8 Hz, 1H), 7.42 (dd, J=8.8, 2.4 Hz, 1H), 4.94-4.91 (m, 1H), 4.89-4.86 (m, 1H), 4.12 (s, 1H), 3.97-3.93 (m, 1H), 3.08 (s, 6H), 3.06-3.04 (m, 1H), 2.91-2.88 (m, 1H), 2.11-2.06 (m, 1H), 1.41-1.35 (m, 1H). ~4:1 mixture of alcohol regioisomers.

Example 145: rac-(1R,2R,3S,4R,5S)—N-(3,4-dichlorophenyl)-5-hydroxy-3-(2-(trifluoromethyl)pyridin-4-yl)-7-oxabicyclo[2.2.1]heptane-2-carboxamide LC-MS: Rt=1.63 min; MS m/z [M+H]$^+$ 447.0. $^1$H NMR (500 MHz, DMSO-d$_6$) δ 10.28 (s, 1H), 8.68 (d, J=5.0 Hz, 1H), 7.97 (d, J=2.4 Hz, 1H), 7.73 (s, 1H), 7.61-7.59 (m, 1H), 7.56 (d, J=8.8 Hz, 1H), 7.41 (dd, J=8.8, 2.5 Hz, 1H), 5.01-4.99 (m, 1H), 4.97-4.93 (m, 1H), 4.28 (s, 1H), 4.04-3.98 (m, 1H), 3.42-3.39 (m, 1H), 3.05-2.99 (m, 1H), 2.13-2.05 (m, 1H), 1.47-1.39 (m, 1H). ~5:1 mixture of alcohol regioisomers.

Examples 145a and 145b (Corresponding to Peak 1 and Peak 2)

(1R,2R,3S,4R,5S)—N-(3,4-dichlorophenyl)-5-hydroxy-3-(2-(trifluoromethyl)pyridin-4-yl)-7-oxabicyclo[2.2.1]heptane-2-carboxamide or (1S,2S,3R,4S,5R)—N-(3,4-dichlorophenyl)-5-hydroxy-3-(2-(trifluoromethyl)pyridin-4-yl)-7-oxabicyclo[2.2.1]heptane-2-carboxamide

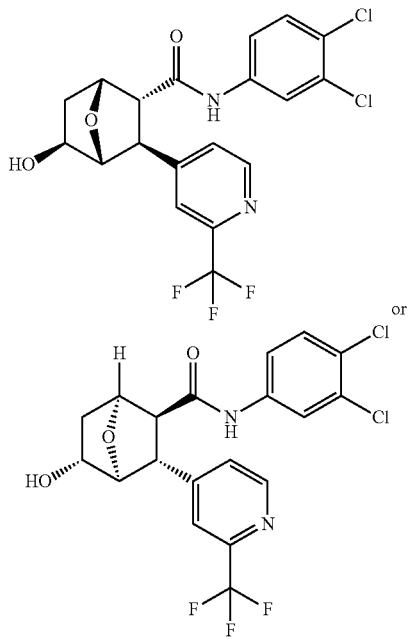

Chiral separation of rac-(1R,2R,3S,4R,5S)—N-(3,4-dichlorophenyl)-5-hydroxy-3-(2-(trifluoromethyl)pyridin-4-yl)-7-oxabicyclo[2.2.1]heptane-2-carboxamide (Example 145) as a ~5:1 mixture of alcohol regioisomers by Supercritical Fluid Chromatography using the following conditions afforded the compounds listed hereafter:

Method Details:
Column: 21×250 mm AD-H @ 30° C.
Mobile Phase: 90% $CO_2$/10% MeOH+0.5% isopropylamine
Detection: UV @ 220 nm
Flow: 2 mL/min Peak 1: SFC Retention Time=3.44 min. LC-MS: Rt=1.71 min; MS m/z [M+H]$^+$ 447.1. $^1$H NMR (400 MHz, DMSO-d$_6$) δ 10.30 (s, 1H), 8.68 (d, J=5.1 Hz, 1H), 7.98 (d, J=2.4 Hz, 1H), 7.73 (s, 1H), 7.61-7.59 (m, 1H), 7.56 (d, J=8.8 Hz, 1H), 7.41 (dd, J=8.8, 2.4 Hz, 1H), 5.03-4.99 (m, 1H), 4.97-4.93 (m, 1H), 4.27 (s, 1H), 4.04-3.98 (m, 1H), 3.43-3.39 (m, 1H), 3.05-2.99 (m, 1H), 2.12-2.05 (m, 1H), 1.47-1.39 (m, 1H).

Peak 2: SFC Retention Time=4.56 min. LC-MS: Rt=1.71 min; MS m/z [M+H]$^+$ 447.0. $^1$H NMR (400 MHz, DMSO-d$_6$) δ 10.30 (s, 1H), 8.68 (d, J=5.1 Hz, 1H), 7.98 (d, J=2.4 Hz, 1H), 7.73 (s, 1H), 7.61-7.59 (m, 1H), 7.56 (d, J=8.8 Hz, 1H), 7.41 (dd, J=8.8, 2.4 Hz, 1H), 5.03-4.99 (m, 1H), 4.97-4.93 (m, 1H), 4.27 (s, 1H), 4.04-3.98 (m, 1H), 3.44-3.38 (m, 1H), 3.05-2.99 (m, 1H), 2.12-2.05 (m, 1H), 1.48-1.39 (m, 1H).

Example 146: (1R,2R,3S,4R,5S)—N-(3,4-dichlorophenyl)-3-(2,3-difluoropyridin-4-yl)-5-hydroxy-7-oxabicyclo[2.2.1]heptane-2-carboxamide

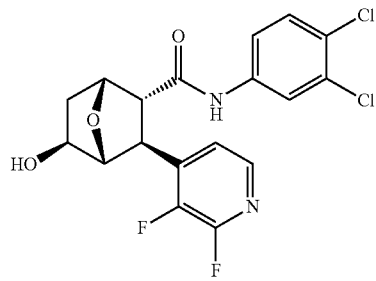 [SMILES: O=C(Nc1ccc(Cl)c(Cl)c1)[C@@H]1[C@@H](c2ccnc(F)c2F)[C@H]2O[C@@H]1C[C@@H]2O]

LC-MS: Rt=1.58 min; MS m/z [M+H]$^+$ 415.0. $^1$H NMR (500 MHz, DMSO-d$_6$) δ 10.32 (s, 1H), 8.01 (d, J=5.2, Hz, 1H), 7.97 (d, J=2.4 Hz, 1H), 7.56 (d, J=8.8 Hz, 1H), 7.42 (dd, J=8.9, 2.5 Hz, 1H), 7.38 (t, J=4.9 Hz, 1H), 5.09-5.04 (m, 1H), 4.96-4.90 (m, 1H), 4.36 (s, 1H), 4.02-3.96 (m, 1H), 3.63-3.58 (m, 1H), 3.02-2.96 (m, 1H), 2.13-2.05 (m, 1H), 1.47-1.40 (m, 1H). ~5:1 mixture of alcohol regioisomers.

Example 147: (1R,2R,3S,4R,5S)—N-(3,4-dichlorophenyl)-3-(2,5-difluoropyridin-4-yl)-5-hydroxy-7-oxabicyclo[2.2.1]heptane-2-carboxamide

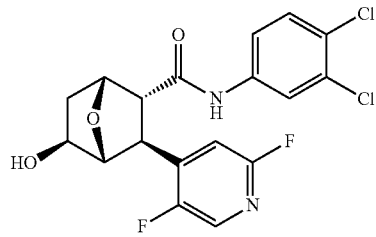 [SMILES: O=C(Nc1ccc(Cl)c(Cl)c1)[C@@H]1[C@@H](c2cc(F)ncc2F)[C@H]2O[C@@H]1C[C@@H]2O]

LC-MS: Rt=1.57 min; MS m/z [M+H]$^+$ 415.0. $^1$H NMR (500 MHz, DMSO-d$_6$) δ 10.30 (s, 1H), 8.18 (d, J=1.3 Hz, 1H), 7.97 (d, J=2.4 Hz, 1H), 7.57 (d, J=8.8 Hz, 1H), 7.42 (dd, J=8.8, 2.5 Hz, 1H), 7.14 (dd, J=4.7, 2.1 Hz, 1H), 5.08-5.01 (m, 1H), 4.94-4.88 (m, 1H), 4.41 (s, 1H), 4.01-3.97 (m, 1H), 3.54-3.50 (m, 1H), 3.02-2.98 (m, 1H), 2.13-2.07 (m, 1H), 1.46-1.37 (m, 1H). ~4:1 mixture of alcohol regioisomers.

Example 148: (1R,2R,3S,4R,5S)—N-(3,4-dichlorophenyl)-5-hydroxy-3-(2-methylpyrimidin-5-yl)-7-oxabicyclo[2.2.1]heptane-2-carboxamide

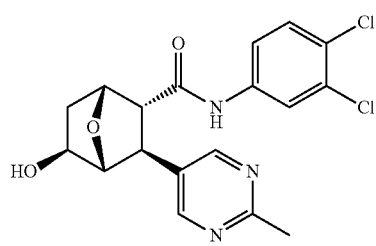 [SMILES: Cc1ncc([C@H]2[C@H]3O[C@H](C[C@@H]3O)[C@@H]2C(=O)Nc2ccc(Cl)c(Cl)c2)cn1]

LC-MS: Rt=1.37 min; MS m/z [M+H]+ 394.0. ¹H NMR (500 MHz, DMSO-d₆) δ 10.28 (s, 1H), 8.56 (s, 2H), 7.97 (dd, J=2.6, 1.0 Hz, 1H), 7.55 (dd, J=8.8, 1.0 Hz, 1H), 7.41 (ddd, J=8.8, 2.5, 1.0 Hz, 1H), 4.99-4.96 (m, 1H), 4.94-4.91 (m, 1H), 4.22 (s, 1H), 4.02-3.97 (m, 1H), 3.26-3.22 (m, 1H), 3.01-2.97 (m, 1H), 2.57 (s, 3H), 2.12-2.06 (m, 1H), 1.44-1.38 (m, 1H). ~4:1 mixture of alcohol regioisomers.

Example 149: (1R,2R,3S,4R,5S)-3-(2-aminopyridin-4-yl)-N-(3,4-dichlorophenyl)-5-hydroxy-7-oxabicyclo[2.2.1]heptane-2-carboxamide

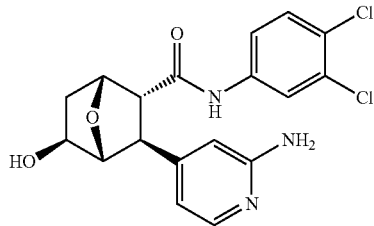 [SMILES: Nc1cc([C@H]2[C@H]3O[C@H](C[C@@H]3O)[C@@H]2C(=O)Nc2ccc(Cl)c(Cl)c2)ccn1]

LC-MS: Rt=1.29 min; MS m/z [M+H]+ 394.0. ¹H NMR (500 MHz, DMSO-d₆) δ 10.31 (s, 1H), 7.98-7.96 (m, 1H), 7.80 (d, J=5.2 Hz, 1H), 7.56 (d, J=8.9 Hz, 1H), 7.44-7.40 (m, 1H), 6.37-6.30 (m, 2H), 5.84 (s, 2H), 4.95-4.91 (m, 1H), 4.85-4.81 (m, 1H), 4.20 (s, 1H), 3.95-3.91 (m, 1H), 3.01-2.98 (m, 1H), 2.90-2.86 (m, 1H), 2.07-2.00 (m, 1H), 1.41-1.35 (m, 1H). ~4:1 mixture of alcohol regioisomers.

Example 150: (1R,2R,3S,4R,5S)—N-(3,4-dichlorophenyl)-5-hydroxy-3-(pyridin-4-yl)-7-oxabicyclo[2.2.1]heptane-2-carboxamide

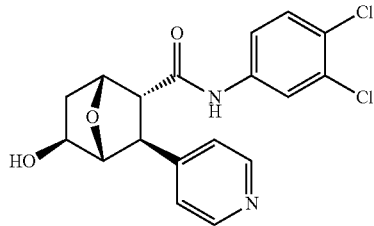 [SMILES: O=C(Nc1ccc(Cl)c(Cl)c1)[C@@H]1[C@@H](c2ccncc2)[C@H]2O[C@@H]1C[C@@H]2O]

LC-MS: Rt=1.25 min; MS m/z [M+H]+ 379.0. ¹H NMR (500 MHz, DMSO-d₆) δ 10.31 (s, 1H), 8.50-8.47 (m, 2H), 7.97 (d, J=2.4 Hz, 1H), 7.56 (d, J=8.8 Hz, 1H), 7.42 (dd, J=8.9, 2.5 Hz, 1H), 7.28-7.24 (m, 2H), 4.99-4.96 (m, 1H), 4.93-4.86 (m, 1H), 4.25 (s, 1H), 4.04-3.97 (m, 1H), 3.25-3.20 (m, 1H), 2.99-2.95 (m, 1H), 2.11-2.04 (m, 1H), 1.45-1.38 (m, 1H). ~4:1 mixture of alcohol regioisomers.

Example 151: (1R,2R,3S,4R,5S)—N-(3,4-dichlorophenyl)-3-(2-fluoropyrimidin-5-yl)-5-hydroxy-7-oxabicyclo[2.2.1]heptane-2-carboxamide

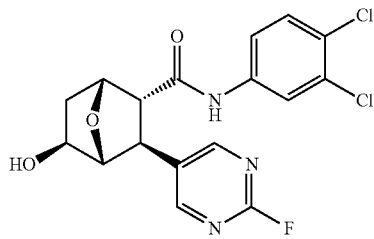 [SMILES: O=C(Nc1ccc(Cl)c(Cl)c1)[C@@H]1[C@@H](c2cnc(F)nc2)[C@H]2O[C@@H]1C[C@@H]2O]

LC-MS: Rt=1.44 min; MS m/z [M+H]+ 398.0. ¹H NMR (400 MHz, DMSO-d₆) δ 10.34 (s, 1H), 8.65 (d, J=1.7 Hz, 2H), 7.99 (d, J=2.4 Hz, 1H), 7.58-7.54 (m, 1H), 7.42 (dd, J=8.8, 2.5 Hz, 1H), 5.04-5.01 (m, 1H), 4.97-4.92 (m, 1H), 4.27 (s, 1H), 4.02-3.95 (m, 1H), 3.39-3.36 (m, 1H), 3.06-3.02 (m, 1H), 2.12-2.04 (m, 1H), 1.46-1.38 (m, 1H). ~2:1 mixture of alcohol regioisomers.

Example 152: (1R,2R,3S,4R,5S)—N-(3,4-dichlorophenyl)-5-hydroxy-3-(1-methyl-1H-pyrazol-4-yl)-7-oxabicyclo[2.2.1]heptane-2-carboxamide

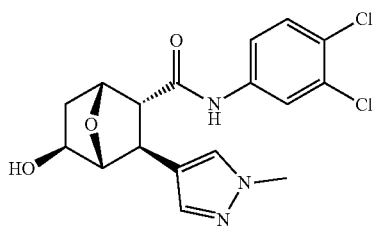 [SMILES: Cn1cc([C@H]2[C@H]3O[C@H](C[C@@H]3O)[C@@H]2C(=O)Nc2ccc(Cl)c(Cl)c2)cn1]

LC-MS: Rt=0.95 min; MS m/z [M+H]+ 382.1. Mixture of alcohol regioisomers.

Example 153: (1R,2R,3S,4R,5S)—N-(3,4-dichlorophenyl)-5-hydroxy-3-(1-methyl-1H-pyrazol-3-yl)-7-oxabicyclo[2.2.1]heptane-2-carboxamide

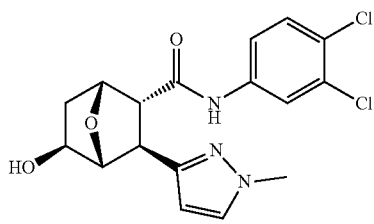 [SMILES: Cn1ccc([C@H]2[C@H]3O[C@H](C[C@@H]3O)[C@@H]2C(=O)Nc2ccc(Cl)c(Cl)c2)n1]

LC-MS: Rt=0.97 min; MS m/z [M+H]+ 382.1. ¹H NMR (500 MHz, DMSO-d₆) δ 10.40 (s, 1H), 7.98 (d, J=2.4 Hz, 1H), 7.58-7.55 (m, 2H), 7.46 (dd, J=8.8, 2.4 Hz, 1H), 6.06 (d, J=2.2 Hz, 1H), 4.95-4.86 (m, 1H), 4.81-4.76 (m, 1H), 4.20 (s, 1H), 3.97-3.90 (m, 1H), 3.75 (s, 3H), 3.27-3.22 (m, 1H), 3.21-3.17 (m, 1H), 2.04-1.97 (m, 1H), 1.38-1.32 (m, 1H). ~4:1 mixture of alcohol regioisomers.

Example 154: (1R,2R,3S,4R,5S)—N-(3,4-dichlorophenyl)-5-hydroxy-3-(2-(trifluoromethyl)pyrimidin-5-yl)-7-oxabicyclo[2.2.1]heptane-2-carboxamide

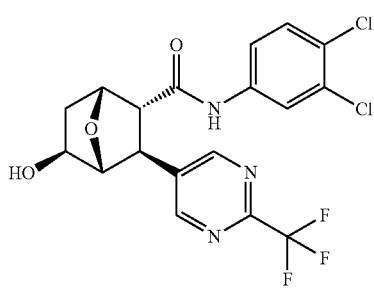 [SMILES: O=C(Nc1ccc(Cl)c(Cl)c1)[C@@H]1[C@@H](c2cnc(C(F)(F)F)nc2)[C@H]2O[C@@H]1C[C@@H]2O]

LC-MS: Rt=1.13 min; MS m/z [M+H]+ 448.1. ¹H NMR (500 MHz, DMSO-d₆) δ 10.33 (s, 1H), 8.93 (s, 2H), 7.98 (d, J=2.4 Hz, 1H), 7.55 (d, J=8.9 Hz, 1H), 7.41 (dd, J=8.8, 2.5 Hz, 1H), 5.09-5.02 (m, 1H), 5.02-4.95 (m, 1H), 4.36 (s, 1H), 4.05-3.98 (m, 1H), 3.47-3.42 (m, 1H), 3.12-3.07 (m, 1H), 2.15-2.06 (m, 1H), 1.50-1.40 (m, 1H). ~5:1 mixture of alcohol regioisomers.

Example 155: (1R,2R,3S,4R,5S)—N-(3,4-dichlorophenyl)-5-methoxy-3-(2-methylpyridin-4-yl)-7-oxabicyclo[2.2.1]heptane-2-carboxamide

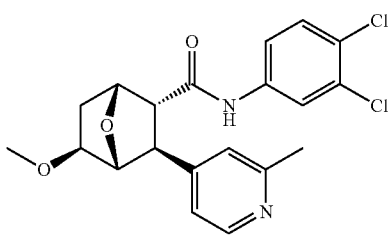 [SMILES: CO[C@H]1C[C@H]2O[C@@H]1[C@H](c1ccnc(C)c1)[C@H]2C(=O)Nc1ccc(Cl)c(Cl)c1]

Example 155 described infra was synthesized according to the protocol described for Example 117 using methyl (1R,4S,5S)-3-bromo-5-methoxy-7-oxabicyclo[2.2.1]hept-2-ene-2-carboxylate and methyl (1S,4S,6R)-3-bromo-6-methoxy-7-oxabicyclo[2.2.1]hept-2-ene-2-carboxylate (Intermediate 1f) and dichloroaniline in Step A and (2-methylpyridin-4-yl)boronic acid in Step C. LC-MS: Rt=1.39 min; MS m/z [M+H]+ 407.0. Mixture of alcohol regioisomers.

Examples 156 and 157 (Corresponding to Peak 1 and Peak 2)

(1S,2R,3S,4R,5S,6R)—N-(3,4-dichlorophenyl)-5,6-dihydroxy-3-(2-methylpyridin-4-yl)-7-oxabicyclo[2.2.1]heptane-2-carboxamide or (1R,2S,3R,4S,5R,6S)—N-(3,4-dichlorophenyl)-5,6-dihydroxy-3-(2-methylpyridin-4-yl)-7-oxabicyclo[2.2.1]heptane-2-carboxamide

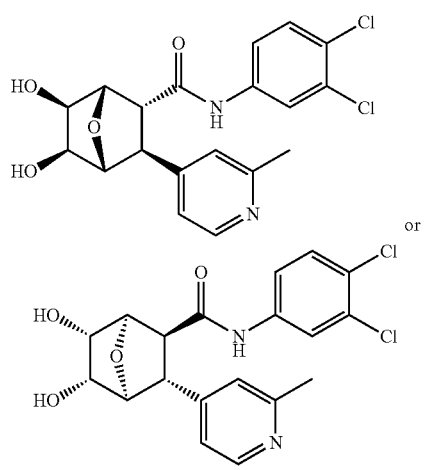

Title compound was prepared from methyl 3-bromo-7-oxabicyclo[2.2.1]hepta-2,5-diene-2-carboxylate (Intermediate 1c) using Steps A-E and Step G as in Scheme 5 followed by separation of enantiomers by chiral chromatography.

Step A: To a solution of the methyl 3-bromo-7-oxabicyclo[2.2.1]hepta-2,5-diene-2-carboxylate (10.0 g, 43.3 mmol) in 1:1 acetone/water (200 mL) was added NMO (5.85 g, 43.3 mmol) at 0° C. followed by dropwise addition of osmium tetroxide (0.220 g, 0.866 mmol) in acetone (15 mL) at 0° C. The resulting reaction mixture was slowly warmed up to RT and then stirred overnight at RT. The solvent was concentrated and the resulting residue was extracted with DCM (100 mL 3×). The combined DCM layers were dried over anhydrous Na₂SO₄, filtered, and concentrated. The resulting residue was purified by FCC to afford methyl 3-bromo-5,6-dihydroxy-7-oxabicyclo[2.2.1]hept-2-ene-2-carboxylate (6.5 g, 54%). ¹H NMR (400 MHz, CDCl₃) δ 5.01 (d, J=1.4 Hz, 1H), 4.75 (d, J=1.4 Hz, 1H), 4.18-3.91 (m, 2H), 3.83 (s, 3H), 3.19 (d, J=6.4 Hz, 1H), 3.03 (d, J=6.3 Hz, 1H).

Step B: To a suspension of methyl 3-bromo-5,6-dihydroxy-7-oxabicyclo[2.2.1]hept-2-ene-2-carboxylate (3.81 g, 14.4 mmol) in toluene (150 mL) was added (dimethoxymethyl)benzene (2.63 g, 17.3 mmol) and pTsOH (137 mg, 0.719 mmol). The resulting reaction mixture was heated at 70° C. for 30 min. The reaction mixture was concentrated and was purified by FCC to afford methyl 6-bromo-2-phenyl-3a,4,7,7a-tetrahydro-4,7-epoxybenzo[d][1,3]dioxole-5-carboxylate as a 2:1 mixture of diastereomers. ¹H NMR (400 MHz, CDCl₃) δ 7.58 (m, 1H), 7.51-7.35 (m, 6.5H), 6.37 (s, 1H), 6.04 (s, 0.5H), 5.32 (d, J=1.2 Hz, 1H), 5.22 (d, J=1.2 Hz, 0.5H), 5.05 (d, J=1.2 Hz, 1H), 4.95 (d, J=1.2 Hz, 0.5H), 4.77-4.68 (m, 2H), 4.68-4.63 (m, 1H), 3.85 (s, 4.5H). 2:1 mixture of diastereomers:

Step C: To a solution of 3,4-dichloroaniline (0.628 g, 3.87 mmol) in toluene (30 mL) was added 2.0 M Me₃Al in toluene (2.10 ml, 4.20 mmol) at 0° C. The reaction mixture was stirred for 1 h and then a solution of methyl 6-bromo-2-phenyl-3a,4,7,7a-tetrahydro-4,7-epoxybenzo[d][1,3]dioxole-5-carboxylate (1.14 g, 3.23 mmol) in toluene (20 mL) was added dropwise at 0° C. The resulting reaction mixture was allowed to warm to RT and was stirred at RT overnight. The reaction mixture was quenched with saturated aqueous NH₄Cl and was diluted with EtOAc and water. The aqueous layer was extracted with EtOAc and the combined organic solvents was washed with water and brine, dried over anhydrous Na₂SO₄, filtered and concentrated. The resulting residue was purified by FCC to afford (3aS,4S,7S,7aS)-6-bromo-N-(3,4-dichlorophenyl)-2-phenyl-3a,4,7,7a-tetrahydro-4,7-epoxybenzo[d][1,3]dioxole-5-carboxamide (450 mg, 26%). LC-MS: Rt=1.76 min; MS m/z [M+H]+ 482.0.

Step D: To a stirring solution of (3aS,4S,7S,7aS)-6-bromo-N-(3,4-dichlorophenyl)-2-phenyl-3a,4,7,7a-tetrahydro-4,7-epoxybenzo[d][1,3]dioxole-5-carboxamide (650 mg, 1.307 mmol) In THF (40 mL) and water (10 mL) at 0° C. was added acetic acid (0.299 mL, 5.23 mmol) followed by the portionwise addition of zinc powder (342 mg, 5.23 mmol). The reaction slurry was allowed to warm to RT and was stirred for 15 minutes. The reaction mixture was filtered and neutralized with saturated aqueous sodium bicarbonate to pH 7. The mixture was extracted with ethyl acetate and the organic layer was washed with water and brine, dried over anhydrous sodium sulfate, filtered, and concentrated. The resulting crude mixture was purified by RP HPLC to afford (3aS,4S,7R,7aR)—N-(3,4-dichlorophenyl)-2-phenyl-3a,4,7,7a-tetrahydro-4,7-epoxybenzo[d][1,3]dioxole-5-carboxamide, which was used directly for the next step. LC-MS: Rt=1.62 and 1.66 min; MS m/z [M+H]$^+$ 404.1.

Step E: A mixture of (3aS,4S,7R,7aR)—N-(3,4-dichlorophenyl)-2-phenyl-3a,4,7,7a-tetrahydro-4,7-epoxybenzo[d][1,3]dioxole-5-carboxamide (180 mg, 0.445 mmol), 2-methyl-4-(4,4,5,5-tetramethyl-1,3,2-dioxaborolan-2-yl)pyridine (117 mg, 0.534 mmol), chloro(1,5-cyclooctadiene)rhodium(I) dimer (11.0 mg, 0.022 mmol), 2,2'-bis(diphenylphosphino)-1,1'-binaphthalene (28 mg, 0.045 mmol), and potassium carbonate (30.8 mg, 0.223 mmol) was charged with 3:1 1,4-dioxane/H$_2$O (16 mL) and was purged with nitrogen. The resulting reaction mixture was warmed at 100° C. for 1 h in the microwave. The reaction mixture was filtered and was purified by RP HPLC to afford (4S,5R,6S,7R)—N-(3,4-dichlorophenyl)-6-(2-methylpyridin-4-yl)-2-phenylhexahydro-4,7-epoxybenzo[d][1,3]dioxole-5-carboxamide. LC-MS: Rt=1.43 min; MS m/z [M+H]$^+$ 497.2.

Step G: To a solution of (4S,5R,6S,7R)—N-(3,4-dichlorophenyl)-6-(2-methylpyridin-4-yl)-2-phenylhexahydro-4,7-epoxybenzo[d][1,3]dioxole-5-carboxamide (133 mg, 0.267 mmol) and 1,2,3,4,5-pentamethylbenzene (119 mg, 0.802 mmol) in DCM (3.0 mL) was added dropwise 1.0 M BCl$_3$ in DCM (1.34 mL, 1.34 mmol) at 0° C. The resulting reaction mixture was stirred for 1 h at 0° C. and then was allowed to warm to RT and was stirred for 1 h. The reaction mixture was quenched with saturated aqueous NaHCO$_3$, and the aqueous layer was extracted with DCM. The combined organic layers were dried over Na$_2$SO$_4$, filtered and concentrated to get the crude product, which was purified by HPLC to afford rac-(1S,2R,3S,4R,5S,6R)—N-(3,4-dichlorophenyl)-5,6-dihydroxy-3-(2-methylpyridin-4-yl)-7-oxabicyclo[2.2.1]heptane-2-carboxamide as a mixture of enantiomers. LC-MS: Rt=1.06 min; MS m/z [M+H]$^+$ 409.1.

Chiral separation of rac-(1S,2R,3S,4R,5S,6R)—N-(3,4-dichlorophenyl)-5,6-dihydroxy-3-(2-methylpyridin-4-yl)-7-oxabicyclo[2.2.1]heptane-2-carboxamide by Supercritical Fluid Chromatography using the following conditions afforded the compounds listed hereafter:
Method Details:
  Column: 21×250 mm IA @ 30° C.
  Mobile Phase: 75% CO$_2$/25% MeOH+0.5% isopropylamine
  Detection: UV @ 220 nm
  Flow: 2 mL/min
  Peak 1: SFC Retention Time=1.47 min. LC-MS: Rt=1.07 min; MS m/z [M+H]$^+$ 409.1. $^1$H NMR (400 MHz, DMSO-d$_6$) δ 10.58 (s, 1H), 8.40 (d, J=5.3 Hz, 1H), 8.01 (d, J=2.4 Hz, 1H), 7.59 (d, J=8.8 Hz, 1H), 7.48 (dd, J=8.8, 2.5 Hz, 1H), 7.23 (d, J=1.7 Hz, 1H), 7.16 (dd, J=5.5, 1.7 Hz, 1H), 4.98 (brs, 1H), 4.83 (brs, 1H), 4.61 (dd, J=5.6, 1.6 Hz, 1H), 4.23 (d, J=1.5 Hz, 1H), 3.92 (q, J=4.6 Hz, 2H), 3.00 (t, J=5.5 Hz, 1H), 2.47 (s, 3H).
  Peak 2: SFC Retention Time=2.54 min. LC-MS: Rt=1.07 min; MS m/z [M+H]$^+$ 409.2.

Examples 158-163 described infra were synthesized according to the protocol described for Example 156 using methyl 3-bromo-7-oxabicyclo[2.2.1]hepta-2,5-diene-2-carboxylate (Intermediate 1c) and various anilines in Step C and various boronic esters/acids in Step E.

Example 158: (1S,2R,3S,4R,5S,6R)-5,6-dihydroxy-3-(2-methylpyridin-4-yl)-N-(3-(trifluoromethyl)phenyl)-7-oxabicyclo[2.2.1]heptane-2-carboxamide

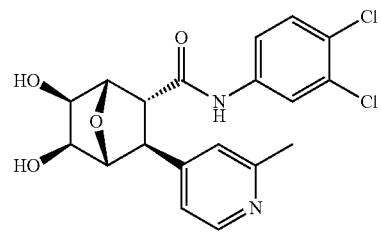 [SMILES: Cc1cc([C@H]2[C@H]3O[C@H]([C@H](O)[C@@H]3O)[C@@H]2C(=O)Nc2ccc(Cl)c(Cl)c2)ccn1]

LC-MS: Rt=1.05 min; MS m/z [M+H]$^+$ 409.2.

Example 159: (1S,2R,3S,4R,5S,6R)-5,6-dihydroxy-3-(pyridin-4-yl)-N-(3-(trifluoromethyl)phenyl)-7-oxabicyclo[2.2.1]heptane-2-carboxamide

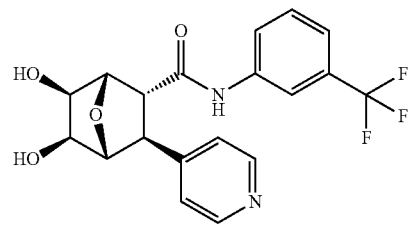 [SMILES: O=C(Nc1cccc(C(F)(F)F)c1)[C@H]1[C@@H]2O[C@@H]([C@@H](O)[C@H]2O)[C@@H]1c1ccncc1]

LC-MS: Rt=1.07 min; MS m/z [M+H]$^+$ 395.2.

Example 160: (1S,2R,3S,4R,5S,6R)—N-(3,4-dichlorophenyl)-5,6-dihydroxy-3-(pyridin-4-yl)-7-oxabicyclo[2.2.1]heptane-2-carboxamide

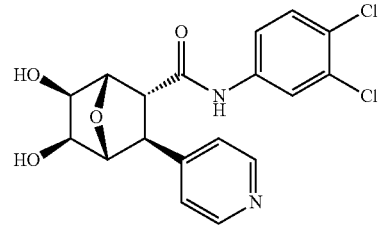 [SMILES: O=C(Nc1ccc(Cl)c(Cl)c1)[C@H]1[C@@H]2O[C@@H]([C@@H](O)[C@H]2O)[C@@H]1c1ccncc1]

LC-MS: Rt=1.08 min; MS m/z [M+H]$^+$ 395.1.

Example 161: (1S,2R,3S,4R,5S,6R)-5,6-dihydroxy-3-(2-methylpyridin-4-yl)-N-(2-(trifluoromethyl)pyridin-4-yl)-7-oxabicyclo[2.2.1]heptane-2-carboxamide

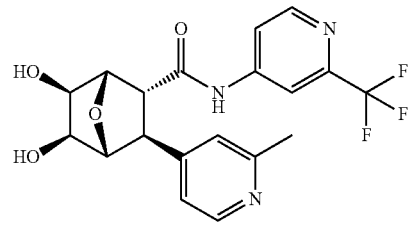 [SMILES: Cc1cc([C@H]2[C@H]3O[C@H]([C@H](O)[C@@H]3O)[C@@H]2C(=O)Nc2ccnc(C(F)(F)F)c2)ccn1]

LC-MS: Rt=0.85 min; MS m/z [M+H]$^+$ 410.2.

Example 162: (1S,2R,3S,4R,5S,6R)—N-(5,6-dichloropyridin-3-yl)-5,6-dihydroxy-3-(2-methylpyridin-4-yl)-7-oxabicyclo[2.2.1]heptane-2-carboxamide

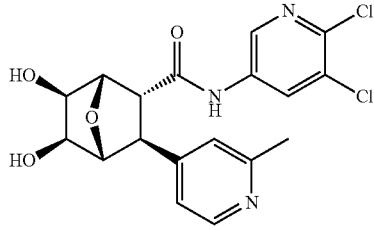 [SMILES: Cc1cc([C@H]2[C@H]3O[C@H]([C@H](O)[C@@H]3O)[C@@H]2C(=O)Nc2cnc(Cl)c(Cl)c2)ccn1]

LC-MS: Rt=0.96 min; MS m/z [M+H]+ 410.1. 1H NMR (400 MHz, DMSO-$d_6$) δ 10.73 (s, 1H), 8.48 (d, J=2.4 Hz, 1H), 8.40-8.36 (m, 2H), 7.18 (s, 1H), 7.12 (dd, J=5.3, 1.7 Hz, 1H), 4.94 (s, 2H), 4.63-4.58 (m, 1H), 4.24-4.21 (m, 1H), 3.96-3.90 (m, 2H), 3.35-3.28 (m, 1H), 3.03-2.97 (m, 1H), 2.45 (s, 3H).

Example 163: (1S,2R,3S,4R,5S,6R)-5,6-dihydroxy-N-(6-methyl-5-(trifluoromethyl)pyridin-3-yl)-3-(2-methylpyridin-4-yl)-7-oxabicyclo[2.2.1]heptane-2-carboxamide

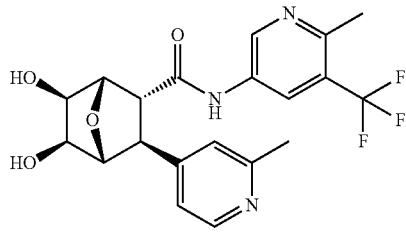 [SMILES: Cc1cc([C@H]2[C@H]3O[C@H]([C@H](O)[C@@H]3O)[C@@H]2C(=O)Nc2cnc(C)c(C(F)(F)F)c2)ccn1]

LC-MS: Rt=0.92 min; MS m/z [M+H]+ 424.2. 1H NMR (400 MHz, DMSO-$d_6$) δ 10.63 (s, 1H), 8.78 (d, J=2.4 Hz, 1H), 8.41 (d, J=2.5 Hz, 1H), 8.39 (d, J=5.5 Hz, 1H), 7.22 (s, 1H), 7.16 (dd, J=5.4, 1.7 Hz, 1H), 4.94 (s, 1H), 4.85 (s, 1H), 4.63-4.58 (m, 1H), 4.24-4.21 (m, 1H), 3.97-3.90 (m, 2H), 3.36-3.32 (m, 1H), 3.05-2.99 (m, 1H), 2.59-2.56 (m, 3H), 2.46 (s, 3H).

Example 164: (1R,2R,3S,4R,5R)—N-(3,4-dichlorophenyl)-5-fluoro-3-(6-methylpyridin-3-yl)-7-oxabicyclo[2.2.1]heptane-2-carboxamide

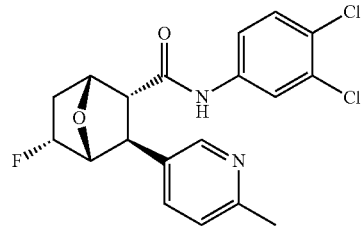 [SMILES: Cc1ccc([C@H]2[C@H]3O[C@H](C[C@H]3F)[C@@H]2C(=O)Nc2ccc(Cl)c(Cl)c2)cn1]

Title compound was prepared from (1R,2R,3S,4R,5S)—N-(3,4-dichlorophenyl)-5-hydroxy-3-(6-methylpyridin-3-yl)-7-oxabicyclo[2.2.1]heptane-2-carboxamide (5a, wherein R$_2$=3,4-dichlorophenyl and Ar=6-methylpyridin-3-yl, Example 138) using Step A as in Scheme 6.

Step A: To a stirring solution of (1R,2R,3S,4R,5S)—N-(3,4-dichlorophenyl)-5-hydroxy-3-(6-methylpyridin-3-yl)-7-oxabicyclo[2.2.1]heptane-2-carboxamide (25 mg, 0.064 mmol) in DCM (1 mL) at room temperature was added Xtalfluor-E (22 mg, 0.095 mmol) and triethylamine trihydrofluoride (0.021 mL, 0.127 mmol). The reaction mixture was stirred for 16 h, was cooled to 0° C. and quenched with saturated aqueous sodium bicarbonate solution. The crude mixture was extracted with DCM 3×. The combined organic layer was dried over anhydrous sodium sulfate, filtered, and concentrated. The crude compound was purified by FCC to afford (1R,2R,3S,4R,5R)—N-(3,4-dichlorophenyl)-5-fluoro-3-(6-methylpyridin-3-yl)-7-oxabicyclo[2.2.1]heptane-2-carboxamide. LC-MS: Rt=1.46 min; MS m/z [M+H]+ 395.0. 1H NMR (500 MHz, DMSO-$d_6$) δ 10.62 (s, 1H), 8.41 (d, J=2.4 Hz, 1H), 7.99 (d, J=2.4 Hz, 1H), 7.59-7.56 (m, 2H), 7.49 (dd, J=8.8, 2.4 Hz, 1H), 7.24 (d, J=8.1 Hz, 1H), 5.27 (d, J=71.0 Hz, 1H), 4.85-4.77 (m, 1H), 3.81-3.76 (m, 1H), 3.15-3.13 (m, 1H), 3.12-3.09 (m, 1H), 2.44 (s, 3H), 1.99-1.91 (m, 2H). >20:1 mixture of alcohol regioisomers.

Example 165: (1R,2R,3S,4R,5R)—N-(3,4-dichlorophenyl)-5-fluoro-3-(2-methoxypyridin-4-yl)-7-oxabicyclo[2.2.1]heptane-2-carboxamide

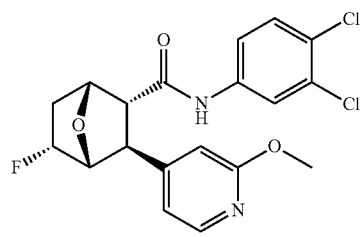 [SMILES: COc1cc([C@H]2[C@H]3O[C@H](C[C@H]3F)[C@@H]2C(=O)Nc2ccc(Cl)c(Cl)c2)ccn1]

Example 165 was synthesized according to the protocol described for Example 164 using (1R,2R,3S,4R,5S)—N-(3,4-dichlorophenyl)-5-hydroxy-3-(2-methoxypyridin-4-yl)-7-oxabicyclo[2.2.1]heptane-2-carboxamide (5a, wherein R$_2$=3,4-dichlorophenyl and Ar=2-methoxypyridin-4-yl, Example 139) in Step A. LC-MS: Rt=1.74 min; MS m/z [M+H]+ 411.0. 1H NMR (500 MHz, DMSO-$d_6$) δ 10.64 (s, 1H), 8.13-8.12 (m, 1H), 7.99 (d, J=2.4 Hz, 1H), 7.58 (d, J=8.8 Hz, 1H), 7.49 (dd, J=8.8, 2.4 Hz, 1H), 6.95-6.92 (m, 1H), 6.75 (s, 1H), 5.31-5.13 (m, 1H), 4.84-4.81 (m, 1H), 3.85 (s, 3H), 3.80-3.76 (m, 1H), 3.25-3.21 (m, 1H), 3.11-3.08 (m, 1H), 1.97-1.91 (m, 2H). ~2:1 mixture of alcohol regioisomers.

Example 166: (1R,2R,3S,4R,5R)—N-(3,4-dichlorophenyl)-5-(dimethylamino)-3-(2-methylpyridin-4-yl)-7-oxabicyclo[2.2.1]heptane-2-carboxamide

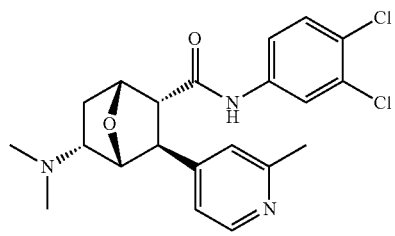 [SMILES: Cc1cc([C@H]2[C@H]3O[C@H](C[C@H]3N(C)C)[C@@H]2C(=O)Nc2ccc(Cl)c(Cl)c2)ccn1]

Title compound was prepared from (1R,2R,3S,4R,5S)—N-(3,4-dichlorophenyl)-5-hydroxy-3-(2-methylpyridin-4-yl)-7-oxabicyclo[2.2.1]heptane-2-carboxamide (5a, wherein R₂=3,4-dichlorophenyl and Ar=2-methylpyridin-4-yl, Example 77) using Steps B and C as in Scheme 6.

Step B: To a stirring solution of (1R,2R,3S,4R,5S)—N-(3,4-dichlorophenyl)-5-hydroxy-3-(2-methylpyridin-4-yl)-7-oxabicyclo[2.2.1]heptane-2-carboxamide (200 mg, 0.509 mmol) in THF (5 mL) at RT was added Dess-Martin reagent (431 mg, 1.02 mmol) and the reaction was stirred at room temperature for 16 h. The reaction mixture was diluted with EtOAc, washed with sat. aq. NaHCO₃ and brine, dried (Na₂SO₄), filtered, and concentrated. The resulting residue was purified by FCC to afford (1R,2R,3S,4R)—N-(3,4-dichlorophenyl)-3-(2-methylpyridin-4-yl)-5-oxo-7-oxabicyclo[2.2.1]heptane-2-carboxamide. LC-MS: Rt=1.22 min; MS m/z [M+H]⁺ 391.0.

Step C: To a stirring solution of (1R,2R,3S,4R)—N-(3,4-dichlorophenyl)-3-(2-methylpyridin-4-yl)-5-oxo-7-oxabicyclo[2.2.1]heptane-2-carboxamide (20 mg, 0.051 mmol) in DCM (2 mL) was added one drop of acetic acid and dimethylamine in THF (0.153 mL, 0.307 mmol). The reaction was cooled to 0° C. and sodium borohydride (4 mg, 0.102 mmol) was added. The reaction was stirred at RT for 30 minutes, then was warmed at 50° C. for 2 h. The reaction mixture was cooled to room temperature and was filtered and the filtrate was concentrated. The crude compound was purified by RP HPLC to afford (1R,2R,3S,4R,5R)—N-(3,4-dichlorophenyl)-5-(dimethylamino)-3-(2-methylpyridin-4-yl)-7-oxabicyclo[2.2.1]heptane-2-carboxamide. LC-MS: Rt=1.12 min; MS m/z [M+H]⁺ 420.1. ¹H NMR (400 MHz, DMSO-d₆) δ 10.21 (s, 1H), 8.35 (d, J=5.1 Hz, 1H), 8.00 (d, J=2.5 Hz, 1H), 7.55 (d, J=8.8 Hz, 1H), 7.43 (dd, J=8.8, 2.5 Hz, 1H), 7.12 (s, 1H), 7.06 (d, J=5.3 Hz, 1H), 4.94-4.87 (m, 1H), 4.48-4.42 (m, 1H), 4.13-4.08 (m, 1H), 3.10-3.04 (m, 1H), 2.43 (s, 3H), 2.42-2.35 (m, 1H), 2.12 (s, 6H), 1.89-1.79 (m, 1H), 1.48-1.40 (m, 1H). >20:1 mixture of alcohol regioisomers.

Examples 167-177 described infra were synthesized according to the protocol described for Example 166 using intermediate 5a and various amines in Step C.

Example 167: (1R,2R,3S,4R,5R)—N-(3,4-dichlorophenyl)-5-(methylamino)-3-(2-methylpyridin-4-yl)-7-oxabicyclo[2.2.1]heptane-2-carboxamide

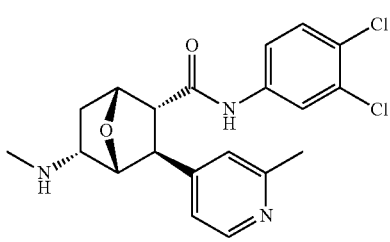 [SMILES: CN[C@@H]1C[C@H]2O[C@@H]1[C@H](c1ccnc(C)c1)[C@H]2C(=O)Nc1ccc(Cl)c(Cl)c1]

LC-MS: Rt=1.10 min; MS m/z [M+H]⁺ 406.2. ¹H NMR (400 MHz, DMSO-d₆) δ 10.44 (s, 1H), 8.37-8.32 (m, 1H), 8.00 (d, J=2.4 Hz, 1H), 7.56 (d, J=8.8 Hz, 1H), 7.45 (dd, J=8.8, 2.5 Hz, 1H), 7.14 (s, 1H), 7.08 (dd, J=5.2, 1.7 Hz, 1H), 4.90-4.84 (m, 1H), 4.49-4.44 (m, 1H), 3.99-3.95 (m, 1H), 3.16 (s, 1H), 3.15-3.11 (m, 1H), 3.09-3.02 (m, 1H), 2.43 (s, 3H), 2.28 (s, 3H), 1.99-1.89 (m, 1H), 1.28-1.20 (m, 1H). >20:1 mixture of alcohol regioisomers.

Example 168: (1R,2R,3S,4R,5R)—N-(3,4-dichlorophenyl)-5-((2-hydroxyethyl)amino)-3-(2-methylpyridin-4-yl)-7-oxabicyclo[2.2.1]heptane-2-carboxamide

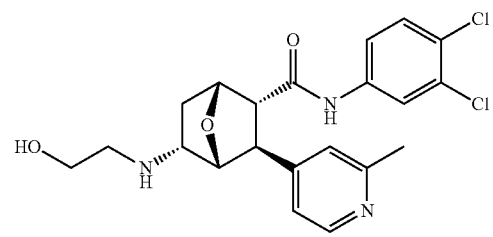

LC-MS: Rt=1.06 min; MS m/z [M+H]⁺ 436.2. ¹H NMR (400 MHz, DMSO-d₆) δ 10.47 (s, 1H), 8.35 (dd, J=5.1, 0.7 Hz, 1H), 8.01 (d, J=2.4 Hz, 1H), 7.56 (d, J=8.8 Hz, 1H), 7.45 (dd, J=8.8, 2.5 Hz, 1H), 7.14 (d, J=1.7 Hz, 1H), 7.08 (dd, J=5.2, 1.7 Hz, 1H), 4.87-4.84 (m, 1H), 4.60-4.54 (m, 1H), 4.48-4.44 (m, 1H), 4.01-3.97 (m, 1H), 3.50-3.43 (m, 2H), 3.22-3.11 (m, 3H), 2.59-2.53 (m, 2H), 2.44 (s, 3H), 2.02-1.93 (m, 1H), 1.28-1.20 (m, 1H). >20:1 mixture of alcohol regioisomers.

Example 169: (1R,2R,3S,4R,5R)—N-(3,4-dichlorophenyl)-3-(2-methylpyridin-4-yl)-5-((tetrahydro-2H-pyran-4-yl)amino)-7-oxabicyclo[2.2.1]heptane-2-carboxamide

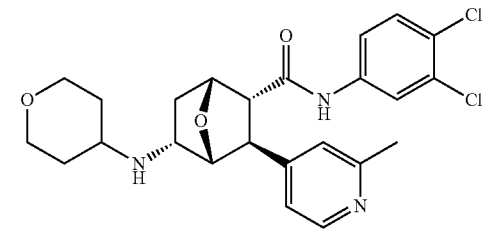 [SMILES: Cc1cc([C@H]2[C@H]3O[C@H](C[C@H]3NC3CCOCC3)[C@@H]2C(=O)Nc2ccc(Cl)c(Cl)c2)ccn1]

LC-MS: Rt=1.16 min; MS m/z [M+H]⁺ 476.2. Mixture of alcohol regioisomers.

Example 170: (1R,2R,3S,4R,5R)—N-(3,4-dichlorophenyl)-5-(((1r,3R)-3-hydroxycyclobutyl)amino)-3-(2-methylpyridin-4-yl)-7-oxabicyclo[2.2.1]heptane-2-carboxamide

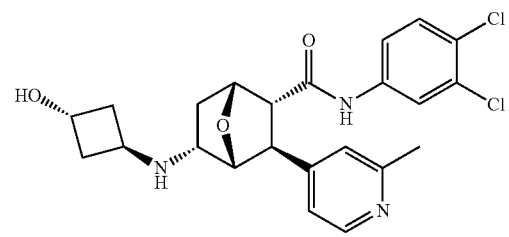 [SMILES: Cc1cc([C@H]2[C@H]3O[C@H](C[C@H]3N[C@H]3C[C@H](O)C3)[C@@H]2C(=O)Nc2ccc(Cl)c(Cl)c2)ccn1]

LC-MS: Rt=1.07 min; MS m/z [M+H]⁺ 462.2. Mixture of alcohol regioisomers.

Example 171: (1R,2R,3S,4R,5R)—N-(3,4-dichloro-phenyl)-3-(2-fluoropyridin-4-yl)-5-(methylamino)-7-oxabicyclo[2.2.1]heptane-2-carboxamide

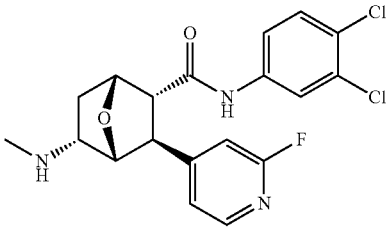 [SMILES: CN[C@@H]1C[C@H]2O[C@@H]1[C@H](c1ccnc(F)c1)[C@H]2C(=O)Nc1ccc(Cl)c(Cl)c1]

LC-MS: Rt=1.26 min; MS m/z [M+H]+ 410.2. 1H NMR (400 MHz, DMSO-d6) δ 10.33 (s, 1H), 8.17 (d, J=5.2 Hz, 1H), 8.00 (d, J=2.4 Hz, 1H), 7.57 (d, J=8.8 Hz, 1H), 7.44 (dd, J=8.8, 2.4 Hz, 1H), 7.28-7.25 (m, 1H), 7.03 (s, 1H), 4.93-4.86 (m, 1H), 4.56-4.51 (m, 1H), 4.14-4.09 (m, 1H), 3.33-3.30 (m, 1H), 3.16-3.12 (m, 1H), 3.10-3.02 (m, 1H), 2.28 (s, 3H), 1.98-1.90 (m, 1H), 1.27-1.21 (m, 1H). >20:1 mixture of alcohol regioisomers.

Example 172: (1R,2R,3S,4R,5R)—N-(3,4-dichloro-phenyl)-5-(dimethylamino)-3-(2-fluoropyridin-4-yl)-7-oxabicyclo[2.2.1]heptane-2-carboxamide

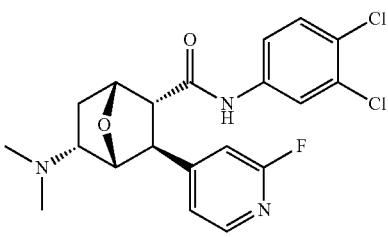 [SMILES: CN(C)[C@@H]1C[C@H]2O[C@@H]1[C@H](c1ccnc(F)c1)[C@H]2C(=O)Nc1ccc(Cl)c(Cl)c1]

LC-MS: Rt=1.25 min; MS m/z [M+H]+ 424.2. 1H NMR (400 MHz, DMSO-d6) δ 10.20 (s, 1H), 8.17 (d, J=5.3 Hz, 1H), 8.00 (d, J=2.4 Hz, 1H), 7.56 (d, J=8.8 Hz, 1H), 7.46-7.42 (m, 1H), 7.25-7.21 (m, 1H), 7.00 (s, 1H), 4.97-4.92 (m, 1H), 4.55-4.51 (m, 1H), 4.25-4.18 (m, 1H), 3.13-3.08 (m, 1H), 2.43-2.37 (m, 1H), 2.12 (s, 6H), 1.90-1.81 (m, 1H), 1.47-1.39 (m, 1H). >20:1 mixture of alcohol regioisomers.

Example 173: (1R,2R,3S,4R,5R)—N-(3,4-dichloro-phenyl)-3-(2-fluoropyridin-4-yl)-5-((2-hydroxyethyl)amino)-7-oxabicyclo[2.2.1]heptane-2-carboxamide

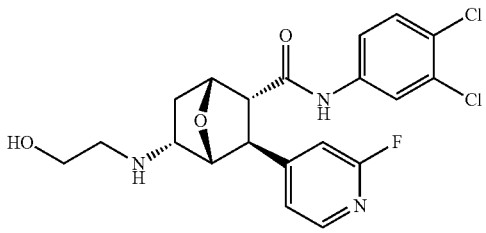 [SMILES: O=C(Nc1ccc(Cl)c(Cl)c1)[C@@H]1[C@@H](c2ccnc(F)c2)[C@H]2O[C@@H]1C[C@H]2NCCO]

LC-MS: Rt=1.21 min; MS m/z [M+H]+ 440.2. 1H NMR (400 MHz, DMSO-d6) δ 10.36 (s, 1H), 8.18 (d, J=5.2 Hz, 1H), 8.00 (d, J=2.4 Hz, 1H), 7.57 (d, J=8.8 Hz, 1H), 7.44 (dd, J=8.8, 2.4 Hz, 1H), 7.28-7.24 (m, 1H), 7.03 (d, J=1.4 Hz, 1H), 4.91-4.84 (m, 1H), 4.59-4.55 (m, 1H), 4.53 (d, J=4.6 Hz, 1H), 4.13 (d, J=5.5 Hz, 1H), 3.50-3.43 (m, 2H), 3.36-3.31 (m, 1H), 3.22-3.13 (m, 2H), 2.62-2.52 (m, 2H), 2.04-1.94 (m, 1H), 1.29-1.22 (m, 1H). >20:1 mixture of alcohol regioisomers.

Example 174: (1R,2R,3S,4R,5R)—N-(5,6-dichloro-pyridin-3-yl)-3-(2-fluoropyridin-4-yl)-5-(methyl-amino)-7-oxabicyclo[2.2.1]heptane-2-carboxamide

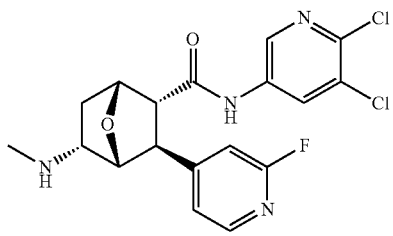 [SMILES: CN[C@@H]1C[C@H]2O[C@@H]1[C@H](c1ccnc(F)c1)[C@H]2C(=O)Nc1cnc(Cl)c(Cl)c1]

LC-MS: Rt=1.11 min; MS m/z [M+H]+ 411.2. 1H NMR (400 MHz, DMSO-d6) δ 10.60 (s, 1H), 8.47 (d, J=2.4 Hz, 1H), 8.40 (d, J=2.4 Hz, 1H), 8.17 (d, J=5.2 Hz, 1H), 7.29-7.25 (m, 1H), 7.04 (s, 1H), 4.94-4.90 (m, 1H), 4.58-4.51 (m, 1H), 4.17-4.12 (m, 1H), 3.33-3.29 (m, 1H), 3.20-3.16 (m, 1H), 3.10-3.04 (m, 1H), 2.27 (s, 3H), 1.99-1.91 (m, 1H), 1.29-1.22 (m, 1H). >20:1 mixture of alcohol regioisomers.

Example 175: (1R,2R,3S,4R,5R)—N-(5,6-dichloro-pyridin-3-yl)-5-(dimethylamino)-3-(2-fluoropyridin-4-yl)-7-oxabicyclo[2.2.1]heptane-2-carboxamide

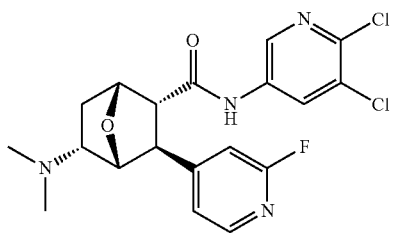

LC-MS: Rt=1.13 min; MS m/z [M+H]+ 425.2. 1H NMR (400 MHz, DMSO-d6) δ 10.46 (s, 1H), 8.47 (d, J=2.4 Hz, 1H), 8.41 (d, J=2.4 Hz, 1H), 8.18 (d, J=5.2 Hz, 1H), 7.26-7.24 (m, 1H), 7.02-7.00 (m, 1H), 4.98-4.94 (m, 1H), 4.57-4.53 (m, 1H), 4.25-4.19 (m, 1H), 3.17-3.11 (m, 1H), 2.44-2.36 (m, 1H), 2.12 (s, 6H), 1.91-1.81 (m, 1H), 1.48-1.38 (m, 1H). >20:1 mixture of alcohol regioisomers.

Example 176: (1R,2R,3S,4R,5R)—N-(5,6-dichloro-pyridin-3-yl)-3-(2-fluoropyridin-4-yl)-5-((2-hy-droxyethyl)amino)-7-oxabicyclo[2.2.1]heptane-2-carboxamide

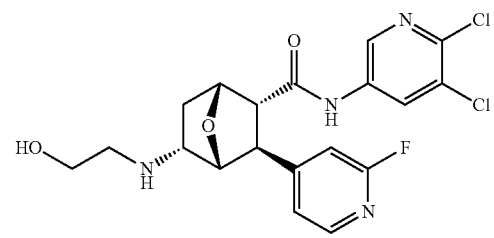

LC-MS: Rt=1.08 min; MS m/z [M+H]+ 441.2. ¹H NMR (400 MHz, DMSO-d₆) δ 10.64 (s, 1H), 8.47 (d, J=2.4 Hz, 1H), 8.42 (d, J=2.3 Hz, 1H), 8.18 (d, J=5.2 Hz, 1H), 7.28-7.25 (m, 1H), 7.03 (s, 1H), 4.92-4.86 (m, 1H), 4.60-4.53 (m, 2H), 4.15 (d, J=5.6 Hz, 1H), 3.50-3.43 (m, 2H), 3.35-3.29 (m, 1H), 3.24-3.15 (m, 2H), 2.63-2.52 (m, 2H), 2.04-1.94 (m, 1H), 1.26 (dd, J=12.8, 4.7 Hz, 1H). >20:1 mixture of alcohol regioisomers.

Example 177: (1R,2R,3S,4R,5R)—N-(3,4-dichlorophenyl)-3-(2-methylpyridin-4-yl)-5-morpholino-7-oxabicyclo[2.2.1]heptane-2-carboxamide

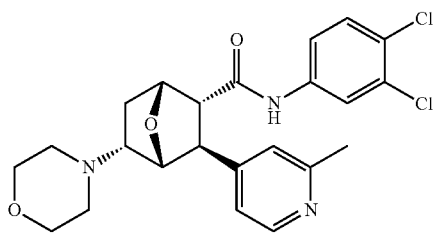 [SMILES: Cc1cc([C@H]2[C@H]3O[C@H](C[C@H]3N3CCOCC3)[C@@H]2C(=O)Nc2ccc(Cl)c(Cl)c2)ccn1]

LC-MS: Rt=1.15 min; MS m/z [M+H]+ 462.1. Mixture of alcohol regioisomers.

Example 178: (1R,2R,3S,4R,5R)—N-(3,4-dichlorophenyl)-5-hydroxy-5-methyl-3-(2-methylpyridin-4-yl)-7-oxabicyclo[2.2.1]heptane-2-carboxamide

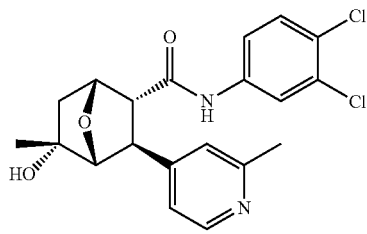 [SMILES: Cc1cc([C@@H]2[C@@H](C(=O)Nc3ccc(Cl)c(Cl)c3)[C@H]3C[C@@](C)(O)[C@@H]2O3)ccn1]

Title compound was prepared from single enantiomer (1R,2R,3S,4R,5S)—N-(3,4-dichlorophenyl)-5-hydroxy-3-(2-methylpyridin-4-yl)-7-oxabicyclo[2.2.1]heptane-2-carboxamide (5a, wherein R₂=3,4-dichlorophenyl and Ar=2-methylpyridin-4-yl, Example 77a) using Steps B and D as in Scheme 6.

Step B: To a stirring solution of (1R,2R,3S,4R,5S)—N-(3,4-dichlorophenyl)-5-hydroxy-3-(2-methylpyridin-4-yl)-7-oxabicyclo[2.2.1]heptane-2-carboxamide (200 mg, 0.509 mmol) in THF (5 mL) at RT was added Dess-Martin reagent (431 mg, 1.017 mmol) and the reaction was stirred at room temperature for 16 h. The reaction mixture was diluted with EtOAc, washed with sat. aq. NaHCO₃ and brine, dried (Na₂SO₄), filtered, and concentrated. The resulting residue was purified by FCC to afford (1R,2R,3S,4R)—N-(3,4-dichlorophenyl)-3-(2-methylpyridin-4-yl)-5-oxo-7-oxabicyclo[2.2.1]heptane-2-carboxamide. LC-MS: Rt=1.22 min; MS m/z [M+H]+ 391.0.

Step D: A solution of (1R,2R,3S,4R)—N-(3,4-dichlorophenyl)-3-(2-methylpyridin-4-yl)-5-oxo-7-oxabicyclo[2.2.1]heptane-2-carboxamide (10.4 mg, 0.027 mmol) in THF (0.5 mL) at RT was treated with MeMgBr, 3.0 M in diethyl ether (35.4 μl, 0.106 mmol) and was stirred for 2 h. Additional MeMgBr, 3.0 M in diethyl ether (35.4 μl, 0.106 mmol) was added and the reaction was stirred at RT for 16 h. The reaction mixture was quenched with sat. aq. NH₄Cl, diluted with EtOAc, washed with water and brine, dried (Na₂SO₄), filtered, and concentrated. The resulting residue was purified by FCC to afford (1R,2R,3S,4R,5R)—N-(3,4-dichlorophenyl)-5-hydroxy-5-methyl-3-(2-methylpyridin-4-yl)-7-oxabicyclo[2.2.1]heptane-2-carboxamide. LC-MS: Rt=1.27 min; MS m/z [M+H]+ 407.2.

Example 179: (1S,2S,3R,4S,5S)—N-(3,4-dichlorophenyl)-5-hydroxy-5-methyl-3-(2-methylpyridin-4-yl)-7-oxabicyclo[2.2.1]heptane-2-carboxamide

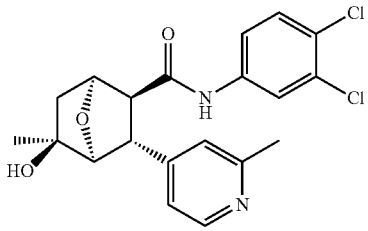 [SMILES: Cc1cc([C@H]2[C@H](C(=O)Nc3ccc(Cl)c(Cl)c3)[C@@H]3C[C@](C)(O)[C@H]2O3)ccn1]

Example 179 was synthesized according to the protocol described for Example 178 using single enantiomer (1S,2S,3R,4S,5R)—N-(3,4-dichlorophenyl)-5-hydroxy-3-(2-methylpyridin-4-yl)-7-oxabicyclo[2.2.1]heptane-2-carboxamide (Example 77c). LC-MS: Rt=1.27 min; MS m/z [M+H]+ 407.2. >20:1 mixture of alcohol regioisomers.

Example 180: (1R,2R,3S,4R,5R)—N-(3,4-dichlorophenyl)-5-hydroxy-3-(2-methylpyridin-4-yl)-7-oxabicyclo[2.2.1]heptane-2-carboxamide

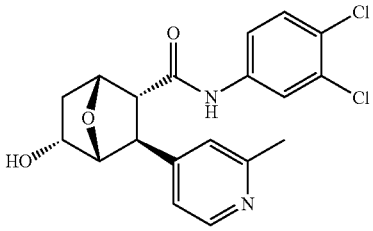 [SMILES: Cc1cc([C@H]2[C@H]3O[C@H](C[C@H]3O)[C@@H]2C(=O)Nc2ccc(Cl)c(Cl)c2)ccn1]

Title compound was prepared from single enantiomer (1R,2R,3S,4R,5S)—N-(3,4-dichlorophenyl)-5-hydroxy-3-(2-methylpyridin-4-yl)-7-oxabicyclo[2.2.1]heptane-2-carboxamide (5a, wherein R₂=3,4-dichlorophenyl and Ar=2-methylpyridin-4-yl, Example 77a) using Steps B and E as in Scheme 6.

Step B: To a stirring solution of (1R,2R,3S,4R,5S)—N-(3,4-dichlorophenyl)-5-hydroxy-3-(2-methylpyridin-4-yl)-7-oxabicyclo[2.2.1]heptane-2-carboxamide (200 mg, 0.509 mmol) in THF (5 mL) at RT was added Dess-Martin reagent (431 mg, 1.017 mmol) and the reaction was stirred at room temperature for 16 h. The reaction mixture was diluted with EtOAc, washed with sat. aq. NaHCO₃ and brine, dried (Na₂SO₄), filtered, and concentrated. The resulting residue was purified by FCC to afford (1R,2R,3S,4R)—N-(3,4-dichlorophenyl)-3-(2-methylpyridin-4-yl)-5-oxo-7-oxabicyclo[2.2.1]heptane-2-carboxamide. LC-MS: Rt=1.22 min; MS m/z [M+H]+ 391.0.

Step E: A solution of 1R,2R,3S,4R)—N-(3,4-dichlorophenyl)-3-(2-methylpyridin-4-yl)-5-oxo-7-oxabicyclo[2.2.1]heptane-2-carboxamide (18 mg, 0.046 mmol) in THF (1 mL) at RT was treated with NaBH$_4$ (6.96 mg, 0.184 mmol) and was stirred at RT for 18 h. The reaction mixture was diluted with sat. aq. NaHCO$_3$ and was extracted with EtOAc. The organic layer was washed with brine, dried (Na$_2$SO$_4$), filtered, and concentrated. The resulting residue was purified by FCC to afford (1R,2R,3S,4R,5R)—N-(3,4-dichlorophenyl)-5-hydroxy-3-(2-methylpyridin-4-yl)-7-oxabicyclo[2.2.1]heptane-2-carboxamide. LC-MS: Rt=1.20 min; MS m/z [M+H]$^+$ 393.1. $^1$H NMR (400 MHz, Acetonitrile-ds) δ 8.59 (s, 1H), 8.35 (dd, J=5.2, 0.8 Hz, 1H), 7.89 (dd, J=2.2, 0.6 Hz, 1H), 7.46-7.38 (m, 2H), 7.18-7.16 (m, 1H), 7.10 (dd, J=5.2, 1.7 Hz, 1H), 4.87-4.79 (m, 1H), 4.42-4.34 (m, 1H), 4.33-4.24 (m, 1H), 4.17-4.13 (m, 1H), 3.65-3.55 (m, 1H), 3.15-3.07 (m, 1H), 2.46 (s, 3H), 2.12-2.02 (m, 1H), 1.54-1.46 (m, 1H). >20:1 mixture of alcohol regioisomers.

Example 181: (1S,2S,3R,4S,5S)—N-(3,4-dichlorophenyl)-5-hydroxy-3-(2-methylpyridin-4-yl)-7-oxabicyclo[2.2.1]heptane-2-carboxamide

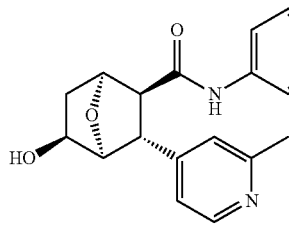

Example 181 was synthesized according to the protocol described for Example 180 using single enantiomer (1S,2S,3R,4S,5R)—N-(3,4-dichlorophenyl)-5-hydroxy-3-(2-methylpyridin-4-yl)-7-oxabicyclo[2.2.1]heptane-2-carboxamide (Example 77c). LC-MS: Rt=1.20 min; MS m/z [M+H]$^+$ 393.1. $^1$H NMR (400 MHz, Acetonitrile-ds) δ 8.60 (s, 1H), 8.36-8.34 (m, 1H), 7.89 (dd, J=2.2, 0.6 Hz, 1H), 7.46-7.39 (m, 2H), 7.17 (s, 1H), 7.10 (dd, J=5.2, 1.7 Hz, 1H), 4.86-4.81 (m, 1H), 4.42-4.37 (m, 1H), 4.31-4.24 (m, 1H), 4.17-4.11 (m, 1H), 3.63-3.57 (m, 1H), 3.15-3.09 (m, 1H), 2.46 (s, 3H), 2.11-2.01 (m, 1H), 1.54-1.45 (m, 1H). >20:1 mixture of alcohol regioisomers.

Example 182. The incorporation of a 5S-hydroxyl group into the oxabicycle core reduces the CYP3A4 inhibition and the intrinsic clearance in both rat and human liver microsomes of the compounds, as shown in Table 1.

TABLE 1

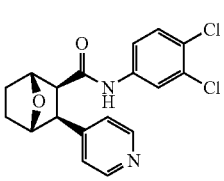 [SMILES: O=C(Nc1ccc(Cl)c(Cl)c1)[C@H]1[C@@H](c2ccncc2)[C@@H]2CC[C@H]1O2] 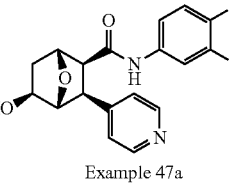 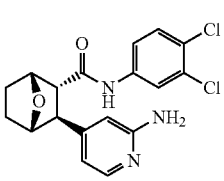 [SMILES: Nc1cc([C@@H]2[C@@H](C(=O)Nc3ccc(Cl)c(Cl)c3)[C@H]3CC[C@@H]2O3)ccn1] 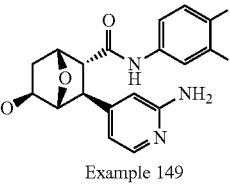

|  | | Example 47a | | Example 149 |
| --- | --- | --- | --- | --- |
| rat liver microsomes CL$_{int}$ (µL/min/mg) | 466 | 7 | 243 | 11 |
| human liver microsomes CL$_{int}$ (µL/min/mg) | 202 | 7 | 38 | 7 |
| CYP3A4 inh. (µM) | 6 | >25 | 5 | 20 |

Biological Assays

The compounds of the present invention were evaluated in the following assays: (1) the Collagen type II assay to measure chondrogenic differentiation; (2) the Alkaline Phosphatase (ALP) activity assay to determine the ability of the compounds to prevent chondrocyte hypertrophy in normal human articular chondrocytes (NHACs) and C3H10T1/2 cell line; and (3) calcium flux assay.

TABLE 2

Reagents used for experimentation

| Description | Company | Catalog number | Dilution/Concentration |
| --- | --- | --- | --- |
| Collagenase, Type II | Worthington Biochemicals | CLS-2 | 0.2 mg/ml |
| Anti-type II collagen | Abcam | 3092 | 1:500 |
| Anti-mouse 647 | Life Technologies | A-21235 | 1:5000 |
| Bovine Serum Albumin (BSA) | | | |
| Triton X-100 | | | |
| Hoescht 33342 | Life Technologies | H3570 | 1:1000 |
| Fast Blue RR Salt | Sigma | F0500-25G | 0.024% w/v |
| Naphthol AS-MX Phosphate Alkaline Solution | Sigma | 855-20ML | 4% v/v |
| Calcium 5 dye | Molecular Devices | R8186 | 100 ml/vial |
| Probenecid | Sigma | P8761-100G | 5 mM |
| HEPES | Hyclone | SH30237.01 | 10 mM |

Cell Culture

Normal human articular chondrocytes (NHACs) were purchased from PromoCell (Heidelberg, Germany) and grown in Chondrocyte Growth Medium (CGM; Lonza, Walkersville, MD). C3H10T1/2 cell line (clone 8) was purchased from ATCC (Manassas, Va.) and grown in DMEM/High glucose supplemented with 10% FBS and antibiotic/antimycotic (ThermoFisher scientific, Waltham, Mass.). Human chondrogenic progenitor cell (CPCs) were derived from human primary articular chondrocytes (Lonza, Walkersville, Md.) which were separated into single cells, clonally grown in Mesenchymal Stem Cell Growth Medium (MSCGM; Lonza, Walkersville Md.) and validated as mesenchymal progenitors through chondrogenic, osteogenic and adipogenic differentiation. The cells were FACS sorted and proven to be >98% positive for CD166 and CD105. CPCs were cultured up to 20 passages with no alteration in the cell profile, growth or differentiation rates identified.

Collagen Type II Assay and Quantitation

To initiate chondrogenesis in primary CPCs, 8000 cells were plated/well in a Costar 96 well plate in MSCGM. After 24 hours the MSCGM was removed and replaced with DMEM containing 1% FBS. The test compound was then added to each well at the indicated dose. The cultures were grown at 37° C. for 18 days. A media supplement of an additional 50 µl of DMEM containing 1% FBS was given 10 days after chondrogenic induction.

To detect the presence of Collagen type II, hCPCs were fixed with 10% formalin for 20 minutes, permeablized with PBS containing 0.1% triton X-100, 0.2 mg/ml of Collagenase 2 for 10 minutes, blocked with PBS containing 5% BSA for 1 hr at room temperature, followed by incubation with primary antibody (anti-type II collagen antibody) in PBS containing 1% BSA overnight at 4° C. Cells were washed 3 times with PBS and incubated with fluorophore-conjugated secondary antibody and Hoechst dye for 1 hour at room temperature, followed by washing with PBS for 3 times.

The total intensity of staining was imaged by fluorescent microscopy and/or quantified by high content imagining with the ImageXpress Micro (Molecular Devices, Sunnyvale, Calif.). Data analyses were performed with the customized multiwavelength cell-scoring application.

Alkaline Phosphatase Staining and Quantitation in NHACs

To initiate differentiation in NHACs, 16,000 cells were plated/well in Costar 96 well plate in CGM media (Lonza). After 24 hours the MSCGM was removed and replaced with DMEM containing 1% FBS. The test compound was then added to each well at the indicated dose. The cultures were grown at 37° C. for 10 days.

To detect the presence of hypertrophic cells, NHACs were fixed with 10% formalin and Hoeschst dye for 20 minutes, rinsed in PBS, then stained with Fast Blue RR Salt with Naphthol AS-MX Phosphate Alkaline Solution. Once cells were observed to turn blue, after approximately 2 hours at 37° C., they were washed with PBS three times.

The total intensity of staining was imaged by fluorescent microscopy, using the 651 wavelength, and/or quantified by high content imagining with the ImageXpress Micro (Molecular Devices, Sunnyvale, Calif.). Data analyses were performed with the customized multiwavelength cell-scoring application.

Alkaline Phosphatase Staining and Quantitation in C3H10T1/2

To initiate differentiation in C3H10T1/2, Clone 8 (ATCC cat #CCL-226), 4,000 cells were plated/well in 384 Perkin Elmer CellCarrier Ultra plate in DMEM/High glucose (HyClone cat #SH30022.01) containing 10% FBS and 1× Antibiotic/Antimycotic (HyClone cat #SV30079.01). After 24 hours the test compound was then added to each well at the indicated dose. The cultures were grown at 37° C. for 6 days.

To detect the presence of hypertrophic cells, C3H10T1/2 were fixed with 4% paraformaldehyde and Hoeschst dye for 20 minutes, rinsed in PBS, then stained with Fast Blue RR Salt with Naphthol AS-MX Phosphate Alkaline Solution. Once cells were observed to turn blue, after approximately 3 hours at 37° C., they were washed with PBS six times.

The ALP staining was imaged by fluorescent microscopy, using the 561 wavelength, and/or quantified by high content imagining with the ImageXpress Micro Confocal (Molecular Devices, Sunnyvale, Calif.). Data analyses were performed with the customized multiwavelength cell-scoring application looking at the number of ALP positive cells per well.

Calcium Flux assay and Quantitation

NHACs were plated in 1536 Greiner plate at 2000 cells/well in 4 ul volume. 24 hours later, 4 ul of Calcium 5 dye solution (Hank's Balanced Salt/HEPES buffer containing 5 mM of Probenecid) was then added and incubated for 1 hour at room temperature. Fluorescence readings at excitation wavelength of 470-495 nm and emission wavelength of 515-575 nm were done using FLIPR high-throughput screening system (Molecular Devices, Sunnyvale, Calif.). The test compound was then added to each well at the indicated dose. Signal was measured prior compound dispense and after using a first interval of 1 second for 60 reads and second interval of 3 second for 20 reads. Data was analyzed using Molecular Devices ScreenWorks® Software.

The activity of the compounds of the present invention in the following assays are summarized in Table 3. Legend: (A) calcium flux assay; (B) collagen Type II assay; (C) alkaline phosphatase assay in NHAC; and (D) alkaline phosphatase assay in C3H10T1/2.

TABLE 3

| Ex No. | | (A) EC$_{50}$ µM (% Efficacy) | (B) EC$_{50}$ µM (% Efficacy) | (C) IC$_{50}$ µM (% Efficacy) | (D) IC$_{50}$ µM (% Efficacy) |
|---|---|---|---|---|---|
| 1 | (1S,2S,4R,5R,6S,7S)-N-(5,6-dichloropyridin-3-yl)-7-(2-methoxypyridin-4-yl)-8-oxatricyclo[3.2.1.0$^{2,4}$]octane-6-carboxamide | 3.4 (164) | | | |
| 2 | rac-(1S,2S,4R,5R,6S,7S)-N-(6-methoxypyridin-3-yl)-7-(6-methylpyridin-3-yl)-8-oxatricyclo[3.2.1.0$^{2,4}$]octane-6-carboxamide | >50 (0) | | | |
| 3 | (1S,2S,4R,5R,6S,7S)-N-(6-methoxypyridin-3-yl)-7-(6-methylpyridin-3-yl)-8-oxatricyclo[3.2.1.0$^{2,4}$]octane-6-carboxamide | 0.30 (45) | | | |

TABLE 3-continued

| Ex No. | | (A) EC$_{50}$ μM (% Efficacy) | (B) EC$_{50}$ μM (% Efficacy) | (C) IC$_{50}$ μM (% Efficacy) | (D) IC$_{50}$ μM (% Efficacy) |
|---|---|---|---|---|---|
| 4 | (1R,2R,4S,5S,6R,7R)-N-(6-methoxypyridin-3-yl)-7-(6-methylpyridin-3-yl)-8-oxatricyclo[3.2.1.0$^{2,4}$]octane-6-carboxamide | >50 (0) | | | |
| 5 | (1R,2S,3S,4R,5S)-N-(4,5-dichloropyridin-2-yl)-5-hydroxy-3-(2-methylpyridin-4-yl)-7-oxabicyclo[2.2.1]heptane-2-carboxamide | >50 (28) | | | |
| 6 | (1R,2S,3S,4R,5S)-N-(5-chloro-6-methylpyridin-3-yl)-5-hydroxy-3-(2-methylpyridin-4-yl)-7-oxabicyclo[2.2.1]heptane-2-carboxamide | >50 (18) | | | |
| 7 | (1R,2S,3S,4R,5S)-N-(5,6-dichloropyridin-3-yl)-5-hydroxy-3-(2-methylpyridin-4-yl)-7-oxabicyclo[2.2.1]heptane-2-carboxamide | >50 (17) | | | |
| 8 | (1S,2R,3R,4S,5R)-N-(5,6-dichloropyridin-3-yl)-5-hydroxy-3-(2-methylpyridin-4-yl)-7-oxabicyclo[2.2.1]heptane-2-carboxamide | >50 (0) | | | |
| 9 | (1R,2S,3S,4R,5S)-5-hydroxy-3-(2-methylpyridin-4-yl)-N-[3-(trifluoromethyl)phenyl]-7-oxabicyclo[2.2.1]heptane-2-carboxamide | >50 (50) | | >31 (62) | >20 (16) |
| 10 | (1S,2S,3S,4S,6R)-6-hydroxy-3-(2-methylpyridin-4-yl)-N-[3-(trifluoromethyl)phenyl]-7-oxabicyclo[2.2.1]heptane-2-carboxamide | >50 (0) | | | |
| 11 | rac-(1R,2S,3S,4R,5S)-N-(5,6-dichloropyridin-3-yl)-5-hydroxy-3-(pyridin-4-yl)-7-oxabicyclo[2.2.1]heptane-2-carboxamide | >50 (0) | | | |
| 11a | (1R,2S,3S,4R,5S)-N-(5,6-dichloropyridin-3-yl)-5-hydroxy-3-(pyridin-4-yl)-7-oxabicyclo[2.2.1]heptane-2-carboxamide | >50 (55) | | | |
| 12 | rac-(1R,2S,3S,4R,5S)-5-hydroxy-3-(pyridin-4-yl)-N-[3-(trifluoromethyl)phenyl]-7-oxabicyclo[2.2.1]heptane-2-carboxamide | >50 (27) | | | |
| 12a | (1R,2S,3S,4R,5S)-5-hydroxy-3-(pyridin-4-yl)-N-[3-(trifluoromethyl)phenyl]-7-oxabicyclo[2.2.1]heptane-2-carboxamide | 0.27 (98) | 2.9 (91) | 48 (65) | >20 (6) |
| 13 | (1S,2S,3S,4S,6R)-6-hydroxy-3-(pyridin-4-yl)-N-[3-(trifluoromethyl)phenyl]-7-oxabicyclo[2.2.1]heptane-2-carboxamide | >50 (22) | | | |
| 14 | (1R,2S,3S,4R,5R)-N-(3,4-dichlorophenyl)-5-fluoro-3-(2-methylpyridin-4-yl)-7-oxabicyclo[2.2.1]heptane-2-carboxamide | 4.5 (68) | | | |
| 15 | (1R,2S,3S,4R,5R)-5-fluoro-N-(6-methoxypyridin-3-yl)-3-(2-methylpyridin-4-yl)-7-oxabicyclo[2.2.1]heptane-2-carboxamide | 8.3 (115) | | | |
| 16 | (1R,2S,3S,4R,5R)-5-fluoro-3-(2-methylpyridin-4-yl)-N-[3-(trifluoromethyl)phenyl]-7-oxabicyclo[2.2.1]heptane-2-carboxamide | >50 (0) | | | |

TABLE 3-continued

| Ex No. | | (A) EC$_{50}$ μM (% Efficacy) | (B) EC$_{50}$ μM (% Efficacy) | (C) IC$_{50}$ μM (% Efficacy) | (D) IC$_{50}$ μM (% Efficacy) |
|---|---|---|---|---|---|
| 17 | (1R,2S,3S,4R,5S)-N-(3,4-dichlorophenyl)-5-fluoro-3-(2-methylpyridin-4-yl)-7-oxabicyclo[2.2.1]heptane-2-carboxamide | 21 (105) | | | |
| 18 | (1R,2S,3S,4R,5S)-5-fluoro-3-(2-methylpyridin-4-yl)-N-[3-(trifluoromethyl)phenyl]-7-oxabicyclo[2.2.1]heptane-2-carboxamide | >50 (0) | | | |
| 19 | (1R,2S,3S,4R,5S)-N-(5,6-dichloropyridin-3-yl)-5-fluoro-3-(2-methylpyridin-4-yl)-7-oxabicyclo[2.2.1]heptane-2-carboxamide | >50 (0) | | | |
| 20 | (1R,2S,3S,4R,5S)-N-(3,4-dichlorophenyl)-5-fluoro-3-(2-methoxypyridin-4-yl)-7-oxabicyclo[2.2.1]heptane-2-carboxamide | 25 (258) | | | |
| 21 | (1R,2S,3S,4R,5S)-3-(2-aminopyrimidin-5-yl)-N-(3,4-dichlorophenyl)-5-fluoro-7-oxabicyclo[2.2.1]heptane-2-carboxamide | >50 (5) | | | |
| 22 | (1R,2S,3S,4R,5S)-N-(3,4-dichlorophenyl)-5-fluoro-3-(6-methylpyridin-3-yl)-7-oxabicyclo[2.2.1]heptane-2-carboxamide | 27 (159) | | | |
| 23 | (1R,2S,3S,4R,5S)-N-(3,4-dichlorophenyl)-5-fluoro-3-(2-fluoropyridin-4-yl)-7-oxabicyclo[2.2.1]heptane-2-carboxamide | 4.2 (128) | | | |
| 24 | rac-(1S,2S,4R,5R,6S,7S)-N-(3,4-dichlorophenyl)-7-(2-methylpyridin-4-yl)-8-oxatricyclo[3.2.1.0$^{2,4}$]octane-6-carboxamide | >50 (54) | | | |
| 24a | (1S,2S,4R,5R,6S,7S)-N-(3,4-dichlorophenyl)-7-(2-methylpyridin-4-yl)-8-oxatricyclo[3.2.1.0$^{2,4}$]octane-6-carboxamide | 6.1 (99) | 0.78 (29) | 30 (100) | >20 (28) |
| 24b | (1R,2R,4S,5S,6R,7R)-N-(3,4-dichlorophenyl)-7-(2-methylpyridin-4-yl)-8-oxatricyclo[3.2.1.0$^{2,4}$]octane-6-carboxamide | >50 (0) | | | |
| 25 | (1S,2S,4R,5R,6S,7S)-N-(3,4-dichlorophenyl)-7-(2-methoxypyridin-4-yl)-8-oxatricyclo[3.2.1.0$^{2,4}$]octane-6-carboxamide | 11 (71) | | | |
| 26 | (1S,2S,4R,5R,6S,7S)-N-(3,4-dichlorophenyl)-7-(2-fluoropyridin-4-yl)-8-oxatricyclo[3.2.1.0$^{2,4}$]octane-6-carboxamide | 17 (52) | | | |
| 27 | (1S,2S,4R,5R,6S,7S)-7-(2-methylpyridin-4-yl)-N-[3-(trifluoromethyl)phenyl]-8-oxatricyclo[3.2.1.0$^{2,4}$]octane-6-carboxamide | 23 (54) | | | |
| 28 | (1S,2S,4R,5R,6S,7S)-N-(3,4-dichlorophenyl)-7-(pyrimidin-5-yl)-8-oxatricyclo[3.2.1.0$^{2,4}$]octane-6-carboxamide | 13 (120) | | 34 (71) | >20 (48) |
| 29 | (1R,2R,4S,5S,6R,7R)-N-(3,4-dichlorophenyl)-7-(pyrimidin-5-yl)-8-oxatricyclo[3.2.1.0$^{2,4}$]octane-6-carboxamide | 23 (167) | | | |

TABLE 3-continued

| Ex No. | | (A) EC$_{50}$ μM (% Efficacy) | (B) EC$_{50}$ μM (% Efficacy) | (C) IC$_{50}$ μM (% Efficacy) | (D) IC$_{50}$ μM (% Efficacy) |
|---|---|---|---|---|---|
| 30 | (1S,2S,4R,5R,6S,7S)-N-(3,4-dichlorophenyl)-7-(2,3-difluoropyridin-4-yl)-8-oxatricyclo[3.2.1.0$^{2,4}$]octane-6-carboxamide | >50 (6) | | | |
| 31 | (1R,2R,4S,5S,6R,7R)-N-(3,4-dichlorophenyl)-7-(2,3-difluoropyridin-4-yl)-8-oxatricyclo[3.2.1.0$^{2,4}$]octane-6-carboxamide | 10 (133) | | | |
| 32 | (1S,2S,4R,5R,6S,7S)-N-(5,6-dichloropyridin-3-yl)-7-(2,3-difluoropyridin-4-yl)-8-oxatricyclo[3.2.1.0$^{2,4}$]octane-6-carboxamide | 13 (143) | | | |
| 33 | (1S,2S,4R,5R,6S,7S)-N-(6-methoxypyridin-3-yl)-7-(pyridin-4-yl)-8-oxatricyclo[3.2.1.0$^{2,4}$]octane-6-carboxamide | 4.6 (49) | | | |
| 34 | (1S,2S,4R,5R,6S,7S)-7-(2,3-difluoropyridin-4-yl)-N-(6-methoxypyridin-3-yl)-8-oxatricyclo[3.2.1.0$^{2,4}$]octane-6-carboxamide | >50 (3) | | | |
| 35 | (1S,2S,4R,5R,6S,7S)-N-(6-methoxypyridin-3-yl)-7-[6-(trifluoromethyl)pyridin-2-yl]-8-oxatricyclo[3.2.1.0$^{2,4}$]octane-6-carboxamide | >50 (0) | | | |
| 36 | (1S,2S,4R,5R,6S,7S)-N-(3,4-dichlorophenyl)-7-(2-fluoropyrimidin-5-yl)-8-oxatricyclo[3.2.1.0$^{2,4}$]}octane-6-carboxamide | 8.6 (124) | | | |
| 37 | (1S,2S,4R,5R,6S,7S)-7-(pyrimidin-5-yl)-N-[3-(trifluoromethyl)phenyl]-8-oxatricyclo[3.2.1.0$^{2,4}$]octane-6-carboxamide | >50 (26) | | | |
| 38 | (1S,2S,4R,5R,6S,7S)-7-(pyridin-4-yl)-N-[3-(trifluoromethyl)phenyl]-8-oxatricyclo[3.2.1.0$^{2,4}$]octane-6-carboxamide | 9.9 (36) | | | |
| 39 | (1S,2S,4R,5R,6S,7S)-7-(2-aminopyrimidin-5-yl)-N-(3,4-dichlorophenyl)-8-oxatricyclo[3.2.1.0$^{2,4}$]octane-6-carboxamide | 0.53 (40) | | | |
| 40 | (1S,2S,4R,5R,6S,7S)-N-(3,4-dichlorophenyl)-7-[2-(morpholin-4-yl)pyrimidin-5-yl]-8-oxatricyclo[3.2.1.0$^{2,4}$]octane-6-carboxamide | >50 (37) | | | |
| 41 | (1S,2S,4R,5R,6S,7S)-7-(2-fluoropyridin-4-yl)-N-[3-(trifluoromethyl)phenyl]-8-oxatricyclo[3.2.1.0$^{2,4}$]octane-6-carboxamide | 24 (121) | | | |
| 42 | (1S,2S,4R,5R,6S,7S)-N-(3,4-dichlorophenyl)-7-(2-methylpyrimidin-5-yl)-8-oxatricyclo[3.2.1.0$^{2,4}$]octane-6-carboxamide | 18 (57) | | | |
| 43 | rac-(1S,2S,4R,5R,6S,7S)-N-(5,6-dichloropyridin-3-yl)-7-(pyridin-4-yl)-8-oxatricyclo[3.2.1.0$^{2,4}$]octane-6-carboxamide | >50 (168) | | | |
| 43a | (1S,2S,4R,5R,6S,7S)-N-(3,4-dichlorophenyl)-7-(pyridin-4-yl)-8-oxatricyclo[3.2.1.0$^{2,4}$]octane-6-carboxamide | >50 (0) | | | |

TABLE 3-continued

| Ex No. | | (A) EC$_{50}$ µM (% Efficacy) | (B) EC$_{50}$ µM (% Efficacy) | (C) IC$_{50}$ µM (% Efficacy) | (D) IC$_{50}$ µM (% Efficacy) |
|---|---|---|---|---|---|
| 43b | (1R,2R,4S,5S,6R,7R)-N-(5,6-dichloropyridin-3-yl)-7-(pyridin-4-yl)-8-oxatricyclo[3.2.1.0$^{2,4}$]octane-6-carboxamide | >50 (3) | | | |
| 44 | (1S,2S,4R,5R,6S,7S)-N-(3,4-dichlorophenyl)-7-(pyridin-4-yl)-8-oxatricyclo[3.2.1.0$^{2,4}$]octane-6-carboxamide | >50 (0) | | | |
| 45 | (1S,2S,4R,5R,6S,7S)-N-(5,6-dichloropyridin-3-yl)-7-(2-methylpyridin-4-yl)-8-oxatricyclo[3.2.1.0$^{2,4}$]octane-6-carboxamide | 14 (32) | | | |
| 46 | (1R,2R,4S,5S,6R,7R)-N-(5,6-dichloropyridin-3-yl)-7-(2-methylpyridin-4-yl)-8-oxatricyclo[3.2.1.0$^{2,4}$]octane-6-carboxamide | >50 (0) | | | |
| 47 | rac-(1R,2S,3S,4R,5S)-N-(3,4-dichlorophenyl)-5-hydroxy-3-(pyridin-4-yl)-7-oxabicyclo[2.2.1]heptane-2-carboxamide | 7.8 (38) | | | |
| 47a | (1R,2S,3S,4R,5S)-N-(3,4-dichlorophenyl)-5-hydroxy-3-(pyridin-4-yl)-7-oxabicyclo[2.2.1]heptane-2-carboxamide | >50 (68) | 2.1 (82) | 33 (88) | >20 (23) |
| 48 | (1R,2S,3S,4R,5S)-N-(3,4-dichlorophenyl)-5-hydroxy-3-(6-methylpyridin-3-yl)-7-oxabicyclo[2.2.1]heptane-2-carboxamide | 22 (80) | | | |
| 49 | rac-(1R,2S,3S,4R,5S)-N-(3,4-dichlorophenyl)-5-hydroxy-3-(2-methoxypyridin-4-yl)-7-oxabicyclo[2.2.1]heptane-2-carboxamide | 11 (77) | | | |
| 49a | (1R,2S,3S,4R,5S)-N-(3,4-dichlorophenyl)-5-hydroxy-3-(2-methoxypyridin-4-yl)-7-oxabicyclo[2.2.1]heptane-2-carboxamide | 0.84 (53) | | | |
| 49b | (1S,2R,3R,4S,5R)-N-(3,4-dichlorophenyl)-5-hydroxy-3-(2-methoxypyridin-4-yl)-7-oxabicyclo[2.2.1]heptane-2-carboxamide | >50 (31) | | | |
| 50 | (1R,2S,3S,4R,5S)-N-(3,4-dichlorophenyl)-5-hydroxy-3-[6-(trifluoromethyl)pyridin-2-yl]-7-oxabicyclo[2.2.1]heptane-2-carboxamide | 21 (308) | | | |
| 51 | (1R,2S,3S,4R,5S)-N-(3,4-dichlorophenyl)-5-hydroxy-3-(pyrimidin-5-yl)-7-oxabicyclo[2.2.1]heptane-2-carboxamide | >50 (0) | | | |
| 52 | rac-(1R,2S,3S,4R,5S)-N-(3,4-dichlorophenyl)-3-(2-fluoropyridin-4-yl)-5-hydroxy-7-oxabicyclo[2.2.1]heptane-2-carboxamide | >50 (4) | | | |
| 52a | (1R,2S,3S,4R,5S)-N-(3,4-dichlorophenyl)-3-(2-fluoropyridin-4-yl)-5-hydroxy-7-oxabicyclo[2.2.1]heptane-2-carboxamide | >50 (96) | 0.49 (80) | 17 (71) | >20 (36) |
| 52b | (1S,2R,3R,4S,5R)-N-(3,4-dichlorophenyl)-3-(2-fluoropyridin-4-yl)-5-hydroxy-7-oxabicyclo[2.2.1]heptane-2-carboxamide | >50 (1) | | | |

TABLE 3-continued

| Ex No. | | (A) EC$_{50}$ μM (% Efficacy) | (B) EC$_{50}$ μM (% Efficacy) | (C) IC$_{50}$ μM (% Efficacy) | (D) IC$_{50}$ μM (% Efficacy) |
|---|---|---|---|---|---|
| 53 | rac-(1R,2S,3S,4R,5S)-N-(3,4-dichlorophenyl)-5-hydroxy-3-(2-methylpyridin-4-yl)-7-oxabicyclo[2.2.1]heptane-2-carboxamide | >50 (43) | | | |
| 53a | (1R,2S,3S,4R,5S)-N-(3,4-dichlorophenyl)-5-hydroxy-3-(2-methylpyridin-4-yl)-7-oxabicyclo[2.2.1]heptane-2-carboxamide | >50 (12) | 13 (44) | 31 (83) | >20 (0) |
| 53b | (1S,2R,3R,4S,5R)-N-(3,4-dichlorophenyl)-5-hydroxy-3-(2-methylpyridin-4-yl)-7-oxabicyclo[2.2.1]heptane-2-carboxamide | >50 (119) | | | |
| 54 | rac-(1R,2S,3S,4R,5S)-N-(3,4-dichlorophenyl)-5-hydroxy-3-[2-(trifluoromethyl)pyridin-4-yl]-7-oxabicyclo[2.2.1]heptane-2-carboxamide | >50 (22) | | | >20 (35) |
| 54a | (1R,2S,3S,4R,5S)-N-(3,4-dichlorophenyl)-5-hydroxy-3-[2-(trifluoromethyl)pyridin-4-yl]-7-oxabicyclo[2.2.1]heptane-2-carboxamide | 3.5 (45) | | | >20 (35) |
| 54b | (1S,2R,3R,4S,5R)-N-(3,4-dichlorophenyl)-5-hydroxy-3-[2-(trifluoromethyl)pyridin-4-yl]-7-oxabicyclo[2.2.1]heptane-2-carboxamide | >50 (16) | | | >20 (46) |
| 55 | (1R,2S,3S,4R,5S)-N-(3,4-dichlorophenyl)-3-[2-(dimethylamino)pyrimidin-5-yl]-5-hydroxy-7-oxabicyclo[2.2.1]heptane-2-carboxamide | >50 (0) | | | |
| 56 | (1R,2S,3S,4R,5S)-N-(3,4-dichlorophenyl)-5-hydroxy-3-(2-methylpyrimidin-5-yl)-7-oxabicyclo[2.2.1]heptane-2-carboxamide | >50 (0) | | | |
| 57 | (1R,2S,3S,4R,5S)-3-(2-aminopyridin-4-yl)-N-(3,4-dichlorophenyl)-5-hydroxy-7-oxabicyclo[2.2.1]heptane-2-carboxamide | >50 (56) | | | |
| 58 | (1R,2S,3S,4R,5S)-N-(3,4-dichlorophenyl)-3-(2,5-difluoropyridin-4-yl)-5-hydroxy-7-oxabicyclo[2.2.1]heptane-2-carboxamide | >50 (0) | | | |
| 59 | (1R,2S,3S,4R,5S)-N-(3,4-dichlorophenyl)-3-(2,3-difluoropyridin-4-yl)-5-hydroxy-7-oxabicyclo[2.2.1]heptane-2-carboxamide | 1.2 (254) | | | |
| 60 | (1R,2S,3S,4R,5S)-3-(2-aminopyrimidin-5-yl)-N-(3,4-dichlorophenyl)-5-hydroxy-7-oxabicyclo[2.2.1]heptane-2-carboxamide | >50 (2) | | | |
| 61 | (1R,2S,3S,4R,5S)-N-(3,4-dichlorophenyl)-3-(2-fluoropyrimidin-5-yl)-5-hydroxy-7-oxabicyclo[2.2.1]heptane-2-carboxamide | >50 (24) | | | |
| 62 | (1R,2S,3S,4R,5S)-N-(3,4-dichlorophenyl)-5-hydroxy-3-[2-(trifluoromethyl)pyrimidin-5-yl]-7-oxabicyclo[2.2.1]heptane-2-carboxamide | 8.2 (61) | | | |

TABLE 3-continued

| Ex No. | | (A) EC$_{50}$ µM (% Efficacy) | (B) EC$_{50}$ µM (% Efficacy) | (C) IC$_{50}$ µM (% Efficacy) | (D) IC$_{50}$ µM (% Efficacy) |
|---|---|---|---|---|---|
| 63 | (1R,2S,3S,4R,5S)-N-(3,4-dichlorophenyl)-5-methoxy-3-(2-methylpyridin-4-yl)-7-oxabicyclo[2.2.1.]heptane-2-carboxamide | >50 (9) | | | |
| 64 | (1R,2S,3S,4R,5R)-N-(3,4-dichlorophenyl)-5-fluoro-3-(6-methylpyridin-3-yl)-7-oxabicyclo[2.2.1.]heptane-2-carboxamide | 21 (253) | | | |
| 65 | (1R,2S,3S,4R,5R)-N-(3,4-dichlorophenyl)-5-fluoro-3-(2-methoxypyridin-4-yl)-7-oxabicyclo[2.2.1.]heptane-2-carboxamide | 18 (169) | | | |
| 66 | (1S,2S,4R,5R,6R,7S)-N-(4-chloro-3-cyanophenyl)-7-(2-methylpyridin-4-yl)-8-oxatricyclo[3.2.1.0$^{2,4}$]octane-6-carboxamide | 20 (179) | | | |
| 67 | (1S,2S,4R,5R,6R,7S)-N-(4-chloro-2-cyanophenyl)-7-(2-methylpyridin-4-yl)-8-oxatricyclo[3.2.1.0$^{2,4}$]octane-6-carboxamide | >50 (39) | | | |
| 68 | (1S,2S,4R,5R,6R,7S)-N-(4-chloro-3-fluorophenyl)-7-(2-methylpyridin-4-yl)-8-oxatricyclo[3.2.1.0$^{2,4}$]octane-6-carboxamide | 15 (306) | | | |
| 69 | (1S,2S,4R,5R,6R,7S)-7-(2-methylpyridin-4-yl)-N-[3-(trifluoromethoxy)phenyl]-8-oxatricyclo[3.2.1.0$^{2,4}$]octane-6-carboxamide | 21 (180) | | | >20 (63) |
| 70 | (1S,2S,4R,5R,6R,7S)-N-(5-methyl-1,3-thiazol-2-yl)-7-(2-methylpyridin-4-yl)-8-oxatricyclo[3.2.1.0$^{2,4}$]octane-6-carboxamide | >50 (25) | | | >20 (1) |
| 71 | (1S,2S,4R,5R,6R,7S)-N-[3-fluoro-4-(trifluoromethoxy)phenyl]-7-(2-methylpyridin-4-yl)-8-oxatricyclo[3.2.1.0$^{2,4}$]octane-6-carboxamide | 6.2 (250) | | | |
| 72 | (1S,2S,4R,5R,6R,7S)-N-(5,6-dichloropyridin-3-yl)-7-(2,3-difluoropyridin-4-yl)-8-oxatricyclo[3.2.1.0$^{2,4}$]octane-6-carboxamide | 7.7 (208) | | | |
| 73 | (1R,2R,4S,5S,6S,7R)-N-(5,6-dichloropyridin-3-yl)-7-(2,3-difluoropyridin-4-yl)-8-oxatricyclo[3.2.1.0$^{2,4}$]octane-6-carboxamide | 16 (127) | | | |
| 74 | (1S,2S,4R,5R,6R,7S)-N-(5,6-dichloropyridin-3-yl)-7-(6-methylpyridin-3-yl)-8-oxatricyclo[3.2.1.0$^{2,4}$]octane-6-carboxamide | 7.7 (90) | | | >20 (83) |
| 75 | (1S,2S,4R,5R,6R,7S)-N-(5,6-dichloropyridin-3-yl)-7-(pyrimidin-5-yl)-8-oxatricyclo[3.2.1.0$^{2,4}$]octane-6-carboxamide | 4.4 (73) | | | >20 (45) |
| 76 | (1S,2S,4R,5R,6R,7S)-N-(5,6-dichloropyridin-3-yl)-7-(2-methoxypyridin-4-yl)-8-oxatricyclo[3.2.1.0$^{2,4}$]octane-6-carboxamide | 5.8 (123) | | | |

TABLE 3-continued

| Ex No. | | (A) EC$_{50}$ μM (% Efficacy) | (B) EC$_{50}$ μM (% Efficacy) | (C) IC$_{50}$ μM (% Efficacy) | (D) IC$_{50}$ μM (% Efficacy) |
|---|---|---|---|---|---|
| 77 | rac-(1R,2R,3S,4R,5S)-N-(3,4-dichlorophenyl)-5-hydroxy-3-(2-methylpyridin-4-yl)-7-oxabicyclo[2.2.1]heptane-2-carboxamide | 26 (49) | | | |
| 77a | (1R,2R,3S,4R,5S)-N-(3,4-dichlorophenyl)-5-hydroxy-3-(2-methylpyridin-4-yl)-7-oxabicyclo[2.2.1]heptane-2-carboxamide | 26 (182) | 0.69 (120) | 3.5 (114) | >20 (45) |
| 77b | (1S,2R,3S,4S,6R)-N-(3,4-dichlorophenyl)-6-hydroxy-3-(2-methylpyridin-4-yl)-7-oxabicyclo[2.2.1]heptane-2-carboxamide | 20 (157) | | | >20 (47) |
| 77c | (1S,2S,3R,4S,5R)-N-(3,4-dichlorophenyl)-5-hydroxy-3-(2-methylpyridin-4-yl)-7-oxabicyclo[2.2.1]heptane-2-carboxamide | 13 (72) | | | 3.9 (72) |
| 77d | (1R,2S,3R,4R,6S)-N-(3,4-dichlorophenyl)-6-hydroxy-3-(2-methylpyridin-4-yl)-7-oxabicyclo[2.2.1]heptane-2-carboxamide | 33 (92) | | | >20 (54) |
| 78 | (1R,2R,3S,4R,5S)-N-[3-chloro-4-(2-fluorophenyl)phenyl]-5-hydroxy-3-(2-methylpyridin-4-yl)-7-oxabicyclo[2.2.1]heptane-2-carboxamide | >50 (70) | | | |
| 79 | (1R,2R,3S,4R,5S)-5-hydroxy-N-(1-methanesulfonylpiperidin-4-yl)-3-(2-methylpyridin-4-yl)-7-oxabicyclo[2.2.1]heptane-2-carboxamide | >50 (113) | | | >20 (34) |
| 80 | (1R,2R,3S,4R,5S)-N-(4,5-dichloropyridin-2-yl)-5-hydroxy-3-(2-methylpyridin-4-yl)-7-oxabicyclo[2.2.1]heptane-2-carboxamide | >50 (32) | | | |
| 81 | (1R,2R,3S,4R,5S)-N-(5-chloro-6-methylpyridin-3-yl)-5-hydroxy-3-(2-methylpyridin-4-yl)-7-oxabicyclo[2.2.1]heptane-2-carboxamide | 2.7 (34) | | | |
| 82 | (1R,2R,3S,4R,5S)-N-(3,4-dichlorophenyl)-5-hydroxy-3-(2-methylpyrimidin-4-yl)-7-oxabicyclo[2.2.1]heptane-2-carboxamide | >50 (74) | | | |
| 83 | (1R,2R,3S,4R,5S)-N-(5,6-dichloropyridin-3-yl)-5-hydroxy-3-(2-methylpyridin-4-yl)-7-oxabicyclo[2.2.1]heptane-2-carboxamide | >50 (38) | 1.5 (150) | 12 (106) | >20 (34) |
| 84 | (1S,2S,3R,4S,5R)-N-(5,6-dichloropyridin-3-yl)-5-hydroxy-3-(2-methylpyridin-4-yl)-7-oxabicyclo[2.2.1]heptane-2-carboxamide | >50 (61) | | | >20 (31) |
| 85 | (1R,2R,3S,4R,5S)-5-hydroxy-3-(2-methylpyridin-4-yl)-N-[3-(trifluoromethyl)phenyl]-7-oxabicyclo[2.2.1]heptane-2-carboxamide | >50 (56) | | | |
| 86 | (1S,2R,3S,4S,6R)-6-hydroxy-3-(2-methylpyridin-4-yl)-N-[3-(trifluoromethyl)phenyl]-7-oxabicyclo[2.2.1]heptane-2-carboxamide | >50 (38) | | | |
| 87 | (1R,2R,3S,4R,5S)-N-(5,6-dichloropyridin-3-yl)-5-hydroxy-3-(pyridin-4-yl)-7-oxabicyclo[2.2.1]heptane-2-carboxamide | >50 (14) | | | |

TABLE 3-continued

| Ex No. | | (A) EC$_{50}$ μM (% Efficacy) | (B) EC$_{50}$ μM (% Efficacy) | (C) IC$_{50}$ μM (% Efficacy) | (D) IC$_{50}$ μM (% Efficacy) |
|---|---|---|---|---|---|
| 88 | (1R,2R,3S,4R,5S)-5-hydroxy-3-(pyridin-4-yl)-N-[3-(trifluoromethyl)phenyl]-7-oxabicyclo[2.2.1]heptane-2-carboxamide | >50 (27) | | | |
| 89 | (1S,2R,3S,4S,6R)-6-hydroxy-3-(pyridin-4-yl)-N-[3-(trifluoromethyl)phenyl]-7-oxabicyclo[2.2.1]heptane-2-carboxamide | >50 (0) | | | |
| 90 | rac-(1R,2R,3S,4R,5S)-N-(5,6-dichloropyridin-3-yl)-3-(2-fluoropyridin-4-yl)-5-hydroxy-7-oxabicyclo[2.2.1]heptane-2-carboxamide | >50 (45) | | | |
| 90a | (1R,2R,3S,4R,5S)-N-(5,6-dichloropyridin-3-yl)-3-(2-fluoropyridin-4-yl)-5-hydroxy-7-oxabicyclo[2.2.1]heptane-2-carboxamide | >50 (101) | 2.3 (65) | >50 (98) | >20 (48) |
| 90b | (1S,2S,3R,4S,5R)-N-(5,6-dichloropyridin-3-yl)-3-(2-fluoropyridin-4-yl)-5-hydroxy-7-oxabicyclo[2.2.1]heptane-2-carboxamide | >50 (44) | | | >20 (45) |
| 91 | (1R,2R,3S,4R,5S)-N-(5,6-dichloropyridin-3-yl)-3-(2,3-difluoropyridin-4-yl)-5-hydroxy-7-oxabicyclo[2.2.1]heptane-2-carboxamide | 4.4 (66) | | | |
| 92 | (1R,2R,3S,4R,5R)-N-(3,4-dichlorophenyl)-5-fluoro-3-(2-methylpyridin-4-yl)-7-oxabicyclo[2.2.1]heptane-2-carboxamide | >50 (57) | | | |
| 93 | (1S,2R,3S,4S,6S)-N-(3,4-dichlorophenyl)-6-fluoro-3-(2-methylpyridin-4-yl)-7-oxabicyclo[2.2.1]heptane-2-carboxamide | >50 (7) | | | |
| 94 | (1S,2S,3R,4S,5S)-N-(3,4-dichlorophenyl)-5-fluoro-3-(2-methylpyridin-4-yl)-7-oxabicyclo[2.2.1]heptane-2-carboxamide | 18 (157) | | | >20 (0) |
| 95 | (1R,2S,3R,4R,6R)-N-(3,4-dichlorophenyl)-6-fluoro-3-(2-methylpyridin-4-yl)-7-oxabicyclo[2.2.1]heptane-2-carboxamide | 11 (113) | | | |
| 96 | (1R,2R,3S,4R,5R)-5-fluoro-3-(2-methylpyridin-4-yl)-N-[3-(trifluoromethyl)phenyl]-7-oxabicyclo[2.2.1]heptane-2-carboxamide | 14 (281) | | | |
| 97 | (1R,2R,3S,4R,5R)-5-fluoro-N-(6-methoxypyridin-3-yl)-3-(2-methylpyridin-4-yl)-7-oxabicyclo[2.2.1]heptane-2-carboxamide | >50 (2) | | | |
| 98 | (1R,2R,3S,4R,5R)-N-(5,6-dichloropyridin-3-yl)-5-fluoro-3-(2-methylpyridin-4-yl)-7-oxabicyclo[2.2.1]heptane-2-carboxamide | 21 (404) | | | |
| 99 | (1R,2R,3S,4R,5R)-5-fluoro-3-(2-methylpyridin-4-yl)-N-[3-(trifluoromethoxy)phenyl]-7-oxabicyclo[2.2.1]heptane-2-carboxamide | 18 (383) | | | |

TABLE 3-continued

| Ex No. | | (A) EC$_{50}$ μM (% Efficacy) | (B) EC$_{50}$ μM (% Efficacy) | (C) IC$_{50}$ μM (% Efficacy) | (D) IC$_{50}$ μM (% Efficacy) |
|---|---|---|---|---|---|
| 100 | (1R,2R,3S,4R,5R)-5-fluoro-N-[3-fluoro-4-(trifluoromethoxy)phenyl]-3-(2-methylpyridin-4-yl)-7-oxabicyclo[2.2.1]heptane-2-carboxamide | 18 (310) | | | |
| 101 | (1R,2R,3S,4R,5R)-5-fluoro-N-(1-methyl-1H-pyrazol-3-yl)-3-(2-methylpyridin-4-yl)-7-oxabicyclo[2.2.1]heptane-2-carboxamide | 29 (62) | | | |
| 102 | (1R,2R,3S,4R,5R)-5-fluoro-N-(5-methyl-1,3-thiazol-2-yl)-3-(2-methylpyridin-4-yl)-7-oxabicyclo[2.2.1]heptane-2-carboxamide | 2.1 (84) | | | |
| 103 | (1R,2R,3S,4R,5S)-N-(3,4-dichlorophenyl)-5-fluoro-3-(2-methoxypyridin-4-yl)-7-oxabicyclo[2.2.1]heptane-2-carboxamide | 24 (153) | | 10 (79) | |
| 104 | (1S,2R,3S,4S,6R)-N-(3,4-dichlorophenyl)-6-fluoro-3-(2-methoxypyridin-4-yl)-7-oxabicyclo[2.2.1]heptane-2-carboxamide | 14 (96) | | | |
| 105 | (1R,2R,3S,4R,5S)-N-(3,4-dichlorophenyl)-5-fluoro-3-(2-methylpyridin-4-yl)-7-oxabicyclo[2.2.1]heptane-2-carboxamide | 8.2 (106) | | 1.7 (68) | |
| 106 | (1S,2R,3S,4S,6R)-N-(3,4-dichlorophenyl)-6-fluoro-3-(2-methylpyridin-4-yl)-7-oxabicyclo[2.2.1]heptane-2-carboxamide | 24 (84) | | | |
| 107 | (1R,2R,3S,4R,5S)-5-fluoro-3-(2-methylpyridin-4-yl)-N-[3-(trifluoromethyl)phenyl]-7-oxabicyclo[2.2.1]heptane-2-carboxamide | 12 (139) | | | |
| 108 | (1S,2R,3S,4S,6R)-6-fluoro-3-(2-methylpyridin-4-yl)-N-[3-(trifluoromethyl)phenyl]-7-oxabicyclo[2.2.1]heptane-2-carboxamide | 27 (137) | | | |
| 109 | (1R,2R,3S,4R,5S)-N-(5,6-dichloropyridin-3-yl)-5-fluoro-3-(2-methylpyridin-4-yl)-7-oxabicyclo[2.2.1]heptane-2-carboxamide | 28 (164) | | | |
| 110 | (1S,2R,3S,4S,6R)-N-(5,6-dichloropyridin-3-yl)-6-fluoro-3-(2-methylpyridin-4-yl)-7-oxabicyclo[2.2.1]heptane-2-carboxamide | 28 (199) | | | |
| 111 | (1R,2R,3S,4R,5S)-N-(3,4-dichlorophenyl)-5-fluoro-3-(2-fluoropyridin-4-yl)-7-oxabicyclo[2.2.1]heptane-2-carboxamide | 28 (87) | | | |
| 112 | (1S,2R,3S,4S,6R)-N-(3,4-dichlorophenyl)-6-fluoro-3-(2-fluoropyridin-4-yl)-7-oxabicyclo[2.2.1]heptane-2-carboxamide | 28 (99) | | | |
| 113 | (1R,2R,3S,4R,5S)-3-(2-aminopyrimidin-5-yl)-N-(3,4-dichlorophenyl)-5-fluoro-7-oxabicyclo[2.2.1]heptane-2-carboxamide | 30 (103) | | | |

TABLE 3-continued

| Ex No. | | (A) EC$_{50}$ μM (% Efficacy) | (B) EC$_{50}$ μM (% Efficacy) | (C) IC$_{50}$ μM (% Efficacy) | (D) IC$_{50}$ μM (% Efficacy) |
|---|---|---|---|---|---|
| 114 | (1S,2R,3S,4S,6R)-3-(2-aminopyrimidin-5-yl)-N-(3,4-dichlorophenyl)-6-fluoro-7-oxabicyclo[2.2.1]heptane-2-carboxamide | 30 (127) | | | |
| 115 | (1R,2R,3S,4R,5S)-N-(3,4-dichlorophenyl)-5-fluoro-3-(6-methylpyridin-3-yl)-7-oxabicyclo[2.2.1]heptane-2-carboxamide | 33 (49) | | | |
| 116 | (1S,2R,3S,4S,6R)-N-(3,4-dichlorophenyl)-6-fluoro-3-(6-methylpyridin-3-yl)-7-oxabicyclo[2.2.1]heptane-2-carboxamide | 23 (58) | | | |
| 117 | (1S,2S,4R,5R,6R,7S)-N-(3,4-dichlorophenyl)-7-(2-methylpyridin-4-yl)-8-oxatricyclo[3.2.1.0$^{2,4}$]octane-6-carboxamide | 3.0 (177) | | | 7.0 (59) |
| 118 | (1S,2S,4R,5R,6R,7S)-N-(3,4-dichlorophenyl)-7-(2-methoxypyridin-4-yl)-8-oxatricyclo[3.2.1.0$^{2,4}$]octane-6-carboxamide | 8.2 (118) | | | |
| 119 | (1S,2S,4R,5R,6R,7S)-N-(3,4-dichlorophenyl)-7-(2-fluoropyridin-4-yl)-8-oxatricyclo[3.2.1.0$^{2,4}$]octane-6-carboxamide | 25 (149) | | | |
| 120 | (1S,2S,4R,5R,6R,7S)-N-(3,4-dichlorophenyl)-7-[6-(trifluoromethyl)pyridin-2-yl]-8-oxatricyclo[3.2.1.0$^{2,4}$]octane-6-carboxamide | 20 (102) | | | 4.4 (119) |
| 121 | rac-(1S,2S,4R,5R,6R,7S)-7-(2-methylpyridin-4-yl)-N-[3-(trifluoromethyl)phenyl]-8-oxatricyclo[3.2.1.0$^{2,4}$]octane-6-carboxamide | 26 (353) | | | |
| 121a | (1S,2S,4R,5R,6R,7S)-7-(2-methylpyridin-4-yl)-N-[3-(trifluoromethyl)phenyl]-8-oxatricyclo[3.2.1.0$^{2,4}$]octane-6-carboxamide | 2.7 (231) | | | 4.5 (80) |
| 121b | (1R,2R,4S,5S,6S,7R)-7-(2-methylpyridin-4-yl)-N-[3-(trifluoromethyl)phenyl]-8-oxatricyclo[3.2.1.0$^{2,4}$]octane-6-carboxamide | 22 (92) | | | |
| 122 | rac-(1S,2S,4R,5R,6R,7S)-N-(3,4-dichlorophenyl)-7-(2,3-difluoropyridin-4-yl)-8-oxatricyclo[3.2.1.0$^{2,4}$]octane-6-carboxamide | 5.0 (32) | | | |
| 122a | (1S,2S,4R,5R,6R,7S)-N-(3,4-dichlorophenyl)-7-(2,3-difluoropyridin-4-yl)-8-oxatricyclo[3.2.1.0$^{2,4}$]octane-6-carboxamide | 25 (160) | | | |
| 122b | (1R,2R,4S,5S,6S,7R)-N-(3,4-dichlorophenyl)-7-(2,3-difluoropyridin-4-yl)-8-oxatricyclo[3.2.1.0$^{2,4}$]octane-6-carboxamide | 17 (217) | | | |
| 123 | (1S,2S,4R,5R,6R,7S)-N-(6-methoxypyridin-3-yl)-7-(6-methylpyridin-3-yl)-8-oxatricyclo[3.2.1.0$^{2,4}$]octane-6-carboxamide | >50 (0) | >20 (48) | | |
| 124 | (1S,2S,4R,5R,6R,7S)-N-(5,6-dichloropyridin-3-yl)-7-(2,3-difluoropyridin-4-yl)-8-oxatricyclo[3.2.1.0$^{2,4}$]octane-6-carboxamide | 2.8 (160) | 17 (59) | | |

TABLE 3-continued

| Ex No. | | (A) EC$_{50}$ μM (% Efficacy) | (B) EC$_{50}$ μM (% Efficacy) | (C) IC$_{50}$ μM (% Efficacy) | (D) IC$_{50}$ μM (% Efficacy) |
|---|---|---|---|---|---|
| 125 | (1S,2S,4R,5R,6R,7S)-N-(6-methoxypyridin-3-yl)-7-(pyridin-oxatricyclo[3.2.1.0$^{2,4}$]octane-6-carboxamide | 17 (162) | | | |
| 126 | rac-(1S,2S,4R,5R,6R,7S)-N-(3,4-dichlorophenyl)-7-(pyrimidin-5-yl)-8-oxatricyclo[3.2.1.0$^{2,4}$]octane-6-carboxamide | 10 (212) | | | |
| 126a | (1S,2S,4R,5R,6R,7S)-N-(3,4-dichlorophenyl)-7-(pyrimidin-5-yl)-8-oxatricyclo[3.2.1.0$^{2,4}$]octane-6-carboxamide | 5.4 (233) | | | |
| 126b | (1R,2R,4S,5S,6S,7R)-N-(3,4-dichlorophenyl)-7-(pyrimidin-5-yl)-8-oxatricyclo[3.2.1.0$^{2,4}$]octane-6-carboxamide | 5.6 (103) | | | >20 (42) |
| 127 | (1S,2S,4R,5R,6R,7S)-7-(2,3-difluoropyridin-4-yl)-N-(6-methoxypyridin-3-yl)-8-oxatricyclo[3.2.1.0$^{2,4}$]octane-6-carboxamide | >50 (62) | | | |
| 128 | (1S,2S,4R,5R,6R,7S)-N-(6-methoxypyridin-3-yl)-7-[6-(trifluoromethyl)pyridin-2-yl]-8-oxatricyclo[3.2.1.0$^{2,4}$]octane-6-carboxamide | >50 (27) | | | >20 (39) |
| 129 | (1S,2S,4R,5R,6R,7S)-N-(3,4-dichlorophenyl)-7-(2-fluoropyrimidin-5-yl)-8-oxatricyclo[3.2.1.0$^{2,4}$]octane-6-carboxamide | 10 (146) | | | |
| 130 | (1S,2S,4R,5R,6R,7S)-7-(pyrimidin-5-yl)-N-[3-(trifluoromethyl)phenyl]-8-oxatricyclo[3.2.1.0$^{2,4}$]octane-6-carboxamide | 10 (237) | | | |
| 131 | (1S,2S,4R,5R,6R,7S)-7-(pyridin-4-yl)-N-[3-(trifluoromethyl)phenyl]-8-oxatricyclo[3.2.1.0$^{2,4}$]octane-6-carboxamide | 19 (360) | | | |
| 132 | (1S,2S,4R,5R,6R,7S)-7-(2-aminopyrimidin-5-yl)-N-(3,4-dichlorophenyl)-8-oxatricyclo[3.2.1.0$^{2,4}$]octane-6-carboxamide | 18 (321) | | | |
| 133 | (1S,2S,4R,5R,6R,7S)-N-(3,4-dichlorophenyl)-7-[2-(morpholin-4-yl)pyrimidin-5-yl]-8-oxatricyclo[3.2.1.0$^{2,4}$]octane-6-carboxamide | 25 (158) | | | |
| 134 | (1S,2S,4R,5R,6R,7S)-7-(2-fluoropyridin-4-yl)-N-[3-(trifluoromethyl)phenyl]-8-oxatricyclo[3.2.1.0$^{2,4}$]octane-6-carboxamide | 19 (249) | | | |
| 135 | (1S,2S,4R,5R,6R,7S)-N-(3,4-dichlorophenyl)-7-(2-methylpyrimidin-5-yl)-8-oxatricyclo[3.2.1.0$^{2,4}$]octane-6-carboxamide | 16 (237) | | | |
| 136 | (1S,2S,4R,5R,6R,7S)-N-(5,6-dichloropyridin-3-yl)-7-(pyridin-4-yl)-8-oxatricyclo[3.2.1.0$^{2,4}$]octane-6-carboxamide | 17 (254) | | | |
| 137 | (1S,2S,4R,5R,6R,7S)-N-(3,4-dichlorophenyl)-7-(pyridin-4-yl)-8-oxatricyclo[3.2.1.0$^{2,4}$]octane-6-carboxamide | 21 (202) | | | |

TABLE 3-continued

| Ex No. | | (A) EC$_{50}$ µM (% Efficacy) | (B) EC$_{50}$ µM (% Efficacy) | (C) IC$_{50}$ µM (% Efficacy) | (D) IC$_{50}$ µM (% Efficacy) |
|---|---|---|---|---|---|
| 138 | (1R,2R,3S,4R,5S)-N-(3,4-dichlorophenyl)-5-hydroxy-3-(6-methylpyridin-3-yl)-7-oxabicyclo[2.2.1]heptane-2-carboxamide | >50 (0) | | | >20 (24) |
| 139 | rac-(1R,2R,3S,4R,5S)-N-(3,4-dichlorophenyl)-5-hydroxy-3-(2-methoxypyridin-4-yl)-7-oxabicyclo[2.2.1]heptane-2-carboxamide | 21 (223) | | | |
| 139a | (1R,2R,3S,4R,5S)-N-(3,4-dichlorophenyl)-5-hydroxy-3-(2-methoxypyridin-4-yl)-7-oxabicyclo[2.2.1]heptane-2-carboxamide | 25 (275) | | | 1.8 (54) |
| 139b | (1S,2S,3R,4S,5R)-N-(3,4-dichlorophenyl)-5-hydroxy-3-(2-methoxypyridin-4-yl)-7-oxabicyclo[2.2.1]heptane-2-carboxamide | 26 (141) | | | 7.7 (82) |
| 140 | (1R,2R,3S,4R,5S)-N-(3,4-dichlorophenyl)-5-hydroxy-3-[6-(trifluoromethyl)pyridin-2-yl]-7-oxabicyclo[2.2.1]heptane-2-carboxamide | 15 (292) | | | |
| 141 | (1R,2R,3S,4R,5S)-N-(3,4-dichlorophenyl)-5-hydroxy-3-(pyrimidin-5-yl)-7-oxabicyclo[2.2.1]heptane-2-carboxamide | 13 (43) | | | |
| 142 | rac-(1R,2R,3S,4R,5S)-N-(3,4-dichlorophenyl)-3-(2-fluoropyridin-4-yl)-5-hydroxy-7-oxabicyclo[2.2.1]heptane-2-carboxamide | 28 (142) | | | |
| 142a | (1R,2R,3S,4R,5S)-N-(3,4-dichlorophenyl)-3-(2-fluoropyridin-4-yl)-5-hydroxy-7-oxabicyclo[2.2.1]heptane-2-carboxamide | 22 (68) | 1.2 (83) | 33 (93) | 6.6 (81) |
| 142b | (1S,2S,3R,4S,5R)-N-(3,4-dichlorophenyl)-3-(2-fluoropyridin-4-yl)-5-hydroxy-7-oxabicyclo[2.2.1]heptane-2-carboxamide | 0.79 (54) | | | |
| 143 | (1R,2R,3S,4R,5S)-3-(2-aminopyrimidin-5-yl)-N-(3,4-dichlorophenyl)-5-hydroxy-7-oxabicyclo[2.2.1]heptane-2-carboxamide | >50 (0) | | | |
| 144 | (1R,2R,3S,4R,5S)-N-(3,4-dichlorophenyl)-3-[2-(dimethylamino)pyrimidin-5-yl]-5-hydroxy-7-oxabicyclo[2.2.1]heptane-2-carboxamide | 30 (183) | | | |
| 145 | (1R,2R,3S,4R,5S)-N-(3,4-dichlorophenyl)-5-hydroxy-3-[2-(trifluoromethyl)pyridin-4-yl]-7-oxabicyclo[2.2.1]heptane-2-carboxamide | 17 (246) | | | |
| 145a | (1R,2R,3S,4R,5S)-N-(3,4-dichlorophenyl)-5-hydroxy-3-[2-(trifluoromethyl)pyridin-4-yl]-7-oxabicyclo[2.2.1]heptane-2-carboxamide | | | | 1.2 (100) |
| 145b | (1S,2S,3R,4S,5R)-N-(3,4-dichlorophenyl)-5-hydroxy-3-(2-(trifluoromethyhpyridin-4-yl)-7-oxabicyclo[2.2.1]heptane-2-carboxamide | | | | 11 (83) |

TABLE 3-continued

| Ex No. | | (A) EC$_{50}$ μM (% Efficacy) | (B) EC$_{50}$ μM (% Efficacy) | (C) IC$_{50}$ μM (% Efficacy) | (D) IC$_{50}$ μM (% Efficacy) |
|---|---|---|---|---|---|
| 146 | (1R,2R,3S,4R,5S)-N-(3,4-dichlorophenyl)-3-(2,3-difluoropyridin-4-yl)-5-hydroxy-7-oxabicyclo[2.2.1]heptane-2-carboxamide | 20 (150) | | | |
| 147 | (1R,2R,3S,4R,5S)-N-(3,4-dichlorophenyl)-3-(2,5-difluoropyridin-4-yl)-5-hydroxy-7-oxabicyclo[2.2.1]heptane-2-carboxamide | 28 (284) | | | |
| 148 | (1R,2R,3S,4R,5S)-N-(3,4-dichlorophenyl)-5-hydroxy-3-(2-methylpyrimidin-5-yl)-7-oxabicyclo[2.2.1]heptane-2-carboxamide | 7.8 (51) | | | 18 (58) |
| 149 | (1R,2R,3S,4R,5S)-3-(2-aminopyridin-4-yl)-N-(3,4-dichlorophenyl)-5-hydroxy-7-oxabicyclo[2.2.1]heptane-2-carboxamide | 26 (112) | | | 8.3 (58) |
| 150 | (1R,2R,3S,4R,5S)-N-(3,4-dichlorophenyl)-5-hydroxy-3-(pyridin-4-yl)-7-oxabicyclo[2.2.1]heptane-2-carboxamide | >50 (5) | | | |
| 151 | (1R,2R,3S,4R,5S)-N-(3,4-dichlorophenyl)-3-(2-fluoropyrimidin-5-yl)-5-hydroxy-7-oxabicyclo[2.2.1]heptane-2-carboxamide | >50 (0) | | | |
| 152 | (1R,2R,3S,4R,5S)-N-(3,4-dichlorophenyl)-5-hydroxy-3-(1-methyl-1H-pyrazol-4-yl)-7-oxabicyclo[2.2.1]heptane-2-carboxamide | 12 (44) | | | 2.0 (61) |
| 153 | (1R,2R,3S,4R,5S)-N-(3,4-dichlorophenyl)-5-hydroxy-3-(1-methyl-1H-pyrazol-3-yl)-7-oxabicyclo[2.2.1]heptane-2-carboxamide | 19 (121) | | | >20 (46) |
| 154 | (1R,2R,3S,4R,5S)-N-(3,4-dichlorophenyl)-5-hydroxy-3-[2-(trifluoromethyl)pyrimidin-5-yl]-7-oxabicyclo[2.2.1]heptane-2-carboxamide | 26 (236) | | | 4.0 (75) |
| 155 | (1R,2R,3S,4R,5S)-N-(3,4-dichlorophenyl)-5-methoxy-3-(2-methylpyridin-4-yl)-7-oxabicyclo[2.2.1]heptane-2-carboxamide | 26 (262) | | | |
| 156 | (1S,2R,3S,4R,5S,6R)-N-(3,4-dichlorophenyl)-5,6-dihydroxy-3-(2-methylpyridin-4-yl)-7-oxabicyclo[2.2.1]heptane-2-carboxamide | 18 (28) | 0.95 (99) | 15 (103) | >20 (42) |
| 157 | (1R,2S,3R,4S,5R,6S)-N-(3,4-dichlorophenyl)-5,6-dihydroxy-3-(2-methylpyridin-4-yl)-7-oxabicyclo[2.2.1]heptane-2-carboxamide | 29 (57) | 2.1 (59) | 32 (84) | >20 (15) |
| 158 | (1S,2R,3S,4R,5S,6R)-5,6-dihydroxy-3-(2-methylpyridin-4-yl)-N-[3-(trifluoromethyl)phenyl]-7-oxabicyclo[2.2.1]heptane-2-carboxamide | >50 (31) | | | |
| 159 | (1S,2R,3S,4R,5S,6R)-5,6-dihydroxy-3-(pyridin-4-yl)-N-[3-(trifluoromethyl)phenyl]-7-oxabicyclo[2.2.1]heptane-2-carboxamide | >50 (11) | | | |
| 160 | (1S,2R,3S,4R,5S,6R)-N-(3,4-dichlorophenyl)-5,6-dihydroxy-3-(pyridin-4-yl)-7-oxabicyclo[2.2.1]heptane-2-carboxamide | >50 (32) | | | |

TABLE 3-continued

| Ex No. | | (A) EC$_{50}$ μM (% Efficacy) | (B) EC$_{50}$ μM (% Efficacy) | (C) IC$_{50}$ μM (% Efficacy) | (D) IC$_{50}$ μM (% Efficacy) |
|---|---|---|---|---|---|
| 161 | (1S,2R,3S,4R,5S,6R)-5,6-dihydroxy-3-(2-methylpyridin-4-yl)-N-[2-(trifluoromethyhpyridin-4-yl]-7-oxabicyclo[2.2.1]heptane-2-carboxamide | >50 (29) | | | |
| 162 | (1S,2R,3S,4R,5S,6R)-N-(5,6-dichloropyridin-3-yl)-5,6-dihydroxy-3-(2-methylpyridin-4-yl)-7-oxabicyclo[2.2.1]heptane-2-carboxamide | >50 (25) | | | |
| 163 | (1S,2R,3S,4R,5S,6R)-5,6-dihydroxy-N-[6-methyl-5-(trifluoromethyl)pyridin-3-yl]-3-(2-methylpyridin-4-yl)-7-oxabicyclo[2.2.1]heptane-2-carboxamide | >50 (23) | | | |
| 164 | (1R,2R,3S,4R,5R)-N-(3,4-dichlorophenyl)-5-fluoro-3-(6-methylpyridin-3-yl)-7-oxabicyclo[2.2.1]heptane-2-carboxamide | >50 (0) | | | |
| 165 | (1R,2R,3S,4R,5R)-N-(3,4-dichlorophenyl)-5-fluoro-3-(2-methoxypyridin-4-yl)-7-oxabicyclo[2.2.1]heptane-2-carboxamide | 6.0 (110) | | | >20 (59) |
| 166 | (1R,2R,3S,4R,5R)-N-(3,4-dichlorophenyl)-5-(dimethylamino)-3-(2-methylpyridin-4-yl)-7-oxabicyclo[2.2.1]heptane-2-carboxamide | 24 (68) | | | >20 (0) |
| 167 | (1R,2R,3S,4R,5R)-N-(3,4-dichlorophenyl)-5-(methylamino)-3-(2-methylpyridin-4-yl)-7-oxabicyclo[2.2.1]heptane-2-carboxamide | 6.9 (83) | | | |
| 168 | (1R,2R,3S,4R,5R)-N-(3,4-dichlorophenyl)-5-[(2-hydroxyethyl)amino]-3-(2-methylpyridin-4-yl)-7-oxabicyclo[2.2.1]heptane-2-carboxamide | 0.32 (114) | | | >20 (0) |
| 169 | (1R,2R,3S,4R,5R)-N-(3,4-dichlorophenyl)-3-(2-methylpyridin-4-yl)-5-[(oxan-4-yl)amino]-7-oxabicyclo[2.2.1]heptane-2-carboxamide | >50 (69) | | | >20 (54) |
| 170 | (1R,2R,3S,4R,5R)-N-(3,4-dichlorophenyl)-3-(2-methylpyridin-4-yl)-5-{[(1r,3r)-3-hydroxycyclobutyl]amino}-7-oxabicyclo[2.2.1]heptane-2-carboxamide | >50 (37) | | | |
| 171 | (1R,2R,3S,4R,5R)-N-(3,4-dichlorophenyl)-3-(2-fluoropyridin-4-yl)-5-(methylamino)-7-oxabicyclo[2.2.1]heptane-2-carboxamide | 24 (237) | | | |
| 172 | (1R,2R,3S,4R,5R)-N-(3,4-dichlorophenyl)-5-(dimethylamino)-3-(2-fluoropyridin-4-yl)-7-oxabicyclo[2.2.1]heptane-2-carboxamide | 16 (177) | | | |
| 173 | (1R,2R,3S,4R,5R)-N-(3,4-dichlorophenyl)-3-(2-fluoropyridin-4-yl)-5-[(2-hydroxyethyl)amino]-7-oxabicyclo[2.2.1]heptane-2-carboxamide | 27 (54) | | | |

TABLE 3-continued

| Ex No. | | (A) EC$_{50}$ μM (% Efficacy) | (B) EC$_{50}$ μM (% Efficacy) | (C) IC$_{50}$ μM (% Efficacy) | (D) IC$_{50}$ μM (% Efficacy) |
|---|---|---|---|---|---|
| 174 | (1R,2R,3S,4R,5R)-N-(5,6-dichloropyridin-3-yl)-3-(2-fluoropyridin-4-yl)-5-(methylamino)-7-oxabicyclo[2.2.1]heptane-2-carboxamide | >50 (37) | | | |
| 175 | (1R,2R,3S,4R,5R)-N-(5,6-dichloropyridin-3-yl)-5-(dimethylamino)-3-(2-fluoropyridin-4-yl)-7-oxabicyclo[2.2.1]heptane-2-carboxamide | 29 (186) | | | |
| 176 | (1R,2R,3S,4R,5R)-N-(5,6-dichloropyridin-3-yl)-3-(2-fluoropyridin-4-yl)-5-[(2-hydroxyethyl)amino]-7-oxabicyclo[2.2.1]heptane-2-carboxamide | 25 (51) | | | |
| 177 | (1R,2R,3S,4R,5R)-N-(3,4-dichlorophenyl)-3-(2-methylpyridin-4-yl)-5-(morpholin-4-yl)-7-oxabicyclo[2.2.1]heptane-2-carboxamide | 22 (211) | 1.5 (34) | >50 (33) | 1.5 (103) |
| 178 | (1 R,2R,3S,4R,5R)-N-(3,4-dichlorophenyl)-5-hydroxy-5-methyl-3-(2-methylpyridin-4-yl)-7-oxabicyclo[2.2.1]heptane-2-carboxamide | >50 (1) | | | |
| 179 | (1S,2S,3R,4S,5S)-N-(3,4-dichlorophenyl)-5-hydroxy-5-methyl-3-(2-methylpyridin-4-yl)-7-oxabicyclo[2.2.1]heptane-2-carboxamide | >50 (22) | | | |
| 180 | (1R,2R,3S,4R,5R)-N-(3,4-dichlorophenyl)-5-hydroxy-3-(2-methylpyridin-4-yl)-7-oxabicyclo[2.2.1]heptane-2-carboxamide | 30 (113) | | | 11 (69) |
| 181 | (1S,2S,3R,4S,5S)-N-(3,4-dichlorophenyl)-5-hydroxy-3-(2-methylpyridin-4-yl)-7-oxabicyclo[2.2.1]heptane-2-carboxamide | 27 (243) | | | >20 (28) |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

The invention claimed is:

1. A compound of Formula I or a pharmaceutically acceptable salt thereof, wherein:

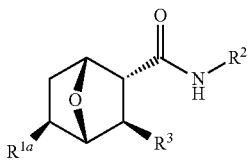

(2A)

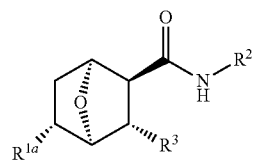

(2G)

$R^{1a}$ is hydroxyl;

$R^2$ is phenyl; a 5- or 6-membered heteroaryl or a 5- or 6-membered heterocyclyl, each having 1 to 3 heteroatoms selected from N, O and S; wherein $R^2$ is unsubstituted or substituted by 1 to 3 substituents independently selected from halo, $C_{1-6}$alkyl, halo-substituted $C_{1-6}$alkyl, $C_{1-6}$alkoxy, halo-substituted $C_{1-6}$alkoxy, cyano, $C_{1-6}$alkylsulfonyl, phenyl unsubstituted or substituted by halo;

$R^3$ is a 5- or 6-membered heteroaryl having 1 to 2 heteroatoms selected from N, O and S; wherein $R^3$ is unsubstituted or substituted by 1 to 3 substituents independently selected from halo, $C_{1-6}$alkyl, halo-substituted $C_{1-6}$alkyl, $C_{1-6}$alkoxy or —NR$^5$R$^6$;

$R^5$ and $R^6$ are independently hydrogen or $C_{1-6}$alkyl;

alternatively, $R^5$ and $R^6$ together with the nitrogen atom to which they are attached form a 5- or 6-membered heterocyclyl having 1-3 heteroatoms selected from N, O and S.

2. The compound of claim 1, wherein $R^2$ is phenyl, pyridyl, pyrazolyl, thiazolyl or piperidinyl, each of which is unsubstituted or substituted by 1 to 2 substituents independently selected from halo, $C_{1-6}$alkyl, halo-substituted $C_{1-6}$alkyl, $C_{1-6}$ alkoxy, halo-substituted $C_{1-6}$alkoxy, cyano, $C_{1-6}$alkylsulfonyl, phenyl unsubstituted or substituted by halo.

3. The compound of claim 1, wherein $R^2$ is selected from:
phenyl substituted by 3,4-dichloro; 2-trifluoromethyl; 3-trifluoromethyl; 3-cyano-4-chloro; 2-cyano-4-chloro; 3-fluoro-4-chloro; 3-trifluoromethoxy; 3-fluoro-4-trifluoromethoxy; or 3-chloro-4-(2-fluorophenyl);
pyridin-4-yl substituted by 6-methoxy or 2-trifluoromethyl;
pyridin-3-yl substituted by 5,6-dichloro; 6-methoxy; 5-chloro-6-methyl or 5-trifluoromethyl-6-methyl;
pyridin-2-yl substituted by 4,5-dichloro;
1H-pyrazol-3-yl substituted 1-methyl;
thiazol-2-yl substituted by 5-methyl; and
piperidin-4-yl substituted by 1-methylsulfonyl.

4. The compound of claim 1, wherein $R^3$ is selected from:
pyridin-4-yl unsubstituted or substituted by 2-methyl; 2-trifluoromethyl; 2-methoxy; 2-amino; 2-fluoro; 2,3-difluoro; or 2,5-difluoro;
pyridin-3-yl unsubstituted or substituted by 6-methyl; 6-methoxy; or 5,6-dichloro;
pyridin-2-yl substituted by 6-trifluoromethyl;
pyrimidin-5-yl unsubstituted or substituted by 2-fluoro, 2-methyl, 2-amino, 2-trifluoromethyl, 2-morpholinyl or 2-di-methylamino;
pyrimidin-4-yl substituted by 2-methyl; and
1H-pyrazol-4-yl or 1H-pyrazolyl-3-yl substituted by 1-methyl.

5. The compound of claim 1, wherein $R^3$ is pyridyl unsubstituted or substituted by 1 to 2 substituents independently selected from fluoro, trifluoromethyl, methyl and methoxy.

6. The compound of claim 1, wherein said compound is (1R,2R,3S,4R,5S)—N-(3,4-dichlorophenyl)-5-hydroxy-3-(2-methylpyridin-4-yl)-7-oxabicyclo[2.2.1]heptane-2-carboxamide or a pharmaceutically acceptable salt thereof.

7. The compound of claim 1, wherein said compound is (1S,2S,3R,4S,5R)—N-(3,4-dichlorophenyl)-5-hydroxy-3-(2-methylpyridin-4-yl)-7-oxabicyclo[2.2.1]heptane-2-carboxamide or a pharmaceutically acceptable salt thereof.

8. The compound of claim 1, wherein said compound is (1R,2R,3S,4R,5S)—N-(3,4-dichlorophenyl)-3-(2-fluoropyridin-4-yl)-5-hydroxy-7-oxabicyclo[2.2.1]heptane-2-carboxamide or a pharmaceutically acceptable salt thereof.

9. The compound of claim 1, wherein said compound is (1S,2S,3R,4S,5R)—N-(3,4-dichlorophenyl)-3-(2-fluoropyridin-4-yl)-5-hydroxy-7-oxabicyclo[2.2.1]heptane-2-carboxamide or a pharmaceutically acceptable salt thereof.

10. The compound of claim 1, wherein said compound is (1R,2R,3S,4R,5S)—N-(3,4-dichlorophenyl)-5-hydroxy-3-(2-(trifluoromethyl)pyridin-4-yl)-7-oxabicyclo[2.2.1]heptane-2-carboxamide or a pharmaceutically acceptable salt thereof.

11. The compound of claim 1, wherein said compound is (1S,2S,3R,4S,5R)—N-(3,4-dichlorophenyl)-5-hydroxy-3-(2-(trifluoromethyl)pyridin-4-yl)-7-oxabicyclo[2.2.1]heptane-2-carboxamide or a pharmaceutically acceptable salt thereof.

12. A pharmaceutical composition comprising a compound according to claim 1 or a pharmaceutically acceptable salt thereof, and one or more pharmaceutically acceptable carriers.

13. A combination comprising a compound according to claim 1 or a pharmaceutically acceptable salt thereof, and one or more therapeutically active agents.

14. A method for treating, ameliorating or preventing arthritis or joint injury, or for cartilage repair in a subject in need thereof, comprising administering a therapeutically effective amount of a compound according to claim 1, and optionally in combination with a second therapeutic agent; thereby treating, ameliorating or preventing arthritis or joint injury, or repairing cartilage, in said subject.

15. A method for treating or ameliorating osteoarthritis in a subject in need thereof, comprising administering a therapeutically effective amount of a compound according to claim 1, and optionally in combination with a second therapeutic agent; thereby treating or ameliorating osteoarthritis, in said subject.

16. The compound of claim 1, wherein $R^3$ is pyridyl, pyrimidinyl or pyrazolyl, each of which is unsubstituted or substituted by 1 to 2 substituents independently selected from halo, $C_{1-6}$alkyl, halo-substituted $C_{1-6}$alkyl, $C_{1-6}$alkoxy or —$NR^5R^6$.

* * * * *